(12) United States Patent
Yadav et al.

(10) Patent No.: US 7,659,120 B2
(45) Date of Patent: Feb. 9, 2010

(54) Δ 15 DESATURASES SUITABLE FOR ALTERING LEVELS OF POLYUNSATURATED FATTY ACIDS IN OLEAGINOUS PLANTS AND YEAST

(75) Inventors: Narendra S. Yadav, Chadds Ford, PA (US); Hongxiang Zhang, Chadds Ford, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 227 days.

(21) Appl. No.: 10/985,254

(22) Filed: Nov. 10, 2004

(65) Prior Publication Data

US 2005/0132442 A1 Jun. 16, 2005

Related U.S. Application Data

(60) Provisional application No. 60/519,191, filed on Nov. 12, 2003.

(51) Int. Cl.
*C12N 15/82* (2006.01)
*C07H 21/04* (2006.01)
*C12N 1/20* (2006.01)

(52) U.S. Cl. .................... 435/419; 435/471; 435/252.3; 536/23.2; 800/281

(58) Field of Classification Search ........................ None
See application file for complete search history.

(56) References Cited

U.S. PATENT DOCUMENTS

| 5,850,026 | A | 12/1998 | DeBonte et al. |
| 5,952,544 | A | 9/1999 | Browse et al. |
| 6,075,183 | A | 6/2000 | Knutzon et al. |
| 6,459,018 | B1 | 10/2002 | Knutzon |
| 2002/0170090 | A1 | 11/2002 | Browse et al. |

FOREIGN PATENT DOCUMENTS

| EP | 0 005 277 A2 | 11/1979 |
| EP | 0 005 277 B1 | 1/1982 |
| WO | WO 98/46764 | 10/1998 |
| WO | WO 98/55625 | 12/1998 |
| WO | 99/64614 A2 | 12/1999 |
| WO | WO 02/26946 A2 | 4/2002 |
| WO | 03/064596 A2 | 8/2003 |
| WO | WO 03/099216 A2 | 12/2003 |
| WO | 2005/003310 A2 | 1/2005 |

OTHER PUBLICATIONS

Broun et al, Science 282:1315-1317, Nov. 13, 1998.*
Van de Loo et al, PNAS, USA 92:6743-6747, Jul. 1995.*
Doerks et al, TIG 14(6): 248-250, Jun. 1998.*
Smith et al, Nature Biotechnology 15: 1222-1223, Nov. 15, 1997.*
Brenner, S.E., TIG 15(4): 132-133, Apr. 1999.*
Bork et al, TIG 12(10): 425-427, Oct 1996.*
DeLuca, V, AgBiotech News and Information 5(6): 225N-229N, 1993.*
Kimura et al, FEBS Lett 435:163-168, 1998.*
Sequence database Accession No. AB014492, Dec. 25, 2002.*
Frederic Domergue et al., Cloning and functional characterization of phaeodactylum tricornutum front-end desaturases involved in eicosapentaenoic acid biosynthesis, Eur. J. Biochem., vol. 269:4105-4113, 2002.
Frederic Beaudoin et al., Heterologous reconstitution in yeast of the polyunsaturated fatty acid biosynthetic pathway, PNAS, vol. 97(12):6421-6426, 2000.
J. M. Dyer et al., Metabolic engineering of *Saccharomyces cerevislae* for production of novel lipid compounds, Appl Microbiol Biotechnol., vol. 59:224-230, 2002.
Darwin W. Reed et al., Characterization of the *Brassica napus* Extraplastidial Linoleate Desaturase by Expression in *Saccharomyces cerevisiae*, Plant Phys., vol. 122:715-720, 2000.
Dauenpen Meesapyodsuk et al., Characterization of the Regiochemistry and Cryptoregiochemistry of a *Caenorhabditis elegans* Fatty Acid Desaturase (FAT-1) Expressed in *Saccharomyces cerevisiae*, Biochemistry, vol. 39:11948-11954, 2000.
James P. Spychalla et al., Identification of an animal w-3 fatty acid desaturase by heterologous expression in *Arabidopsis*, Proc. Natl. Acad. Sci., vol. 1142-1147, 1997.
National Center for Biotechnology Information General Identifier No. 46127025, Accession No. XP_388066, Apr. 29, 2004.
C. Ratledge, Microbial Oils and Fats: An Assessment of Their Commercial Potential, Prog. Ind. Microbiol., vol. 16:119-206, 1982.
Kimura, M. et al., *Gibberella zeae* gene for fatty acid desaturase, partial cds., Database GeneSeq, Database Accession No. AB014492, Dec. 25, 2002.
Tocher, D. R. et al., Recent Advances in the Biochemistry and Molecular Biology of Fatty Acyl Desaturases, Prog. Lipid Res., Aug. 7, 1998, p. 73-117, vol. 37, No. 2/3, Elsevier Science Ltd.

* cited by examiner

*Primary Examiner*—Elizabeth F McElwain

(57) ABSTRACT

The present invention relates to fungal Δ-15 fatty acid desaturases that are able to catalyze the conversion of linoleic acid (18:2, LA) to alpha-linolenic acid (18:3, ALA). Nucleic acid sequences encoding the desaturases, nucleic acid sequences which hybridize thereto, DNA constructs comprising the desaturase genes, and recombinant host plants and microorganisms expressing increased levels of the desaturases are described. Methods of increasing production of specific omega-3 and omega-6 fatty acids by over-expression of the Δ-15 fatty acid desaturases are also described herein.

34 Claims, 9 Drawing Sheets

Figure 5

Pair Distances of Untitled ClustalW (Slow/Accurate, Gonnet)

Percent Similarity in upper triangle
Percent Divergence in lower triangle

|  | Nc 1 | Fg 1 | Fm 1 | Mg 1 | An 1 | Yl d12d | Nc 2 | Fg 2 | Fm 2 | Mg 2 | An 2 |  |
|---|---|---|---|---|---|---|---|---|---|---|---|---|
| Nc 1 | *** | 55.2 | 54.8 | 56.2 | 46.2 | 35.9 | 40.3 | 40.1 | 40.3 | 41.5 | 39.6 | Nc 1 |
| Fg 1 | 59.0 | *** | 88.8 | 59.8 | 46.2 | 40.2 | 43.7 | 42.4 | 42.4 | 43.9 | 44.4 | Fg 1 |
| Fm 1 | 59.8 | 11.9 | *** | 60.9 | 46.8 | 42.0 | 43.8 | 43.8 | 43.5 | 43.5 | 44.5 | Fm 1 |
| Mg 1 | 54.2 | 53.3 | 51.0 | *** | 48.0 | 41.1 | 45.2 | 43.7 | 43.1 | 42.1 | 42.6 | Mg 1 |
| An 1 | 78.8 | 84.8 | 83.0 | 81.6 | *** | 38.9 | 43.4 | 41.6 | 40.4 | 42.4 | 40.6 | An 1 |
| Yl d12d | 116.2 | 103.6 | 97.1 | 102.4 | 109.1 | *** | 52.5 | 52.3 | 51.3 | 53.0 | 53.0 | Yl d12d |
| Nc 2 | 109.2 | 97.8 | 97.5 | 93.0 | 98.4 | 73.4 | *** | 65.8 | 67.6 | 69.7 | 66.4 | Nc 2 |
| Fg 2 | 103.7 | 99.4 | 95.0 | 97.9 | 104.0 | 72.1 | 39.1 | *** | 95.0 | 72.1 | 61.6 | Fg 2 |
| Fm 2 | 108.8 | 102.0 | 98.3 | 99.6 | 108.9 | 76.4 | 41.0 | 5.2 | *** | 70.0 | 61.2 | Fm 2 |
| Mg 2 | 104.6 | 97.0 | 98.3 | 103.0 | 101.7 | 72.2 | 38.3 | 34.8 | 38.2 | *** | 56.3 | Mg 2 |
| An 2 | 111.1 | 95.4 | 95.1 | 101.3 | 107.9 | 71.9 | 42.0 | 52.2 | 52.6 | 45.7 | *** | An 2 |

SEQUENCE LISTING

```
<160> NUMBER OF SEQ ID NOS: 109

<210> SEQ ID NO 1
<211> LENGTH: 1209
<212> TYPE: DNA
<213> ORGANISM: Fusarium monoliforme

<400> SEQUENCE: 1
atggcgactc gacagcgaac tgccaccact gttgtggtcg aggaccttcc caaggtcact      60
cttgaggcca agtctgaacc tgtgttcccc gatatcaaga ccatcaagga tgccattccc     120
gcgcactgct tccagccctc gctcgtcacc tcattctact acgtcttccg cgattttgcc     180
```

```
atggtctctg ccctcgtctg ggctgctctc acctacatcc ccagcatccc cgaccagacc      240
ctccgcgtcg cagcttggat ggtctacggc ttcgtccagg gtctgttctg caccggtgtc      300
tggattctcg gccatgagtg cggccacggt gctttctctc tccacggaaa ggtcaacaat      360
gtgaccggct ggttcctcca ctcgttcctc ctcgtcccct acttcagctg gaagtactct      420
caccaccgcc accaccgctt caccggccac atggatctcg acatggcttt cgtcgccaag      480
actgagccca agccctccaa gtcgctcatg attgctggca ttgacgtcgc cgagcttgtt      540
gaggacaccc ccgctgctca gatggtcaag ctcatcttcc accagctttt cggatggcag      600
gcgtacctct tcttcaacgc tagctctggc aagggcagca agcagtggga gcccaagact      660
ggcctctcca gtggttccg agtcagtcac ttcgagccta ccagcgctgt cttccgcccc      720
aacgaggcca tcttcatcct catctccgat atcggtcttg ctctaatggg aactgctctg      780
tactttgctt ccaagcaagt tggtgtttcg accattctct tcctctacct tgttccctac      840
ctgtgggttc accactggct cgttgccatt acctacctcc accaccacca caccgagctc      900
cctcactaca ccgctgaggg ctggacctac gtcaagggag ctctcgccac tgtcgaccgt      960
gagtttggct tcatcggaaa gcacctcttc cacggtatca ttgagaagca cgttgttcac     1020
catctcttcc ctaagatccc cttctacaag gctgacgagg ccaccgaggc catcaagccc     1080
gtcattggcg accactactg ccacgacgac cgaagcttcc tgggccagct gtggaccatc     1140
ttcggcacgc tcaagtacgt cgagcacgac cctgcccgac ccggtgccat gcgatggaac     1200
aaggactag                                                             1209
```

<210> SEQ ID NO 2
<211> LENGTH: 402
<212> TYPE: PRT
<213> ORGANISM: Fusarium monoliforme

<400> SEQUENCE: 2

```
Met Ala Thr Arg Gln Arg Thr Ala Thr Thr Val Val Glu Asp Leu
1               5                   10                  15

Pro Lys Val Thr Leu Glu Ala Lys Ser Glu Pro Val Phe Pro Asp Ile
                20                  25                  30

Lys Thr Ile Lys Asp Ala Ile Pro Ala His Cys Phe Gln Pro Ser Leu
            35                  40                  45

Val Thr Ser Phe Tyr Tyr Val Phe Arg Asp Phe Ala Met Val Ser Ala
        50                  55                  60

Leu Val Trp Ala Ala Leu Thr Tyr Ile Pro Ser Ile Pro Asp Gln Thr
65                  70                  75                  80

Leu Arg Val Ala Ala Trp Met Val Tyr Gly Phe Val Gln Gly Leu Phe
                85                  90                  95

Cys Thr Gly Val Trp Ile Leu Gly His Glu Cys Gly His Gly Ala Phe
            100                 105                 110

Ser Leu His Gly Lys Val Asn Asn Val Thr Gly Trp Phe Leu His Ser
        115                 120                 125

Phe Leu Leu Val Pro Tyr Phe Ser Trp Lys Tyr Ser His His Arg His
    130                 135                 140

His Arg Phe Thr Gly His Met Asp Leu Asp Met Ala Phe Val Pro Lys
145                 150                 155                 160

Thr Glu Pro Lys Pro Ser Lys Ser Leu Met Ile Ala Gly Ile Asp Val
                165                 170                 175

Ala Glu Leu Val Glu Asp Thr Pro Ala Ala Gln Met Val Lys Leu Ile
            180                 185                 190
```

```
Phe His Gln Leu Phe Gly Trp Gln Ala Tyr Leu Phe Asn Ala Ser
            195                 200                 205

Ser Gly Lys Gly Ser Lys Gln Trp Glu Pro Lys Thr Gly Leu Ser Lys
        210                 215                 220

Trp Phe Arg Val Ser His Phe Glu Pro Thr Ser Ala Val Phe Arg Pro
225                 230                 235                 240

Asn Glu Ala Ile Phe Ile Leu Ile Ser Asp Ile Gly Leu Ala Leu Met
                245                 250                 255

Gly Thr Ala Leu Tyr Phe Ala Ser Lys Gln Val Gly Val Ser Thr Ile
            260                 265                 270

Leu Phe Leu Tyr Leu Val Pro Tyr Leu Trp Val His Trp Leu Val
        275                 280                 285

Ala Ile Thr Tyr Leu His His His Thr Glu Leu Pro His Tyr Thr
        290                 295                 300

Ala Glu Gly Trp Thr Tyr Val Lys Gly Ala Leu Ala Thr Val Asp Arg
305                 310                 315                 320

Glu Phe Gly Phe Ile Gly Lys His Leu Phe His Gly Ile Ile Glu Lys
                325                 330                 335

His Val Val His His Leu Phe Pro Lys Ile Pro Phe Tyr Lys Ala Asp
            340                 345                 350

Glu Ala Thr Glu Ala Ile Lys Pro Val Ile Gly Asp His Tyr Cys His
            355                 360                 365

Asp Asp Arg Ser Phe Leu Gly Gln Leu Trp Thr Ile Phe Gly Thr Leu
        370                 375                 380

Lys Tyr Val Glu His Asp Pro Ala Arg Pro Gly Ala Met Arg Trp Asn
385                 390                 395                 400

Lys Asp

<210> SEQ ID NO 3
<211> LENGTH: 1434
<212> TYPE: DNA
<213> ORGANISM: Fusarium monoliforme

<400> SEQUENCE: 3
atggcgtcca cttcggctct gcccaagcag aaccctgcgc ttagacgcac cgtcacctca      60
actactgtga cggattctga gtctgccgcc gtctctcctt cagactctcc ccgccactcg     120
gcctcttcca catcgctctc gtccatgtcc gaggttgata tcgccaagcc caagtccgag     180
tatggtgtca tgctcgacac ctacggcaac cagttcgagg ttcccgactt taccatcaag     240
gacatctaca tgccatccc taagcactgc ttcaagcgct ccgctctcaa gggatacggt     300
tatatcctcc gcgacattgt cctcctgact accactttca gcatctggta caactttgtg     360 accccgaat atatcccctc accccgcc cgcgctggtc tgtgggccgt gtacaccgtt       420
cttcagggtc ttttcggtac tggtctctgg gttattgccc atgagtgcgg tcacggtgct     480
ttctccgatt ctcgcatcat caacgacatt actggctggg ttcttcactc ttccctcctt     540 gtccctact tcagctggca aatctcccac cgaaagcacc acaaggccac tggcaacatg     600
gagcgtgaca tggtcttcgt tccccgaacc cgcgagcagc aggctactcg tctcggaaag     660 atgaccacg agctcgctca tcttactgag gagaccccg ctttcactct tctcatgctc     720
gtccttcagc agctcgttgg ctggcccaac tacctcatca ccaatgttac cggccacaac     780
taccacgagc gccagcgtga gggtcgcggc aagggcaagc ataacggcct cggcggtggt     840
gttaaccact tcgatccccg cagccctctg tacgagaaca gtgacgctaa gctcatcgtc     900
```

-continued

```
ctcagcgata ttggtatcgg tctgatggcc actgctctgt acttcctcgt tcagaagttc    960
ggtttctaca acatggccat ctggtacttt gttccctacc tctgggttaa ccactggctc   1020
gttgccatca ccttcctcca gcacaccgac cctacccttc cccactacac caacgacgag   1080
tggaacttcg tccgtggtgc cgctgctacc attgaccgtg agatgggctt catcggccgc   1140
caccttctcc acggcatcat cgagactcat gtcctccacc actacgtcag cagcatcccc   1200
ttctacaacg cggacgaggc caccgaggcc attaagccca tcatgggcaa gcactaccgg   1260
gctgatgtcc aggatggtcc tcgtggcttc atccgcgcca tgtaccgcag tgcgcgtatg   1320
tgccagtggg ttgagcccag cgctggtgcc gagggtgctg gtaagggtgt tctgttcttc   1380
cgcaaccgca acaacgtggg caccccccc gctgttatca agcccgttgc ttaa          1434

<210> SEQ ID NO 4
<211> LENGTH: 477
<212> TYPE: PRT
<213> ORGANISM: Fusarium monoliforme

<400> SEQUENCE: 4

Met Ala Ser Thr Ser Ala Leu Pro Lys Gln Asn Pro Ala Leu Arg Arg
1               5                   10                  15

Thr Val Thr Ser Thr Thr Val Thr Asp Ser Glu Ser Ala Ala Val Ser
            20                  25                  30

Pro Ser Asp Ser Pro Arg His Ser Ala Ser Ser Thr Ser Leu Ser Ser
        35                  40                  45

Met Ser Glu Val Asp Ile Ala Lys Pro Lys Ser Glu Tyr Gly Val Met
    50                  55                  60

Leu Asp Thr Tyr Gly Asn Gln Phe Glu Val Pro Asp Phe Thr Ile Lys
65                  70                  75                  80

Asp Ile Tyr Asn Ala Ile Pro Lys His Cys Phe Lys Arg Ser Ala Leu
                85                  90                  95

Lys Gly Tyr Gly Tyr Ile Leu Arg Asp Ile Val Leu Leu Thr Thr Thr
            100                 105                 110

Phe Ser Ile Trp Tyr Asn Phe Val Thr Pro Glu Tyr Ile Pro Ser Thr
        115                 120                 125

Pro Ala Arg Ala Gly Leu Trp Ala Val Tyr Thr Val Leu Gln Gly Leu
    130                 135                 140

Phe Gly Thr Gly Leu Trp Val Ile Ala His Glu Cys Gly His Gly Ala
145                 150                 155                 160

Phe Ser Asp Ser Arg Ile Ile Asn Asp Ile Thr Gly Trp Val Leu His
                165                 170                 175

Ser Ser Leu Leu Val Pro Tyr Phe Ser Trp Gln Ile Ser His Arg Lys
            180                 185                 190

His His Lys Ala Thr Gly Asn Met Glu Arg Asp Met Val Phe Val Pro
        195                 200                 205

Arg Thr Arg Glu Gln Gln Ala Thr Arg Leu Gly Lys Met Thr His Glu
    210                 215                 220

Leu Ala His Leu Thr Glu Glu Thr Pro Ala Phe Thr Leu Leu Met Leu
225                 230                 235                 240

Val Leu Gln Gln Leu Val Gly Trp Pro Asn Tyr Leu Ile Thr Asn Val
                245                 250                 255

Thr Gly His Asn Tyr His Glu Arg Gln Arg Glu Gly Arg Gly Lys Gly
            260                 265                 270

Lys His Asn Gly Leu Gly Gly Gly Val Asn His Phe Asp Pro Arg Ser
```

```
                275                 280                 285
Pro Leu Tyr Glu Asn Ser Asp Ala Lys Leu Ile Val Leu Ser Asp Ile
    290                 295                 300
Gly Ile Gly Leu Met Ala Thr Ala Leu Tyr Phe Leu Val Gln Lys Phe
305                 310                 315                 320
Gly Phe Tyr Asn Met Ala Ile Trp Tyr Phe Val Pro Tyr Leu Trp Val
                325                 330                 335
Asn His Trp Leu Val Ala Ile Thr Phe Leu Gln His Thr Asp Pro Thr
                340                 345                 350
Leu Pro His Tyr Thr Asn Asp Glu Trp Asn Phe Val Arg Gly Ala Ala
                355                 360                 365
Ala Thr Ile Asp Arg Glu Met Gly Phe Ile Gly Arg His Leu Leu His
    370                 375                 380
Gly Ile Ile Glu Thr His Val Leu His His Tyr Val Ser Ser Ile Pro
385                 390                 395                 400
Phe Tyr Asn Ala Asp Glu Ala Thr Glu Ala Ile Lys Pro Ile Met Gly
                405                 410                 415
Lys His Tyr Arg Ala Asp Val Gln Asp Gly Pro Arg Gly Phe Ile Arg
                420                 425                 430
Ala Met Tyr Arg Ser Ala Arg Met Cys Gln Trp Val Glu Pro Ser Ala
                435                 440                 445
Gly Ala Glu Gly Ala Gly Lys Gly Val Leu Phe Phe Arg Asn Arg Asn
    450                 455                 460
Asn Val Gly Thr Pro Pro Ala Val Ile Lys Pro Val Ala
465                 470                 475

<210> SEQ ID NO 5
<211> LENGTH: 1206
<212> TYPE: DNA
<213> ORGANISM: Aspergillus nidulans

<400> SEQUENCE: 5
atggctgcaa ctgcaacaac cctagcagag attgaaaaga aaaagaagaa aataactctg      60
cagacaatca aaaatgcgat tcccaaacac tgcttcaacc gctctctcct catttcctct     120
gcctacgtcg tccgcgatct cctctacgcc tccgtcctct tctactttgc cctgcacatt     180
gacaccctct tttcctcgca actcctccgc atcctcgcct ggaccgccta cggtttcatg     240
caaggctgcg tcggcaccgg aatctggatc ctcgcacacg aatgcggcca tggagctttc     300
tccccatacc aaacgtggaa cgatgtcgtc ggatggacat tgcactccct cctgatggtc     360
ccgtatttca gctggaagat cacgcacgct cgacaccacc ggtacacaaa caacacagag     420
cgagatacag catttgtccc ctggacagag aaggaataca cactcgccc gcgctacttc     480
cctgcctggt ttgagatgtt tgaggacacg cccgtctaca accttattag cctactggcg     540
catcagatcg caggatggca gatgtatctc tgttttacg ttagcgccgg cgcaaagagt      600
aagcctgtac gcagggaaa acagagcggg tggtttggag ccagcagag cgccagccac       660
tttgatccgg gcagttcgct gtggacggaa aaccagcggc atctgattgc gatttcggac     720
ctggggttgc tgcttgttgc ggcggcaaat tggtaccttg cgcagcaagt gggcgtgctc     780
cgcatggtgc tgatctatgt tgtgccgtac ttctgggtgc accattggct gtgggcgatc     840
acgtacctcc accacacaca ccctcgatc ccgcactaca ctgatagcac ctggacgttc      900
accaaaggcg ctctgtccac cgtcgaccgc gacttcggtt tcatcgggcg gcatttcttc     960
caccatatca ttgaccacca gtcgtgcat cacttgttta accggatccc gttctaccat     1020
```

```
gccgaggagg cgactaatgc cattattccc gtactcgggg acatgtatca tcgcgaagag   1080
accggcttct tgtggagttt aatggagacg tacaagaact gtcggtttgt aggcgttgaa   1140
aatgatgttg gaaaggaggg cgttttgcat tgggttttg aggagaagaa gggtgccaaa   1200
gcggaa                                                              1206
```

<210> SEQ ID NO 6
<211> LENGTH: 401
<212> TYPE: PRT
<213> ORGANISM: Aspergillus nidulans

<400> SEQUENCE: 6

```
Met Ala Ala Thr Ala Thr Thr Leu Ala Glu Ile Glu Lys Lys Lys Glu
1               5                   10                  15

Glu Ile Thr Leu Gln Thr Ile Lys Asn Ala Ile Pro Lys His Cys Phe
            20                  25                  30

Asn Arg Ser Leu Leu Ile Ser Ser Ala Tyr Val Val Arg Asp Leu Leu
        35                  40                  45

Tyr Ala Ser Val Leu Phe Tyr Phe Ala Leu His Ile Asp Thr Leu Phe
    50                  55                  60

Ser Ser Gln Leu Leu Arg Ile Leu Ala Trp Thr Ala Tyr Gly Phe Met
65                  70                  75                  80

Gln Gly Cys Val Gly Thr Gly Ile Trp Ile Leu Ala His Glu Cys Gly
                85                  90                  95

His Gly Ala Phe Ser Pro Tyr Gln Thr Trp Asn Asp Val Val Gly Trp
            100                 105                 110

Thr Leu His Ser Leu Leu Met Val Pro Tyr Phe Ser Trp Lys Ile Thr
        115                 120                 125

His Ala Arg His His Arg Tyr Thr Asn Asn Thr Glu Arg Asp Thr Ala
    130                 135                 140

Phe Val Pro Trp Thr Glu Lys Glu Tyr Asp Thr Arg Pro Arg Tyr Phe
145                 150                 155                 160

Pro Ala Trp Phe Glu Met Phe Glu Asp Thr Pro Val Tyr Asn Leu Ile
                165                 170                 175

Ser Leu Leu Ala His Gln Ile Ala Gly Trp Gln Met Tyr Leu Cys Phe
            180                 185                 190

Tyr Val Ser Ala Gly Ala Lys Ser Lys Pro Val Pro Gln Gly Lys Gln
        195                 200                 205

Ser Gly Trp Phe Gly Gly Gln Gln Ser Ala Ser His Phe Asp Pro Gly
    210                 215                 220

Ser Ser Leu Trp Thr Glu Asn Gln Arg His Leu Ile Ala Ile Ser Asp
225                 230                 235                 240

Leu Gly Leu Leu Val Ala Ala Ala Asn Trp Tyr Leu Ala Gln Gln
                245                 250                 255

Val Gly Val Leu Arg Met Val Leu Ile Tyr Val Pro Tyr Phe Trp
            260                 265                 270

Val His His Trp Leu Val Ala Ile Thr Tyr Leu His Thr His Pro
        275                 280                 285

Ser Ile Pro His Tyr Thr Asp Ser Thr Trp Thr Phe Thr Lys Gly Ala
    290                 295                 300

Leu Ser Thr Val Asp Arg Asp Phe Gly Phe Ile Gly Arg His Phe Phe
305                 310                 315                 320

His His Ile Ile Asp His His Val Val His Leu Phe Asn Arg Ile
                325                 330                 335
```

```
Pro Phe Tyr His Ala Glu Glu Ala Thr Asn Ala Ile Ile Pro Val Leu
            340                 345                 350

Gly Asp Met Tyr His Arg Glu Glu Thr Gly Phe Leu Trp Ser Leu Met
        355                 360                 365

Glu Thr Tyr Lys Asn Cys Arg Phe Val Gly Val Glu Asn Asp Val Gly
    370                 375                 380

Lys Glu Gly Val Leu His Trp Val Phe Glu Glu Lys Lys Gly Ala Lys
385                 390                 395                 400

Ala

<210> SEQ ID NO 7
<211> LENGTH: 1416
<212> TYPE: DNA
<213> ORGANISM: Aspergillus nidulans

<400> SEQUENCE: 7
atgtcgtcta ctgccctccc gaagcgcgtt gcgctgcatc gcaacccgac taccgactct      60
tcggtcccca gctccgtctc ggtctccccg ctggactcgc ccgtcagtc tccgtcgtcg     120 acttcgctct cgtcaatggc ctcggatgcg ggcaagggag acttgggcaa gatgctcgac     180
acctatggca atgagttcaa gatccccgac tacaccatca aggatatccg tgatgccatt     240
ccgtcccact gctacaaccg gtctgctatc aggagtctgt cctatgtctt ccgtgatctc     300
gccgtcctcg cttccgtctt ctacgtcttc cacaaatacg tgaccccgga gaccgtccct     360
tcgtacccgg cgcgtgttgc gctgtggact ctctacactg tcgtccaggg tctgttcggt     420
accggtattt gggttcttgc tcacgagtgt ggacaccagg cgttctctac ttccaaggtg     480
ctcaacgaca ctgttggctg gatcctgcat tcggctctgc tggtccccta tttctcgtgg     540
aagatctctc acggcaagca ccacaaggcc accggtaacc tggctcgtga catggtcttc     600
gtccccaaga cccgcgaggt gtacgcctcc cgcatcaaga gaccatcta cgacctgaac     660 gaggtgatgg aggagacccc cttggccact gccacccact ccatcctgca gcagctgttc     720
ggctggccct tgtacctgct caccaacgtt accggtcacg caaccacga cgccagcct     780 gaaggccgcg gcaagggcaa gcgtaacggc tacttcaccg gcgtcaacca cttcaacccc     840
aacagccctc tgttcgaggc caaggacgcc aagctcatca ttctgagtga tatcggcctc     900
gccatcaccg ccagcatcct gtacctgatc ggctccaagt tcggctggat gaacttgctc     960
gtctggtacg gtatccccta cctctgggtg aaccactggc ttgttgccat cacctactc    1020 cagcacaccg accccactct ccccactac cagcccgagt cctggacctt cgcccgcggt    1080
gccgctgcca ccattgaccg cgagttcggc ttcatcggcc gtcacattct ccacggcatc    1140
atcgagaccc acgtcctcca ccactacgtc agcaccatcc ccttctacca cgccgacgag    1200
gccagcgagg ctatcaagaa ggtcatgggc tcgcactacc gcagcgaggc acacaccggt    1260
cctctgggct tcctcaaggc tctctggacc agcgcccgtg tctgccactg ggtcgagccc    1320
accgaaggca ccaagggcga gaacgctggt gtcttgttct ccgcaacac caacggcatc    1380 ggtgttcctc ccattaagct gaccaagcct aactaa                             1416

<210> SEQ ID NO 8
<211> LENGTH: 471
<212> TYPE: PRT
<213> ORGANISM: Aspergillus nidulans

<400> SEQUENCE: 8
```

-continued

```
Met Ser Ser Thr Ala Leu Pro Lys Arg Val Ala Leu His Arg Asn Pro
1               5                   10                  15

Thr Thr Asp Ser Ser Val Pro Ser Ser Val Ser Pro Leu Asp
            20              25              30

Ser Pro Arg Gln Ser Pro Ser Ser Thr Ser Leu Ser Ser Met Ala Ser
            35              40              45

Asp Ala Gly Lys Gly Asp Leu Gly Lys Met Leu Asp Thr Tyr Gly Asn
        50              55              60

Glu Phe Lys Ile Pro Asp Tyr Thr Ile Lys Asp Ile Arg Asp Ala Ile
65              70              75                  80

Pro Ser His Cys Tyr Asn Arg Ser Ala Ile Arg Ser Leu Ser Tyr Val
                85              90                  95

Phe Arg Asp Leu Ala Val Leu Ala Ser Val Phe Tyr Val Phe His Lys
            100             105             110

Tyr Val Thr Pro Glu Thr Val Pro Ser Tyr Pro Ala Arg Val Ala Leu
            115             120             125

Trp Thr Leu Tyr Thr Val Val Gln Gly Leu Phe Gly Thr Gly Ile Trp
        130             135             140

Val Leu Ala His Glu Cys Gly His Gln Ala Phe Ser Thr Ser Lys Val
145             150             155                 160

Leu Asn Asp Thr Val Gly Trp Ile Leu His Ser Ala Leu Leu Val Pro
                165             170             175

Tyr Phe Ser Trp Lys Ile Ser His Gly Lys His His Lys Ala Thr Gly
            180             185             190

Asn Leu Ala Arg Asp Met Val Phe Val Pro Lys Thr Arg Glu Val Tyr
        195             200             205

Ala Ser Arg Ile Lys Lys Thr Ile Tyr Asp Leu Asn Glu Val Met Glu
        210             215             220

Glu Thr Pro Leu Ala Thr Ala Thr His Ser Ile Leu Gln Gln Leu Phe
225             230             235             240

Gly Trp Pro Leu Tyr Leu Leu Thr Asn Val Thr Gly His Asp Asn His
            245             250             255

Glu Arg Gln Pro Glu Gly Arg Gly Lys Gly Lys Arg Asn Gly Tyr Phe
            260             265             270

Thr Gly Val Asn His Phe Asn Pro Asn Ser Pro Leu Phe Glu Ala Lys
        275             280             285

Asp Ala Lys Leu Ile Ile Leu Ser Asp Ile Gly Leu Ala Ile Thr Ala
        290             295             300

Ser Ile Leu Tyr Leu Ile Gly Ser Lys Phe Gly Trp Met Asn Leu Leu
305             310             315             320

Val Trp Tyr Gly Ile Pro Tyr Leu Trp Val Asn His Trp Leu Val Ala
            325             330             335

Ile Thr Tyr Leu Gln His Thr Asp Pro Thr Leu Pro His Tyr Gln Pro
            340             345             350

Glu Ser Trp Thr Phe Ala Arg Gly Ala Ala Thr Ile Asp Arg Glu
        355             360             365

Phe Gly Phe Ile Gly Arg His Ile Leu His Gly Ile Ile Glu Thr His
        370             375             380

Val Leu His His Tyr Val Ser Thr Ile Pro Phe Tyr His Ala Asp Glu
385             390             395             400

Ala Ser Glu Ala Ile Lys Lys Val Met Gly Ser His Tyr Arg Ser Glu
            405             410             415

Ala His Thr Gly Pro Leu Gly Phe Leu Lys Ala Leu Trp Thr Ser Ala
```

```
                  420           425            430
Arg Val Cys His Trp Val Glu Pro Thr Glu Gly Thr Lys Gly Glu Asn
            435                 440                 445

Ala Gly Val Leu Phe Phe Arg Asn Thr Asn Gly Ile Gly Val Pro Pro
        450                 455                 460

Ile Lys Leu Thr Lys Pro Asn
465                 470

<210> SEQ ID NO 9
<211> LENGTH: 1185
<212> TYPE: DNA
<213> ORGANISM: Magnaporthe grisea

<400> SEQUENCE: 9
atgtccacca ccgtcactca gcggccgggc gccgctagcc gcgctgaagc caagcccaag      60
gagcagcaat ttccagacat caacaccatc aggaatgcta tccccgcaca ctgttttgag     120
gcatctctgg tgacttcagt tggttacttg gtgcgagatg tggccctcat caccgctctc     180
ggctgggccg ccttgaccta cattccccaa attccggatt cgactttgcg ctggaccgcc     240
tgggccgctt acggctttgt tcagggtctc tttggcaccg gtctctggat tctgcccac      300 gagtgcggcc acggtgcttt cagcaagcac acgcgcatta caacattct ggctgggcc       360 gcccactcgg ccctgctggt accgtacttc agctggaagt tctctcacca ccgccaccac     420
aacttcaccg ccacatgga aaggacatg gcctttgtgc cccccaggc tgccgaccgc        480 gagtcccgcg ccagcttgct gtcccgcttc ggcatcgacc tcgaggtctt tgaggatacc     540
cccatctttc agcttgctcg cctcgtgagc caccagctct tcggctggca gacttacctg     600
ctcttcaacg ccacctgcgg caaggagtct ctgcagaaca gggtgccgc gtggttccgc      660 cagagccact ttgagcccac ctctgccgtc ttccgctcca gcgaggccct ctacatcgcc     720
atctctgaca ttggcctggc catcgttgcc gccgccatct actggggctc caccaaggtc     780
ggcgccggca ccatgttcct cctctacgcc gttccctaca tgtgggttca ccactggctc     840
gtcgccatca cctaccttca ccacaccaac aaggaggtgc accactacga ggccgacagc     900
tggacctttg tcaagggtgc cgtcgccact gtcgaccgtg actttggttt cattgaccgc     960
cacctgttcc acggtatcat ggaacccac gtcgcccacc atctgttccc tgcattccc      1020 ttttacaagg cagaggaggc caccgaggcc atcaagcctg tcctcggaga cctttaccac    1080
agcgacaatc gccccttcat gcaggctctg tggagcaact tcaccacctg caagtacgtc    1140
gagaaggacc ccaaggttcc cggcgccatg aggtgggccg attga                    1185

<210> SEQ ID NO 10
<211> LENGTH: 394
<212> TYPE: PRT
<213> ORGANISM: Magnaporthe grisea

<400> SEQUENCE: 10

Met Ser Thr Thr Val Thr Gln Arg Pro Gly Ala Ala Ser Arg Ala Glu
1               5                   10                  15

Ala Lys Pro Lys Glu Gln Gln Phe Pro Asp Ile Asn Thr Ile Arg Asn
            20                  25                  30

Ala Ile Pro Ala His Cys Phe Glu Ala Ser Leu Val Thr Ser Val Gly
        35                  40                  45

Tyr Leu Val Arg Asp Val Ala Leu Ile Thr Ala Leu Gly Trp Ala Ala
    50                  55                  60
```

-continued

```
Leu Thr Tyr Ile Pro Gln Ile Pro Asp Ser Thr Leu Arg Trp Thr Ala
65                  70                  75                  80

Trp Ala Ala Tyr Gly Phe Val Gln Gly Leu Phe Gly Thr Gly Leu Trp
                85                  90                  95

Ile Leu Ala His Glu Cys Gly His Gly Ala Phe Ser Lys His Thr Arg
            100                 105                 110

Ile Asn Asn Ile Leu Gly Trp Ala Ala His Ser Ala Leu Leu Val Pro
        115                 120                 125

Tyr Phe Ser Trp Lys Phe Ser His His Arg His His Asn Phe Thr Gly
    130                 135                 140

His Met Glu Lys Asp Met Ala Phe Val Pro Pro Gln Ala Ala Asp Arg
145                 150                 155                 160

Glu Ser Arg Ala Ser Leu Leu Ser Arg Phe Gly Ile Asp Leu Glu Val
                165                 170                 175

Phe Glu Asp Thr Pro Ile Phe Gln Leu Ala Arg Leu Val Ser His Gln
            180                 185                 190

Leu Phe Gly Trp Gln Thr Tyr Leu Leu Phe Asn Ala Thr Cys Gly Lys
        195                 200                 205

Glu Ser Leu Gln Asn Lys Gly Ala Ala Trp Phe Arg Gln Ser His Phe
    210                 215                 220

Glu Pro Thr Ser Ala Val Phe Arg Ser Ser Glu Ala Leu Tyr Ile Ala
225                 230                 235                 240

Ile Ser Asp Ile Gly Leu Ala Ile Val Ala Ala Ala Ile Tyr Trp Gly
                245                 250                 255

Ser Thr Lys Val Gly Ala Gly Thr Met Phe Leu Leu Tyr Ala Val Pro
            260                 265                 270

Tyr Met Trp Val His His Trp Leu Val Ala Ile Thr Tyr Leu His His
        275                 280                 285

Thr Asn Lys Glu Val His His Tyr Glu Ala Asp Ser Trp Thr Phe Val
    290                 295                 300

Lys Gly Ala Val Ala Thr Val Asp Arg Asp Phe Gly Phe Ile Asp Arg
305                 310                 315                 320

His Leu Phe His Gly Ile Ile Gly Thr His Val Ala His His Leu Phe
                325                 330                 335

Pro Arg Ile Pro Phe Tyr Lys Ala Glu Glu Ala Thr Glu Ala Ile Lys
            340                 345                 350

Pro Val Leu Gly Asp Leu Tyr His Ser Asp Asn Arg Pro Phe Met Gln
        355                 360                 365

Ala Leu Trp Ser Asn Phe Thr Thr Cys Lys Tyr Val Glu Lys Asp Pro
    370                 375                 380

Lys Val Pro Gly Ala Met Arg Trp Ala Asp
385                 390
```

<210> SEQ ID NO 11
<211> LENGTH: 1656
<212> TYPE: DNA
<213> ORGANISM: Magnaporthe grisea

<400> SEQUENCE: 11

```
atgccttcca ccagatcgac cacatcgggc attgcccagg agaagactcc tatgaggcga      60
acgaccacct cggccactgt cgaatcggac gtctcagctc cgggaaccgc tgttcagtcg     120
cctatggact cgccccgcca ctctgcctcg tccacctcac tctcttcact ctcttccgtt     180
gatgcggcgg ccgagaagaa atccaacgag tctgtcggca aactcgtcga cacgtacggc     240
```

-continued

```
aacaccttg  agatccctga  cttcaccatc  aaggacatcc  acgatgccat  tccaaagcac   300
tgctttgaac  gctctgctat  tcgtagcttg  agctacgtcg  cccgtgatat  ggtcctcctg   360
gcgacgacct  tctacgtgtt  ccacaactac  gtgacaccag  agtacattcc  ctcgaagccg   420
gctcgtgctg  gtctgtgggc  catttacacg  gtgctccagg  gcctcttcgg  caccggaatc   480
tgggttcttg  cccatgagtg  tggccaccag  gctttctcgc  cttccaagac  catcaacaac   540
acggttggct  ggattctcca  ctcgtctctg  ctggttccgt  acttcagctg  gcagatgtca   600
cacagcaagc  accacaaggc  cactggccat  attgagcgcg  acatggtctt  tgtgccccgc   660
acccgggagg  agcacgccag  caggatcggc  cgcatggtcc  acgagctgtc  ggagttgacc   720
gaggagacgc  ctattgccac  ccttatccac  ttggttgggc  agcagctgat  cggctggcct   780
ctgtacatca  tcactaacaa  gaccggtcac  aactaccacg  agcgccagcg  tgagggccgt   840
ggcaagggca  agaagaacgg  tcttttcact  ggcgtcaacc  acttcaaccc  cagcagccct   900
ctgtacgaga  caaggacgc   cggaaaggtg  cttctcagcg  acctgggtgt  cggccttgtt   960
atcgctggcc  tcgtgtacct  ttgccaaact  ttcggcaccc  agaacatgct  ggtttggtac  1020
tttatcccct  acctctgggt  gaaccactgg  ctcgttgcca  ttacattcct  tcagcacacc  1080
gaccctcgc   ttccgcacta  tactgccgag  gaatggaact  tcgtccgagg  tgccgctgcc  1140
acgatcgatc  gcgagtttgg  cttcgtcggc  cgccacctgc  ttcacggtat  cattgagacc  1200
cacgtcctgc  accactatgt  cagcacgatc  ccctttaca   acgccgacga  ggctactgat  1260
gccatcaaga  aggtgatggg  caagcactac  cgcagcgaca  ctgccggcgg  ccctgctggc  1320
ttccttaagt  cactctggac  gagtagccgc  atgtgccaat  gggttgagcc  cagcgccgag  1380
gctgagggta  gtggcaaggg  tgtcctgttc  ttccgcaacc  acaacaagat  cggcactcct  1440
cctatcaaga  tgtctgctca  gaaaattaga  ctatgcaatg  accttcttgg  catgcataag  1500
ggaaagaatc  aaatgaatgg  atcaagggag  cgccgcggcg  gacaaagtag  tttaaagagg  1560
gtgagaaatc  agcgatcgac  aaatatgaac  gaatcacaca  tgacggtgtt  ccgggcattc  1620
cgaacttgga  gctcatgcac  gcgcgcgtcc  acatga                              1656
```

<210> SEQ ID NO 12
<211> LENGTH: 551
<212> TYPE: PRT
<213> ORGANISM: Magnaporthe grisea

<400> SEQUENCE: 12

```
Met Pro Ser Thr Arg Ser Thr Thr Ser Gly Ile Ala Gln Glu Lys Thr
  1               5                  10                  15

Pro Met Arg Arg Thr Thr Thr Ser Ala Thr Val Glu Ser Asp Val Ser
             20                  25                  30

Ala Pro Gly Thr Ala Val Gln Ser Pro Met Asp Ser Pro Arg His Ser
         35                  40                  45

Ala Ser Ser Thr Ser Leu Ser Ser Leu Ser Ser Val Asp Ala Ala Ala
     50                  55                  60

Glu Lys Lys Ser Asn Glu Ser Val Gly Lys Leu Val Asp Thr Tyr Gly
 65                  70                  75                  80

Asn Thr Phe Glu Ile Pro Asp Phe Thr Ile Lys Asp Ile His Asp Ala
                 85                  90                  95

Ile Pro Lys His Cys Phe Glu Arg Ser Ala Ile Arg Ser Leu Ser Tyr
            100                 105                 110

Val Ala Arg Asp Met Val Leu Leu Ala Thr Thr Phe Tyr Val Phe His
        115                 120                 125
```

-continued

```
Asn Tyr Val Thr Pro Glu Tyr Ile Pro Ser Lys Pro Ala Arg Ala Gly
        130                 135                 140

Leu Trp Ala Ile Tyr Thr Val Leu Gln Gly Leu Phe Gly Thr Gly Ile
145                 150                 155                 160

Trp Val Leu Ala His Glu Cys Gly His Gln Ala Phe Ser Pro Ser Lys
                165                 170                 175

Thr Ile Asn Asn Thr Val Gly Trp Ile Leu His Ser Ser Leu Leu Val
            180                 185                 190

Pro Tyr Phe Ser Trp Gln Met Ser His Ser Lys His His Lys Ala Thr
        195                 200                 205

Gly His Ile Glu Arg Asp Met Val Phe Val Pro Arg Thr Arg Glu Glu
    210                 215                 220

His Ala Ser Arg Ile Gly Arg Met Val His Glu Leu Ser Glu Leu Thr
225                 230                 235                 240

Glu Glu Thr Pro Ile Ala Thr Leu Ile His Leu Val Gly Gln Gln Leu
                245                 250                 255

Ile Gly Trp Pro Leu Tyr Ile Ile Thr Asn Lys Thr Gly His Asn Tyr
            260                 265                 270

His Glu Arg Gln Arg Glu Gly Arg Gly Lys Gly Lys Lys Asn Gly Leu
        275                 280                 285

Phe Thr Gly Val Asn His Phe Asn Pro Ser Ser Pro Leu Tyr Glu Asn
    290                 295                 300

Lys Asp Ala Gly Lys Val Leu Leu Ser Asp Leu Gly Val Gly Leu Val
305                 310                 315                 320

Ile Ala Gly Leu Val Tyr Leu Cys Gln Thr Phe Gly Thr Gln Asn Met
                325                 330                 335

Leu Val Trp Tyr Phe Ile Pro Tyr Leu Trp Val Asn His Trp Leu Val
            340                 345                 350

Ala Ile Thr Phe Leu Gln His Thr Asp Pro Ser Leu Pro His Tyr Thr
        355                 360                 365

Ala Glu Glu Trp Asn Phe Val Arg Gly Ala Ala Thr Ile Asp Arg
    370                 375                 380

Glu Phe Gly Phe Val Gly Arg His Leu Leu His Gly Ile Ile Glu Thr
385                 390                 395                 400

His Val Leu His His Tyr Val Ser Thr Ile Pro Phe Tyr Asn Ala Asp
                405                 410                 415

Glu Ala Thr Asp Ala Ile Lys Lys Val Met Gly Lys His Tyr Arg Ser
            420                 425                 430

Asp Thr Ala Gly Gly Pro Ala Gly Phe Leu Lys Ser Leu Trp Thr Ser
        435                 440                 445

Ser Arg Met Cys Gln Trp Val Glu Pro Ser Ala Glu Ala Glu Gly Ser
    450                 455                 460

Gly Lys Gly Val Leu Phe Phe Arg Asn His Asn Lys Ile Gly Thr Pro
465                 470                 475                 480

Pro Ile Lys Met Ser Ala Gln Lys Ile Arg Leu Cys Asn Asp Leu Leu
                485                 490                 495

Gly Met His Lys Gly Lys Asn Gln Met Asn Gly Ser Arg Glu Arg Arg
            500                 505                 510

Gly Gly Gln Ser Ser Leu Lys Arg Val Arg Asn Gln Arg Ser Thr Asn
        515                 520                 525

Met Asn Glu Ser His Met Thr Val Phe Arg Ala Phe Arg Thr Trp Ser
    530                 535                 540
```

```
Ser Cys Thr Arg Ala Ser Thr
545                 550
```

<210> SEQ ID NO 13
<211> LENGTH: 1290
<212> TYPE: DNA
<213> ORGANISM: Neurospora crassa

<400> SEQUENCE: 13

```
atgacggtca ccacccgcag ccacaaggcc gcggccgcca ccgagcccga ggttgtcagc      60
accggcgttg acgccgtctc tgctgctgct ccctcctcct cctcctcctc ttccagccaa     120
aagtcggccg agcccatcga ataccccgac atcaagacca tccgcgacgc catccccgac     180
cactgcttcc gcccgcgcgt ctggatctcc atggcctact tcatccgcga cttcgccatg     240
gccttttggcc tcggctacct cgcctggcag tacatccccc tgatcgcctc caccccgctc     300
cgctacggcg cctgggctct gtacggctac ctccagggtc tcgtctgcac gggcatctgg     360
attctggcgc acgagtgcgg ccacggcgcc ttctcgaggc acacgtggtt caacaacgtc     420
atggggtgga ttggccactc cttcctcttg gtcccttact tcagctggaa gttcagccac     480
catcgccacc atcgcttcac cggccacatg gagaaggaca tggcgtttgt gcctgccacc     540
gaggctgatc gcaaccagag gaagctggcc aacttgtaca tggacaagga cacggccgag     600
atgtttgagg atgtgcccat tgtccagctc gtcaagctca tcgcccacca gctggccggc     660
tggcagatgt acctcctctt caacgtctcc gccggtaagg gcagcaagca gtgggagact     720
ggcaagggcg catgggctg gttgagggtt agccactttg agccttcctc tgctgtgttc     780
cgcaactccg aggccatcta cattgccctg tccgatcttg gtctcatgat catgggctat     840
atcctctacc aggccgcgca ggttgttggc tggcagatgg taggtctgct gtacttccag     900
cagtacttct gggttcacca ttggttggtc gccatcactt acctccacca cacccacgag     960
gaagtccacc actttgacgc cgactcgtgg accttcgtca agggcgctct cgccaccgtc    1020
gaccgcgatt ttggcttcat tggcaagcac ctcttccaca acattatcga ccaccacgtc    1080
gtccaccact tgttccctcg catccccttc tactacgccg aagaagccac caactcgatc    1140
cgccccatgc tcggccccct ctaccaccgc gacgaccgct ccttcatggg ccagctgtgg    1200
tacaacttca cccactgcaa gtgggtcgtt ccggaccccc aggtcccgg cgcgcttatt    1260
tgggcgcaca ccgttcagag cacccagtaa                                   1290
```

<210> SEQ ID NO 14
<211> LENGTH: 429
<212> TYPE: PRT
<213> ORGANISM: Neurospora crassa

<400> SEQUENCE: 14

```
Met Thr Val Thr Thr Arg Ser His Lys Ala Ala Ala Thr Glu Pro
1               5                   10                  15

Glu Val Val Ser Thr Gly Val Asp Ala Val Ser Ala Ala Pro Ser
                20                  25                  30

Ser Ser Ser Ser Ser Ser Gln Lys Ser Ala Glu Pro Ile Glu Tyr
                35                  40                  45

Pro Asp Ile Lys Thr Ile Arg Asp Ala Ile Pro Asp His Cys Phe Arg
                50                  55                  60

Pro Arg Val Trp Ile Ser Met Ala Tyr Phe Ile Arg Asp Phe Ala Met
65              70                  75                  80

Ala Phe Gly Leu Gly Tyr Leu Ala Trp Gln Tyr Ile Pro Leu Ile Ala
```

```
                 85                  90                  95
Ser Thr Pro Leu Arg Tyr Gly Ala Trp Ala Leu Tyr Gly Tyr Leu Gln
            100                 105                 110
Gly Leu Val Cys Thr Gly Ile Trp Ile Leu Ala His Glu Cys Gly His
            115                 120                 125
Gly Ala Phe Ser Arg His Thr Trp Phe Asn Asn Val Met Gly Trp Ile
            130                 135                 140
Gly His Ser Phe Leu Leu Val Pro Tyr Phe Ser Trp Lys Phe Ser His
145                 150                 155                 160
His Arg His His Arg Phe Thr Gly His Met Glu Lys Asp Met Ala Phe
                165                 170                 175
Val Pro Ala Thr Glu Ala Asp Arg Asn Gln Arg Lys Leu Ala Asn Leu
            180                 185                 190
Tyr Met Asp Lys Glu Thr Ala Glu Met Phe Glu Asp Val Pro Ile Val
            195                 200                 205
Gln Leu Val Lys Leu Ile Ala His Gln Leu Ala Gly Trp Gln Met Tyr
            210                 215                 220
Leu Leu Phe Asn Val Ser Ala Gly Lys Gly Ser Lys Gln Trp Glu Thr
225                 230                 235                 240
Gly Lys Gly Gly Met Gly Trp Leu Arg Val Ser His Phe Glu Pro Ser
                245                 250                 255
Ser Ala Val Phe Arg Asn Ser Glu Ala Ile Tyr Ile Ala Leu Ser Asp
            260                 265                 270
Leu Gly Leu Met Ile Met Gly Tyr Ile Leu Tyr Gln Ala Ala Gln Val
            275                 280                 285
Val Gly Trp Gln Met Val Gly Leu Leu Tyr Phe Gln Gln Tyr Phe Trp
            290                 295                 300
Val His His Trp Leu Val Ala Ile Thr Tyr Leu His His Thr His Glu
305                 310                 315                 320
Glu Val His His Phe Asp Ala Asp Ser Trp Thr Phe Val Lys Gly Ala
                325                 330                 335
Leu Ala Thr Val Asp Arg Asp Phe Gly Phe Ile Gly Lys His Leu Phe
            340                 345                 350
His Asn Ile Ile Asp His His Val Val His Leu Phe Pro Arg Ile
            355                 360                 365
Pro Phe Tyr Tyr Ala Glu Glu Ala Thr Asn Ser Ile Arg Pro Met Leu
            370                 375                 380
Gly Pro Leu Tyr His Arg Asp Asp Arg Ser Phe Met Gly Gln Leu Trp
385                 390                 395                 400
Tyr Asn Phe Thr His Cys Lys Trp Val Val Pro Asp Pro Gln Val Pro
                405                 410                 415
Gly Ala Leu Ile Trp Ala His Thr Val Gln Ser Thr Gln
            420                 425

<210> SEQ ID NO 15
<211> LENGTH: 1446
<212> TYPE: DNA
<213> ORGANISM: Neurospora crassa

<400> SEQUENCE: 15
atggcgtccg tctcctctgc ccttcccgag ggcaacaagc ctgccctgcg caggacccaa      60
accgaggcca cctccgactc atacccggt accgctgatg cctctccctt cgactctccc      120
cttgagcgct cggcctccaa cacctcgctt tcttcccagg cctctgacaa cgtcaagacc      180
```

-continued

```
gacaaggccg agttcggcaa gctgctcgac acgtatggca acgagttcga ggtccccgac    240
ttcaccatca aggacatccg cgatgccatc cccgcccact gctttgagcg ttcggctctt    300
cacagcttgg cgcacgtcgt ccgcgacatc atttacctca ccgtcacttt ttacgtctgg    360
aacaagtatg tcactcccga gtacatcccc atgaaggctg cccgtgtcgt cctctggggt    420
ctgtacacct tcatgcaggg ccttttcggc accggtctct gggttcttgc ccatgagtgc    480
ggtcaccagg ctttctcccc gtccaggttg atcaacgaca ccgtcggctg ggtcctccac    540
tctgcccttc tcgtccccta cttctcgtgg aagttctccc acagcaagca ccacaaggcc    600
accggcaaca tcgagcgtga catggtcttc gttcctcgga cccgcgagca gtttgcgtct    660
cgcatcggcc gtttcgtcca tgagatttcc gagttgaccg aggagacccc catctacacc    720
ttgatccacc ttatcggtca gcagctcatc ggctggccca actacctcat gaccaacgtc    780
accggccaca acttccacga gaggcagcgc gagggtcgtg gcaagggcaa gaagaacggc    840
tggttcactg gtgtcaacca cttcaacccc agctctcccc tctatgagga gcgtgaggcc    900
ccctggatca tcgtctccga catcggtatc gctatcgccg ccaccgccct catctacctc    960
ggcaacacct tcggctggtc caacatgttc gtctggtact tccttcccta cctctgggtc   1020
aaccactggc ttgttgccat cacctacctc cagcacaccg accctcgct ccccactac    1080 accctgatc agtggaactt tgtccgtggt gccgccgcga ctattgaccg cgagttcggc   1140
ttcatcggcc gtcacctcct ccacggcatt atcgagaccc acgttctcca ccactacgtc   1200
agcaccattc ccttttacca cgccgacgag gcctccgagg ccatcaagaa ggtcatgggc   1260
cgtcactacc gcgctgacgt ccaagatggc cccatcggtt tcatcaaggc catgtggaag   1320
gctgctcgtt ggtgccagtg ggttgagcct accgagggcg ctgagggtaa gggcaagggc   1380
gtcttgttct accgcaacca gaacggtctc ggtgtcaagc ctgccaagct ccccaaaacc   1440
aactaa                                                              1446
```

<210> SEQ ID NO 16
<211> LENGTH: 481
<212> TYPE: PRT
<213> ORGANISM: Neurospora crassa

<400> SEQUENCE: 16

```
Met Ala Ser Val Ser Ser Ala Leu Pro Glu Gly Asn Lys Pro Ala Leu
1               5                   10                  15

Arg Arg Thr Gln Thr Glu Ala Thr Ser Asp Ser Tyr Pro Gly Thr Ala
            20                  25                  30

Asp Ala Ser Pro Phe Asp Ser Pro Leu Glu Arg Ser Ala Ser Asn Thr
        35                  40                  45

Ser Leu Ser Ser Gln Ala Ser Asp Asn Val Lys Thr Asp Lys Ala Glu
    50                  55                  60

Phe Gly Lys Leu Leu Asp Thr Tyr Gly Asn Glu Phe Glu Val Pro Asp
65                  70                  75                  80

Phe Thr Ile Lys Asp Ile Arg Asp Ala Ile Pro Ala His Cys Phe Glu
                85                  90                  95

Arg Ser Ala Leu His Ser Leu Ala His Val Val Arg Asp Ile Ile Tyr
            100                 105                 110

Leu Thr Val Thr Phe Tyr Val Trp Asn Lys Tyr Val Thr Pro Glu Tyr
        115                 120                 125

Ile Pro Met Lys Ala Ala Arg Val Val Leu Trp Gly Leu Tyr Thr Phe
    130                 135                 140
```

-continued

```
Met Gln Gly Leu Phe Gly Thr Gly Leu Trp Val Leu Ala His Glu Cys
145                 150                 155                 160

Gly His Gln Ala Phe Ser Pro Ser Arg Leu Ile Asn Asp Thr Val Gly
                165                 170                 175

Trp Val Leu His Ser Ala Leu Leu Val Pro Tyr Phe Ser Trp Lys Phe
            180                 185                 190

Ser His Ser Lys His His Lys Ala Thr Gly Asn Ile Glu Arg Asp Met
        195                 200                 205

Val Phe Val Pro Arg Thr Arg Glu Gln Phe Ala Ser Arg Ile Gly Arg
    210                 215                 220

Phe Val His Glu Ile Ser Glu Leu Thr Glu Glu Thr Pro Ile Tyr Thr
225                 230                 235                 240

Leu Ile His Leu Ile Gly Gln Gln Leu Ile Gly Trp Pro Asn Tyr Leu
                245                 250                 255

Met Thr Asn Val Thr Gly His Asn Phe His Glu Arg Gln Arg Glu Gly
            260                 265                 270

Arg Gly Lys Gly Lys Lys Asn Gly Trp Phe Thr Gly Val Asn His Phe
        275                 280                 285

Asn Pro Ser Ser Pro Leu Tyr Glu Glu Arg Glu Ala Pro Trp Ile Ile
    290                 295                 300

Val Ser Asp Ile Gly Ile Ala Ile Ala Ala Thr Ala Leu Ile Tyr Leu
305                 310                 315                 320

Gly Asn Thr Phe Gly Trp Ser Asn Met Phe Val Trp Tyr Phe Leu Pro
                325                 330                 335

Tyr Leu Trp Val Asn His Trp Leu Val Ala Ile Thr Tyr Leu Gln His
            340                 345                 350

Thr Asp Pro Ser Leu Pro His Tyr Thr Pro Asp Gln Trp Asn Phe Val
        355                 360                 365

Arg Gly Ala Ala Ala Thr Ile Asp Arg Glu Phe Gly Phe Ile Gly Arg
    370                 375                 380

His Leu Leu His Gly Ile Ile Glu Thr His Val Leu His His Tyr Val
385                 390                 395                 400

Ser Thr Ile Pro Phe Tyr His Ala Asp Glu Ala Ser Glu Ala Ile Lys
                405                 410                 415

Lys Val Met Gly Arg His Tyr Arg Ala Asp Val Gln Asp Gly Pro Ile
            420                 425                 430

Gly Phe Ile Lys Ala Met Trp Lys Ala Ala Arg Trp Cys Gln Trp Val
        435                 440                 445

Glu Pro Thr Glu Gly Ala Glu Gly Lys Gly Lys Gly Val Leu Phe Tyr
    450                 455                 460

Arg Asn Gln Asn Gly Leu Gly Val Lys Pro Ala Lys Leu Pro Lys Thr
465                 470                 475                 480

Asn
```

<210> SEQ ID NO 17
<211> LENGTH: 1212
<212> TYPE: DNA
<213> ORGANISM: Fusarium graminearium

<400> SEQUENCE: 17

```
atggccacca gacagcgaac tgccaccact gttgtggtcg agaaggacct gcccaaggtc      60
actctcgagg ccacttctca gcctcaattc cccgacatca agaccatcaa ggatgccatc     120
cccgcccact gcttccagcc ctcgctcatc acctcatact actatgtcgt ccgcgacttc     180
```

-continued

```
gccatggtcg gctccctcgt ctgggccgcc ctcacctaca tccccggcat tgaggaccag    240
tacctccgcg tcgccgcctg gatggcctac ggcttcctcc agggtctctt ctgcaccgga    300
atctggattc tcggtcatga gtgcggccac ggtgccttct ctacccacag caagctcaac    360
aatgtgaccg gctggttcct ccactcgttc ctcatggtcc cctatttcag ctggaagtac    420
tctcaccacc gtcaccaccg cttcaccggc acatggatc tcgacatggc ctttgtcccc    480
cgcacttcgc ccaagccttc tttgtctttc cgcattgctg gtatggacgt cgctgagctg    540
attgaggaca cccccattgc ccaggccgtc aagctcatct ccaccagct cttcggatgg    600
caggtgtaca ccttcttcaa cgccagctct ggcaagggta gcaagcagtg ggagcccaag    660
agcggcttgg ccagctggtt ccgcgtcagc cacttcgagc ccaccagcgc tgtcttccgc    720
cccgccgagg ctcctttcat cctcatctcc gacattggtc tcgccctcac tggaactgct    780
ctgtactttg cttccaagga ggtcggcgtt ccaccgttc tctacctcta cctcgtcccc    840
tacctctggg tccaccactg gctcgtcgcc atcacctacc tccaccacca ccacaccgag    900
cttccccact acaccgccga gggctggacc tacgtcaagg gtgctctcgc tactgttgac    960
cgcgagtttg gcttcattgg caagcaccttt ttccacggca tcattgagaa gcacgtcatt   1020
caccacctgt tccctaagat cccttctac aaggctgacg aggccaccga ggccatcaag     1080
cccatcatcg cgaccacta ctgccacgac accgcagct tccttggcca gctctggacc     1140
atctttggca gcctcaagta cgtcgagcac gaccccgccg tccctggtgc catgcgctgg   1200
gccaaggagt ag                                                        1212
```

<210> SEQ ID NO 18
<211> LENGTH: 403
<212> TYPE: PRT
<213> ORGANISM: Fusarium graminearium

<400> SEQUENCE: 18

```
Met Ala Thr Arg Gln Arg Thr Ala Thr Thr Val Val Glu Lys Asp
1               5                   10                  15

Leu Pro Lys Val Thr Leu Glu Ala Thr Ser Gln Pro Gln Phe Pro Asp
            20                  25                  30

Ile Lys Thr Ile Lys Asp Ala Ile Pro Ala His Cys Phe Gln Pro Ser
        35                  40                  45

Leu Ile Thr Ser Tyr Tyr Val Val Arg Asp Phe Ala Met Val Gly
    50                  55                  60

Ser Leu Val Trp Ala Ala Leu Thr Tyr Ile Pro Gly Ile Glu Asp Gln
65                  70                  75                  80

Tyr Leu Arg Val Ala Ala Trp Met Ala Tyr Gly Phe Leu Gln Gly Leu
                85                  90                  95

Phe Cys Thr Gly Ile Trp Ile Leu Gly His Glu Cys Gly His Gly Ala
            100                 105                 110

Phe Ser Thr His Ser Lys Leu Asn Asn Val Thr Gly Trp Phe Leu His
        115                 120                 125

Ser Phe Leu Met Val Pro Tyr Phe Ser Trp Lys Tyr Ser His His Arg
    130                 135                 140

His His Arg Phe Thr Gly His Met Asp Leu Asp Met Ala Phe Val Pro
145                 150                 155                 160

Arg Thr Ser Pro Lys Pro Ser Leu Ser Phe Arg Ile Ala Gly Met Asp
                165                 170                 175

Val Ala Glu Leu Ile Glu Asp Thr Pro Ile Ala Gln Ala Val Lys Leu
            180                 185                 190
```

```
Ile Phe His Gln Leu Phe Gly Trp Gln Val Tyr Thr Phe Phe Asn Ala
            195                 200                 205

Ser Ser Gly Lys Gly Ser Lys Gln Trp Glu Pro Lys Ser Gly Leu Ala
        210                 215                 220

Ser Trp Phe Arg Val Ser His Phe Glu Pro Thr Ser Ala Val Phe Arg
225                 230                 235                 240

Pro Ala Glu Ala Pro Phe Ile Leu Ile Ser Asp Ile Gly Leu Ala Leu
                245                 250                 255

Thr Gly Thr Ala Leu Tyr Phe Ala Ser Lys Glu Val Gly Val Ser Thr
            260                 265                 270

Val Leu Tyr Leu Tyr Leu Val Pro Tyr Leu Trp Val His His Trp Leu
        275                 280                 285

Val Ala Ile Thr Tyr Leu His His His Thr Glu Leu Pro His Tyr
            290                 295                 300

Thr Ala Glu Gly Trp Thr Tyr Val Lys Gly Ala Leu Ala Thr Val Asp
305                 310                 315                 320

Arg Glu Phe Gly Phe Ile Gly Lys His Leu Phe His Gly Ile Ile Glu
                325                 330                 335

Lys His Val Ile His His Leu Phe Pro Lys Ile Pro Phe Tyr Lys Ala
            340                 345                 350

Asp Glu Ala Thr Glu Ala Ile Lys Pro Ile Ile Gly Asp His Tyr Cys
        355                 360                 365

His Asp Asp Arg Ser Phe Leu Gly Gln Leu Trp Thr Ile Phe Gly Ser
370                 375                 380

Leu Lys Tyr Val Glu His Asp Pro Ala Val Pro Gly Ala Met Arg Trp
385                 390                 395                 400

Ala Lys Glu

<210> SEQ ID NO 19
<211> LENGTH: 1371
<212> TYPE: DNA
<213> ORGANISM: Fusarium graminearium

<400> SEQUENCE: 19
tcaaccacgg cgacggatac tgagtctgct gccgtttctc cttcagactc tccccgccat      60
tcggcctctt ccacctcgct ctcgtctctt tccgagattg atatcgccaa gcccaaggcc     120
gaatatggtg ttatgcttga cacctatggc aacaagttcg aggttcccga cttcaccatc     180
aaggagatct acaatgccat ccccaagcac tgcttccagc gctccgctct caagggatac     240
ggatacatcc tccgcgacat tgtccttctt gctaccacct ttagcatctg gtacaactat     300 gtgaccccg agtacatccc tagcactccc gcccgcgctg gtctctgggc tgtctacact     360
gttctccagg gtcttttcgg taccggtctc tgggtcatcg ctcacgagtg tggccacggt     420
gctttctccg actctcgcct tatcaacgac atcaccggct gggtcctcca ctcttctctc     480
ctcgtcccct acttcagctg gcaaatctcc caccgaaagc accacaaggc taccggaaac     540
atggagcgtg acatggtctt tgttccccga actcgcgagc agcaggctac tcgtctcggc     600
aagatgaccc acgagcttgc tcacctcact gaggagaccc ccgtcttcac tctgatcatg     660
cttgttctcc agcagctcgt cggctggccc aactacctca tgaccaacgt tactggccac     720
aactaccacg agcgtcagaa ggagggccgt ggcaagggca gcacaacgg tctcggcggc     780 ggtgtcaacc actttgatcc ccgcagccct ctttacgagc acagcgatgc taagctcatt     840
gtcttgagtg atattggtat cggtctgatg ggtaccgctc tgtacttcct cgtccagaag     900
```

-continued

```
tttggctttt acaacatggc catctggtac tttgtccctt acctttgggt caaccactgg    960
ctcgtcgcca ttactttcct ccagcacacc gaccctaccc ttccccacta caccaacgac   1020
gagtggaact tgtccgcgg tgctgctgct accatcgatc gtgagatggg tttcattggc    1080
cgacacctcc tccacggtat catcgagact cacgtcctcc accactacgt cagcagcatc   1140
cccttctaca acgccgacga ggctaccgag gctatcaagc tgtcatggg caagcactac    1200 cgtgccgacg tccaggatgg tccccgtggt ttcattcgtg ccatgtaccg cagtgcccgt   1260
atgtgccagt gggttgagcc cagcgctgag gccgagggtg ctggcaaggg tgttctgttc   1320
ttccgcaacc gcaacaaggt tggcactgct cctgccgtcc tcaaggctta g            1371
```

<210> SEQ ID NO 20
<211> LENGTH: 456
<212> TYPE: PRT
<213> ORGANISM: Fusarium graminearium

<400> SEQUENCE: 20

```
Ser Thr Thr Ala Thr Asp Thr Glu Ser Ala Ala Val Ser Pro Ser Asp
1               5                   10                  15

Ser Pro Arg His Ser Ala Ser Ser Thr Ser Leu Ser Ser Leu Ser Glu
                20                  25                  30

Ile Asp Ile Ala Lys Pro Lys Ala Glu Tyr Gly Val Met Leu Asp Thr
            35                  40                  45

Tyr Gly Asn Lys Phe Glu Val Pro Asp Phe Thr Ile Lys Glu Ile Tyr
        50                  55                  60

Asn Ala Ile Pro Lys His Cys Phe Gln Arg Ser Ala Leu Lys Gly Tyr
65                  70                  75                  80

Gly Tyr Ile Leu Arg Asp Ile Val Leu Ala Thr Thr Phe Ser Ile
                85                  90                  95

Trp Tyr Asn Tyr Val Thr Pro Glu Tyr Ile Pro Ser Thr Pro Ala Arg
            100                 105                 110

Ala Gly Leu Trp Ala Val Tyr Thr Val Leu Gln Gly Leu Phe Gly Thr
        115                 120                 125

Gly Leu Trp Val Ile Ala His Glu Cys Gly His Gly Ala Phe Ser Asp
    130                 135                 140

Ser Arg Leu Ile Asn Asp Ile Thr Gly Trp Val Leu His Ser Ser Leu
145                 150                 155                 160

Leu Val Pro Tyr Phe Ser Trp Gln Ile Ser His Arg Lys His His Lys
                165                 170                 175

Ala Thr Gly Asn Met Glu Arg Asp Met Val Phe Val Pro Arg Thr Arg
            180                 185                 190

Glu Gln Gln Ala Thr Arg Leu Gly Lys Met Thr His Glu Leu Ala His
        195                 200                 205

Leu Thr Glu Glu Thr Pro Val Phe Thr Leu Ile Met Leu Val Leu Gln
    210                 215                 220

Gln Leu Val Gly Trp Pro Asn Tyr Leu Met Thr Asn Val Thr Gly His
225                 230                 235                 240

Asn Tyr His Glu Arg Gln Lys Glu Gly Arg Gly Lys Gly Lys His Asn
                245                 250                 255

Gly Leu Gly Gly Gly Val Asn His Phe Asp Pro Arg Ser Pro Leu Tyr
            260                 265                 270

Glu His Ser Asp Ala Lys Leu Ile Val Leu Ser Asp Ile Gly Ile Gly
        275                 280                 285
```

```
Leu Met Gly Thr Ala Leu Tyr Phe Leu Val Gln Lys Phe Gly Phe Tyr
    290                 295                 300

Asn Met Ala Ile Trp Tyr Phe Val Pro Tyr Leu Trp Val Asn His Trp
305                 310                 315                 320

Leu Val Ala Ile Thr Phe Leu Gln His Thr Asp Pro Thr Leu Pro His
                325                 330                 335

Tyr Thr Asn Asp Glu Trp Asn Phe Val Arg Gly Ala Ala Thr Ile
                340                 345                 350

Asp Arg Glu Met Gly Phe Ile Gly Arg His Leu Leu His Gly Ile Ile
            355                 360                 365

Glu Thr His Val Leu His His Tyr Val Ser Ser Ile Pro Phe Tyr Asn
    370                 375                 380

Ala Asp Glu Ala Thr Glu Ala Ile Lys Pro Val Met Gly Lys His Tyr
385                 390                 395                 400

Arg Ala Asp Val Gln Asp Gly Pro Arg Gly Phe Ile Arg Ala Met Tyr
                405                 410                 415

Arg Ser Ala Arg Met Cys Gln Trp Val Glu Pro Ser Ala Glu Ala Glu
            420                 425                 430

Gly Ala Gly Lys Gly Val Leu Phe Phe Arg Asn Arg Asn Lys Val Gly
    435                 440                 445

Thr Ala Pro Ala Val Leu Lys Ala
    450                 455

<210> SEQ ID NO 21
<211> LENGTH: 19
<212> TYPE: DNA
<213> ORGANISM: Artificial Sequence
<220> FEATURE:
<223> OTHER INFORMATION: Primer TEF5'

<400> SEQUENCE: 21
agagaccggg ttggcggcg                                            19

<210> SEQ ID NO 22
<211> LENGTH: 30
<212> TYPE: DNA
<213> ORGANISM: Artificial Sequence
<220> FEATURE:
<223> OTHER INFORMATION: Primer TEF3'

<400> SEQUENCE: 22
ttggatcctt tgaatgattc ttatactcag                                30

<210> SEQ ID NO 23
<211> LENGTH: 29
<212> TYPE: DNA
<213> ORGANISM: Artificial Sequence
<220> FEATURE:
<223> OTHER INFORMATION: Primer XPR5'

<400> SEQUENCE: 23
tttccgcggc ccgagattcc ggcctcttc                                 29

<210> SEQ ID NO 24
<211> LENGTH: 31
<212> TYPE: DNA
<213> ORGANISM: Artificial Sequence
<220> FEATURE:
<223> OTHER INFORMATION: Primer XPR3'

<400> SEQUENCE: 24
```
tttccgcgga cacaatatct ggtcaaattt c    31

<210> SEQ ID NO 25
<211> LENGTH: 39
<212> TYPE: DNA
<213> ORGANISM: Artificial Sequence
<220> FEATURE:
<223> OTHER INFORMATION: Primer YL5

<400> SEQUENCE: 25 ccccctcga ggtcgatggt gtcgataagc ttgatatcg    39

<210> SEQ ID NO 26
<211> LENGTH: 39
<212> TYPE: DNA
<213> ORGANISM: Artificial Sequence
<220> FEATURE:
<223> OTHER INFORMATION: Primer YL6

<400> SEQUENCE: 26
cgatatcaag cttatcgaca ccatcgacct cgaggggg    39

<210> SEQ ID NO 27
<211> LENGTH: 35
<212> TYPE: DNA
<213> ORGANISM: Artificial Sequence
<220> FEATURE:
<223> OTHER INFORMATION: Primer YL9

<400> SEQUENCE: 27
tggtaaataa atgatgtcga ctcaggcgac gacgg    35

<210> SEQ ID NO 28
<211> LENGTH: 35
<212> TYPE: DNA
<213> ORGANISM: Artificial Sequence
<220> FEATURE:
<223> OTHER INFORMATION: Primer YL10

<400> SEQUENCE: 28
ccgtcgtcgc ctgagtcgac atcatttatt tacca    35

<210> SEQ ID NO 29
<211> LENGTH: 37
<212> TYPE: DNA
<213> ORGANISM: Artificial Sequence
<220> FEATURE:
<223> OTHER INFORMATION: Primer YL7

<400> SEQUENCE: 29
caaccgattt cgacagttaa ttaataattt gaatcga    37

<210> SEQ ID NO 30
<211> LENGTH: 37
<212> TYPE: DNA
<213> ORGANISM: Artificial Sequence
<220> FEATURE:
<223> OTHER INFORMATION: Primer YL8

<400> SEQUENCE: 30
tcgattcaaa ttattaatta actgtcgaaa tcggttg    37

<210> SEQ ID NO 31
<211> LENGTH: 36
<212> TYPE: DNA
<213> ORGANISM: Artificial Sequence
<220> FEATURE:
<223> OTHER INFORMATION: Primer YL3

<400> SEQUENCE: 31
gtataagaat cattcaccat ggatccacta gttcta     36

<210> SEQ ID NO 32
<211> LENGTH: 36
<212> TYPE: DNA
<213> ORGANISM: Artificial Sequence
<220> FEATURE:
<223> OTHER INFORMATION: Primer YL4

<400> SEQUENCE: 32
tagaactagt ggatccatgg tgaatgattc ttatac     36

<210> SEQ ID NO 33
<211> LENGTH: 30
<212> TYPE: DNA
<213> ORGANISM: Artificial Sequence
<220> FEATURE:
<223> OTHER INFORMATION: Primer YL1

<400> SEQUENCE: 33
cagtgccaaa agccaaggca ctgagctcgt     30

<210> SEQ ID NO 34
<211> LENGTH: 31
<212> TYPE: DNA
<213> ORGANISM: Artificial Sequence
<220> FEATURE:
<223> OTHER INFORMATION: Primer YL2

<400> SEQUENCE: 34
gacgagctca gtgccttggc ttttggcact g     31

<210> SEQ ID NO 35
<211> LENGTH: 33
<212> TYPE: DNA
<213> ORGANISM: Artificial Sequence
<220> FEATURE:
<223> OTHER INFORMATION: Primer YL61

<400> SEQUENCE: 35
acaattccac acaacgtacg agccggaagc ata     33

<210> SEQ ID NO 36
<211> LENGTH: 33
<212> TYPE: DNA
<213> ORGANISM: Artificial Sequence
<220> FEATURE:
<223> OTHER INFORMATION: Primer YL62

<400> SEQUENCE: 36
tatgcttccg gctcgtacgt tgtgtggaat tgt     33

<210> SEQ ID NO 37
<211> LENGTH: 971
<212> TYPE: DNA
<213> ORGANISM: Yarrowia lipolytica

<400> SEQUENCE: 37
gacgcagtag gatgtcctgc acgggtcttt tgtggggtg tggagaaagg ggtgcttgga     60
gatggaagcc ggtagaaccg ggctgcttgt gcttggagat ggaagccggt agaaccgggc    120

```
tgcttggggg gatttggggc cgctgggctc caaagagggg taggcatttc gttgggggtta      180
cgtaattgcg gcatttgggt cctgcgcgca tgtcccattg gtcagaatta gtccggatag      240
gagacttatc agccaatcac agcgccggat ccacctgtag gttgggttgg gtgggagcac      300
ccctccacag agtagagtca aacagcagca gcaacatgat agttgggggt gtgcgtgtta      360
aaggaaaaaa aagaagcttg ggttatattc ccgctctatt tagaggttgc gggatagacg      420
ccgacggagg gcaatggcgc catggaacct tgcggatatc gatacgccgc ggcggactgc      480
gtccgaacca gctccagcag cgttttttcc gggccattga gccgactgcg accccgccaa      540
cgtgtcttgg cccacgcact catgtcatgt tggtgttggg aggccacttt ttaagtagca      600
caaggcacct agctcgcagc aaggtgtccg aaccaaagaa gcggctgcag tggtgcaaac      660
ggggcggaaa cggcgggaaa aagccacggg ggcacgaatt gaggcacgcc ctcgaatttg      720
agacgagtca cggcccccatt cgcccgcgca atggctcgcc aacgcccggt cttttgcacc     780
acatcaggtt accccaagcc aaacctttgt gttaaaaagc ttaacatatt ataccgaacg      840
taggtttggg cgggcttgct ccgtctgtcc aaggcaacat ttatataagg gtctgcatcg      900
ccggctcaat tgaatctttt ttcttcttct cttctctata ttcattcttg aattaaacac      960
acatcaacat g                                                           971
```

<210> SEQ ID NO 38
<211> LENGTH: 30
<212> TYPE: DNA
<213> ORGANISM: Artificial Sequence
<220> FEATURE:
<223> OTHER INFORMATION: Primer YL211

<400> SEQUENCE: 38
tttgtcgacg cagtaggatg tcctgcacgg      30

<210> SEQ ID NO 39
<211> LENGTH: 34
<212> TYPE: DNA
<213> ORGANISM: Artificial Sequence
<220> FEATURE:
<223> OTHER INFORMATION: Primer YL212

<400> SEQUENCE: 39
tttccatggt tgatgtgtgt ttaattcaag aatg      34

<210> SEQ ID NO 40
<211> LENGTH: 18
<212> TYPE: DNA
<213> ORGANISM: Artificial Sequence
<220> FEATURE:
<223> OTHER INFORMATION: Primer GPDsense

<400> SEQUENCE: 40
atacgagatc gtcaaggg      18

<210> SEQ ID NO 41
<211> LENGTH: 26
<212> TYPE: DNA
<213> ORGANISM: Artificial Sequence
<220> FEATURE:
<223> OTHER INFORMATION: Primer GPDantisense

<400> SEQUENCE: 41
gcggccgcgg attgatgtgt gtttaa      26

```
<210> SEQ ID NO 42
<211> LENGTH: 26
<212> TYPE: DNA
<213> ORGANISM: Artificial Sequence
<220> FEATURE:
<223> OTHER INFORMATION: Degenerate primer P73
<220> FEATURE:
<221> NAME/KEY: misc_feature
<222> LOCATION: (24)..(24)
<223> OTHER INFORMATION: n is a, c, g, or t

<400> SEQUENCE: 42
tgggtcctgg gccaygartg yggnca                                         26

<210> SEQ ID NO 43
<211> LENGTH: 9
<212> TYPE: PRT
<213> ORGANISM: Artificial Sequence
<220> FEATURE:
<223> OTHER INFORMATION: Consensus sequence in delta12 desaturases

<400> SEQUENCE: 43

Trp Val Leu Gly His Glu Cys Gly His
1               5

<210> SEQ ID NO 44
<211> LENGTH: 30
<212> TYPE: DNA
<213> ORGANISM: Artificial Sequence
<220> FEATURE:
<223> OTHER INFORMATION: Degenerate primer P76
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t

<400> SEQUENCE: 44
ggtggcctcc tcggcgtgrt araanggnat                                     30

<210> SEQ ID NO 45
<211> LENGTH: 10
<212> TYPE: PRT
<213> ORGANISM: Artificial Sequence
<220> FEATURE:
<223> OTHER INFORMATION: Consensus sequence in delta12 desaturases
<220> FEATURE:
<221> NAME/KEY: MISC_FEATURE
<222> LOCATION: (1)..(1)
<223> OTHER INFORMATION: Xaa = Met or Ile

<400> SEQUENCE: 45

Xaa Pro Phe Tyr His Ala Glu Glu Ala Thr
1               5                   10

<210> SEQ ID NO 46
<211> LENGTH: 29
<212> TYPE: DNA
<213> ORGANISM: Artificial Sequence
<220> FEATURE:
<223> OTHER INFORMATION: Primer P99

<400> SEQUENCE: 46
ggcaagctta acgccccgct gtttgagaa                                      29

<210> SEQ ID NO 47
```

```
<211> LENGTH: 36
<212> TYPE: DNA
<213> ORGANISM: Artificial Sequence
<220> FEATURE:
<223> OTHER INFORMATION: Primer P100

<400> SEQUENCE: 47
tgacgttgtt agatctacgt gggtctcgat gatgtc                              36

<210> SEQ ID NO 48
<211> LENGTH: 35
<212> TYPE: DNA
<213> ORGANISM: Artificial Sequence
<220> FEATURE:
<223> OTHER INFORMATION: Primer P101

<400> SEQUENCE: 48
gacccacgta gatctaacaa cgtcaccgga tgggt                               35

<210> SEQ ID NO 49
<211> LENGTH: 29
<212> TYPE: DNA
<213> ORGANISM: Artificial Sequence
<220> FEATURE:
<223> OTHER INFORMATION: Primer P102

<400> SEQUENCE: 49
cgggaattcg gggttgaagt ggttgacag                                      29

<210> SEQ ID NO 50
<211> LENGTH: 16
<212> TYPE: DNA
<213> ORGANISM: Artificial Sequence
<220> FEATURE:
<223> OTHER INFORMATION: Primer P119

<400> SEQUENCE: 50
taataacgcc agggtt                                                    16

<210> SEQ ID NO 51
<211> LENGTH: 22
<212> TYPE: DNA
<213> ORGANISM: Artificial Sequence
<220> FEATURE:
<223> OTHER INFORMATION: Primer P120

<400> SEQUENCE: 51
gtagaagggc attcgagaca cg                                             22

<210> SEQ ID NO 52
<211> LENGTH: 22
<212> TYPE: DNA
<213> ORGANISM: Artificial Sequence
<220> FEATURE:
<223> OTHER INFORMATION: Primer P121

<400> SEQUENCE: 52
tgtgcccaag gaccgaaagg ag                                             22

<210> SEQ ID NO 53
<211> LENGTH: 28
<212> TYPE: DNA
<213> ORGANISM: Artificial Sequence
<220> FEATURE:
<223> OTHER INFORMATION: Primer P122

<400> SEQUENCE: 53
```

```
tgcaggtagg tgatggccac gagttggg                                          28

<210> SEQ ID NO 54
<211> LENGTH: 1936
<212> TYPE: DNA
<213> ORGANISM: Yarrowia lipolytica
<220> FEATURE:
<221> NAME/KEY: CDS
<222> LOCATION: (283)..(1539)

<400> SEQUENCE: 54
cgtagttata tacaagaggt agatgcgtgc tggtgttaga ggggctctca ggattaggag      60
gaaaatttga cattggccct caacatataa cctcgggtgt gcctctgttt accctcagct     120
tttgcttgtc cccaagtcag tcacgccagg ccaaaaaggt tggtggattg acagggagaa     180
aaaaaaaagc ctagtgggtt taaactcgag gtaagacatt gaaatatata ccggtcggca     240
tcctgagtcc ctttctcgta ttccaacaga ccgaccatag aa atg gat tcg acc       294
                                                Met Asp Ser Thr
                                                  1 acg cag acc aac acc ggc acc ggc aag gtg gcc gtg cag ccc ccc acg      342
Thr Gln Thr Asn Thr Gly Thr Gly Lys Val Ala Val Gln Pro Pro Thr
  5              10                  15                  20 gcc ttc att aag ccc att gag aag gtg tcc gag ccc gtc tac gac acc      390
Ala Phe Ile Lys Pro Ile Glu Lys Val Ser Glu Pro Val Tyr Asp Thr
             25                  30                  35 ttt ggc aac gag ttc act cct cca gac tac tct atc aag gat att ctg      438
Phe Gly Asn Glu Phe Thr Pro Pro Asp Tyr Ser Ile Lys Asp Ile Leu
         40                  45                  50 gat gcc att ccc cag gag tgc tac aag cgg tcc tac gtt aag tcc tac      486
Asp Ala Ile Pro Gln Glu Cys Tyr Lys Arg Ser Tyr Val Lys Ser Tyr
     55                  60                  65 tcg tac gtg gcc cga gac tgc ttc ttt atc gcc gtt ttt gcc tac atg      534
Ser Tyr Val Ala Arg Asp Cys Phe Phe Ile Ala Val Phe Ala Tyr Met
 70                  75                  80 gcc tac gcg tac ctg cct ctt att ccc tcg gct tcc ggc cga gct gtg      582
Ala Tyr Ala Tyr Leu Pro Leu Ile Pro Ser Ala Ser Gly Arg Ala Val
85                  90                  95                 100 gcc tgg gcc atg tac tcc att gtc cag ggt ctg ttt ggc acc ggt ctg      630
Ala Trp Ala Met Tyr Ser Ile Val Gln Gly Leu Phe Gly Thr Gly Leu
                105                 110                 115 tgg gtt ctt gcc cac gag tgt ggc cac tct gct ttc tcc gac tct aac      678
Trp Val Leu Ala His Glu Cys Gly His Ser Ala Phe Ser Asp Ser Asn
            120                 125                 130 acc gtc aac aac gtc acc gga tgg gtt ctg cac tcc tcc atg ctg gtc      726
Thr Val Asn Asn Val Thr Gly Trp Val Leu His Ser Ser Met Leu Val
        135                 140                 145 cct tac tac gcc tgg aag ctg acc cac tcc atg cac cac aag tcc act      774
Pro Tyr Tyr Ala Trp Lys Leu Thr His Ser Met His His Lys Ser Thr
    150                 155                 160 ggt cac ctc acc cgt gat atg gtg ttt gtg ccc aag gac cga aag gag      822
Gly His Leu Thr Arg Asp Met Val Phe Val Pro Lys Asp Arg Lys Glu
165                 170                 175                 180 ttt atg gag aac cga ggc gcc cat gac tgg tct gag ctt gct gag gac      870
Phe Met Glu Asn Arg Gly Ala His Asp Trp Ser Glu Leu Ala Glu Asp
                185                 190                 195 gct ccc ctc atg acc ctc tac ggc ctc atc acc cag cag gtg ttt gga      918
Ala Pro Leu Met Thr Leu Tyr Gly Leu Ile Thr Gln Gln Val Phe Gly
            200                 205                 210 tgg cct ctg tat ctg ctg tct tac gtt acc gga cag aag tac ccc aag      966
```

```
Trp Pro Leu Tyr Leu Leu Ser Tyr Val Thr Gly Gln Lys Tyr Pro Lys
        215                 220                 225 ctc aac aaa tgg gct gtc aac cac ttc aac ccc aac gcc ccg ctg ttt    1014
Leu Asn Lys Trp Ala Val Asn His Phe Asn Pro Asn Ala Pro Leu Phe
    230                 235                 240 gag aag aag gac tgg ttc aac atc tgg atc tct aac gtc ggt att ggt    1062
Glu Lys Lys Asp Trp Phe Asn Ile Trp Ile Ser Asn Val Gly Ile Gly
245                 250                 255                 260 atc acc atg tcc gtc atc gca tac tcc atc aac cga tgg ggc ctg gct    1110
Ile Thr Met Ser Val Ile Ala Tyr Ser Ile Asn Arg Trp Gly Leu Ala
                265                 270                 275 tcc gtc acc ctc tac tac ctg atc ccc tac ctg tgg gtc aac cac tgg    1158
Ser Val Thr Leu Tyr Tyr Leu Ile Pro Tyr Leu Trp Val Asn His Trp
            280                 285                 290 ctc gtg gcc atc acc tac ctg cag cac acc gac ccc act ctg ccc cac    1206
Leu Val Ala Ile Thr Tyr Leu Gln His Thr Asp Pro Thr Leu Pro His
        295                 300                 305 tac cac gcc gac cag tgg aac ttc acc cga gga gcc gcc gcc acc atc    1254
Tyr His Ala Asp Gln Trp Asn Phe Thr Arg Gly Ala Ala Ala Thr Ile
    310                 315                 320 gac cga gag ttt ggc ttc atc ggc tcc ttc tgc ttc cat gac atc atc    1302
Asp Arg Glu Phe Gly Phe Ile Gly Ser Phe Cys Phe His Asp Ile Ile
325                 330                 335                 340 gag acc cac gtt ctg cac cac tac gtg tct cga att ccc ttc tac aac    1350
Glu Thr His Val Leu His His Tyr Val Ser Arg Ile Pro Phe Tyr Asn
                345                 350                 355 gcc cga atc gcc act gag aag atc aag aag gtc atg ggc aag cac tac    1398
Ala Arg Ile Ala Thr Glu Lys Ile Lys Lys Val Met Gly Lys His Tyr
            360                 365                 370 cga cac gac gac acc aac ttc atc aag tct ctt tac act gtc gcc cga    1446
Arg His Asp Asp Thr Asn Phe Ile Lys Ser Leu Tyr Thr Val Ala Arg
        375                 380                 385 acc tgc cag ttt gtt gaa ggt aag gaa ggc att cag atg ttt aga aac    1494
Thr Cys Gln Phe Val Glu Gly Lys Glu Gly Ile Gln Met Phe Arg Asn
    390                 395                 400 gtc aat gga gtc gga gtt gct cct gac ggc ctg cct tct aaa aag        1539
Val Asn Gly Val Gly Val Ala Pro Asp Gly Leu Pro Ser Lys Lys
405                 410                 415 tagagctaga aatgttattt gattgtgttt taactgaaca gcaccgagcc cgaggctaag   1599
ccaagcgaag ccgaggggtt gtgtagtcca tggacgtaac gagtaggcga tatcaccgca   1659
ctcggcactg cgtgtctgcg ttcatgggcg aagtcacatt acgctgacaa ccgttgtagt   1719 ttcccttta g tatcaatact gttacaagta ccggtctcgt actcgtactg atacgaatct   1779
gtgggaagaa gtcaccctta tcagaccttc atactgatgt ttcggatatc aatagaactg   1839
gcatagagcc gttaaagaag tttcacttaa tcactccaac cctcctactt gtagattcaa   1899
gcagatcgat aagatggatt tgatggtcag tgctagc                            1936

<210> SEQ ID NO 55
<211> LENGTH: 419
<212> TYPE: PRT
<213> ORGANISM: Yarrowia lipolytica

<400> SEQUENCE: 55

Met Asp Ser Thr Thr Gln Thr Asn Thr Gly Thr Gly Lys Val Ala Val
1               5                   10                  15

Gln Pro Pro Thr Ala Phe Ile Lys Pro Ile Glu Lys Val Ser Glu Pro
            20                  25                  30
```

-continued

Val Tyr Asp Thr Phe Gly Asn Glu Phe Thr Pro Pro Asp Tyr Ser Ile
        35                  40                  45

Lys Asp Ile Leu Asp Ala Ile Pro Gln Glu Cys Tyr Lys Arg Ser Tyr
    50                  55                  60

Val Lys Ser Tyr Ser Tyr Val Ala Arg Asp Cys Phe Phe Ile Ala Val
65                  70                  75                  80

Phe Ala Tyr Met Ala Tyr Ala Tyr Leu Pro Leu Ile Pro Ser Ala Ser
                85                  90                  95

Gly Arg Ala Val Ala Trp Ala Met Tyr Ser Ile Val Gln Gly Leu Phe
                100                 105                 110

Gly Thr Gly Leu Trp Val Leu Ala His Glu Cys Gly His Ser Ala Phe
            115                 120                 125

Ser Asp Ser Asn Thr Val Asn Val Thr Gly Trp Val Leu His Ser
    130                 135                 140

Ser Met Leu Val Pro Tyr Tyr Ala Trp Lys Leu Thr His Ser Met His
145                 150                 155                 160

His Lys Ser Thr Gly His Leu Thr Arg Asp Met Val Phe Val Pro Lys
                165                 170                 175

Asp Arg Lys Glu Phe Met Glu Asn Arg Gly Ala His Asp Trp Ser Glu
            180                 185                 190

Leu Ala Glu Asp Ala Pro Leu Met Thr Leu Tyr Gly Leu Ile Thr Gln
        195                 200                 205

Gln Val Phe Gly Trp Pro Leu Tyr Leu Leu Ser Tyr Val Thr Gly Gln
    210                 215                 220

Lys Tyr Pro Lys Leu Asn Lys Trp Ala Val Asn His Phe Asn Pro Asn
225                 230                 235                 240

Ala Pro Leu Phe Glu Lys Lys Asp Trp Phe Asn Ile Trp Ile Ser Asn
                245                 250                 255

Val Gly Ile Gly Ile Thr Met Ser Val Ile Ala Tyr Ser Ile Asn Arg
            260                 265                 270

Trp Gly Leu Ala Ser Val Thr Leu Tyr Tyr Leu Ile Pro Tyr Leu Trp
        275                 280                 285

Val Asn His Trp Leu Val Ala Ile Thr Tyr Leu Gln His Thr Asp Pro
    290                 295                 300

Thr Leu Pro His Tyr His Ala Asp Gln Trp Asn Phe Thr Arg Gly Ala
305                 310                 315                 320

Ala Ala Thr Ile Asp Arg Glu Phe Gly Phe Ile Gly Ser Phe Cys Phe
                325                 330                 335

His Asp Ile Ile Glu Thr His Val Leu His His Tyr Val Ser Arg Ile
            340                 345                 350

Pro Phe Tyr Asn Ala Arg Ile Ala Thr Glu Lys Ile Lys Lys Val Met
        355                 360                 365

Gly Lys His Tyr Arg His Asp Asp Thr Asn Phe Ile Lys Ser Leu Tyr
    370                 375                 380

Thr Val Ala Arg Thr Cys Gln Phe Val Glu Gly Lys Glu Gly Ile Gln
385                 390                 395                 400

Met Phe Arg Asn Val Asn Gly Val Gly Val Ala Pro Asp Gly Leu Pro
                405                 410                 415

Ser Lys Lys

<210> SEQ ID NO 56
<211> LENGTH: 36
<212> TYPE: DNA
<213> ORGANISM: Artificial Sequence

```
<220> FEATURE:
<223> OTHER INFORMATION: Primer P192

<400> SEQUENCE: 56
aaatatgcgg ccgcacaatg gcgactcgac agcgaa                                 36

<210> SEQ ID NO 57
<211> LENGTH: 34
<212> TYPE: DNA
<213> ORGANISM: Artificial Sequence
<220> FEATURE:
<223> OTHER INFORMATION: Primer P193

<400> SEQUENCE: 57
tttatagcgg ccgcctagtc cttgttccat cgca                                   34

<210> SEQ ID NO 58
<211> LENGTH: 10
<212> TYPE: DNA
<213> ORGANISM: Yarrowia lipolytica
<220> FEATURE:
<221> NAME/KEY: misc_feature
<222> LOCATION: (8)..(8)
<223> OTHER INFORMATION: n is a, c, g, or t

<400> SEQUENCE: 58 mammatgnhs                                                              10

<210> SEQ ID NO 59
<211> LENGTH: 38
<212> TYPE: DNA
<213> ORGANISM: Artificial Sequence
<220> FEATURE:
<223> OTHER INFORMATION: Primer P186

<400> SEQUENCE: 59
agactccatg gccaccaccg tcactcagcg gccgggcg                               38

<210> SEQ ID NO 60
<211> LENGTH: 38
<212> TYPE: DNA
<213> ORGANISM: Artificial Sequence
<220> FEATURE:
<223> OTHER INFORMATION: Primer P187

<400> SEQUENCE: 60
gaaattgctg ctccttgggc ttggcttcag cgcggcta                               38

<210> SEQ ID NO 61
<211> LENGTH: 38
<212> TYPE: DNA
<213> ORGANISM: Artificial Sequence
<220> FEATURE:
<223> OTHER INFORMATION: Primer P188

<400> SEQUENCE: 61
ctagccgcgc tgaagccaag cccaaggagc agcaattt                               38

<210> SEQ ID NO 62
<211> LENGTH: 38
<212> TYPE: DNA
<213> ORGANISM: Artificial Sequence
<220> FEATURE:
<223> OTHER INFORMATION: Primer P189

<400> SEQUENCE: 62
```
ccttgtaaaa gggaatgcga gggaacagat ggtgggcg                                38

<210> SEQ ID NO 63
<211> LENGTH: 38
<212> TYPE: DNA
<213> ORGANISM: Artificial Sequence
<220> FEATURE:
<223> OTHER INFORMATION: Primer P190

<400> SEQUENCE: 63
gtcgcccacc atctgttccc tcgcattccc ttttacaa                                38

<210> SEQ ID NO 64
<211> LENGTH: 38
<212> TYPE: DNA
<213> ORGANISM: Artificial Sequence
<220> FEATURE:
<223> OTHER INFORMATION: Primer P191

<400> SEQUENCE: 64
cttagcggcc gctcaatcgg cccacctcat ggcgccgg                                38

<210> SEQ ID NO 65
<211> LENGTH: 36
<212> TYPE: DNA
<213> ORGANISM: Artificial Sequence
<220> FEATURE:
<223> OTHER INFORMATION: Primer PFg1UP1

<400> SEQUENCE: 65
atccgcggcc gcacatggcc accagacagc gaactg                                  36

<210> SEQ ID NO 66
<211> LENGTH: 36
<212> TYPE: DNA
<213> ORGANISM: Artificial Sequence
<220> FEATURE:
<223> OTHER INFORMATION: Primer PFg1LP1

<400> SEQUENCE: 66
gtggcctcga gagtgacctt gggcaggtcc ttctcg                                  36

<210> SEQ ID NO 67
<211> LENGTH: 35
<212> TYPE: DNA
<213> ORGANISM: Artificial Sequence
<220> FEATURE:
<223> OTHER INFORMATION: Primer PFg1UP2

<400> SEQUENCE: 67
aaggacctgc ccaaggtcac tctcgaggcc acttc                                   35

<210> SEQ ID NO 68
<211> LENGTH: 34
<212> TYPE: DNA
<213> ORGANISM: Artificial Sequence
<220> FEATURE:
<223> OTHER INFORMATION: Primer PFg1LP2

<400> SEQUENCE: 68
aggtaggtga tggcgacgag ccagtggtgg accc                                    34

<210> SEQ ID NO 69
<211> LENGTH: 36
<212> TYPE: DNA
<213> ORGANISM: Artificial Sequence

```
<220> FEATURE:
<223> OTHER INFORMATION: Primer PFg1UP3

<400> SEQUENCE: 69
ggtccaccac tggctcgtcg ccatcaccta cctcca                                    36

<210> SEQ ID NO 70
<211> LENGTH: 35
<212> TYPE: DNA
<213> ORGANISM: Artificial Sequence
<220> FEATURE:
<223> OTHER INFORMATION: Primer PFg1LP3

<400> SEQUENCE: 70
gtagaagggg atcttaggga acaggtggtg aatga                                     35

<210> SEQ ID NO 71
<211> LENGTH: 44
<212> TYPE: DNA
<213> ORGANISM: Artificial Sequence
<220> FEATURE:
<223> OTHER INFORMATION: Primer PFg1UP4

<400> SEQUENCE: 71
cattcaccac ctgttcccta agatcccctt ctacaaggct gacg                           44

<210> SEQ ID NO 72
<211> LENGTH: 36
<212> TYPE: DNA
<213> ORGANISM: Artificial Sequence
<220> FEATURE:
<223> OTHER INFORMATION: Primer PFg1LP4

<400> SEQUENCE: 72
cttttgcggc cgctctactc cttggcccag cgcatg                                    36

<210> SEQ ID NO 73
<211> LENGTH: 34
<212> TYPE: DNA
<213> ORGANISM: Artificial Sequence
<220> FEATURE:
<223> OTHER INFORMATION: synthetic oligonucleotide

<400> SEQUENCE: 73
aagcttgcat gcctgcaggt cgactcgacg tacg                                      34

<210> SEQ ID NO 74
<211> LENGTH: 280
<212> TYPE: DNA
<213> ORGANISM: soybean albumin transcription terminator

<400> SEQUENCE: 74
tctagaggat ccaaggccgc gaagttaaaa gcaatgttgt cacttgtcgt actaacacat          60
gatgtgatag tttatgctag ctagctataa cataagctgt ctctgagtgt gttgtatatt         120
aataaagatc atcactggtg aatggtgatc gtgtacgtac cctacttagt aggcaatgga         180
agcacttaga gtgtgctttg tgcatggcct tgcctctgtt ttgagacttt tgtaatgttt         240
tcgagtttaa atctttgcct ttgcgtacgt gggcggatcc                               280

<210> SEQ ID NO 75
<211> LENGTH: 32
<212> TYPE: DNA
<213> ORGANISM: Artificial Sequence
<220> FEATURE:
```

<210> SEQ ID NO 76
<211> LENGTH: 36
<212> TYPE: DNA
<213> ORGANISM: Artificial Sequence
<220> FEATURE:
<223> OTHER INFORMATION: synthetic oligonucleotide

<400> SEQUENCE: 75
tttggatcct ctagacgtac gcaaaggcaa ag                              32

<210> SEQ ID NO 76
<211> LENGTH: 36
<212> TYPE: DNA
<213> ORGANISM: Artificial Sequence
<220> FEATURE:
<223> OTHER INFORMATION: synthetic oligonucleotide

<400> SEQUENCE: 76
aaaggatcca aggccgcgaa gttaaaagca atgttg                          36

<210> SEQ ID NO 77
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 77
ggatctcctg caggatctgg ccggccggat ctcgtac                         37

<210> SEQ ID NO 78
<211> LENGTH: 9088
<212> TYPE: DNA
<213> ORGANISM: Artificial Sequence
<220> FEATURE:
<223> OTHER INFORMATION: plasmid pKR578
<220> FEATURE:
<221> NAME/KEY: misc_feature
<222> LOCATION: (6951)..(6951)
<223> OTHER INFORMATION: n is a, c, g, or t

<400> SEQUENCE: 78
ggccgcgaca caagtgtgag agtactaaat aaatgctttg gttgtacgaa atcattacac    60
taaataaaat aatcaaagct tatatatgcc ttccgctaag gccgaatgca agaaattgg    120 ttctttctcg ttatcttttg ccacttttac tagtacgtat taattactac ttaatcatct   180
ttgtttacgg ctcattatat ccggtctaga ggatccaagg ccgcgaagtt aaaagcaatg   240
ttgtcacttg tcgtactaac acatgatgtg atagtttatg ctagctagct ataacataag   300
ctgtctctga gtgtgttgta tattaataaa gatcatcact ggtgaatggt gatcgtgtac   360
gtaccctact tagtaggcaa tggaagcact tagagtgtgc tttgtgcatg gccttgcctc   420
tgttttgaga cttttgtaat gttttcgagt ttaaatcttt gcctttgcgt acggatccgt   480
cgacggcgcg cccgatcatc cggatatagt tcctcctttc agcaaaaaac ccctcaagac   540
ccgtttagag gccccaaggg gttatgctag ttattgctca gcggtggcag cagccaactc   600
agcttccttt cgggctttgt tagcagccgg atcgatccaa gctgtacctc actattcctt   660
tgccctcgga cgagtgctgg ggcgtcggtt tccactatcg cgagtacttc tacacagcc    720 atcggtccag acggccgcgc ttctgcgggc gatttgtgta cgcccgacag tcccggctcc   780
ggatcggacg attgcgtcgc atcgaccctg cgcccaagct gcatcatcga aattgccgtc   840
aaccaagctc tgatagagtt ggtcaagacc aatgcggagc atatacgccc ggagccgcgg   900
cgatcctgca agctccggat gcctccgctc gaagtagcgc gtctgctgct ccatacaagc   960
caaccacggc ctccagaaga agatgttggc gacctcgtat tgggaatccc cgaacatcgc  1020
ctcgctccag tcaatgaccg ctgttatgcg gccattgtcc gtcaggacat tgttggagcc  1080

-continued

```
gaaatccgcg tgcacgaggt gccggacttc ggggcagtcc tcggcccaaa gcatcagctc    1140
atcgagagcc tgcgcgacgg acgcactgac ggtgtcgtcc atcacagttt gccagtgata    1200
cacatgggga tcagcaatcg cgcatatgaa atcacgccat gtagtgtatt gaccgattcc    1260
ttgcggtccg aatgggccga acccgctcgt ctggctaaga tcggccgcag cgatcgcatc    1320
catagcctcc gcgaccggct gcagaacagc gggcagttcg gtttcaggca ggtcttgcaa    1380
cgtgacaccc tgtgcacggc gggagatgca ataggtcagg ctctcgctga attccccaat    1440
gtcaagcact tccggaatcg ggagcgcggc cgatgcaaag tgccgataaa cataacgatc    1500
tttgtagaaa ccatcggcgc agctatttac ccgcaggaca tatccacgcc ctcctacatc    1560
gaagctgaaa gcacgagatt cttcgccctc cgagagctgc atcaggtcgg agacgctgtc    1620
gaacttttcg atcagaaact tctcgacaga cgtcgcggtg agttcaggct tttccatggg    1680
tatatctcct tcttaaagtt aaacaaaatt atttctagag ggaaaccgtt gtggtctccc    1740
tatagtgagt cgtattaatt tcgcgggatc gagatcgatc caattccaat cccacaaaaa    1800
tctgagctta acagcacagt tgctcctctc agagcagaat cgggtattca cacccctcat    1860
atcaactact acgttgtgta taacggtcca catgccggta tatacgatga ctggggttgt    1920
acaaaggcgg caacaaacgg cgttcccgga gttgcacaca agaaatttgc cactattaca    1980
gaggcaagag cagcagctga cgcgtacaca acaagtcagc aaacagacag gttgaacttc    2040
atccccaaag gagaagctca actcaagccc aagagctttg ctaaggccct aacaagccca    2100
ccaaagcaaa aagcccactg gctcacgcta ggaaccaaaa ggcccagcag tgatccagcc    2160
ccaaaagaga tctcctttgc cccggagatt acaatggacg atttcctcta tctttacgat    2220
ctaggaagga agttcgaagg tgaaggtgac gacactatgt tcaccactga taatgagaag    2280
gttagcctct tcaatttcag aaagaatgct gacccacaga tggttagaga ggcctacgca    2340
gcaggtctca tcaagacgat ctacccgagt aacaatctcc aggagatcaa ataccttccc    2400
aagaaggtta agatgcagt caaaagattc aggactaatt gcatcaagaa cacagagaaa    2460
gacatatttc tcaagatcag aagtactatt ccagtatgga cgattcaagg cttgcttcat    2520
aaaccaaggc aagtaataga gattggagtc tctaaaaagg tagttcctac tgaatctaag    2580
gccatgcatg gagtctaaga ttcaaatcga ggatcaaaca gaactcgccg tgaagactgg    2640
cgaacagttc atacagagtc ttttacgact caatgacaag aagaaaatct tcgtcaacat    2700
ggtggagcac gacactctgg tctactccaa aaatgtcaaa gatacagtct cagaagacca    2760
aagggctatt gagactttc aacaaaggat aatttcggga aacctcctcg gattccattg    2820
cccagctatc tgtcacttca tcgaaaggac agtagaaaag gaaggtggct cctacaaatg    2880
ccatcattgc gataaaggaa aggctatcat tcaagatgcc tctgccgaca gtggtcccaa    2940
agatggaccc ccaccacga ggagcatcgt ggaaaaagaa gacgttccaa ccacgtcttc    3000
aaagcaagtg gattgatgtg acatctccac tgacgtaagg gatgacgcac aatcccacta    3060
tccttcgcaa gacccttcct ctatataagg aagttcattt catttggaga ggacacgctc    3120
gagctcattt ctctattact tcagccataa caaaagaact cttttctctt cttattaaac    3180
catgaaaaag cctgaactca ccgcgacgtc tgtcgagaag tttctgatcg aaaagttcga    3240
cagcgtctcc gacctgatgc agctctcgga gggcgaagaa tctcgtgctt tcagcttcga    3300
tgtaggaggg cgtggatatg tcctgcgggt aaatagctgc gccgatggtt tctacaaaga    3360
tcgttatgtt tatcggcact ttgcatcggc cgcgctcccg attccggaag tgcttgacat    3420
```

```
tggggaattc agcgagagcc tgacctattg catctcccgc cgtgcacagg gtgtcacgtt   3480
gcaagacctg cctgaaaccg aactgcccgc tgttctgcag ccggtcgcgg aggccatgga   3540
tgcgatcgct gcggccgatc ttagccagac gagcgggttc ggcccattcg gaccgcaagg   3600
aatcggtcaa tacactacat ggcgtgattt catatgcgcg attgctgatc cccatgtgta   3660
tcactggcaa actgtgatgg acgacaccgt cagtgcgtcc gtcgcgcagg ctctcgatga   3720
gctgatgctt tgggccgagg actgcccgga agtccggcac ctcgtgcacg cggatttcgg   3780
ctccaacaat gtcctgacgg acaatggccg cataacagcg gtcattgact ggagcgaggc   3840
gatgttcggg gattcccaat acgaggtcgc caacatcttc ttctggaggc cgtggttggc   3900
ttgtatggag cagcagacgc gctacttcga gcggaggcat ccggagcttg caggatcgcc   3960
gcggctccgg gcgtatatgc tccgcattgg tcttgaccaa ctctatcaga gcttggttga   4020
cggcaatttc gatgatgcag cttgggcgca gggtcgatgc gacgcaatcg tccgatccgg   4080
agccgggact gtcgggcgta cacaaatcgc ccgcagaagc gcggccgtct ggaccgatgg   4140
ctgtgtagaa gtactcgccg atagtggaaa ccgacgcccc agcactcgtc cgagggcaaa   4200
ggaatagtga ggtacctaaa gaaggagtgc gtcgaagcag atcgttcaaa catttggcaa   4260
taaagtttct taagattgaa tcctgttgcc ggtcttgcga tgattatcat ataatttctg   4320
ttgaattacg ttaagcatgt aataattaac atgtaatgca tgacgttatt tatgagatgg   4380
gtttttatga ttagagtccc gcaattatac atttaatacg cgatagaaaa caaaatatag   4440
cgcgcaaact aggataaatt atcgcgcgcg gtgtcatcta tgttactaga tcgatgtcga   4500
atcgatcaac ctgcattaat gaatcggcca acgcgcgggg agaggcggtt tgcgtattgg   4560
gcgctcttcc gcttcctcgc tcactgactc gctgcgctcg gtcgttcggc tgcggcgagc   4620
ggtatcagct cactcaaagg cggtaatacg gttatccaca gaatcagggg ataacgcagg   4680
aaagaacatg tgagcaaaag gccagcaaaa ggccaggaac cgtaaaaagg ccgcgttgct   4740
ggcgtttttc cataggctcc gcccccctga cgagcatcac aaaaatcgac gctcaagtca   4800
gaggtggcga aacccgacag gactataaag ataccaggcg tttccccctg gaagctccct   4860
cgtgcgctct cctgttccga ccctgccgct taccggatac ctgtccgcct ttctcccttc   4920
gggaagcgtg gcgctttctc aatgctcacg ctgtaggtat ctcagttcgg tgtaggtcgt   4980
tcgctccaag ctgggctgtg tgcacgaacc cccgttcag cccgaccgct gcgccttatc   5040
cggtaactat cgtcttgagt ccaacccggt aagacacgac ttatcgccac tggcagcagc   5100
cactggtaac aggattagca gagcgaggta tgtaggcggt gctacagagt tcttgaagtg   5160
gtggcctaac tacggctaca ctagaaggac agtatttggt atctgcgctc tgctgaagcc   5220
agttaccttc ggaaaaagag ttggtagctc ttgatccggc aaacaaacca ccgctggtag   5280
cggtggtttt tttgtttgca agcagcagat tacgcgcaga aaaaaaggat ctcaagaaga   5340
tcctttgatc ttttctacgg ggtctgacgc tcagtggaac gaaaactcac gttaagggat   5400
tttggtcatg acattaacct ataaaaatag gcgtatcacg aggccctttc gtctcgcgcg   5460
tttcggtgat gacggtgaaa acctctgaca catgcagctc ccggagacgg tcacagcttg   5520
tctgtaagcg gatgccggga gcagacaagc ccgtcagggc gcgtcagcgg gtgttggcgg   5580
gtgtcggggc tggcttaact atgcggcatc agagcagatt gtactgagag tgcaccatat   5640
ggacatattg tcgttagaac gcggctacaa ttaatacata accttatgta tcatacacat   5700
acgatttagg tgcactata gaacggcgcg ccaagcttgg atctcctgca ggatctggcc   5760
ggccggatct cgtacgtcct cgaagagaag ggttaataac acattttta acattttaa   5820
```

```
cacaaattttt agttatttaa aaatttatta aaaaatttaa aataagaaga ggaactctttt    5880
aaataaatct aacttacaaa atttatgatt tttaataagt tttcaccaat aaaaaatgtc    5940
ataaaaatat gttaaaaagt atattatcaa tattctcttt atgataaata aaagaaaaa    6000
aaaaataaaa gttaagtgaa aatgagattg aagtgacttt aggtgtgtat aaatatatca    6060
accccgccaa caattatttt aatccaaata tattgaagta tattattcca tagcctttat    6120
ttatttatat atttattata taaaagcttt atttgttcta ggttgttcat gaaatatttt    6180
tttggtttta tctccgttgt aagaaaatca tgtgctttgt gtcgccactc actattgcag    6240
cttttttcatg cattggtcag attgacggtt gattgtattt ttgttttta tggtttgtg    6300
ttatgactta agtcttcatc tctttatctc ttcatcaggt ttgatggtta cctaatatgg    6360
tccatgggta catgcatggt taaattaggt ggccaacttt gttgtgaacg atagaattt    6420
ttttatatta agtaaactat ttttatatta tgaaataata ataaaaaaaa tattttatca    6480
ttattaacaa aatcatatta gttaatttgt taactctata ataaaagaaa tactgtaaca    6540
ttcacattac atggtaacat cttttccaccc tttcatttgt tttttgtttg atgacttttt    6600
ttcttgttta aatttatttc ccttctttta aatttggaat acattatcat catatataaa    6660
ctaaaatact aaaaacagga ttacacaaat gataaataat aacacaaata tttataaatc    6720
tagctgcaat atatttaaac tagctatatc gatattgtaa aataaaacta gctgcattga    6780
tactgataaa aaaatatcat gtgctttctg gactgatgat gcagtatact tttgacattg    6840
cctttattt attttcaga aagcttct tagttctggg ttcttcatta tttgtttccc    6900
atctccattg tgaattgaat catttgcttc gtgtcacaaa tacaatttag ntaggtacat    6960
gcattggtca gattcacggt ttattatgtc atgacttaag ttcatggtag tacattacct    7020
gccacgcatg cattatattg gttagatttg ataggcaaat ttggttgtca acaatataaa    7080
tataaataat gtttttatat tacgaaataa cagtgatcaa aacaaacagt tttatcttta    7140
ttaacaagat tttgtttttg tttgatgacg tttttttaatg tttacgcttt cccccttctt    7200
ttgaatttag aacactttat catcataaaa tcaaatacta aaaaaattac atatttcata    7260
aataataaca caaatatttt taaaaaatct gaaataataa tgaacaatat tacatattat    7320
cacgaaaatt cattaataaa aatattatat aaataaaatg taatagtagt tatatgtagg    7380
aaaaaagtac tgcacgcata atatatacaa aaagattaaa atgaactatt ataaataata    7440
acactaaatt aatggtgaat catatcaaaa taatgaaaaa gtaaataaaa tttgtaatta    7500
acttctatat gtattacaca cacaaataat aaataatagt aaaaaaaatt atgataaata    7560
tttaccatct cataagatat ttaaaataat gataaaaata tagattattt tttatgcaac    7620
tagctagcca aaaagagaac acgggtatat ataaaaagag tacctttaaa ttctactgta    7680
cttcctttat tcctgacgtt tttatatcaa gtggacatac gtgaagattt taattatcag    7740
tctaaatatt tcattagcac ttaatacttt tctgttttat tcctatccta taagtagtcc    7800
cgattctccc aacattgctt attcacacaa ctaactaaga aagtcttcca tagccccca    7860
agcggccgca caatggcgac tcgacagcga actgccacca ctgttgtggt cgaggaccttt    7920
cccaaggtca ctcttgaggc caagtctgaa cctgtgttcc ccgatatcaa gaccatcaag    7980
gatgccattc ccgcgcactg cttccagccc tcgctcgtca cctcattcta ctacgtcttc    8040
cgcgattttg ccatggtctc tgccctcgtc tgggctgctc tcacctacat ccccagcatc    8100
cccgaccaga ccctccgcgt cgcagcttgg atggtctacg gcttcgtcca gggtctgttc    8160
```

-continued

```
tgcaccggtg tctggattct cggccatgag tgcggccacg gtgctttctc tctccacgga      8220
aaggtcaaca atgtgaccgg ctggttcctc cactcgttcc tcctcgtccc ctacttcagc      8280
tggaagtact ctcaccaccg ccaccaccgc ttcaccggcc acatggatct cgacatggct      8340
ttcgtcccca agactgagcc caagccctcc aagtcgctca tgattgctgg cattgacgtc      8400
gccgagcttg ttgaggacac ccccgctgct cagatggtca agctcatctt ccaccagctt      8460
ttcggatggc aggcgtacct cttcttcaac gctagctctg gcaagggcag caagcagtgg      8520
gagcccaaga ctggcctctc caagtggttc cgagtcagtc acttcgagcc taccagcgct      8580
gtcttccgcc ccaacgaggc catcttcatc ctcatctccg atatcggtct tgctctaatg      8640
ggaactgctc tgtactttgc ttccaagcaa gttggtgttt cgaccattct cttcctctac      8700
cttgttccct acctgtgggt tcaccactgg ctcgttgcca ttacctacct ccaccaccac      8760
cacaccgagc tccctcacta caccgctgag ggctggacct acgtcaaggg agctctcgcc      8820
actgtcgacc gtgagtttgg cttcatcgga aagcacctct tccacggtat cattgagaag      8880
cacgttgttc accatctctt ccctaagatc cccttctaca aggctgacga ggccaccgag      8940
gccatcaagc ccgtcattgg cgaccactac tgccacgacg accgaagctt cctgggccag      9000
ctgtggacca tcttcggcac gctcaagtac gtcgagcacg accctgcccg accggtgcc      9060 atgcgatgga acaaggacta ggctaggc                                         9088
```

<210> SEQ ID NO 79
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 79

```
gcccccatc ctttgaaagc ctgt                                              24
```

<210> SEQ ID NO 80
<211> LENGTH: 34
<212> TYPE: DNA
<213> ORGANISM: Artificial Sequence
<220> FEATURE:
<223> OTHER INFORMATION: synthetic oligonucleotide

<400> SEQUENCE: 80

```
cgcggatccg agagcctcag catcttgagc agaa                                  34
```

<210> SEQ ID NO 81
<211> LENGTH: 2012
<212> TYPE: DNA
<213> ORGANISM: Glycine max

<400> SEQUENCE: 81

```
atcttaggcc cttgattata tggtgtttag atggattcac atgcaagttt ttatttcaat      60
cccttttcct ttgaataact gaccaagaac aacaagaaaa aaaaaaaag aaaaggatca      120 ttttgaaagg atattttcg ctcctattca aatactgtat ttttaccaaa aaaactgtat      180
ttttcctaca ctctcaagct ttgttttcg cttcgactct catgatttcc ttcatatgcc      240
aatcactcta tttataaatg gcataaggta gtgtgaacaa ttgcaaagct tgtcatcaaa      300
agcttgcaat gtacaaatta atgttttca tgcctttcaa aattatctgc accccctagc      360
tattaatcta acatctaagt aaggctagtg aattttttcg aatagtcatg cagtgcatta      420
atttccccgt gactattttg gctttgactc caacactggc cccgtacatc cgtccctcat      480
```

-continued

```
tacatgaaaa gaaatattgt ttatattctt aattaaaaat attgtccctt ctaaattttc      540
atatagttaa ttattatatt acttttttct ctattctatt agttctattt tcaaattatt      600
atttatgcat atgtaaagta cattatattt ttgctatata cttaaatatt tctaaattat      660
taaaaaaaga ctgatatgaa aaatttattc tttttaaagc tatatcattt tatatatact      720 ttttctttc tttctttca ttttctattc aatttaataa gaataaaatt ttgtaaattt       780
ttatttatca atttataaaa atatttact ttatatgttt tttcacattt ttgttaaaca      840
aatcatatca ttatgattga aagagaggaa attgacagtg agtaataagt gatgagaaaa      900
aaatgtgtta tttcctaaaa aaacctaaa caaacatgta tctactctct atttcatcta      960
tctctcattt cattttctc tttatctctt tctttatttt tttatcatat catttcacat     1020
taattatttt tactctcttt attttttctc tctatccctc tcttatttcc actcatatat     1080
acactccaaa attggggcat gcctttatca ctactctatc tcctccacta aatcatttaa     1140
atgaaactga aaagcattgg caagtctcct cccctcctca agtgatttcc aactcagcat     1200
tggcatctga ttgattcagt atatctattg catgtgtaaa agtctttcca caatacataa     1260
ctattaatta atcttaaata aataaaggat aaaatatttt tttttcttca taaaattaaa     1320
atatgttatt ttttgtttag atgtatattc gaataaatct aaatatatga taatgatttt     1380
ttatattgat taaacatata atcaatatta aatatgatat ttttttatat aggttgtaca     1440
cataatttta taaggataaa aaatatgata aaaataaatt ttaaatattt ttatatttac     1500
gagaaaaaaa aatatttag ccataaataa atgaccagca tattttacaa ccttagtaat      1560
tcataaattc ctatatgtat atttgaaatt aaaaacagat aatcgttaag ggaaggaatc     1620
ctacgtcatc tcttgccatt tgttttcat gcaaacagaa agggacgaaa aaccacctca     1680
ccatgaatca ctcttcacac cattttact agcaaacaag tctcaacaac tgaagccagc     1740
tctctttccg tttcttttta caacactttc tttgaaatag tagtatttt ttttcacatg     1800 atttattaac gtgccaaaag atgcttattg aatagagtgc acatttgtaa tgtactacta     1860
attagaacat gaaaaagcat tgttctaaca cgataatcct gtgaaggcgt taactccaaa     1920
gatccaattt cactatataa attgtgacga aagcaaaatg aattcacata gctgagagag     1980
aaaggaaagg ttaactaaga agcaatactt ca                                   2012
```

<210> SEQ ID NO 82
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 82

```
ggtccaatat ggaacgatga gttgata                                          27
```

<210> SEQ ID NO 83
<211> LENGTH: 35
<212> TYPE: DNA
<213> ORGANISM: Artificial Sequence
<220> FEATURE:
<223> OTHER INFORMATION: synthetic oligonucleotide

<400> SEQUENCE: 83

```
cgcggatccg ctggaactag aagagagacc taaga                                 35
```

<210> SEQ ID NO 84

<211> LENGTH: 1408
<212> TYPE: DNA
<213> ORGANISM: Glycine max

<400> SEQUENCE: 84

| | | | | | |
|---|---|---|---|---|---|
| aactaaaaaa | agctctcaaa | ttacattttg | agttgtttca | ggttccattg | ccttattgct | 60 |
| aaaactccaa | ctaaaataac | aaatagcaca | tgcaggtgca | aacaaacacgt | tactctgatg | 120 |
| aaggtgatgt | gcctctagca | gtctagctta | tgaggctcgc | tgcttatcaa | cgattcatca | 180 |
| ttccccaaga | cgtgtacgca | gattaaacaa | tggacaaaac | ttcaatcgat | tatagaataa | 240 |
| taattttaac | agtgccgact | tttttctgta | aacaaaggc | cagaatcata | tcgcacatca | 300 |
| tcttgaatgc | agtgtcgagt | ttggaccatt | tgagtacaaa | gccaatattg | aatgattttt | 360 |
| cgattttaca | tgtgtgaatc | agacaaaagt | gcatgcaatc | acttgcaagt | aaattaagga | 420 |
| tactaatcta | ttcctttcat | tttatatgct | ccactttat | ataaaaaaat | atacattatt | 480 |
| atatatgcat | tattaattat | tgcagtatta | tgctattggt | tttatggccc | tgctaaataa | 540 |
| cctaaatgag | tctaactatt | gcatatgaat | caaatgaagg | aagaatcatg | atctaaacct | 600 |
| gagtacccaa | tgcaataaaa | tgcgtcctat | tacctaaact | tcaaacacac | attgccatcg | 660 |
| gacgtataaa | ttaatgcata | taggttattt | tgagaaaaga | aaacatcaaa | agctctaaaa | 720 |
| cttctttaa | ctttgaaata | agctgataaa | aatacgcttt | aaatcaactg | tgtgctgtat | 780 |
| ataagctgca | atttcacatt | ttaccaaacc | gaaacaagaa | tggtaacagt | gaggcaaaaa | 840 |
| tttgaaaaat | gtcctacttc | acattcacat | caaattaatt | acaactaaat | aaataaacat | 900 |
| cgtgattcaa | gcagtaatga | agtcgaaat | cagatagaat | atacacgttt | aacatcaatt | 960 |
| gaattttttt | ttaaatggat | atatacaagt | ttactatttt | atatataatg | aaaattcatt | 1020 |
| ttgtgttagc | acaaaactta | cagaaagaga | taaatttaa | ataaagagaa | ttatatccaa | 1080 |
| ttttataatc | caaataatc | aaattaaaga | atattggcta | gatagaccgg | cttttttcact | 1140 |
| gccctgctg | gataatgaaa | attcatatca | aaacaataca | gaagttctag | tttaataata | 1200 |
| aaaaagttgg | caaactgtca | ttccctgttg | gtttttaagc | caaatcacaa | ttcaattacg | 1260 |
| tatcagaaat | taatttaaac | caaatatata | gctacgaggg | aacttcttca | gtcattacta | 1320 |
| gctagctcac | taatcactat | atatacgaca | tgctacaagt | gaagtgacca | tatcttaatt | 1380 |
| tcaaatcata | aaattcttcc | accaagtt | | | | 1408 |

<210> SEQ ID NO 85
<211> LENGTH: 898
<212> TYPE: DNA
<213> ORGANISM: Glycine max

<400> SEQUENCE: 85

| | | | | | |
|---|---|---|---|---|---|
| tatatatgtg | agggtagagg | gtatcacatg | agctctggat | ttccataatg | aaaaggaatc | 60 |
| agaaaaaaga | aagggtttg | caactaaaaa | cttgggaaag | aacaaaggtt | taatcttggg | 120 |
| atcggtgacc | aaacctcttt | ttgataccat | cttccattta | atctagaata | tgaaaataag | 180 |
| tggataataa | aaaagaaaaa | tgatatttaa | tctaagttca | aacaactcga | ttagtccttt | 240 |
| cctcagttat | aaaaggaaa | acaaaacaac | gtacaactca | atcagatttc | aatttgctta | 300 |
| ttttgtttca | actcaatatt | tagctttaa | taattaacta | aggttttat | attatatta | 360 |
| gaattttttt | tctcctttta | ttttatttgc | atgtatatta | ggagttgtcc | aatgataatt | 420 |
| attcttaat | aatgaatcat | tagtcttaca | tcattacatg | atacacatgt | atgagatgtc | 480 |
| cactccatct | cttgttaatt | tgatgggcat | ccattactta | tcaaccatcc | gccatagtta | 540 |

```
tctggttgtg tattttgtta tctgttggta ctctggagta gcatgcataa cgctatattt      600
ttatttctag gatcatgcat atacgcgcaa accaaagaac agagaccgat gtaaagacaa      660
aacatagagt atcctttcca aaacaacgtc caagttcata aaatagagac gaaatgcaag      720
cacagcacac ataagtggat gatcaagatg ggctcgtcca tgccacgcac accaacacac      780
gtcaagcagc aagccctccc gtggccaaat gtgcatgcat acatgttaac aagagcttgc      840
ataactataa atagccctaa tctcactcca tgtttcatcg tccaataata tatatact       898

<210> SEQ ID NO 86
<211> LENGTH: 36
<212> TYPE: DNA
<213> ORGANISM: Artificial Sequence
<220> FEATURE:
<223> OTHER INFORMATION: synthetic oligonucleotide

<400> SEQUENCE: 86
cgcggatcct atatatgtga gggtagaggg tatcac                                36

<210> SEQ ID NO 87
<211> LENGTH: 44
<212> TYPE: DNA
<213> ORGANISM: Artificial Sequence
<220> FEATURE:
<223> OTHER INFORMATION: synthetic oligonucleotide

<400> SEQUENCE: 87
gaattcgcgg ccgcagtata tatattattg gacgatgaaa catg                       44

<210> SEQ ID NO 88
<211> LENGTH: 690
<212> TYPE: DNA
<213> ORGANISM: Glycine max

<400> SEQUENCE: 88
tagcctaagt acgtactcaa aatgccaaca aataaaaaaa aagttgcttt aataatgcca      60
aaacaaatta ataaaacact tacaacaccg gatttttttt aattaaaatg tgccatttag     120
gataaatagt taatatttt aataattatt taaaaagccg tatctactaa aatgattttt     180
atttggttga aaatattaat atgtttaaat caacacaatc tatcaaaatt aaactaaaaa     240
aaaaataagt gtacgtggtt aacattagta cagtaatata agaggaaaat gagaaattaa     300
gaaattgaaa gcgagtctaa ttttaaatt atgaacctgc atatataaaa ggaaagaaag     360
aatccaggaa gaaaagaaat gaaaccatgc atggtcccct cgtcatcacg agtttctgcc     420
atttgcaata gaaacactga aacacctttc tctttgtcac ttaattgaga tgccgaagcc     480
acctcacacc atgaacttca tgaggtgtag cacccaaggc ttccatagcc atgcatactg     540
aagaatgtct caagctcagc accctacttc tgtgacgttg tccctcattc accttcctct     600
cttccctata aataaccacg cctcaggttc tccgcttcac aactcaaaca ttctcctcca     660
ttggtcctta aacactcatc agtcatcacc                                     690

<210> SEQ ID NO 89
<211> LENGTH: 36
<212> TYPE: DNA
<213> ORGANISM: Artificial Sequence
<220> FEATURE:
<223> OTHER INFORMATION: synthetic oligonucleotide

<400> SEQUENCE: 89
```

```
cgcggatcct agcctaagta cgtactcaaa atgcca                              36

<210> SEQ ID NO 90
<211> LENGTH: 41
<212> TYPE: DNA
<213> ORGANISM: Artificial Sequence
<220> FEATURE:
<223> OTHER INFORMATION: synthetic oligonucleotide

<400> SEQUENCE: 90
gaattcgcgg ccgcggtgat gactgatgag tgtttaagga c                        41

<210> SEQ ID NO 91
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 91
atctagacgt acgtcctcga agagaaggg                                      29

<210> SEQ ID NO 92
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 92
ttctagacgt acggatataa tg                                             22

<210> SEQ ID NO 93
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 93
tgcggccgca tgagccg                                                   17

<210> SEQ ID NO 94
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 94
acgtacggta ccatctgcta atattttaaa tc                                  32

<210> SEQ ID NO 95
<211> LENGTH: 12456
<212> TYPE: DNA
<213> ORGANISM: Artificial Sequence
<220> FEATURE:
<223> OTHER INFORMATION: plasmid pKR585
<220> FEATURE:
<221> NAME/KEY: misc_feature
<222> LOCATION: (1201)..(1201)
<223> OTHER INFORMATION: n is a, c, g, or t

<400> SEQUENCE: 95
ggatctggcc ggccggatct cgtacgtcct cgaagagaag ggttaataac acatttttta    60 acattttttaa cacaaatttt agttatttaa aaatttatta aaaaatttaa aataagaaga  120
```

-continued

```
ggaactcttt aaataaatct aacttacaaa atttatgatt tttaataagt tttcaccaat      180
aaaaaatgtc ataaaaatat gttaaaaagt atattatcaa tattctcttt atgataaata      240
aaaagaaaaa aaaaataaaa gttaagtgaa aatgagattg aagtgacttt aggtgtgtat      300
aaatatatca accccgccaa caatttattt aatccaaata tattgaagta tattattcca      360
tagcctttat ttatttatat atttattata taaaagcttt atttgttcta ggttgttcat      420
gaaatatttt tttggtttta tctccgttgt aagaaaatca tgtgctttgt gtcgccactc      480
actattgcag ctttttcatg cattggtcag attgacggtt gattgtattt ttgtttttta      540
tggttttgtg ttatgactta agtcttcatc tctttatctc ttcatcaggt ttgatggtta      600
cctaatatgg tccatgggta catgcatggt taaattaggt ggccaacttt gttgtgaacg      660
atagaattt ttttatatta agtaaactat ttttatatta tgaataata ataaaaaaaa        720
tattttatca ttattaacaa aatcatatta gttaatttgt taactctata ataaagaaa       780
tactgtaaca ttcacattac atggtaacat ctttccaccc tttcatttgt tttttgtttg      840
atgactttt ttcttgttta aatttatttc ccttcttta aatttggaat acattatcat        900
catatataaa ctaaaatact aaaaacagga ttacacaaat gataataat aacacaaata       960
tttataaatc tagctgcaat atatttaaac tagctatatc gatattgtaa aataaaacta     1020
gctgcattga tactgataaa aaaatatcat gtgctttctg gactgatgat gcagtatact     1080
tttgacattg cctttatttt attttcaga aaagctttct tagttctggg ttcttcatta      1140
tttgtttccc atctccattg tgaattgaat catttgcttc gtgtcacaaa tacaatttag     1200
ntaggtacat gcattggtca gattcacggt ttattatgtc atgacttaag ttcatggtag     1260
tacattacct gccacgcatg cattatattg gttagatttg ataggcaaat ttggttgtca     1320
acaatataaa tataataat gttttatat tacgaaataa cagtgatcaa aacaaacagt       1380
tttatcttta ttaacaagat tttgttttg tttgatgacg tttttttaatg tttacgcttt     1440
cccccttctt ttgaatttag aacactttat catcataaaa tcaaatacta aaaaattac      1500
atatttcata aataataaca caaatatttt taaaaaatct gaaataataa tgaacaatat     1560
tacatattat cacgaaaatt cattaataaa aatattatat aaataaaatg taatagtagt     1620
tatatgtagg aaaaaagtac tgcacgcata atatatacaa aaagattaaa atgaactatt     1680
ataaataata acactaaatt aatggtgaat catatcaaaa taatgaaaaa gtaaataaaa     1740
tttgtaatta acttctatat gtattacaca cacaaataaa aataatagt aaaaaaaatt      1800
atgataaata tttaccatct cataagatat ttaaaataat gataaaaata tagattatttt   1860
tttatgcaac tagctagcca aaaagagaac acgggtatat ataaaagag taccttaaa       1920
ttctactgta cttcctttat tcctgacgtt tttatatcaa gtggacatac gtgaagattt     1980
taattatcag tctaaatatt tcattagcac ttaaacttt tctgttttat tcctatccta      2040
taagtagtcc cgattctccc aacattgctt attcacacaa ctaactaaga aagtcttcca     2100
tagccccca agcggccgca caatggcgac tcgacagcga actgccacca ctgttgtggt      2160
cgaggacctt cccaaggtca ctcttgaggc caagtctgaa cctgtgttcc ccgatatcaa     2220
gaccatcaag gatgccattc ccgcgcactg cttccagccc tcgctcgtca cctcattcta    2280
ctacgtcttc cgcgatttg ccatggtctc tgccctcgtc tgggctgctc tcacctacat      2340
ccccagcatc cccgaccaga ccctccgcgt gcagcttgg atggtctacg gcttcgtcca     2400
gggtctgttc tgcaccggtg tctggattct cggccatgag tgcggccacg gtgctttctc    2460
```

```
tctccacgga aaggtcaaca atgtgaccgg ctggttcctc cactcgttcc tcctcgtccc   2520
ctacttcagc tggaagtact ctcaccaccg ccaccaccgc ttcaccggcc acatggatct   2580
cgacatggct ttcgtcccca agactgagcc caagccctcc aagtcgctca tgattgctgg   2640
cattgacgtc gccgagcttg ttgaggacac ccccgctgct cagatggtca agctcatctt   2700
ccaccagctt ttcggatggc aggcgtacct cttcttcaac gctagctctg caagggcag   2760 caagcagtgg gagcccaaga ctggcctctc caagtggttc cgagtcagtc acttcgagcc   2820
taccagcgct gtcttccgcc caacgaggc catcttcatc ctcatctccg atatcggtct   2880
tgctctaatg ggaactgctc tgtactttgc ttccaagcaa gttggtgttt cgaccattct   2940
cttcctctac cttgttccct acctgtgggt tcaccactgg ctcgttgcca ttacctacct   3000
ccaccaccac cacaccgagc tccctcacta caccgctgag ggctggacct acgtcaaggg   3060
agctctcgcc actgtcgacc gtgagtttgg cttcatcgga aagcacctct tccacggtat   3120
cattgagaag cacgttgttc accatctctt ccctaagatc cccttctaca aggctgacga   3180
ggccaccgag gccatcaagc ccgtcattgg cgaccactac tgccacgacg accgaagctt   3240
cctgggccag ctgtggacca tcttcggcac gctcaagtac gtcgagcacg accctgcccg   3300
acccggtgcc atgcgatgga caaggacta ggctaggcgg ccgcgacaca agtgtgagag   3360
tactaaataa atgctttggt tgtacgaaat cattacacta aataaaataa tcaaagctta   3420
tatatgcctt ccgctaaggc cgaatgcaaa gaaattggtt ctttctcgtt atcttttgcc   3480
acttttacta gtacgtatta attactactt aatcatcttt gtttacggct cattatatcc   3540
ggtctagagg atccaaggcc gcgaagttaa aagcaatgtt gtcacttgtc gtactaacac   3600
atgatgtgat agtttatgct agctagctat aacataagct gtctctgagt gtgttgtata   3660
ttaataaaga tcatcactgg tgaatggtga tcgtgtacgt accctactta gtaggcaatg   3720
gaagcactta gagtgtgctt tgtgcatggc cttgcctctg ttttgagact tttgtaatgt   3780
tttcgagttt aaatctttgc ctttgcgtac ggatccgtcg acggcgcgcc cgatcatccg   3840
gatatagttc ctcctttcag caaaaaaccc ctcaagaccc gtttagaggc cccaaggggt   3900
tatgctagtt attgctcagc ggtggcagca gccaactcag cttcctttcg gctttgtta   3960 gcagccggat cgatccaagc tgtacctcac tattcctttg ccctcggacg agtgctgggg   4020
cgtcggtttc cactatcggc gagtacttct acacagccat cggtccagac ggccgcgctt   4080
ctgcgggcga tttgtgtacg cccgacagtc ccggctccgg atcggacgat gcgtcgcat   4140 cgaccctgcg cccaagctgc atcatcgaaa ttgccgtcaa ccaagctctg atagagttgg   4200
tcaagaccaa tgcggagcat atacgcccgg agccgcggcg atcctgcaag ctccggatgc   4260
ctccgctcga agtagcgcgt ctgctgctcc atacaagcca accacggcct ccagaagaag   4320
atgttggcga cctcgtattg ggaatccccg aacatcgcct cgctccagtc aatgaccgct   4380
gttatgcggc cattgtccgt caggacattg ttggagccga atccgcgtg cacgaggtgc   4440 cggacttcgg ggcagtcctc ggcccaaagc atcagctcat cgagagcctg cgcgacggac   4500
gcactgacgg tgtcgtccat cacagtttgc cagtgataca catggggatc agcaatcgcg   4560
catatgaaat cacgccatgt agtgtattga ccgattcctt gcggtccgaa tgggccgaac   4620
ccgctcgtct ggctaagatc ggccgcagcg atcgcatcca tagcctccgc gaccggctgc   4680
agaacagcgg gcagttcggt ttcaggcagg tcttgcaacg tgacaccctg tgcacggcgg   4740
gagatgcaat aggtcaggct ctcgctgaat tccccaatgt caagcacttc cggaatcggg   4800
agcgcggccg atgcaaagtg ccgataaaca taacgatctt tgtagaaacc atcggcgcag   4860
```

```
ctatttaccc gcaggacata tccacgccct cctacatcga agctgaaagc acgagattct    4920
tcgccctccg agagctgcat caggtcggag acgctgtcga acttttcgat cagaaacttc    4980
tcgacagacg tcgcggtgag ttcaggcttt tccatgggta tatctccttc ttaaagttaa    5040
acaaaattat ttctagaggg aaaccgttgt ggtctcccta tagtgagtcg tattaatttc    5100
gcgggatcga gatcgatcca attccaatcc cacaaaaatc tgagcttaac agcacagttg    5160
ctcctctcag agcagaatcg ggtattcaac accctcatat caactactac gttgtgtata    5220
acggtccaca tgccggtata tacgatgact ggggttgtac aaaggcggca acaaacggcg    5280
ttcccggagt tgcacacaag aaatttgcca ctattacaga ggcaagagca gcagctgacg    5340
cgtacacaac aagtcagcaa acagacaggt tgaacttcat ccccaaagga gaagctcaac    5400
tcaagcccaa gagctttgct aaggccctaa caagcccacc aaagcaaaaa gcccactggc    5460
tcacgctagg aaccaaaagg cccagcagtg atccagcccc aaaagagatc tcctttgccc    5520
cggagattac aatggacgat tcctctatc tttacgatct aggaaggaag ttcgaaggtg    5580
aaggtgacga cactatgttc accactgata atgagaaggt tagcctcttc aatttcagaa    5640
agaatgctga cccacagatg gttagagagg cctacgcagc aggtctcatc aagacgatct    5700
acccgagtaa caatctccag gagatcaaat accttcccaa gaaggttaaa gatgcagtca    5760
aaagattcag gactaattgc atcaagaaca cagagaaaga catatttctc aagatcagaa    5820
gtactattcc agtatggacg attcaaggct tgcttcataa accaaggcaa gtaatagaga    5880
ttggagtctc taaaaaggta gttcctactg aatctaaggc catgcatgga gtctaagatt    5940
caaatcgagg atctaacaga actcgccgtg aagactggcg aacagttcat acagagtctt    6000
ttacgactca atgacaagaa gaaaatcttc gtcaacatgg tggagcacga cactctggtc    6060
tactccaaaa atgtcaaaga tacagtctca gaagaccaaa gggctattga cttttcaa    6120
caaaggataa tttcgggaaa cctcctcgga ttccattgcc cagctatctg tcacttcatc    6180
gaaaggacag tagaaaagga aggtggctcc tacaaatgcc atcattgcga taaaggaaag    6240
gctatcattc aagatgcctc tgccgacagt ggtcccaaag atggacccccc acccacgagg    6300
agcatcgtgg aaaaagaaga cgttccaacc acgtcttcaa agcaagtgga ttgatgtgac    6360
atctccactg acgtaaggga tgacgcacaa tcccactatc cttcgcaaga cccttcctct    6420
atataaggaa gttcatttca tttggagagg acacgctcga gctcatttct ctattacttc    6480
agccataaca aaagaactct tttctcttct tattaaacca tgaaaaagcc tgaactcacc    6540
gcgacgtctg tcgagaagtt tctgatcgaa aagttcgaca gcgtctccga cctgatgcag    6600
ctctcggagg gcgaagaatc tcgtgctttc agcttcgatg taggagggcg tggatatgtc    6660
ctgcgggtaa atagctgcgc cgatggtttc tacaaagatc gttatgttta tcggcacttt    6720
gcatcggccg cgctcccgat tccggaagtg cttgacattg gggaattcag cgagagcctg    6780
acctattgca tctcccgccg tgcacagggt gtcacgttgc aagacctgcc tgaaaccgaa    6840
ctgcccgctg ttctgcagcc ggtcgcgag gccatggatg cgatcgctgc ggccgatctt    6900
agccagacga gcgggttcgg cccattcgga ccgcaaggaa tcggtcaata cactacatgg    6960
cgtgatttca tatgcgcgat tgctgatccc catgtgtatc actggcaaac tgtgatggac    7020
gacaccgtca gtgcgtccgt cgcgcaggct ctcgatgagc tgatgctttg gccgaggac    7080
tgccccgaag tccggcacct cgtgcacgcg gatttcggct ccaacaatgt cctgacggac    7140
aatggccgca taacagcggt cattgactgg agcgaggcga tgttcgggga ttcccaatac    7200
```

```
gaggtcgcca acatcttctt ctggaggccg tggttggctt gtatggagca gcagacgcgc    7260
tacttcgagc ggaggcatcc ggagcttgca ggatcgccgc ggctccgggc gtatatgctc    7320
cgcattggtc ttgaccaact ctatcagagc ttggttgacg gcaatttcga tgatgcagct    7380
tgggcgcagg gtcgatgcga cgcaatcgtc cgatccggag ccgggactgt cgggcgtaca    7440
caaatcgccc gcagaagcgc ggccgtctgg accgatggct gtgtagaagt actcgccgat    7500
agtggaaacc gacgcccag cactcgtccg agggcaaagg aatagtgagg tacctaaaga    7560
aggagtgcgt cgaagcagat cgttcaaaca tttggcaata agtttcttaa gattgaatc    7620
ctgttgccgg tcttgcgatg attatcatat aatttctgtt gaattacgtt aagcatgtaa    7680
taattaacat gtaatgcatg acgttattta tgagatgggt ttttatgatt agagtcccgc    7740
aattatacat ttaatacgcg atagaaaaca aaatatagcg cgcaaactag gataaattat    7800
cgcgcgcggt gtcatctatg ttactagatc gatgtcgaat cgatcaacct gcattaatga    7860
atcggccaac gcgcggggag aggcggtttg cgtattgggc gctcttccgc ttcctcgctc    7920
actgactcgc tgcgctcggt cgttcggctg cggcgagcgg tatcagctca ctcaaaggcg    7980
gtaatacggt tatccacaga atcagggat aacgcaggaa agaacatgtg agcaaaaggc    8040
cagcaaaagg ccaggaaccg taaaaaggcc gcgttgctgg cgttttttcca taggctccgc    8100
cccctgacg agcatcacaa aaatcgacgc tcaagtcaga ggtggcgaaa cccgacagga    8160
ctataaagat accaggcgtt tcccctgga agctccctcg tgcgctctcc tgttccgacc    8220
ctgccgctta ccggatacct gtccgccttt ctcccttcgg gaagcgtggc gctttctcaa    8280
tgctcacgct gtaggtatct cagttcggtg taggtcgttc gctccaagct gggctgtgtg    8340
cacgaaccc ccgttcagcc cgaccgctgc gccttatccg gtaactatcg tcttgagtcc    8400
aacccggtaa gacacgactt atcgccactg gcagcagcca ctggtaacag gattagcaga    8460
gcgaggtatg taggcggtgc tacagagttc ttgaagtggt ggcctaacta cggctacact    8520
agaaggacag tatttggtat ctgcgctctg ctgaagccag ttaccttcgg aaaaagagtt    8580
ggtagctctt gatccggcaa acaaaccacc gctggtagcg gtggtttttt tgtttgcaag    8640
cagcagatta cgcgcagaaa aaaaggatct caagaagatc ctttgatctt ttctacgggg    8700
tctgacgctc agtggaacga aaactcacgt taagggattt tggtcatgac attaacctat    8760
aaaaataggc gtatcacgag gccctttcgt ctcgcgcgtt tcggtgatga cggtgaaaac    8820
ctctgacaca tgcagctccc ggagacggtc acagcttgtc tgtaagcgga tgccgggagc    8880
agacaagccc gtcagggcgc gtcagcgggt gttggcgggt gtcggggctg gcttaactat    8940
gcggcatcag agcagattgt actgagagtg caccatatgg acatattgtc gttagaacgc    9000
ggctacaatt aatacataac cttatgtatc atacacatac gatttaggtg acactataga    9060
acggcgcgcc aagcttggat ctcctgcagc ccggggatc cgcccacgta cggtaccatc    9120
tgctaatatt ttaaatcaca tgcaagagag gaggcatggt tccattttct accttcacat    9180
tatttgagaa aaacgaactt gttctgtgtt ttatttttgc ccttcacatt agtacaacgt    9240
ggaagactca tggttacaca gaatcataca taagtacaat gcttgtccct aagaaaacaa    9300
gcactcgttg tattgaacct ttacggctca tgcggccgcg aattcactag tgattgaatt    9360
cgcggccgct tagtccgact tggccttggc ggccgcggcc gactctttga gcgtgaagat    9420
ctgcgccgtc tcgggcacag cgccgtagtt gacaaagagg tgcgcggtct tgaagaaggc    9480
cgtgatgatg ggctcgtcgt tcctgcgcac gaggtgcggg tacgcggccg caaagtgctt    9540
ggtggcttcg ttgagcttgt agtgcggaat gatcgggaac aagtggtgga cctggtgcgt    9600
```

```
gccaatgtgg tggctcaggt tgtccacgaa cgcgccgtac gagcggtcga cgctcgagag    9660
gttgcccttg acgtacgtcc actccgagtc gccgtaccac ggcgtcgctt cgtcgttgtg    9720
gtgcaagaag tcgtaatga cgaggaacga agcaaagaca aagagcggcg catagtagta    9780
gaggcccatg acggcaaagc cgagcgagta tgtgaggtac gcgtacgcgg cgaagaaggc    9840
ggcccagacg ccgagcgaca cgatgacggc cgacgcgcgg cgaaggagga gcgggtccca    9900
cgggtcaaag tggctcatcg tgcgcggggc atacccgacc ttcaagtaga caaaccacgc    9960
accgccgagc gtgtagaccc attggcgcac gtcctggagg tccttgaccg accggtgcgg   10020
gtaaaagatc tcgtccttat caatgttgcc cgtgttcttg tggtggtggc ggtgcgtcac   10080
gcgccagctc tcgaacggcg tcaaaatcgc agagtgcatg atgcagccga tgataaagtt   10140
gacgctgtgg tagcgcgaga aggccgagtg gccgcagtcg tggccgaccg tgaagaagcc   10200
ccagaagatg acgccctgca cgtagatgta ggtggcgcaa acgagcgcgt ggagcagaac   10260
gttatcggca atgaacggcg tcgagcgcgc cgcgtagagc agcgccgccg aggccgacgc   10320
gttgaagatc gcgcgggccg tgtagtagag cgagaggccg aggttcgact caaagcacgc   10380
gttcgggatc gagtgcttga gctccgtgag cgtcgggaac tcgaccttcg tcttatcctc   10440
agtcatgcgg ccgctgaagt attgcttctt agttaacctt tcctttctct ctcagctatg   10500
tgaattcatt ttgctttcgt cacaatttat atagtgaaat tggatcttg gagttaacgc    10560 cttcacagga ttatcgtgtt agaacaatgc ttttcatgt tctaattagt agtacattac    10620
aaatgtgcac tctattcaat aagcatcttt tggcacgtta ataaatcatg tgaaaaaaaa   10680
atactactat ttcaaagaaa gtgttgtaaa aagaaacgga aagagagctg gcttcagttg   10740
ttgagacttg tttgctagta aaaatggtgt gaagagtgat tcatggtgag gtggtttttc    10800
gtccctttct gtttgcatga aaacaaatg gcaagagatg acgtaggatt ccttcccta    10860 acgattatct gtttttaatt tcaaatatac atataggaat ttatgaatta ctaaggttgt   10920
aaaatatgct ggtcatttat ttatggctaa aatattttt tttctcgtaa atataaaat    10980 atttaaaatt tattttatc atattttta tccttataaa attatgtgta caacctatat    11040 aaaaaatat catatttaat attgattata tgtttaatca atataaaaaa tcattatcat    11100
atatttagat ttattcgaat atacatctaa acaaaaaata acatatttta attttatgaa   11160 gaaaaaaaa tattttatcc tttatttatt taagattaat taatagttat gtattgtgga    11220 aagacttta cacatgcaat agatatactg aatcaattag atgccaatgc tgagttgaa    11280 atcacttgag gaggggagga gacttgccaa tgcttttcag tttcatttaa atgatttagt   11340
ggaggagata gagtagtgat aaaggcatgc cccaattttg gagtgtatat atgagtggaa   11400
ataagagagg gatagagaga aaaataaag agagtaaaaa taattaatgt gaaatgatat    11460 gataaaaaa taagaaaga gataagagaa aaatgaaat gagagataga tgaaatagag    11520
agtagataca tgtttgttta ggttttttt aggaaataac acatttttt ctcatcactt    11580 attactcact gtcaatttcc tctctttcaa tcataatgat atgatttgtt taacaaaaat   11640
gtgaaaaaac atataaagta aatatttt ataattgat aaataaaaat ttacaaaatt    11700
tatttcttat taaattgaat agaaatgaa agaaagaaa agaaaagta tatataaaat    11760 gatatagctt taaaagaat aaattttca tatcagtctt tttttaataa tttagaaata   11820
tttaagtata tagcaaaaat ataatgtact ttacatatgc ataaataata atttgaaaat   11880
agaactaata gaatagagaa aaaagtaata taataattaa ctatatgaaa atttagaagg   11940
```

-continued

```
gacaatattt ttaattaaga atataaacaa tatttctttt catgtaatga gggacggatg   12000
tacggggcca gtgttggagt caaagccaaa atagtcacgg ggaaattaat gcactgcatg   12060
actattcgaa aaaattcact agccttactt agatgttaga ttaatagcta gggggtgcag   12120
ataattttga aaggcatgaa aaacattaat ttgtacattg caagcttttg atgacaagct   12180
ttgcaattgt tcacactacc ttatgccatt tataaataga gtgattggca tatgaaggaa   12240
atcatgagag tcgaagcgaa aaacaaagct tgagagtgta ggaaaaatac agttttttg    12300 gtaaaaatac agtatttgaa taggagcgaa aaatatcctt tcaaaatgat cctttctttt   12360
tttttttttt ttcttgttgt tcttggtcag ttattcaaag gaaaagggat tgaaataaaa   12420
acttgcatgt gggatcgtac gtcgagtcga cctgca                             12456
```

<210> SEQ ID NO 96
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 96
ttgcggccgc aaaccatggc tgctgctccc ag                                 32

<210> SEQ ID NO 97
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 97
aagcggccgc ttactgcgcc ttac                                          24

<210> SEQ ID NO 98
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 98
ttcctgcagg ctagcctaag tacgtactc                                     29

<210> SEQ ID NO 99
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 99
aagcggccgc ggtgatgact g                                             21

<210> SEQ ID NO 100
<211> LENGTH: 36
<212> TYPE: DNA
<213> ORGANISM: Artificial Sequence
<220> FEATURE:
<223> OTHER INFORMATION: synthetic oligonucleotide

<400> SEQUENCE: 100
tttctagacg tacgtcccctt cttatctttg atctcc                            36

<210> SEQ ID NO 101
<211> LENGTH: 34
<212> TYPE: DNA
<213> ORGANISM: Artificial Sequence
<220> FEATURE:
<223> OTHER INFORMATION: synthetic oligonucleotide

<400> SEQUENCE: 101
gcggccgcag ttggatagaa tatatgtttg tgac                          34

<210> SEQ ID NO 102
<211> LENGTH: 41
<212> TYPE: DNA
<213> ORGANISM: Artificial Sequence
<220> FEATURE:
<223> OTHER INFORMATION: synthetic oligonucleotide

<400> SEQUENCE: 102
ctatccaact gcggccgcat ttcgcaccaa atcaatgaaa g                  41

<210> SEQ ID NO 103
<211> LENGTH: 38
<212> TYPE: DNA
<213> ORGANISM: Artificial Sequence
<220> FEATURE:
<223> OTHER INFORMATION: synthetic oligonucleotide

<400> SEQUENCE: 103
aatctagacg tacgtgaagg ttaaacatgg tgaatatg                      38

<210> SEQ ID NO 104
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 104
gcggccgcat gggaacggac caag                                     24

<210> SEQ ID NO 105
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 105
gcggccgcct actcttcctt ggga                                     24

<210> SEQ ID NO 106
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 106
gcggccgcat ggagtcgatt gcgc                                     24

<210> SEQ ID NO 107
<211> LENGTH: 24
<212> TYPE: DNA
<213> ORGANISM: Artificial Sequence
<220> FEATURE:
<223> OTHER INFORMATION: synthetic oligonucleotide -continued

```
<400> SEQUENCE: 107
gcggccgctt actgcaactt cctt                                              24

<210> SEQ ID NO 108
<211> LENGTH: 16
<212> TYPE: DNA
<213> ORGANISM: Artificial Sequence
<220> FEATURE:
<223> OTHER INFORMATION: synthetic oligonucleotide

<400> SEQUENCE: 108
tcagggcgcg ccagtc                                                       16

<210> SEQ ID NO 109
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 109
gtacgactgg cgcgccctga at                                                22
```

Δ 15 DESATURASES SUITABLE FOR ALTERING LEVELS OF POLYUNSATURATED FATTY ACIDS IN OLEAGINOUS PLANTS AND YEAST

This application claims the benefit of U.S. Provisional Application No. 60/519,191, filed Nov. 12, 2003.

FIELD OF THE INVENTION

This invention is in the field of biotechnology. More specifically, this invention pertains to the identification of nucleic acid fragments encoding Δ-15 fatty acid desaturase enzymes useful for disrupting or enhancing the production of polyunsaturated fatty acids in plants and organisms, including those microorganisms known as oleaginous yeast.

BACKGROUND OF THE INVENTION

It has long been recognized that certain polyunsaturated fatty acids, or PUFAs, are important biological components of healthy cells. For example, such PUFAs are recognized as:
"Essential" fatty acids that can not be synthesized de novo in mammals and instead must be obtained either in the diet or derived by further desaturation and elongation of linoleic acid (LA) or α-linolenic acid (ALA);
Constituents of plasma membranes of cells, where they may be found in such forms as phospholipids or triglycerides;
Necessary for proper development, particularly in the developing infant brain, and for tissue formation and repair; and,
Precursors to several biologically active eicosanoids of importance in mammals, including prostacyclins, eicosanoids, leukotrienes and prostaglandins.

In the 1970's, observations of Greenland Eskimos linked a low incidence of heart disease and a high intake of long-chain omega-3 PUFAs (Dyerberg, J. et al., *Amer. J. Clin Nutr.* 28:958-966 (1975); Dyerberg, J. et al., *Lancet* 2(8081):117-119 (Jul. 15, 1978)). More recent studies have confirmed the cardiovascular protective effects of omega-3 PUFAs (Shimokawa, H., *World Rev Nutr Diet,* 88:100-108 (2001); von Schacky, C., and Dyerberg, J., *World Rev Nutr Diet,* 88:90-99 (2001)). Further, it has been discovered that several disorders respond to treatment with omega-3 fatty acids, such as the rate of restenosis after angioplasty, symptoms of inflammation and rheumatoid arthritis, asthma, psoriasis and eczema. Gamma-linolenic acid (GLA, an omega-6 PUFA) has been shown to reduce increases in blood pressure associated with stress and to improve performance on arithmetic tests. GLA and dihomo-gamma-linolenic acid (DGLA, another omega-6 PUFA) have been shown to inhibit platelet aggregation, cause vasodilation, lower cholesterol levels and inhibit proliferation of vessel wall smooth muscle and fibrous tissue (Brenner et al., *Adv. Exp. Med. Biol.* 83: 85-101 (1976)). Administration of GLA or DGLA, alone or in combination with eicosapentaenoic acid (EPA, an omega-3 PUFA), has been shown to reduce or prevent gastrointestinal bleeding and other side effects caused by non-steroidal anti-inflammatory drugs (U.S. Pat. No. 4,666,701). Further, GLA and DGLA have been shown to prevent or treat endometriosis and premenstrual syndrome (U.S. Pat. No. 4,758,592) and to treat myalgic encephalomyelitis and chronic fatigue after viral infections (U.S. Pat. No. 5,116,871). Other evidence indicates that PUFAs may be involved in the regulation of calcium metabolism, suggesting that they may be useful in the treatment or prevention of osteoporosis and kidney or urinary tract stones. Finally, PUFAs can be used in the treatment of cancer and diabetes (U.S. Pat. No. 4,826,877; Horrobin et al., *Am. J. Clin. Nutr.* 57 (Suppl.): 732S-737S (1993)).

PUFAs are generally divided into two major classes (consisting of the omega-6 and the omega-3 fatty acids) that are derived by desaturation and elongation of the essential fatty acids, LA and ALA, respectively. Despite a variety of commercial sources of PUFAs from natural sources [e.g., seeds of evening primrose, borage and black currants; filamentous fungi (*Mortierella*), *Porphyridium* (red alga), fish oils and marine plankton (*Cyclotella, Nitzschia, Crypthecodinium*)], there are several disadvantages associated with these methods of production. First, natural sources such as fish and plants tend to have highly heterogeneous oil compositions. The oils obtained from these sources therefore can require extensive purification to separate or enrich one or more of the desired PUFAs. Natural sources are also subject to uncontrollable fluctuations in availability (e.g., due to weather, disease, or over-fishing in the case of fish stocks); and, crops that produce PUFAs often are not competitive economically with hybrid crops developed for food production. Large-scale fermentation of some organisms that naturally produce PUFAs (e.g., *Porphyridium, Mortierella*) can also be expensive and/or difficult to cultivate on a commercial scale.

As a result of the limitations described above, extensive work has been conducted toward: 1.) the development of recombinant sources of PUFAs that are easy to produce commercially; and 2.) modification of fatty acid biosynthetic pathways, to enable production of desired PUFAs. For example, advances in the isolation, cloning and manipulation of fatty acid desaturase and elongase genes from various organisms have been made over the last several years. Knowledge of these gene sequences offers the prospect of producing a desired fatty acid and/or fatty acid composition in novel host organisms that do not naturally produce PUFAs. The literature reports a number of examples in *Saccharomyces cerevisiae*, such as: Domergue, F., et al. (*Eur. J. Biochem.* 269:4105-4113 (2002)), wherein two desaturases from the marine diatom *Phaeodactylum tricornutum* were cloned into *S. cerevisiae*, leading to the production of EPA; Beaudoin F., et al. (*Proc. Natl. Acad. Sci. U.S.A.* 97(12):6421-6 (2000)), wherein the omega-3 and omega-6 PUFA biosynthetic pathways were reconstituted in *S. cerevisiae*, using genes from *Caenorhabditis elegans*; Dyer, J. M., et al. (*Appl. Env. Microbiol.,* 59:224-230 (2002)), wherein plant fatty acid desaturases (FAD2 and FAD3) were expressed in *S. cerevisiae*, leading to the production of ALA; and, U.S. Pat. No. 6,136,574 (Knutzon et al., Abbott Laboratories), wherein one desaturase from *Brassica napus* and two desaturases from the fungus *Mortierella alpina* were cloned into *S. cerevisiae*, leading to the production of LA, GLA, ALA and STA.

There remains a need, however, for an appropriate plant and/or microbial system in which these types of genes can be expressed to provide for economical production of commercial quantities of one or more PUFAs. Additionally, a need exists for oils enriched in specific PUFAs, notably EPA and DHA.

One class of microorganisms that has not been previously examined as a production platform for PUFAs are the oleaginous yeast. These organisms can accumulate oil up to 80% of their dry cell weight. The technology for growing oleaginous yeast with high oil content is well developed (for example, see EP 0 005 277B1; Ratledge, C., *Prog. Ind. Microbiol.* 16:119-206 (1982)), and may offer a cost advantage compared to commercial micro-algae fermentation for production of ω-3- or ω-6 PUFAs. Whole yeast cells may also represent a convenient way of encapsulating omega-3- or omega-6 PUFA-enriched oils for use in functional foods and animal feed supplements.

Despite the advantages noted above, most oleaginous yeast are naturally deficient in omega-6 PUFAs, since naturally produced PUFAs in these organisms are usually limited to 18:2 fatty acids. Thus, the problem to be solved is to develop an oleaginous yeast that accumulates oils enriched in omega-3 and/or omega-6 fatty acids. Toward this end, it is not only necessary to introduce the required desaturases and elongases that allow for the synthesis and accumulation of omega-3 and/or omega-6 fatty acids in oleaginous yeast, but also to increase the availability of the 18:3 substrate (i.e., ALA for ω-3 production). Generally, the availability of this substrate is controlled by the activity of Δ-15 desaturases that catalyze the conversion of LA to ALA.

There were a variety of known Δ-15 desaturases disclosed in the public literature, including those from photosynthetic organisms (e.g., plants) and *Caenorhabditis elegans* at the time that the instant invention was made. These desaturases are not known to be effective for altering fatty acid composition in oleaginous yeast and are not preferred for use in oleaginous yeast. Furthermore, heterologous expression of these desaturases in the non-oleaginous yeast *Saccharomyces cerevisiae* has resulted in production of less than 5% ALA (Reed, D. et al. *Plant Physiol.* 122:715-720 (2000); Meesapy-odsuk, D. et al. *Biochem.* 39:11948-11954 (2000); WO 2003/099216). Thus, there is need for the identification and isolation of genes encoding Δ-15 desaturases that are able to support production of high levels of 18:3 (ALA) and higher ratios of omega-3 to omega-6 fatty acids in oleaginous microorganisms (e.g., oleaginous yeast) for use in the production of PUFAs.

The instant invention concerns, inter alia, isolation of the gene encoding a Δ-15 desaturase from the fungus *Fusarium moniliforme* and demonstrating surprisingly efficient conversion of 18:2 (LA) to 18:3 (ALA) upon expression in an oleaginous yeast. Orthologs of this Δ-15 desaturase were identified in *Magnaporthe grisea, Fusarium graminearium, Aspergilius nidulans* and *Neurospora crassa*. Upon further experimental analysis of the *Fusarium moniliforme* and *Magnaporthe grisea* desaturases' activity, however, it was surprisingly shown that both Δ-15 desaturases also have Δ-1 2 desaturase activity (and thus the enzymes are characterized herein as having bifunctional Δ-12/Δ-15 desaturase activity).

In addition to the interest in oleaginous yeast as a production platform for PUFAs, there has also been interest in plants as an alternative production platform for PUFAs.

WO 02/26946, published Apr. 4, 2002, describes isolated nucleic acid fragments encoding FAD4, FAD5, FAD5-2 and FAD6 fatty acid desaturase family members which are expressed in LCPUFA-producing organisms, e.g., *Thraustochytrium, Pythium irregulare, Schizichytrium* and *Crypthecodinium*. It is indicated that constructs containing the desaturase genes can be used in any expression system including plants, animals, and microorganisms for the production of cells capable of producing LCPUFAs.

WO 02/26946, published Apr. 4, 2002, describes FAD4, FAD5, FAD5-2, and FAD6 fatty acid desaturase members and uses thereof to produce long chain polyunsaturated fatty acids.

WO 98/55625, published Dec. 19, 1998, describes the production of polyunsaturated fatty acids by expression of polyketide-like synthesis genes in plants.

WO 98/46764, published Oct. 22, 1998, describes compositions and methods for preparing long chain fatty acids in plants, plant parts and plant cells which utilize nucleic acid sequences and constructs encoding fatty acid desaturases, including Δ-5 desaturases, Δ-6 desaturases and Δ-12 desaturases.

U.S. Pat. No. 6,075,183, issued to Knutzon et al. on Jun. 13, 2000, describes methods and compositions for synthesis of long chain polyunsaturated fatty acids in plants.

U.S. Pat. No. 6,459,018, issued to Knutzon on Oct. 1, 2002, describes a method for producing stearidonic acid in plant seed utilizing a construct comprising a DNA sequence encoding a Δ-six desaturase.

Spychalla et al., *Proc. Natl. Acad. Sci. USA*, Vol. 94, 1142-1147 (February 1997), describes the isolation and characterization of a cDNA from *C. elegans* that, when expressed in *Arabidopsis*, encodes a fatty acid desaturase which can catalyze the introduction of an omega-3 double bond into a range of 18- and 20-carbon fatty acids.

SUMMARY OF THE INVENTION

The present invention provides a newly discovered fungal Δ15 desaturase enzyme and the nucleic acid sequences encoding the same. This enzyme, and a fungal ortholog identified herein, are unique in their ability to perform both Δ15 and Δ12 desaturation reactions. Additionally, the invention provides host cells expressing the present fungal Δ15 desaturase enzyme.

Accordingly the invention provides an isolated nucleic acid fragment encoding a fungal Δ15 desaturase enzyme, selected from the group consisting of:
  (a) an isolated nucleic acid fragment encoding the amino acid sequence as set forth in SEQ ID NO:2;
  (b) an isolated nucleic acid fragment that hybridizes with (a) under the following hybridization conditions: 0.1× SSC, 0.1% SDS, 65° C. and washed with 2×SSC, 0.1% SDS followed by 0.1×SSC, 0.1% SDS; or,
  an isolated nucleic acid fragment that is complementary to (a) or (b).

Alternatively the invention provides an isolated nucleic acid fragment comprising a first nucleotide sequence encoding a Δ15 desaturase enzyme of at least 402 amino acids that has at least 86% identity based on the Clustal method of alignment when compared to a polypeptide having the sequence as set forth in SEQ ED NO:2;
  or a second nucleotide sequence comprising the complement of the first nucleotide sequence.

Additionally the invention provides polypeptides encoded by the nucleic acids described herein as well as geneic chimera and transformed host comprising the same. Preferred host cells for use in the invention include, but are not limited to plants, algae, bacteria, yeast and fungi In another embodiment the invention provides a method for the production of α-linolenic acid comprising:
  a) providing a host cell comprising:
    (i) an isolated nucleic acid fragment encoding a protein having Δ15 desaturase activity that has at least 46.2% identity based on the Clustal method of alignment when compared to a polypeptide having the sequence as set forth in SEQ ID NO:2; and
    (ii) a source of linoleic acid;
  b) growing the host cell of step (a) under conditions wherein the nucleic acid fragment encoding a protein having Δ15 desaturase activity is expressed and the linoleic acid is converted to α-linolenic acid; and
  c) optionally recovering the α-linolenic acid of step (b).

Similarly the invention provides a method for the production of α-linolenic acid comprising:

a) providing a host cell comprising:
  (i) an isolated nucleic acid fragment encoding a protein having Δ15 desaturase activity that has at least 46.2% identity based on the Clustal method of alignment when compared to a polypeptide having the sequence as set forth in SEQ ID NO:2; and
  (ii) a source of oleic acid;
b) growing the host cell of step (a) under conditions wherein the nucleic acid fragment encoding a protein having Δ15 desaturase activity is expressed and the oleic acid is converted to α-linolenic acid; and
c) optionally recovering the α-linolenic acid of step (b).

Alternatively the invention provides a method for the production of ω-3 fatty acids in a host cell comprising:
a) providing a host cell comprising:
  (i) an isolated nucleic acid fragment encoding a protein having Δ15 desaturase activity that has at least 46.2% identity based on the Clustal method of alignment when compared to a polypeptide having the sequence as set forth in SEQ ID NO:2; and
  (ii) genes encoding a functional ω-3/ω-6 fatty acid biosynthetic pathway;
b) providing a source of desaturase substrate consisting of oleic acid;
c) growing the host cell of step (a) with the desaturase substrate of step (b) under conditions wherein ω-3 fatty acids are produced; and
d) optionally recovering the ω-3 fatty acids of step (c).

In an alternate embodiment the invention provides a method of increasing the ratio of ω-3 fatty acids to ω-6 fatty acids in a host cell producing ω-3 fatty acids to ω-6 fatty acids comprising:
a) providing a host cell producing ω-3 fatty acids and ω-6 fatty acids;
b) introducing into the host cell of (a) an isolated nucleic acid fragment encoding a protein having at least 46.2% identity based on the Clustal method of alignment when compared to a polypeptide having the sequence as set forth in SEQ ID NO:2, wherein the polypeptide binds both oleic acid and linoleic acid as an enzyme substrate, wherein the ratio of ω-3 fatty acids to ω-6 fatty acids are increased.

Additionally the invention provides microbial oils produced by the methods of the invention.

In another embodiment, the invention concerns a recombinant construct for altering the total fatty acid profile of mature seeds of an oilseed plant to produce an oil having an omega 3:omega 6 ratio greater than 0.4 said construct comprising an isolated nucleic acid fragment selected from the group consisting of:
  (a) an isolated nucleic acid fragment encoding all or part of the amino acid sequence as set forth in SEQ ID NO:2;
  (b) an isolated nucleic acid fragment that hybridizes with (a) when washed with: 0.1×SSC, 0.1% SDS, 65° C.;
  (c) an isolated nucleic acid fragment encoding an amino acid sequence having at least 46.2% sequence identity with the amino acid sequences set forth in SEQ ID NOs:2, 6, 10, 14, 18 based on the Clustal V method of alignment; or
  (d) an isolated nucleic acid fragment that is completely complementary to (a), (b), or (c)
  wherein said isolated nucleic acid fragment is operably linked to at least one regulatory sequence.

In a second embodiment, this invention concerns oilseed plants, plant cells, plant tissues or plant parts comprising in their genomes the recombinant construct of the invention.

In a third embodiment, this inventions also concerns seeds obtained from such plants, oil obtained from these seeds and by-products obtained from the processing of this oil.

In a fourth embodiment, this invention concerns use of the oil of the invention in food, animal feed or an industrial application and use of the by-products of the invention in food or animal feed.

In a fifth embodiment, this invention concerns a method for increasing the ratio of omega-3 fatty acids to omega-6 fatty acids in an oilseed plant comprising:
  a) transforming an oilseed plant cell of with the recombinant construct of the invention;
  b) regenerating an oilseed plant from the transformed plant cell of step (a);
  c) selecting those transformed plants having an increased ratio of omega-3 fatty acids to omega-6 fatty acid compared to the ratio of omega-3 fatty acids to omega-6 fatty acid in an untransformed plant.

In a sixth embodiment, this invention concerns oilseed plants made by this method, seeds obtained from such plants, oil obtained from these seeds, use of this oil in food or animal feed, by-products obtained from the processing of this oil and use of these by-products in food or animal feed.

In a seventh embodiment, this invention concerns a method for producing alpha-linolenic acid in seed of an oilseed plant wherein the alpha-linolenic acid content of the oil in the seed is at least 25% of the total fatty acid content of the seed oil, said method comprising:
  a) transforming an oilseed plant cell of with the recombinant construct of the invention;
  b) regenerating an oilseed plant from the transformed plant cell of step (a);
  c) selecting those transformed plants having at least 25% alpha-linolenic acid of the total fatty acid content of the seed oil.

In an eighth embodiment, this invention concerns oilseed plants made by this method, seeds obtained from such plants, oil obtained from these seeds, use of this oil in food or animal feed, by-products obtained from the processing of this oil and use of these by-products in food or animal feed.

In yet another embodiment, the invention concerns a recombinant construct for altering the total fatty acid profile of mature seeds of an oilseed plant to produce an oil having an omega 3 to omega 6 ratio greater than 2, wherein said oil has an eicosapentaenoic acid content greater than 2%, said construct comprising an isolated nucleic acid fragment selected from the group consisting of:
  (a) an isolated nucleic acid fragment encoding all or part of the amino acid sequence as set forth in SEQ ID NO:2;
  (b) an isolated nucleic acid fragment that hybridizes with (a) when washed with 0.1×SSC, 0.1% SDS, 65° C.;
  (c) an isolated nucleic acid fragment encoding an amino acid sequence having at least 46.2% sequence identity with the amino acid sequences set forth in SEQ ID NOs:2, 6, 10, 14, 18 based on the Clustal V method of alignment; or
  (d) an isolated nucleic acid fragment that is completely complementary to (a), (b), or (c)
  wherein said isolated nucleic acid fragment is operably linked to at least one regulatory sequence.

In a further embodiment, this invention concerns oilseed plants, plant cells, plant tissues, or plant parts comprising in their genomes the recombinant construct of the invention. The invention also concerns the seeds obtained from such plants, oil obtained from these seeds, use of this oil in food or animal feed, by-products obtained from the processing of this oil and use of these by-products in food or animal feed.

Additionally the invention provides microbial oils produced by the methods of the invention.

In another embodiment, the present invention concerns a method for producing eicosapentaenoic acid in seed of an oilseed plant to produce an oil having an omega 3 to omega 6 ratio greater than 2, wherein said oil has an eicosapentaenoic acid content greater than 2% of the total fatty acid content of the seed oil, said method comprising:

a) transforming an oilseed plant cell of with the recombinant construct of the present invention;

b) regenerating an oilseed plant from the transformed plant cell of step (a);

c) selecting those transformed plants having at least 2% eicosapentaenoic acid of the total fatty acid content of the seed oil.

In a further embodiment, this invention concerns oilseed plants, plant cells, plant tissues, or plant parts comprising in their genomes the recombinant construct of the invention. The invention also concerns the seeds obtained from such plants, oil obtained from these seeds, use of this oil in food or animal feed, by-products obtained from the processing of this oil and use of these by-products in food or animal feed.

Additionally the invention provides microbial oils produced by the methods of the invention.

Biological Deposits

The following plasmids have been deposited with the American Type Culture Collection (ATCC), 10801 University Boulevard, Manassas, Va. 20110-2209, and bears the following designation, accession number and date of deposit.

| Plasmid | Accession Number | Date of Deposit |
|---------|------------------|-----------------|
| pKR274  | ATCC PTA-4988    | Jan. 30, 2003   |
| pKKE2   | ATCC PTA-4987    | Jan. 30, 2003   |
| pKR578  | ATCC PTA-6280    | Nov. 4, 2004    |
| pKR585  | ATCC PTA-6279    | Nov. 3, 2004    |

BRIEF DESCRIPTION OF THE DRAWINGS AND SEQUENCE DESCRIPTIONS

FIG. 5 shows a pairwise comparison (% Identity) between and among proteins from different filamentous fungi having homology to the *Yarrowia lipolytica* Δ12 desaturase enzyme using a ClustalW analysis (Megalign program of DNASTAR sofware).

Figure 1:
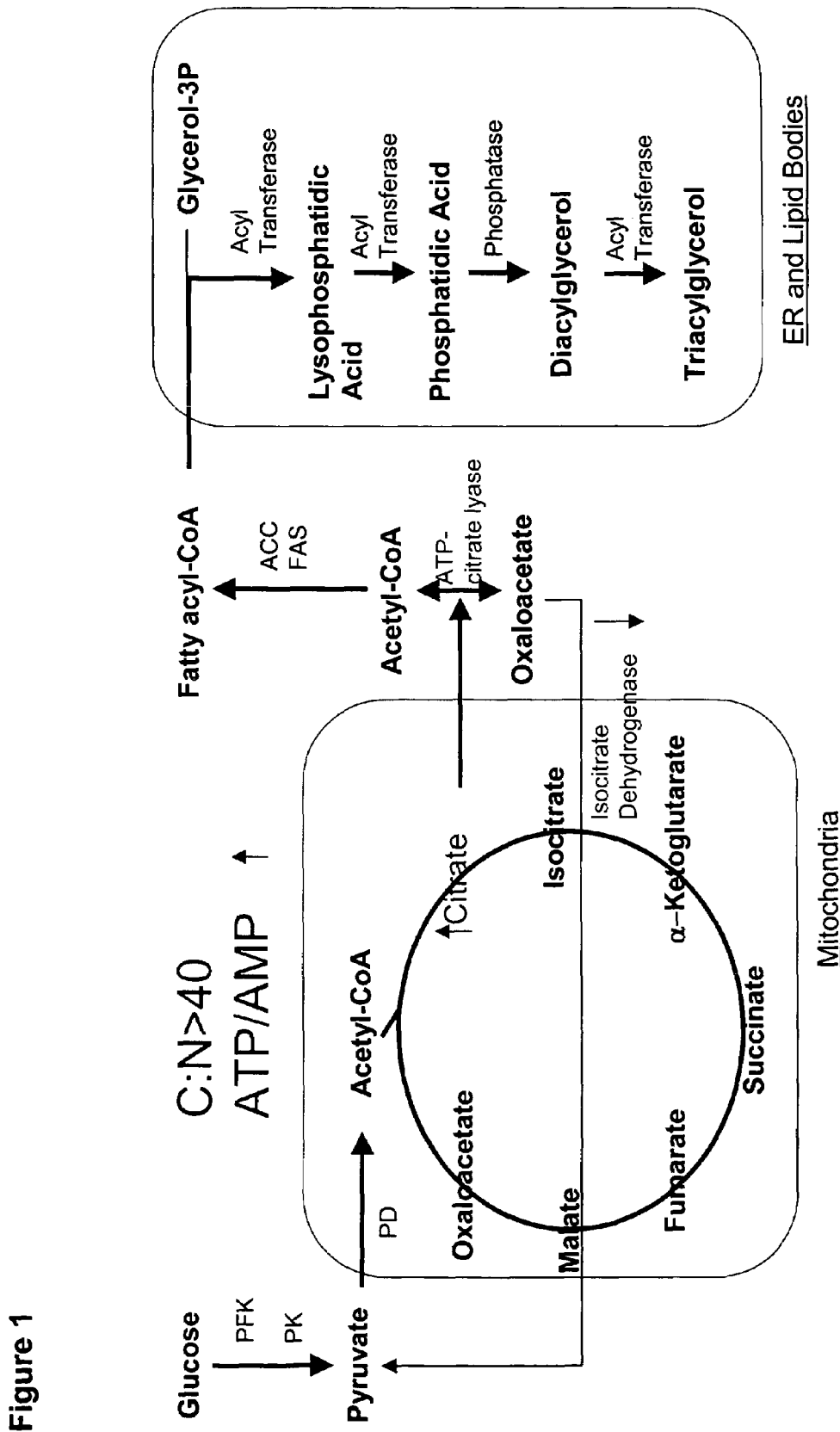
FIG. 1 shows a schematic illustration of the biochemical mechanism for lipid accumulation in oleaginous yeast.

The invention can be more fully understood from the following detailed description and the accompanying sequence descriptions, which form a part of this application.

The following sequences comply with 37 C.F.R. §1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NOs:1-20, 54 and 55 are ORFs encoding genes or proteins as identified in Table 1.

TABLE 1

Summary Of Desaturase Gene And Protein SEQ ID Numbers

| Description | ORF Nucleic acid SEQ ID NO. | Protein SEQ ID NO. |
|-------------|----------------------------|--------------------|
| *Fusarium moniliforme* sub-family 1 desaturase (Δ15/Δ12 desaturase) | 1 (1209 bp) | 2 (402 AA) |
| *Fusarium moniliforme* sub-family 2 desaturase | 3 (1434 bp) | 4 (477 AA) |
| *Aspergillus nidulans* sub-family 1 desaturase (Δ15 desaturase) | 5 (1206 bp) | 6 (401 AA) |
| *Aspergillus nidulans* sub-family 2 desaturase | 7 (1416 bp) | 8 (471 AA) |
| *Magnaporthe grisea* sub-family 1 desaturase (Δ15 desaturase) | 9 (1185 bp) | 10 (394 AA) |
| *Magnaporthe grisea* sub-family 2 desaturase | 11 (1656 bp) | 12 (551 AA) |
| *Neurospora crassa* sub-family 1 desaturase (Δ15 desaturase) | 13 (1290 bp) | 14 (429 AA) |
| *Neurospora crassa* sub-family 2 desaturase | 15 (1446 bp) | 16 (481 AA) |
| *Fusarium graminearum* sub-family 1 desaturase (Δ15 desaturase) | 17 (1212 bp) | 18 (403 AA) |
| *Fusarium graminearum* sub-family 2 desaturase | 19 (1371 bp) | 20 (456 AA) |
| *Yarrowia lipolytica* Δ12 desaturase | 54 (1936 bp) | 55 (419 AA) |

SEQ ID NOs:21 and 22 are primers TEF 5' and TEF 3', respectively, used to isolate the TEF promoter.

SEQ ID NOs:23 and 24 are primers XPR 5' and XPR 3', respectively, used to isolate the XPR2 transcriptional terminator.

SEQ ID NOs:25-36 correspond to primers YL5, YL6, YL9, YL10, YL7, YL8, YL3, YL4, YL1, YL2, YL61 and YL62, respectively, used for plasmid construction.

SEQ ID NO:37 corresponds to a 971 bp fragment designated as "GPDPro", and identified as the putative glyceraldehyde-3-phosphate dehydrogenase promoter in *Yarrowia lipolytica*.

SEQ ID NOs:38 and 39 are primers YL211 and YL212, respectively, used for amplifying a DNA fragment including the glyceraldehyde-3-phosphate-dehydrogenase (GPD) promoter of *Yarrowia lipolytica*.

SEQ ID NOs:40 and 41 are primers GPD sense and GPDantisense, respectively, used for re-amplifying the GPD promoter.

SEQ ID NOs:42 and 44 are the degenerate primers identified as P73 and P76, respectively, used for the isolation of a *Yarrowia lipolytica* Δ12 desaturase gene.

SEQ ID NOs:43 and 45 are the amino acid consensus sequences that correspond to the degenerate primers P73 and P76, respectively.

SEQ ID NOs:46-49 correspond to primers P99, P100, P101 and P102, respectively, used for targeted disruption of the native *Y. lipolytica* Δ12 desaturase gene.

SEQ ID NOs:50-53 correspond to primers P119, P120, P121 and P122, respectively, used to screen for targeted integration of the disrupted *Y. lipolytica* Δ12 desaturase gene.

SEQ ID NOs:56 and 57 are primers P192 and P193, respectively, used to amplify the *Fusarium moniliforme* Δ15 desaturase ("Fm1") coding region.

SEQ ID NO:58 corresponds to the codon-optimized translation initiation site for genes optimally expressed in *Yarrowia* sp.

SEQ ID NOs:59-64 are primers P186, P187, P188, P189, P190 and P191, respectively, used to amplify the *Magnaporthe grisea* Δ15 desaturase ("Mg1").

SEQ ID NOs:65-72 are primers PFg1UP1, PFg1LP1, PFg1UP2, PFg1LP2, PFg1UP3, PFg1LP3, PFg1UP4 and PFg1LP4, respectively, used to amplify the *Fusarium graminearium* Δ15 desaturase ("Fg1").

SEQ ID NO:73 is the multiple restriction enzyme site sequence introduced upstream of the Kti promoter as described in Example 6.

SEQ ID NO:74 sets forth the sequence of the soy albumin transcription terminator with restriction enzyme sites as described in Example 6.

SEQ ID NO:75 is the primer oSalb-12 used for amplification of the albumin transcription terminator.

SEQ ID NO:76 is primer oSalb-13 used for amplification of the albumin transcription terminator.

SEQ ID NO:77 is the multiple restriction enzyme site sequence introduced in front of the beta-conglycinin promoter as described in Example 6.

SEQ ID NO:78 is the complete sequence of plasmid pKR578 described in Example 11 and FIG. 5.

SEQ. ID. NO:79 sets forth oligonucleotide primer GSP1 used to amplify the soybean annexin promoter.

SEQ. ID. NO:80 sets forth oligonucleotide primer GSP2 used to amplify the soybean annexin promoter.

SEQ. ID. NO:81 sets forth the sequence of the annexin promoter.

SEQ. ID. NO:82 sets forth oligonucleotide primer GSP3 used to amplify the soybean BD30 promoter.

SEQ ID NO:83 sets forth oligonucleotide primer GSP4 used to amplify the soybean BD30 promoter.

SEQ. ID. NO:84 sets forth the sequence of the soybean BD30 promoter.

SEQ. ID. NO:85 sets forth the sequence of the soybean β-conglycinin β-subunit promoter.

SEQ. ID. NO:86 sets forth oligonucleotide primer β-con oligo Bam used to amplify the promoter for soybean β-conglycinin β-subunit.

SEQ. ID. NO:87 sets forth oligonucleotide primer β-con oligo Not used to amplify the promoter for soybean β-conglycinin β-subunit.

SEQ. ID. NO:88 sets forth the sequence of the soybean glycinin Gly-1 promoter.

SEQ. ID. NO:89 sets forth oligonucleotide primer glyoligo Bam used to amplify the Gly-1 promoter.

SEQ. ID. NO:90 sets forth oligonucleotide primer glyoligo Not used to amplify the Gly-1 promoter.

SEQ ID NO:91 is primer oKTi5 used for amplification of the Kti/NotI/Kti 3' cassette.

SEQ ID NO:92 is primer oKTi6-used for amplification of the Kti/NotI/Kti 3' cassette.

SEQ ID NO:93 is primer oSBD30-1 used for amplification of the soybean BD30 3' transcription terminator.

SEQ ID NO:94 is primer oSBD30-2 used for amplification of the soybean BD30 3' transcription terminator.

Figure 6:
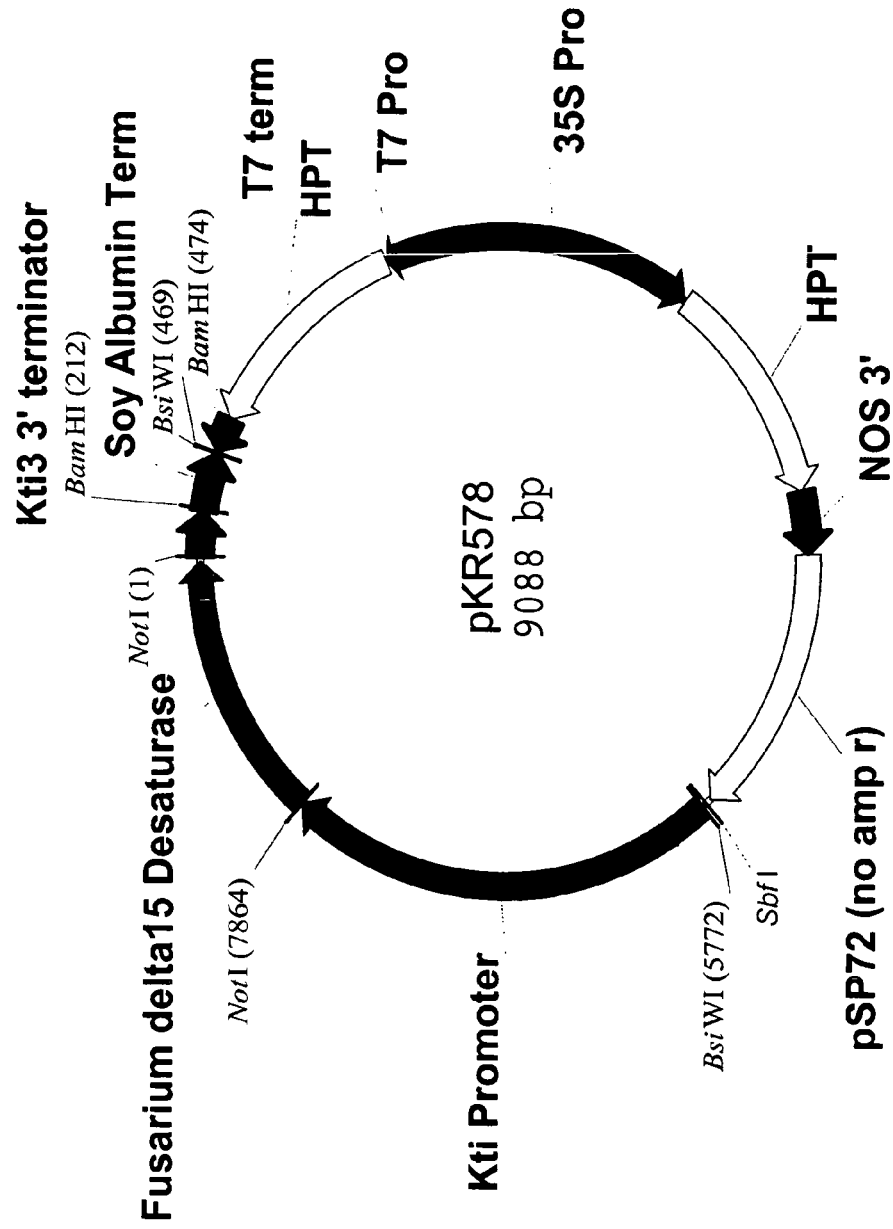
FIG. 6 is a schematic depiction of plasmid pKR578 (see Example 11).

SEQ ID NO:95 is the complete sequence of plasmid pKR585 described in Example 13 and FIG. 6.

SEQ ID NO:96 is primer oCGR5-1 used for amplification of the *M. alpina* delta-6 desaturase.

SEQ ID NO:97 is primer oCGR5-2 used for amplification of the *M. alpina* delta-6 desaturase.

SEQ ID NO:98 is primer oSGly-1 used for amplification of the glycinin Gy1 promoter.

SEQ ID NO:99 is primer oSGly-2 used for amplification of the glycinin Gy1 promoter, SEQ ID NO:100 is primer LegPro5' used for amplification of the legA2 promoter sequence.

SEQ ID NO:101 is primer LegPro3' used for amplification of the legA2 promoter sequence.

SEQ ID NO:102 is primer LegTerm5' used for amplification of the leg2A transcription terminator.

SEQ ID NO:103 is primer LegTerm3' used for amplification of the leg2A transcription terminator.

SEQ ID NO:104 is primer CGR4forward used for the amplification of the *M. alpina* desaturase.

SEQ ID NO:105 is primer CGR4reverse used for amplification of the *M. alpina* desaturase.

SEQ ID NO:106 is the forward primer, RPB2forward, used for amplification of the *Mortierella alpine* elongase.

SEQ ID NO:107 is the reverse primer, RPB2reverse, used for amplification of the *Mortierella alpine* elongase.

SEQ ID NO:108 is primer Asc5 used to form the AscI liker.

SEQ ID NO:109 is primer Asc3 used to form the AscI liker.

DETAILED DESCRIPTION OF THE INVENTION

All patents, patent applications, and publications cited are incorporated herein by reference in their entirety.

This invention concerns the isolation and confirmation of the identity of a *Fusarium moniliforme* gene and a *Magnaporthe grisea* gene encoding a Δ15 desaturase and identified their orthologs in other fungi. Additionally, methods and compositions are provided which permit modification of the long-chain polyunsaturated fatty acid (PUFA) content and composition of plants, in particular, oilseed plants and oleaginous organisms, including oleaginous yeast (e.g., *Yarrowia lipolytica*) and plants (e.g., soybean, corn and sunflower). The Δ15 desaturase enzymes of the present invention are additionally distinguished by their ability to act upon two enzymatic substrates, oleic acid and linoleic acid.

The invention relates to novel Δ15 desaturase enzymes and genes encoding the same that may be used for the manipulation of biochemical pathways for the production of healthful PUFAs. Thus, the subject invention finds many applications. PUFAs, or derivatives thereof, made by the methodology disclosed herein can be used as dietary substitutes, or supplements, particularly infant formulas, for patients undergoing intravenous feeding or for preventing or treating malnutrition. Alternatively, the purified PUFAs (or derivatives thereof) may be incorporated into cooking oils, fats or margarines formulated so that in normal use the recipient would receive the desired amount for dietary supplementation. The PUFAs may also be incorporated into infant formulas, nutritional supplements or other food products and may find use as anti-inflammatory or cholesterol lowering agents. Optionally, the compositions may be used for pharmaceutical use (human or veterinary). In this case, the PUFAs are generally administered orally but can be administered by any route by which they may be successfully absorbed, e.g., parenterally (e.g., subcutaneously, intramuscularly or intravenously), rectally, vaginally or topically (e.g., as a skin ointment or lotion).

Supplementation of humans or animals with PUFAs produced by recombinant means can result in increased levels of the added PUFAs, as well as their metabolic derivatives. For example, treatment with arachidonic acid (ARA) can result not only in increased levels of ARA, but also downstream products of ARA such as prostaglandins. Complex regulatory mechanisms can make it desirable to combine various PUFAs, or add different conjugates of PUFAs, in order to prevent, control or overcome such mechanisms to achieve the desired levels of specific PUFAs in an individual.

In the context of this disclosure, a number of terms shall be utilized.

"Open reading frame" is abbreviated ORF.

"Polymerase chain reaction" is abbreviated PCR.

"American Type Culture Collection" is abbreviated ATCC.

"Polyunsaturated fatty acid(s)" is abbreviated PUFA(s).

The term "*Fusarium moniliforme*" is synonymous with *Fusarium verticilloides*.

A "food analog" is a food-like product manufactured to resemble its food counterpart, whether meat, cheese, milk or the like, and is intended to have the appearance, taste, and texture of its counterpart. Thus, the term "food" as used herein also encompasses food analogs.

"Aquaculture feed" refers to feed used in aquafarming which concerns the propagation, cultivation or farming of aquatic organisms, animals and/or plants in fresh or marine waters. The term "animal feed" as used herein also encompasses aquaculture feed.

The term "fatty acids" refers to long-chain aliphatic acids (alkanoic acids) of varying chain length, from about $C_{12}$ to $C_{22}$ (although both longer and shorter chain-length acids are known). The predominant chain lengths are between $C_{16}$ and $C_{22}$. The structure of a fatty acid is represented by a simple notation system of "X:Y", where X is the total number of C atoms in the particular fatty acid and Y is the number of double bonds.

Generally, fatty acids are classified as saturated or unsaturated. The term "saturated fatty acids" refers to those fatty acids that have no "double bonds" between their carbon backbone. In contrast, "unsaturated fatty acids" have "double bonds" along their carbon backbones (which are most commonly in the cis-configuration). "Monounsaturated fatty acids" have only one "double bond" along the carbon backbone (e.g., usually between the $9^{th}$ and $10^{th}$ carbon atom as for palmitoleic acid (16:1) and oleic acid (18:1)), while "polyunsaturated fatty acids" (or "PUFAs") have at least two double bonds along the carbon backbone (e.g., between the $9^{th}$ and $10^{th}$, and $12^{th}$ and $13^{th}$ carbon atoms for linoleic acid (18:2); and between the $9^{th}$ and $10^{th}$, $12^{th}$ and $13^{th}$, and $15^{th}$ and $16^{th}$ for α-linolenic acid (18:3)).

"PUFAs" can be classified into two major families (depending on the position (n) of the first double bond nearest the methyl end of the fatty acid carbon chain). Thus, the "omega-6 fatty acids" (ω-6 or n-6) have the first unsaturated double bond six carbon atoms from the omega (methyl) end of the molecule and additionally have a total of two or more double bonds, with each subsequent unsaturation occurring 3 additional carbon atoms toward the carboxyl end of the molecule. In contrast, the "omega-3 fatty acids" (ω-3 or n-3) have the first unsaturated double bond three carbon atoms away from the omega end of the molecule and additionally have a total of three or more double bonds, with each subsequent unsaturation occurring 3 additional carbon atoms toward the carboxyl end of the molecule.

For the purposes of the present disclosure, the omega-reference system will be used to indicate the number of carbons, the number of double bonds and the position of the double bond closest to the omega carbon, counting from the omega carbon (which is numbered 1 for this purpose). This nomenclature is shown below in Table 2, in the column titled "Shorthand Notation". The remainder of the Table summarizes the common names of ω-3 and ω-6 fatty acids, the abbreviations that will be used throughout the specification, and each compound's chemical name.

TABLE 2

Nomenclature Of Polyunsaturated Fatty Acids

| Common Name | Abbreviation | Chemical Name | Shorthand Notation |
|---|---|---|---|
| Linoleic | LA | cis-9,12-octadecadienoic | 18:2 ω-6 |
| γLinolenic | GLA | cis-6, 9, 12-octadecatrienoic | 18:3 ω-6 |
| Eicosadienoic | EDA | cis-11, 14-eicosadienoic | 20:2 ω-6 |
| Dihomo-γ-Linolenic | DGLA | cis-8, 11, 14-eicosatrienoic | 20:3 ω-6 |
| Arachidonic | ARA | cis-5, 8, 11, 14-eicosatetraenoic | 20:4 ω-6 |
| αLinolenic | ALA | cis-9, 12, 15-octadecatrienoic | 18:3 ω-3 |
| Stearidonic | STA | cis-6, 9, 12, 15-octadecatetraenoic | 18:4 ω-3 |
| Eicosatrienoic | ETrA | cis-11, 14, 17-eicosatrienoic | 20:3 ω-3 |
| Eicosa-tetraenoic | ETA | cis-8, 11, 14, 17-eicosatetraenoic | 20:4 ω-3 |
| Eicosa-pentaenoic | EPA | cis-5, 8, 11, 14, 17-eicosapentaenoic | 20:5 ω-3 |
| Docosa-pentaenoic | DPA | cis-7, 10, 13, 16, 19-docosapentaenoic | 22:5 ω-3 |
| Docosa-hexaenoic | DHA | cis-4, 7, 10, 13, 16, 19-docosahexaenoic | 22:6 ω-3 |

Specifically, an omega-3 fatty acid is hereby defined as being from the following list of fatty acids where numbers in brackets indicate the position of double bonds from the carboxy-terminus of the fatty acid: alpha-linolenic acid [ALA; 18:3(9,12,15)], stearidonic acid [STA; 18:4(6,9,12,15)], eicosatetraenoic acid [ETA; 20:4(8,11,14,17)], eicosapentaenoic acid [EPA; 20:5(5,8,11,14,17)], docosapentaenoic acid [DPA; 22:5(7,10,13,16,19)] and docosahexaenoic acid [DHA; 22:6(4,7,10,13,16,19)].

Similarly, an omega-6 fatty acid is hereby defined as being from the following list of fatty acids where numbers in brackets indicate the position of double bonds from the carboxy-terminus of the fatty acid: linoleic acid [LA; 18:2(9,12)], gamma-linolenic acid [GLA; 18:3(6,9,12)], dihomo-gamma-linolenic acid [HGLA or DGLA; 20:3(8,11,14)], arachidonic acid [ARA; 20:4(5,8,11,14)] and docosatetraenoic acid [DTA; 22:4(7,10,13,16)].

The term "concentration" as applied to the concentratin of any individual fatty acid is hereby given to mean the amount of the particular fatty acid divided by the total amount of all of the fatty acids in a sample. The concentration of omega-3 fatty acids is defined as the amount of all omega-3 fatty acids (as defined above) divided by the total amount of all of the fatty acids in a sample. The concentration of omega-6 fatty acids is defined as the amount of all omega-6 fatty acids (as defined above) divided by the total amount of all of the fatty acids in a sample. The fatty acid concentration is typically expressed as a weight percent (wt. %-mass of individual fatty acid divided by mass of all fatty acids time 100%) or mole percent (mol %-mols of individual fatty acid divided by total mols of fatty acids times 100%).

The term "ratio of omega-3 to omega-6 fatty acids" or "omega-3 to omega-6 ratio" (n-3/n-6) is hereby defined as the concentration of omega-3 fatty acids divided by the concentration of omega-6 fatty acids (wt. % omega-3/wt. % omega-6 or mol % omega-3/mol % omega-6).

The term "essential fatty acid" refers to a particular PUFA that an individual must ingest in order to survive, being unable to synthesize the particular essential fatty acid de novo. Linoleic (18:2, ω-6) and linoleic (18:3, ω-3) fatty acids are "essential fatty acids", since humans cannot synthesize them and have to obtain them in their diet.

The term "fat" refers to a lipid substance that is solid at 25° C. and usually saturated.

The term "oil" refers to a lipid substance that is liquid at 25° C. and usually polyunsaturated. PUFAs are found in the oils of some algae, oleaginous yeast and filamentous fungi. "Microbial oils" or "single cell oils" are those oils naturally produced by microorganisms during their lifespan. Such oils can contain long-chain PUFAs.

The term "PUFA biosynthetic pathway enzyme" refers to any of the following enzymes (and genes which encode said enzymes) associated with the biosynthesis of a PUFA, including: a Δ4 desaturase, a Δ5 desaturase, a Δ6 desaturase, a Δ12 desaturase, a Δ15 desaturase, a Δ17 desaturase, a Δ9 desaturase, a Δ8 desaturase and/or an elongase(s).

Figure 2:
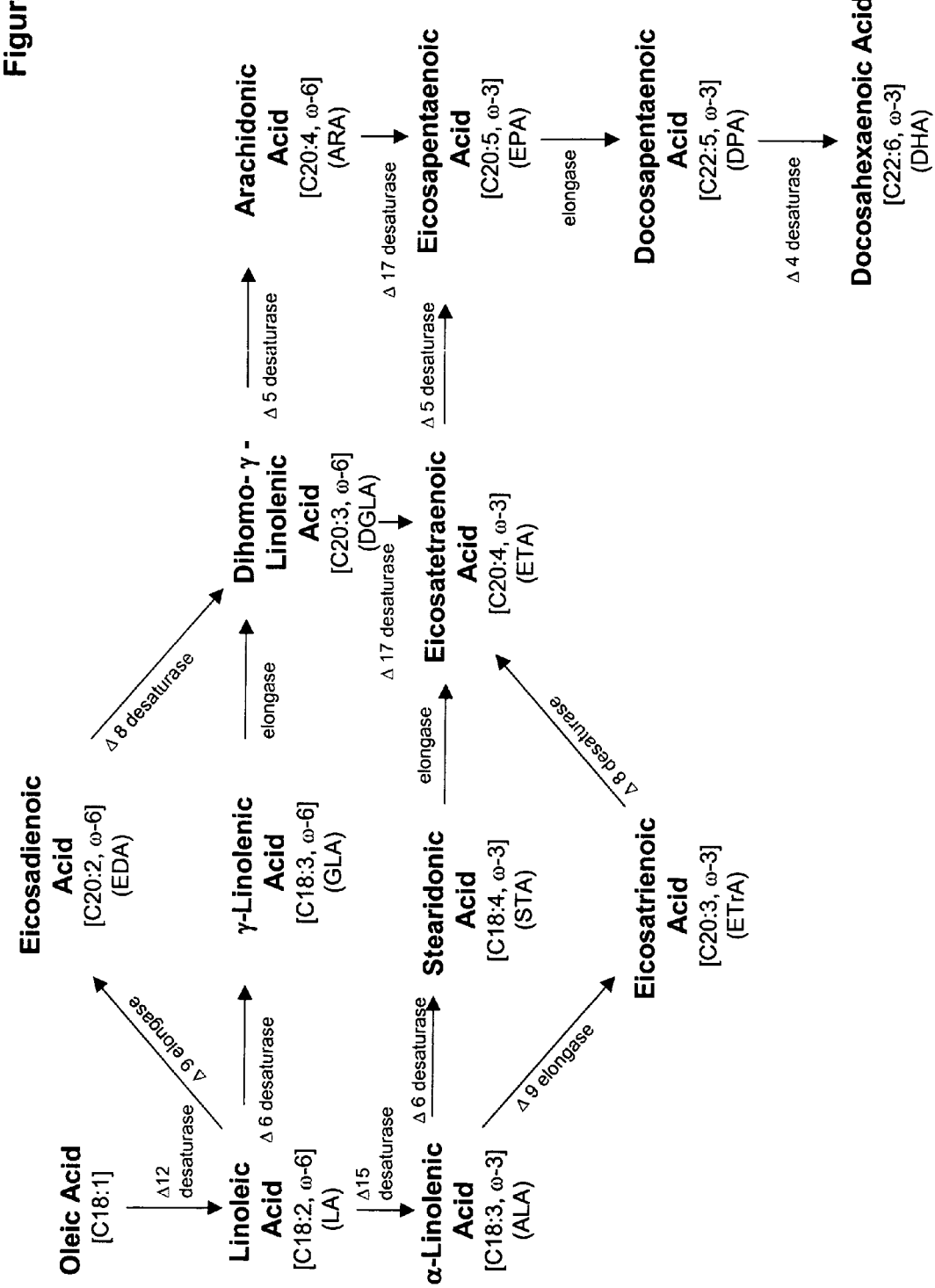
FIG. 2 illustrates the omega-3 and omega-6 fatty acid biosynthetic pathways.

The term "ω-3/ω-6 fatty acid biosynthetic pathway" refers to a set of genes which, when expressed under the appropriate conditions encode enzymes that catalyze the production of either or both ω-3 and ω-6 fatty acids. Typically the genes involved in the ω-3/ω-6 fatty acid biosynthetic pathway encode some or all of the following enzymes: Δ12 desaturase, Δ6 desaturase, elongase, Δ5 desaturase, Δ17 desaturase, Δ15 desaturase, Δ9 desaturase, Δ8 desaturase and Δ4 desaturase. A representative pathway is illustrated in FIG. 2, providing for the conversion of oleic acid through various intermediates to DHA, which demonstrates how both ω-3 and ω-6 fatty acids may be produced from a common source. The pathway is naturally divided into two portions where one portion will generate ω-3 fatty acids and the other portion, only ω-6 fatty acids. That portion that only generates ω-3 fatty acids will be referred to herein as the ω-3 fatty acid biosynthetic pathway, whereas that portion that generates only ω-6 fatty acids will be referred to herein as the ω-6 fatty acid biosynthetic pathway.

In humans there is evidence showing a lowering effect of ω-3 fatty acids on blood triacylglycerol levels. Other evidence supports a protective role against suffering a fatal heart attack. Both linoleic and α-linolenic acids are precursors for the synthesis of the eicosonoids derived from their longer chain metabolites. During synthesis these metabolites compete for the same enzymes. Those derived from α-linolenic acid (ω-3) tend to have less potent inflammatory and immunological effects than those derived from linoleic acid (ω-6). Alpha-linolenic acid also gives rise to docosahexaenoic acid (DHA), a major constituent of the human brain and retina. The richest sources of alpha-linolenic acid are some seed oils, such as linseed oil, rapeseed oil, soya oil and some nuts, particularly walnuts. The very long chain ω-3 fatty acids DHA and eicosapentaenoic acid (EPA), which can be made in the body from alpha-linolenic acid, are provided in fish oils and the flesh of oil-rich fish (not tinned tuna). Oils from flax, such as linseed oil that is rich in α-linolenic acid, also have industrial applications as "drying oils" for use in varnishes and paints.

The term "functional" as used herein in context with the ω-3/ω-6 fatty acid biosynthetic pathway means that some (or all on the genes in the pathway express active enzymes. It should be understood that "ω-3/ω-6 fatty acid biosynthetic pathway" or "functional ω-3/ω-6 fatty acid biosynthetic pathway" does not imply that all the genes listed in the above paragraph are required, as a number of fatty acid products will only require the expression of a subset of the genes of this pathway.

The term "desaturase" refers to a polypeptide that can desaturate, i.e., introduce a double bond, in one or more fatty acids to produce a mono- or polyunsaturated fatty acid or precursor which is of interest. Despite use of the omega-reference system throughout the specification in reference to specific fatty acids, it is more convenient to indicate the activity of a desaturase by counting from the carboxyl end of the substrate using the A-system. Of particular interest herein are Δ15 desaturases that desaturate a fatty acid between the $15^{th}$ and $16^{th}$ carbon atoms numbered from the carboxyl-terminal end of the molecule and that catalyze the conversion of LA to ALA. Other desaturases relevant to the present disclosure include: Δ12 desaturases that catalyze the conversion of oleic acid to LA; Δ17 desaturases that catalyze the conversion of DGLA to ETA and/or ARA to EPA; Δ6 desaturases that catalyze the conversion of LA to GLA and/or ALA to STA; Δ5 desaturases that catalyze the conversion of DGLA to ARA and/or ETA to EPA; Δ4 desaturases that catalyze the conversion of DPA to DHA; Δ8 desaturases that catalyze the conversion of EDA to DGLA and/or ETrA to ETA; and Δ9 desaturases that catalyze the conversion of palmitate to palmitoleic acid (16:1) and/or stearate to oleic acid (18:1). In the art, Δ15 and Δ17 desaturases are also occassionally referred to as "omega-3 desaturases", "w-3 desaturases", and/or "ω-3 desaturases". Some desaturases have activities on two or more substrates (e.g., the substrates of the *Saprolegnia diclina* Δ17 desaturase include ARA and DGLA, those of the *Caenorhabditis elegans* ω-3 desaturase include LA and GLA, and those of the *Fusarium moniliforme* Δ-15 desaturase described herein include LA, GLA and DGLA)

The term "bifunctional" as it refers to Δ15 desaturases of the invention means that the polypeptide has the ability to use both oleic acid and linoleic acid as an enzymatic substrate. By "enzymatic substrate" it is meant that the polypeptide binds the substrate at an active site and acts upon it in a catalytic manner.

The term "proteins having homology to the *Yarrowia lipolytica* Δ-12 desaturase" refers to the proteins identified herein as SEQ ID NOs:2, 4, 6, 8, 10, 12, 14, 16, 18 and 20, and that have homology to the *Y. lipolytica* desaturase identified herein as SEQ ID NO:55 (characterized in co-pending U.S. patent application Ser. No. 10/840,325, herein incorporated by reference in its entirety). Phylogenetic analysis determined that these proteins (i.e., SEQ ID NOs:2, 4, 6, 8, 10, 12, 14, 16, 18 and 20) clustered into two distinct sub-families, referred to herein as "Sub-family 1" and "Sub-family 2". Specifically, the Sub-family 1 proteins (i.e., SEQ ID NOs:2, 6, 10, 14 and 18) appear to encode Δ-15 desaturases as characterized herein. In contrast, the Sub-family 2 proteins encode proteins with Δ-12 desaturase activity (i.e., SEQ ID NOs:4, 8, 12, 16 and 20; see co-pending U.S. Provisional Application 60/570679, herein incorporated by reference in its entirety).

The terms "conversion efficiency" and "percent substrate conversion" refer to the efficiency by which a particular enzyme (e.g., a desaturase or elongase) can convert substrate to product. The conversion efficiency is measured according to the following formula: ([product]/[substrate+product])*100, where 'product' includes the immediate product and all products in the pathway derived from it. In the present Application, it is desirable to identify those Δ-15 desaturases characterized by a high percent substrate conversion (([18:3]/[18: 2+18:3])*100) when expressed in eukaryotic organisms, such as oleaginous yeast hosts; thus, for example, a conversion efficiency to ALA of at least about 50% is useful, a conversion efficiency to ALA of at least about 80% is preferred, while a conversion efficiency to ALA of at least about 90% is particularly suitable, and a conversion efficiency to ALA of at least about 95% is most preferred.

The term "elongase" refers to a polypeptide that can elongate a fatty acid carbon chain to produce an acid that is 2 carbons longer than the fatty acid substrate that the elongase acts upon. This process of elongation occurs in a multi-step mechanism in association with fatty acid synthase, whereby CoA is the acyl carrier (Lassner et al., *The Plant Cell* 8:281-292 (1996)). Briefly, malonyl-CoA is condensed with a long-chain acyl-CoA to yield $CO_2$ and a β-ketoacyl-CoA (where the acyl moiety has been elongated by two carbon atoms). Subsequent reactions include reduction to β-hydroxyacyl-CoA, dehydration to an enoyl-CoA, and a second reduction to yield the elongated acyl-CoA. Examples of reactions catalyzed by elongases are the conversion of GLA to DGLA, STA to ETA, and EPA to DPA. Accordingly, elongases can have different specificities. For example, a $C_{16/18}$ elongase will prefer a $C_{16}$ substrate, a $C_{18/20}$ elongase will prefer a $C_{18}$ substrate and a $C_{20/22}$ elongase will prefer a $C_{20}$ substrate. In like manner, a Δ-9 elongase is able to catalyze the conversion of LA and ALA to EDA and ETrA, respectively.

The term "oleaginous" refers to those organisms that tend to store their energy source in the form of lipid (Weete, In: Fungal Lipid Biochemistry, $2^{nd}$ ed., Plenum, 1980). These include oilseed plants (e.g., soybean, corn, safflower, sunflower, canola, rapeseed, flax, maize and primrose) and microorganisms (e.g., *Thraustochytrium* sp., *Schizochytrium* sp., *Mortierella* sp. and certain oleaginous yeast).

The term "oleaginous yeast" refers to those microorganisms classified as yeasts that can make oil. Generally, the cellular oil or triacylglycerol content of oleaginous microorganisms follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.* 57:419-25 (1991)). It is not uncommon for oleaginous microorganisms to accumulate in excess of about 25% of their dry cell weight as oil. Examples of oleaginous yeast include, but are no means limited to, the following genera: *Yarrowia, Candida, Rhodotorula, Rhodosporidium, Cryptococcus, Trichosporon* and *Lipomyces*.

The term "fermentable carbon substrate" means a carbon source that a microorganism will metabolize to derive energy. Typical carbon substrates of the invention include, but are not limited to: monosaccharides, oligosaccharides, polysaccharides, alkanes, fatty acids, esters of fatty acids, monoglycerides, carbon dioxide, methanol, formaldehyde, formate and carbon-containing amines.

The term "codon-optimized" as it refers to genes or coding regions of nucleic acid fragments for transformation of various hosts, refers to the alteration of codons in the gene or coding regions of the nucleic acid fragments to reflect the typical codon usage of the host organism without altering the polypeptide for which the DNA codes.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA. The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of chimeric genes to produce the desired phenotype in a transformed plant. Chimeric genes can be designed for use in suppression by linking a nucleic acid fragment or subfragment thereof, whether or not it encodes an active enzyme, in the sense or antisense orientation relative to a plant promoter sequence.

A nucleic acid fragment is "hybridizable" to another nucleic acid fragment, such as a cDNA, genomic DNA, or RNA molecule, when a single-stranded form of the nucleic acid fragment can anneal to the other nucleic acid fragment under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, $2^{nd}$ ed., Cold Spring Harbor Laboratory: Cold Spring Harbor, N.Y. (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washed with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art.

The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least about 30 nucleotides. Furthermore, the skilled artisan will recognize that the temperature and wash solution salt concentration may be adjusted as necessary according to factors such as length of the probe.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.* 215:403-410 (1993)). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches the complete amino acid and nucleotide sequence encoding particular fungal proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable of hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing, as well as those substantially similar nucleic acid sequences.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data. Part I* (Griffin, A. M., and Griffin, H. G., Eds.) Humania: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences is performed using the Clustal method of alignment (Higgins and Sharp, *CABIOS.* 5:151153 (1989)) with default parameters (GAP PENALTY=10, GAP LENGTH PENALTY=10), unless otherwise specified. Default parameters for pairwise alignments using the Clustal method are: KTUPLE 1, GAP PENALTY=3, WINDOW=5 and DIAGONALS SAVED=5.

Suitable nucleic acid fragments (isolated polynucleotides of the present invention) encode polypeptides that are at least about 70% identical, preferably at least about 75% identical, and more preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

The terms "homology", "homologous", "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

The term "ortholog" or "orthologous sequences" refers herein to a relationship where sequence divergence follows speciation (i.e., homologous sequences in different species arose from a common ancestral gene during speciation). In contrast, the term "paralogous" refers to homologous sequences within a single species that arose by gene duplication. One skilled in the art will be familiar with techniques required to identify homologous, orthologous and paralogous sequences.

Moreover, the skilled artisan recognizes that substantially similar nucleic acid sequences encompassed by this invention are also defined by their ability to hybridize, under moderately stringent conditions (for example, 0.5×SSC, 0.1% SDS, 60° C.) with the sequences exemplified herein, or to any portion of the nucleotide sequences disclosed herein and which are functionally equivalent to any of the nucleic acid sequences disclosed herein. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions involves a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions involves the use of higher temperatures in which the washes are identical to those above except for the temperature of the final two 30 min washes in 0.2×SSC, 0.5% SDS was increased to 60° C. Another preferred set of highly stringent conditions involves the use of two final washes in 0.1×SSC, 0.1% SDS at 65° C.

"Codon degeneracy" refers to the nature in the genetic code permitting variation of the nucleotide sequence without effecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Chemically synthesized", as related to a sequence of DNA, means that the component nucleotides were assembled in vitro. Manual chemical synthesis of DNA may be accomplished using well-established procedures; or automated chemical synthesis can be performed using one of a number of commercially available machines. "Synthetic genes" can be assembled from oligonucleotide building blocks that are chemically synthesized using procedures known to those skilled in the art. These building blocks are ligated and annealed to form gene segments that are then enzymatically assembled to construct the entire gene. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell, where sequence information is available.

"Gene" refers to a nucleic acid fragment that expresses a specific protein, and that may refer to the coding region alone or may include regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene that is introduced into the host organism by gene transfer. Foreign genes can comprise native genes introduced into a non-native organism, native genes introduced into a new location within the native host, or chimeric genes. A "transgene" is a gene that has been introduced into the genome by a transformation procedure. A "codon-optimized gene" is a gene having its frequency of codon usage designed to mimic the frequency of preferred codon usage of the host cell.

An "allele" is one of several alternative forms of a gene occupying a given locus on a chromosome. When all the alleles present at a given locus on a chromosome are the same that plant is homozygous at that locus. If the alleles present at a given locus on a chromosome differ that plant is heterozygous at that locus.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing sites, effector binding sites and stem-loop structures.

"Promoter" refers to a DNA sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. Promoters that cause a gene to be expressed in most cell types at most times are commonly referred to as "constitutive promoters". New promoters of various types useful in plant cells are constantly being discovered; numerous examples may be found in the compilation by Okamuro, J. K., and Goldberg, R. B. (1989) *Biochemistry of Plants* 15:1-82.

The "translation leader sequence" refers to a polynucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Mol. Biotechnol.* 3:225-236).

The terms "3' non-coding sequences" and "transcription terminator" refer to DNA sequences located downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA" or "mRNA" refers to the RNA that is without introns and that can be translated into protein by the cell. "cDNA" refers to a double-stranded DNA that is complementary to, and derived from, mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; WO 99/28508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated and yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., the coding sequence is under the transcriptional control of the promoter). Coding sequences can be operably linked to regulatory sequences in sense or antisense orientation. In another example, complementary RNA regions can be operably linked, either directly or indirectly, 5' to the target mRNA, or 3' to the target mRNA, or within the target mRNA, or a first complementary region is 5' and its complement is 3' to the target mRNA.

The term "expression", as used herein, refers to the production of a functional end-product e.g., a mRNA or a protein (precursor or mature).

The term "expression cassette" as used herein, refers to a discrete nucleic acid fragment into which a nucleic acid sequence or fragment can be moved.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

"Transformation" refers to the transfer of a nucleic acid fragment into a host organism, resulting in genetically stable inheritance. The nucleic acid fragment may be a plasmid that replicates autonomously, for example; or, it may integrate into the genome of the host organism. Host organisms containing the transformed nucleic acid fragments are referred to as "transgenic" or "recombinant" or "transformed" organisms.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance. Host organisms containing the transformed nucleic acid fragments are referred to as "transgenic" organisms.

"Antisense inhibition" refers to the production of antisense RNA transcripts capable of suppressing the expression of the target protein. "Co-suppression" refers to the production of sense RNA transcripts capable of suppressing the expression of identical or substantially similar foreign or endogenous genes (U.S. Pat. No. 5,231,020). Co-suppression constructs in plants previously have been designed by focusing on overexpression of a nucleic acid sequence having homology to an endogenous mRNA, in the sense orientation, which results in the reduction of all RNA having homology to the overexpressed sequence (see Vaucheret et al. (1998) *Plant J.* 16:651-659; and Gura (2000) *Nature* 404:804-808). The overall efficiency of this phenomenon is low, and the extent of the RNA reduction is widely variable. Recent work has described the use of "hairpin" structures that incorporate all, or part, of an mRNA encoding sequence in a complementary orientation that results in a potential "stem-loop" structure for the expressed RNA (PCT Publication WO 99/53050 published on Oct. 21,1999 and more recently, Applicants' assignee's PCT Application having international publication number WO 02/00904 published on Jan. 3, 2002). This increases the frequency of co-suppression in the recovered transgenic plants. Another variation describes the use of plant viral sequences to direct the suppression, or "silencing", of proximal mRNA encoding sequences (PCT Publication WO 98/36083 published on Aug. 20, 1998). Both of these co-suppressing phenomena have not been elucidated mechanistically, although genetic evidence has begun to unravel this complex situation (Elmayan et al. (1998) *Plant Cell* 10:1747-1757).

The polynucleotide sequences used for suppression do not necessarily have to be 100% complementary to the polynucleotide sequences found in the gene to be suppressed. For example, suppression of all the subunits of the soybean seed storage protein β-conglycinin has been accomplished using a polynucleotide derived from a portion of the gene encoding the α subunit (U.S. Pat. No. 6,362,399). β-conglycinin is a heterogeneous glycoprotein composed of varying combinations of three highly negatively charged subunits identified as α, α' and β. The polynucleotide sequences encoding the α and α' subunits are 85% identical to each other while the polynucleotide sequences encoding the β subunit are 75 to 80% identical to the α and α' subunits. Thus, polynucleotides that are at least 75% identical to a region of the polynucleotide that is target for suppression have been shown to be effective in suppressing the desired target. The polynucleotide should be at least 80% identical, preferably at least 90% identical, most preferably at least 95% identical, or the polynucleotide may be 100% identical to the desired target.

The terms "plasmid", "vector" and "cassette" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing e.g., a promoter fragment and DNA sequence for a selected gene product along with appropriate 3' untranslated sequence into a cell.

"Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

The term "recombinant" refers to an artificial combination of two otherwise separated segments of sequence, e.g., by chemical synthesis or by the manipulation of isolated segments of nucleic acids by genetic engineering techniques.

The terms "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such construct may be used by itself or may be used in conjunction with a vector. If a vector is used then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., (1985) *EMBO J.* 4:2411-2418; De Almeida et al., (1989) *Mol. Gen. Genetics* 218:78-86), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others.

The term "homologous recombination" refers to the exchange of DNA fragments between two DNA molecules (during cross over). The fragments that are exchanged are flanked by sites of identical nucleotide sequences between the two DNA molecules (i.e., "regions of homology"). The term "regions of homology" refer to stretches of nucleotide sequence on nucleic acid fragments that participate in homologous recombination that have homology to each other. Effective homologous recombination will take place where these regions of homology are at least about 10 bp in length where at least about 50 bp in length is preferred. Typically fragments that are intended for recombination contain at least two regions of homology where targeted gene disruption or replacement is desired.

"PCR" or "Polymerase Chain Reaction" is a technique for the synthesis of large quantities of specific DNA segments, consists of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps is referred to as a cycle.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.* 215:403-410 (1990)); 3.) DNASTAR (DNASTAR, Inc. Madison, Wis.); 4.) Sequencher (Gene Codes Corporation, Ann Arbor, Mich.); and 5.) the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

Standard recombinant DNA and molecular cloning techniques used herein are well known in the art and are described by Sambrook, J., Fritsch, E. F. and Maniatis, T., *Molecular Cloning: A Laboratory Manual,* 2nd ed., Cold Spring Harbor Laboratory: Cold Spring Harbor, N.Y. (1989) (hereinafter "Maniatis"); by Silhavy, T. J., Bennan, M. L. and Enquist, L. W., *Experiments with Gene Fusions,* Cold Spring Harbor Laboratory: Cold Spring Harbor, N.Y. (1984); and by Ausubel, F. M. et al., *Current Protocols in Molecular Biology,* published by Greene Publishing Assoc. and Wiley-Interscience (1987).

Microbial Biosynthesis Of Fatty Acids

In general, lipid accumulation in oleaginous microorganisms is triggered in response to the overall carbon to nitrogen ratio present in the growth medium (FIG. 1). When cells have exhausted available nitrogen supplies (e.g., when the carbon to nitrogen ratio is greater than about 40), the depletion of cellular adenosine monophosphate (AMP) leads to the cessation of AMP-dependent isocitrate dehydrogenase activity in the mitochondria and the accumulation of citrate, transport of citrate into the cytosol, and subsequent cleavage of the citrate by ATP-citrate lyase to yield acetyl-CoA. Acetyl-CoA is the principle building block for de novo biosynthesis of fatty acids. Although any compound that can effectively be metabolized to produce acetyl-CoA can serve as a precursor of fatty acids, glucose is the primary source of carbon in this type of reaction (FIG. 1). Glucose is converted to pyruvate via glycolysis, and pyruvate is then transported into the mitochondria where it can be converted to acetyl-CoA by pyruvate dehydrogenase ("PD"). Since acetyl-CoA can not be transported directly across the mitochondrial membrane into the cytoplasm, the two carbons from acetyl-CoA condense with oxaloacetate to yield citrate (catalyzed by citrate synthase). Citrate is transported directly into the cytoplasm, where it is cleaved by ATP-citrate lyase to regenerate acetyl-CoA and oxaloacetate. The oxaloacetate reenters the tricarboxylic acid cycle, via conversion to malate.

The synthesis of malonyl-CoA is the first committed step of fatty acid biosynthesis, which takes place in the cytoplasm. Malonyl-CoA is produced via carboxylation of acetyl-CoA by acetyl-CoA carboxylase ("ACC"). Fatty acid synthesis is catalyzed by a multi-enzyme fatty acid synthase complex ("FAS") and occurs by the condensation of eight two-carbon fragments (acetyl groups from acetyl-CoA) to form a 16-carbon saturated fatty acid, palmitate. More specifically, FAS catalyzes a series of 7 reactions, which involve the following (Smith, S. *FASEB J,* 8(15):1248-59 (1994)):

1. Acetyl-CoA and malonyl-CoA are transferred to the acyl carrier protein (ACP) of FAS. The acetyl group is then transferred to the malonyl group, forming β-ketobutyryl-ACP and releasing $CO_2$.
2. The β-ketobutyryl-ACP undergoes reduction (via β-ketoacyl reductase) and dehydration (via β-hydroxyacyl dehydratase) to form a trans-monounsaturated fatty acyl group.
3. The double bond is reduced by NADPH, yielding a saturated fatty-acyl group two carbons longer than the initial one. The butyryl-group's ability to condense with a new malonyl group and repeat the elongation process is then regenerated.

4. When the fatty acyl group becomes 16 carbons long, a thioesterase activity hydrolyses it, releasing free palmitate.

Palmitate (16:0) is the precursor of longer chain saturated and unsaturated fatty acids (e.g., stearic (18:0), palmitoleic (16:1) and oleic (18:1) acids) through the action of elongases and desaturases present in the endoplasmic reticulum membrane. Palmitate and stearate (as CoA and/or ACP esters) are converted to their unsaturated derivatives, palmitoleic (16:1) and oleic (18:1) acids, respectively, by the action of a Δ-9 desaturase.

Triacylglycerols (the primary storage unit for fatty acids) are formed by the esterification of two molecules of acyl-CoA to glycerol-3-phosphate to yield 1,2-diacylglycerol phosphate (commonly identified as phosphatidic acid) (FIG. 1). The phosphate is then removed, by phosphatidic acid phosphatase, to yield 1,2-diacylglycerol. Triacylglycerol is formed upon the addition of a third fatty acid, for example, by the action of a diacylglycerol-acyl transferase.

Biosynthesis Of Omega Fatty Acids

Simplistically, the metabolic process that converts LA to GLA, DGLA and ARA (the ω-6 pathway) and ALA to STA, ETA, EPA, DPA and DHA (the ω-3 pathway) involves elongation of the carbon chain through the addition of two-carbon units and desaturation of the molecule through the addition of double bonds (FIG. 2). This requires a series of special desaturation and elongation enzymes present in the endoplasmic reticulum membrane.

ω-6 Fatty Acids

Oleic acid is converted to LA (18:2), the first of the ω-6 fatty acids, by the action of a Δ-12 desaturase. Subsequent ω-6 fatty acids are produced as follows: 1.) LA is converted to GLA by the action of a Δ-6 desaturase; 2.) GLA is converted to DGLA by the action of an elongase; and 3.) DGLA is converted to ARA by the action of a Δ-5 desaturase.

Omega-3 Fatty Acids

Linoleic acid (LA) is converted to ALA, the first of the ω-3 fatty acids, by the action of a Δ-15 desaturase. Subsequent ω-3 fatty acids are produced in a series of steps similar to that for the ω-6 fatty acids. Specifically: 1.) ALA is converted to STA by the activity of a Δ6 desaturase; 2.) STA is converted to ETA by the activity of an elongase; and 3.) ETA is converted to EPA by the activity of a Δ5 desaturase. Alternatively, ETA and EPA can be produced from DGLA and ARA, respectively, by the activity of a Δ17 desaturase. EPA can be further converted to DHA by the activity of an elongase and a Δ4 desaturase.

In alternate embodiments, a Δ9 elongase is able to catalyze the conversion of LA and ALA to EDA and ETrA, respectively. A Δ8 desaturase then converts these products to DGLA and ETA, respectively.

Genes Involved In Omega Fatty Acid Production

Many microorganisms, including algae, bacteria, molds and yeast, can synthesize PUFAs and omega fatty acids in the ordinary course of cellular metabolism. Particularly well-studied are fungi including *Schizochytrium aggregatm*, species of the genus *Thraustochytrium* and *Morteriella alpina*. Additionally, many dinoflagellates (Dinophyceaea) naturally produce high concentrations of PUFAs. As such, a variety of genes involved in oil production have been identified through genetic means and the DNA sequences of some of these genes are publicly available (non-limiting examples are shown below in Table 3):

TABLE 3

Some Publicly Available Genes Involved In PUFA Production

| Genbank Accession No. | Description |
|---|---|
| AY131238 | *Argania spinosa* Δ6 desaturase |
| Y055118 | *Echium pitardii* var. *pitardii* Δ6 desaturase |
| AY055117 | *Echium gentianoides* Δ6 desaturase |
| AF296076 | *Mucor rouxii* Δ6 desaturase |
| AF007561 | *Borago officinalis* Δ6 desaturase |
| L11421 | *Synechocystis* sp. Δ6 desaturase |
| NM_031344 | *Rattus norvegicus* Δ6 fatty acid desaturase |
| AF465283, AF465281, AF110510 | *Mortierella alpina* Δ6 fatty acid desaturase |
| AF465282 | *Mortierella isabellina* Δ6 fatty acid desaturase |
| AF419296 | *Pythium irregulare* Δ6 fatty acid desaturase |
| AB052086 | *Mucor circinelloides* D6d mRNA for Δ6 fatty acid desaturase |
| AJ250735 | *Ceratodon purpureus* mRNA for Δ6 fatty acid desaturase |
| AF126799 | *Homo sapiens* Δ6 fatty acid desaturase |
| AF126798 | *Mus musculus* Δ6 fatty acid desaturase |
| AF199596, AF226273 | *Homo sapiens* Δ5 desaturase |
| AF320509 | *Rattus norvegicus* liver Δ5 desaturase |
| AB072976 | *Mus musculus* D5D mRNA for Δ5 desaturase |
| AF489588 | *Thraustochytrium* sp. ATCC21685 Δ5 fatty acid desaturase |
| AJ510244 | *Phytophthora megasperma* mRNA for Δ5 fatty acid desaturase |
| AF419297 | *Pythium irregulare* Δ5 fatty acid desaturase |
| AF07879 | *Caenorhabditis elegans* Δ5 fatty acid desaturase |
| AF067654 | *Mortierella alpina* Δ5 fatty acid desaturase |
| AB022097 | *Dictyostelium discoideum* mRNA for Δ5 fatty acid desaturase |
| AF489589.1 | *Thraustochytrium* sp. ATCC21685 Δ4 fatty acid desaturase |
| AX464731 | *Mortierella alpina* elongase gene (also WO 00/12720) |
| AAG36933 | *Emericella nidulans* oleate Δ2 desaturase |
| AF110509, AB020033 | *Mortierella alpina* Δ12 fatty acid desaturase mRNA |
| AAL13300 | *Mortierella alpina* Δ12 fatty acid desaturase |
| AF417244 | *Mortierella alpina* ATCC 16266 Δ12 fatty acid desaturase gene |
| AF161219 | *Mucor rouxii* Δ12 desaturase mRNA |
| X86736 | *Spiruline platensis* Δ12 desaturase |
| AF240777 | *Caenorhabditis elegans* Δ12 desaturase |
| AB007640 | *Chlamydomonas reinhardtii* Δ12 desaturase |
| AB075526 | *Chlorella vulgaris* Δ12 desaturase |
| AP002063 | *Arabidopsis thaliana* microsomal Δ12 desaturase |
| NP_441622, BAA18302, BAA02924 | *Synechocystis* sp. PCC 6803 Δ15 desaturase |
| AAL36934 | *Perilla frutescens* Δ15 desaturase |
| AF338466 | *Acheta domesticus* Δ9 desaturase 3 mRNA |
| AF438199 | *Picea glauca* desaturase Δ9 (Des9) mRNA |
| E11368 | *Anabaena* Δ9 desaturase |
| E11367 | *Synechocystis* Δ9 desaturase |
| D83185 | *Pichia angusta* DNA for Δ9 fatty acid desaturase |
| U90417 | *Synechococcus vulcanus* Δ9 acyl-lipid fatty acid desaturase (desC) gene |
| AF085500 | *Mortierella alpina* Δ9 desaturase mRNA |
| AY504633 | *Emericella nidulans* Δ9 stearic acid desaturase (sdeB) gene |
| NM_069854 | *Caenorhabditis elegans* essential fatty acid desaturase, stearoyl-CoA desaturase (39.1 kD) (fat-6) complete mRNA |
| AF230693 | *Brassica oleracea* cultivar Rapid Cycling stearoyl-ACP desaturase (Δ9-BO-1) gene, exon sequence |
| AX464731 | *Mortierella alpina* elongase gene (also WO 02/08401) |

TABLE 3-continued

Some Publicly Available Genes Involved In PUFA Production

| Genbank Accession No. | Description |
| --- | --- |
| NM_119617 | *Arabidopsis thaliana* fatty acid elongase 1 (FAE1) (At4g34520) mRNA |
| NM_134255 | *Mus musculus* ELOVL family member 5, elongation of long chain fatty acids (yeast) (Elovl5), mRNA |
| NM_134383 | *Rattus norvegicus* fatty acid elongase 2 (rELO2), mRNA |
| NM_134382 | *Rattus norvegicus* fatty acid elongase 1 (rELO1), mRNA |
| NM_068396, NM_068392, NM_070713, NM_068746, NM_064685 | *Caenorhabditis elegans* fatty acid ELOngation (elo-6), (elo-5), (elo-2), (elo-3), and (elo-9) mRNA |

Additionally, the patent literature provides many additional DNA sequences of genes (and/or details concerning several of the genes above and their methods of isolation) involved in oil production. See, for example: U.S. Pat. No. 5,968,809 (Δ6 desaturases); U.S. Pat. No. 5,972,664 and U.S. Pat. No. 6,075,183 (Δ5 desaturases); WO 91/13972 and U.S. Pat. No. 5,057,419 (Δ9 desaturases); U.S. 2003/0196217 A1 (Δ17 desaturases); WO 02/090493 (Δ4 desaturases); WO 94/11516, U.S. Pat. No. 5,443,974, and U.S. patent application Ser, No. 10/840,325 (Δ12 desaturases); WO 00/12720 and U.S. 2002/0139974A1 (elongases). Each of these patents and applications are herein incorporated by reference in their entirety.

Of particular interest herein are Δ15 desaturases, and more specifically, Δ15 desaturases that are suitable for heterologous expression in oleaginous yeast (e.g., *Yarrowia lipolytica*). Genes encoding Δ15 desaturase are known in the art. For example, they have previously been cloned from plants (e.g., *Arabidopsis, Brassica napus, Glycine max* (WO 93/11245)), cyanobacteria and *C. elegans*. Additionally, following the Applicants' invention described herein, fungal Δ15 desaturases from *Neurospora crassa, Botrytis cinerea* and *Aspergillus nidulans* were disclosed in WO 03/099216 (published Dec. 4, 2003).

Many factors affect the choice of a specific polypeptide having Δ15 desaturase activity that is to be expressed in a host cell for production of PUFAs (optionally in combination with other desaturases and elongases). Depending upon the host cell, the availability of substrate, and the desired end product(s), several polypeptides are of interest. However, considerations for choosing a specific polypeptide having desaturase activity include the substrate specificity of the polypeptide, whether the polypeptide or a component thereof is a rate-limiting enzyme, whether the desaturase is essential for synthesis of a desired PUFA, and/or co-factors required by the polypeptide. The expressed polypeptide preferably has parameters compatible with the biochemical environment of its location in the host cell. For example, the polypeptide may have to compete for substrate with other enzymes in the host cell. Analyses of the $K_M$ and specific activity of the polypeptide are therefore considered in determining the suitability of a given polypeptide for modifying PUFA production in a given host cell. The polypeptide used in a particular host cell is one which can function under the biochemical conditions present in the intended host cell but otherwise can be any polypeptide having Δ15 desaturase activity capable of modifying the desired fatty acids (i.e., LA). Thus, the sequences may be derived from any source, e.g., isolated from a natural source (from bacteria, algae, fungi, plants, animals, etc.), produced via a semi-synthetic route or synthesized de novo.

For the purposes of the present invention herein, however, it is useful for the polypeptide having Δ15 desaturase activity to have a conversion efficiency (i.e., ([18:3]/[18:2+18:3]) *100) of at least about 50% when expressed in the desired eukaryotic host cell, wherein a conversion efficiency of at least about 80% is more desirable, a conversion efficiency of at least about 90% is particularly suitable, and a conversion efficiency of at least about 95% is most preferred.

Identification Of Novel Fungal Δ15 Desaturases

Several fungi, including the filamentous fungi *Magnaporthe grisea, Neurospora crassa, Aspergillus nidulans, Fusarium graminearium* and *Fusarium moniliforme* are known tomake 18:3 (WO 03/099216; WO 03/099216). In view of the teachings and discoveries disclosed herein each of these fungi are expected to have Δ15 desaturase enzyme activity. These sequences will be particularly for expression of the genes in oleaginous yeast (e.g., *Yarrowia lipolytica*).

A novel Δ15 desaturase from *Fusarium moniliforme* was identified, by sequence comparison using the *Yarrowia lipolytica* Δ12 desaturase protein sequence (SEQ ID NO:55) as a query sequence. Specifically, this Yarrowia query sequence was used to search putative encoded protein sequences of a proprietary DuPont expressed sequence tag (EST) library of *Fusarium moniliforme* strain M-8114 (E.I. du Pont de Nemours and Co., Inc., Wilmington, Del.). This resulted in the identification of two homologous sequences, Fm1 (SEQ ID NO:2) and Fm2 (SEQ ID NO:4), encoded by the nucleotide sequences of SEQ ID NOs:1 and 3, respectively.

The *Yarrowia* Δ12 desaturase sequence was also used as a query against public databases of several filamentous fungi; specifically, homologous protein sequences were identified in *Aspergillus nidulans* (SEQ ID NOs:6 and 8), *Magnaporthe grisea* (SEQ ID NOs:10 and 12), *Neurospora crassa* (SEQ ID NOs:14 and 16) and *Fusarium graminearium* (SEQ ID NOs: 18 and 20). Subsequent phylogenetic and homology analysis, based on comparison of these sequences (i.e., SEQ ID NOs: 2, 4, 6, 8, 10, 12, 14, 16, 18 and 20) using the method of Clustal W (slow, accurate, Gonnet option; Thompson et al. *Nucleic Acids Res.* 22:4673-4680 (1994)), revealed two distinct "sub-families" of proteins having homology with the *Yarrowia* Δ12 desaturase. Specifically, all proteins of "sub-family 1" (SEQ ID NOs: 2, 6, 10, 14 and 18) were at least 46.2% identical to each other and were less than 39.6% identical to the proteins of "sub-family 2" (SEQ ID NOs: 4, 8, 12, 16 and 20) (FIGS. 4 and 5; Clustal method of alignment (supra)). The proteins of sub-family 2 were at least 56.3% identical to each other.

Since *Yarrowia* is only able to synthesize 18:2 (but not 18:3) while each of the filamentous fungi described above can make both 18:2 and ALA, and since *Yarrowia* has a single Δ12 desaturase while each of the filamentous fungi had two homologs to the *Yarrowia* Δ12 desaturase, Applicants postulated that one of the sub-families of desaturases in these organisms represented Δ12 desaturases and the other represented Δ15 desaturases. This hypothesis was tested by determining the activity of a representative protein(s) within each of the two sub-families using expression analysis. Specifically, Fm2 was expressed in *Yarrowia lipolytica* and found to encode aΔΔ12 desaturase (see co-pending U.S. Provisional Application 60/570679), while Fm1 and Mg1 were expressed in *Y. lipolytica* as described herein and were characterized as Δ15 desaturases (additionally having some Δ12 desaturase activity).

The *Fusarium moniliforme* Δ15 desaturase nucleotide and deduced amino acid sequences (i.e., SEQ ID NOs:1 and 2, respectively) were compared to public database sequences using a Blastp 2.2.5 program of alignment, with the following parameters: Expect value of 10, Matrix of BLOSUM62, and filter for low complexity (Altschul et al., *Nucleic Acid Res.* 25(17):3389-3402 (1997)). Thus, the *Fusarium moniliforme* Δ15 desaturase nucleotide sequence was most similar to the *Gibberella zeae* PH-1 sequence provided as GenBank Accession No. XM_388066.1 (86% identical over a length of 573 bp). GenBank Accession No. XM_388066.1 corresponds to the *Gibberella zeae* PH-1 protein of GenBank Accession No. XP_388066.1 and SEQ ID NO:17 herein (i.e., the *Fusarium graminearium* Δ15 desaturase ORF). Direct comparison reveals that the *F. moniliforme* and *F. graminearium* Δ15 desaturase ORFs are 87.4% identical over a length of 1211 bp.

Comparison of the *Fusarium moniliforme* Δ15 desaturase deduced amino acid sequence to public databases reveals that the most closely related sequence based on percent identity is GenBank Accession No. XM_388066.1 (89% over the length of 193 amino acids). This is a partial amino acid sequence that corresponds to SEQ ID NO:18 herein, encoding the full length *Fusarium graminearium* Δ15 desaturase that is 88.8% identical over its full length of 403 amino acids.

More preferred amino acid fragments are at least about 70%-80% identical to the sequence herein, where those sequences that are 85%-90% identical are particularly suitable and those sequences that are about 95% identical are most preferred. Similarly, preferred Δ15 desaturase encoding nucleic acid sequences corresponding to the instant ORF are those encoding active proteins and which are at least about 70%-80% identical to the nucleic acid sequence encoding the *F. moniliforme* Δ15 desaturase reported herein, where those sequences that are 85%-90% identical are particularly suitable and those sequences that are about 95% identical are most preferred. Useful percent identities for practicing the present invention include, but are not limited to 45.4%, 46.2%, 47%, 50%, 55%, 60%, 65%, 70%, 75%, 80%, 85%, 90%, 95%, or 100%. It is believed that any integer percentage between 46% and 100% would be useful.

Identification and Isolation Of Homologs

The Δ15 desaturase nucleic acid fragment of the instant invention may be used to identify and isolate genes encoding homologous proteins from the same or other bacterial, algal, fungal or plant species.

Identification Techniques

For example, a substantial portion of the *Fusarium moniliforme* Δ15 desaturase amino acid or nucleotide sequence described herein can be used to putatively identify related polypeptides or genes, either by manual evaluation of the sequence by one skilled in the art, or by computer-automated sequence comparison and identification using algorithms such as BLAST (Basic Local Alignment Search Tool; Altschul, S. F., et al., *J. Mol. Biol.* 215:403-410 (1993)) and ClustalW (Megalign program of DNASTAR software). As described above, use of the *Yarrowia lipolytica* Δ12 desaturase (SEQ ID NO:55) permitted the identification of a suite of fungal desaturases which, upon analysis, clustered as two distinct sub-families of proteins (i.e., sub-family 1 and sub-family 2). Subfamily-1 comprised the *Fusarium moniliforme* Δ15 desaturase described above, as well as the proteins whose coding DNA sequences are found within the following:

Contig 1.122 (scaffold 9) in the *Aspergillus nidulans* genome project (sponsored by the Center for Genome Research (CGR), Cambridge, Mass.) (SEQ ID NO:6);

Locus MG08474.1 in contig 2.1597 in the *Magnaporthe grisea* genome project (sponsored by the CGR and International Rice Blast Genome Consortium) (SEQ ID NO:10);

GenBank Accession No. AABX01000577 (*Neurospora crassa*) (SEQ ID NO:14); and

Contig 1.320 in the *Fusarium graminearium* genome project (sponsored by the CGR and the International *Gibberella zeae* Genomics Consortium (IGGR)); BAA33772.1 (SEQ ID NO:18).

Each of the above proteins were hypothesized to encode a Δ15 desaturase. This hypothesis was confirmed for *Aspergillus nidulans* and *Neurospora crassa* in WO 03/099216 and confirmed herein for *Magnaporthe grisea.*

Analysis of the above proteins reveals that these proteins have at least 46.2% sequence identity to the *Fusarium moniliforme* Δ15 desaturase (SEQ ID NO:2), according to the Clustal method of alignment (supra) (FIG. 5). Additionally, the Δ15 desaturases of sub-family 1 in the present invention were also compared to other known Δ15 desaturase proteins; however, the Δ15 desaturases of sub-family 1 herein are more homologous to the proteins of sub-family 2 (39.6% identity) than they are to any other known Δ15 desaturases. One skilled in the art would be able to use similar methodology to identify other orthologous proteins that would also cluster within sub-family 1 (identified herein as Δ15 desaturases).

Alternatively, any of the instant desaturase sequences (i.e., SEQ ID NOs:1, 2, 5, 6, 9, 10, 13, 14, 17, 18) may be employed as hybridization reagents for the identification of homologs. The basic components of a nucleic acid hybridization test include a probe, a sample suspected of containing the gene or gene fragment of interest and a specific hybridization method. Probes of the present invention are typically single-stranded nucleic acid sequences that are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions that will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed. Optionally, a chaotropic agent may be added. The chaotropic agent stabilizes nucleic acids by inhibiting nuclease activity. Furthermore, the chaotropic agent allows sensitive and stringent hybridization of short oligonucleotide probes at room temperature (Van Ness and Chen, *Nucl. Acids Res.* 19:5143-5151 (1991)). Suitable chaotropic agents include guanidinium chloride, guanidinium thiocyanate, sodium thiocyanate, lithium tetrachloroacetate, sodium perchlorate, rubidium tetrachloroacetate, potassium iodide, and cesium trifluoroacetate, among others. Typically, the chaotropic agent will be present at a final concentration of about 3 M. If desired, one can add formamide to the hybridization mixture, typically 30-50% (v/v).

Various hybridization solutions can be employed. Typically, these comprise from about 20 to 60% volume, preferably 30%, of a polar organic solvent. A common hybridization solution employs about 30-50% v/v formamide, about 0.15 to 1 M sodium chloride, about 0.05 to 0.1 M buffers (e.g., sodium citrate, Tris-HCl, PIPES or HEPES (pH range about 6-9)), about 0.05 to 0.2% detergent (e.g., sodium dodecylsulfate), or between 0.5-20 mM EDTA, FICOLL (Pharmacia Inc.) (about 300-500 kdal), polyvinylpyrrolidone (about 250-500 kdal), and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol glycine. Other additives may also be included, such as volume exclusion agents that include a variety of polar water-soluble or swellable agents (e.g., polyethylene glycol), anionic polymers (e.g., polyacrylate or polymethylacrylate) and anionic saccharidic polymers (e.g., dextran sulfate).

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

Isolation Methods

The *Fusarium moniliforme* Δ15 desaturase nucleic acid fragment of the instant invention (or any of the Δ15 desaturases identified herein [SEQ ID NOs:5, 6, 9, 10, 13, 14, 17 and 18]) may be used to isolate genes encoding homologous proteins from the same or other bacterial, algal, fungal or plant species. Isolation of homologous genes using sequence-dependent protocols is well known in the art. Examples of sequence-dependent protocols include, but are not limited to: 1.) methods of nucleic acid hybridization; 2.) methods of DNA and RNA amplification, as exemplified by various uses of nucleic acid amplification technologies [e.g., polymerase chain reaction (PCR), Mullis et al., U.S. Pat. No. 4,683,202; ligase chain reaction (LCR), Tabor, S. et al., *Proc. Acad. Sci. USA* 82:1074 (1985); or strand displacement amplification (SDA), Walker, et al., *Proc. Natl. Acad. Sci. U.S.A.,* 89:392 (1992)]; and 3.) methods of library construction and screening by complementation.

For example, genes encoding similar proteins or polypeptides to the desaturases described herein could be isolated directly by using all or a portion of the instant nucleic acid fragments as DNA hybridization probes to screen libraries from any desired yeast or fungus using methodology well known to those skilled in the art (wherein those yeast or fungus producing ALA [or ALA-derivatives] would be preferred). Specific oligonucleotide probes based upon the instant nucleic acid sequences can be designed and synthesized by methods known in the art (Maniatis, supra). Moreover, the entire sequences can be used directly to synthesize DNA probes by methods known to the skilled artisan (e.g., random primers DNA labeling, nick translation or end-labeling techniques), or RNA probes using available in vitro transcription systems. In addition, specific primers can be designed and used to amplify a part of (or full-length of) the instant sequences. The resulting amplification products can be labeled directly during amplification reactions or labeled after amplification reactions, and used as probes to isolate full-length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotide as specific hybridization probes in the Diagnosis of Genetic Disorders", in *Human Genetic Diseases: A Practical Approach*, K. E. Davis Ed., (1986) pp 33-50, IRL: Herndon, Va.; and Rychlik, W., In *Methods in Molecular Biology*, White, B. A. Ed., (1993) Vol. 15, pp 31-39, PCR Protocols: Current Methods and Applications. Humania: Totowa, N.J.).

Generally two short segments of the instant sequences may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding microbial genes. Alternatively, the second primer sequence may be based upon sequences derived from the cloning vector. For example, the skilled artisan can follow the RACE protocol (Frohman et al., *PNAS USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (Gibco/BRL, Gaithersburg, Md.), specific 3' or 5' cDNA fragments can be isolated (Ohara et al., *PNAS USA* 86:5673 (1989); Loh et al., *Science* 243:217 (1989)).

Availability of the instant nucleotide and deduced amino acid sequences facilitates immunological screening of DNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen DNA expression libraries to isolate full-length DNA clones of interest (Lerner, R. A. *Adv. Immunol.* 36:1 (1984); Maniatis, supra).

Gene Optimization for Improved Heterologous Expression

A variety of techniques can be utilized to improve the expression of a particular Δ15 desaturase of interest in an alternative host. Two such techniques include codon-optimization and mutagenesis of the gene.

Codon Optimization

For some embodiments, it may be desirable to modify a portion of the codons encoding polypeptides having Δ15 desaturase activity, for example, to enhance the expression of genes encoding those polypeptides in an alternative host (i.e., oleaginous yeast).

In general, host preferred codons can be determined within a particular host species of interest by examining codon usage in proteins (preferably those proteins expressed in the largest amount) and determining which codons are used with highest frequency. Then, the coding sequence for the polypeptide of interest having desaturase activity can be synthesized in whole or in part using the codons preferred in the host species.

All (or portions) of the DNA also can be synthesized to remove any destabilizing sequences or regions of secondary structure that would be present in the transcribed mRNA. All (or portions) of the DNA also can be synthesized to alter the base composition to one more preferable in the desired host cell.

In preferred embodiments of the invention, the Δ15 desaturases from e.g., *Fusarium moniliforme, Aspergillus nidulans, Magnaporthe grisea, Neurospora crassa* and *Fusarium graminearium* could be codon-optimized prior to their expression in a heterologous oleaginous yeast host, such as *Yarrowia lipolytica*.

Mutagenesis

Methods for synthesizing sequences and bringing sequences together are well established in the literature. For example, in vitro mutagenesis and selection, site-directed mutagenesis, error prone PCR (Melnikov et al., *Nucleic Acids Research*, 27(4):1056-1062 (Feb. 15, 1999)), "gene shuffling" (U.S. Pat. No. 5,605,793; U.S. Pat. No. 5,811,238; U.S. Pat. No. 5,830,721; and U.S. Pat. No. 5,837,458) or other means can be employed to obtain mutations of naturally occurring desaturase genes, such as the Δ15 desaturases described herein. This would permit production of a polypeptide having desaturase activity in vivo with more desirable physical and kinetic parameters for function in the host cell (e.g., a longer half-life or a higher rate of production of a desired PUFA).

If desired, the regions of a desaturase polypeptide important for enzymatic activity can be determined through routine mutagenesis, expression of the resulting mutant polypeptides and determination of their activities. Mutants may include deletions, insertions and point mutations, or combinations thereof. A typical functional analysis begins with deletion mutagenesis to determine the N- and C-terminal limits of the protein necessary for function, and then internal deletions, insertions or point mutants are made to further determine regions necessary for function. Other techniques such as cassette mutagenesis or total synthesis also can be used. Deletion mutagenesis is accomplished, for example, by using exonucleases to sequentially remove the 5' or 3' coding regions. Kits are available for such techniques. After deletion, the coding region is completed by ligating oligonucleotides containing start or stop codons to the deleted coding region after the 5' or 3' deletion, respectively. Alternatively, oligonucleotides encoding start or stop codons are inserted into the coding region by a variety of methods including site-directed mutagenesis, mutagenic PCR or by ligation onto DNA digested at existing restriction sites. Internal deletions can similarly be made through a variety of methods including the use of existing restriction sites in the DNA, by use of mutagenic primers via site-directed mutagenesis or mutagenic PCR. Insertions are made through methods such as linker-scanning mutagenesis, site-directed mutagenesis or mutagenic PCR. Point mutations are made through techniques such as site-directed mutagenesis or mutagenic PCR.

Chemical mutagenesis also can be used for identifying regions of a desaturase polypeptide important for activity. A mutated construct is expressed, and the ability of the resulting altered protein to function as a desaturase is assayed. Such structure-function analysis can determine which regions may be deleted, which regions tolerate insertions, and which point mutations allow the mutant protein to function in substantially the same way as the native desaturase. All such mutant proteins and nucleotide sequences encoding them that are derived from the desaturase genes described herein are within the scope of the present invention.

Thus, the present invention comprises the complete sequences of the Δ15 desaturase genes as reported in the accompanying Sequence Listing, the complement of those complete sequences, substantial portions of those sequences, codon-optimized desaturases derived therefrom, and those sequences that are substantially homologous thereto.

Microbial Production Of ω-3 And/Or ω-6 Fatty Acids

Microbial production of ω-3 and/or ω-6 fatty acids can have several advantages over purification from natural sources such as fish or plants.

For example:
1.) Many microbes are known with greatly simplified oil compositions compared with those of higher organisms, making purification of desired components easier;
2.) Microbial production is not subject to fluctuations caused by external variables, such as weather and food supply;
3.) Microbially produced oil is substantially free of contamination by environmental pollutants;
4.) Microbes can provide PUFAs in particular forms which may have specific uses; and
5.) Microbial oil production can be manipulated by controlling culture conditions, notably by providing particular substrates for microbially expressed enzymes, or by addition of compounds or genetic engineering approaches to suppress undesired biochemical pathways.

In addition to these advantages, production of ω-3 and/or ω-6 fatty acids 30 from recombinant microbes provides the ability to alter the naturally occurring microbial fatty acid profile by providing new biosynthetic pathways in the host or by suppressing undesired pathways, thereby increasing levels of desired PUFAs (or conjugated forms thereof) and decreasing levels of undesired PUFAs (see co-pending U.S. patent application Ser. No. 10/840579, herein incorporated entirely by reference).

Methods for Production of Various ω-3 and/or ω-6 Fatty Acids

It is expected that introduction of chimeric genes encoding the Δ15 desaturases described herein, under the control of the appropriate promoters will result in increased production of ALA in the transformed host organism. As such, the present invention encompasses a method for the direct production of PUFAs comprising exposing a fatty acid substrate (i.e., LA) to the PUFA enzyme(s) described herein (e.g., the *Fusarium moniliforme* Δ15 desaturase), such that the substrate is converted to the desired fatty acid product (i.e., ALA). More specifically, it is an object of the present invention to provide a method for the production of ALA in a microorganism (e.g., oleaginous yeast), wherein the microorganism is provided:
(a) an isolated nucleic acid fragment encoding a fungal protein having Δ15 desaturase activity that has at least 46.2% identity based on the Clustal method of alignment when compared to a polypeptide having the sequence as set forth in SEQ ID NO:2; and,
(b) a source of desaturase substrate consisting of LA;

wherein the yeast is grown under conditions such that the chimeric desaturase gene is expressed and the LA is converted to ALA, and wherein the ALA is optionally recovered. Thus, this method minimally includes the use of the following Δ15 desaturases: SEQ ID NOs:2, 6, 10, 14 and 18, as described herein.

Alternatively, each PUFA gene and its corresponding enzyme product described herein can be used indirectly for the production of ω-3 PUFAs. Indirect production of ω-3 PUFAs occurs wherein the fatty acid substrate is converted indirectly into the desired fatty acid product, via means of an intermediate step(s) or pathway intermediate(s). Thus, it is contemplated that the Δ15 desaturases described herein may be expressed in conjunction with one or more genes that encode other enzymes, such that a series of reactions occur to produce a desired product. In a preferred embodiment, for example, a host organism may be co-transformed with a vector comprising additional genes encoding enzymes of the PUFA biosynthetic pathway to result in higher levels of production of ω-3 fatty acids (e.g., ALA, STA, ETA, EPA, DPA and DHA). Specifically, for example, it may be desirable to over-express any one of the Δ15 desaturases described herein in host cells that are also expressing: 1.) a gene encoding aΔA12 desaturase for the overproduction of ALA (wherein production is increased relative to expression of the Δ15 desaturase alone); 2.) a gene encoding a Δ6 desaturase (and optionally a Δ12 desaturase) for the overproduction of STA; 3.) genes encoding a Δ6 desaturase and high-affinity elongase (and optionally a Δ12 desaturase) for the overproduction of ETA; and 4.) genes encoding a Δ6 desaturase, high-affinity elongase and Δ5 desaturase (and optionally a Δ12 desaturase) for the overproduction of EPA. As is well known to one skilled in the art, various other combinations of the following enzymatic activities may be useful to express in a host in conjunction with the desaturase(s) herein: a Δ4 desaturase, a Δ5 desaturase, a Δ6 desaturase, a Δ12 desaturase, a Δ17 desaturase, a Δ9 desaturase, a Δ8 desaturase, and/or an elongase (see FIG. 2). The particular genes included within a particular expression cassette will depend on the host cell (and its PUFA profile and/or desaturase profile), the availability of substrate and the desired end product(s).

In alternative embodiments, it may be useful to disrupt a host organism's native Δ15 desaturase, based on the complete sequences described herein, the complement of those complete sequences, substantial portions of those sequences, codon-optimized desaturases derived therefrom and those sequences that are substantially homologous thereto. For example, the targeted disruption of the Δ15 desaturase in a host organism produces a mutant strain that is unable to synthesize ALA. This mutant strain could be useful for the production of "pure" ω-6 fatty acids (without co-synthesis of ω-3 fatty acids).

Expression Systems, Cassettes and Vectors

The genes and gene products of the instant sequences described herein may be expressed in heterologous microbial host cells, particularly in the cells of oleaginous yeast (e.g., *Yarrowia lipolytica*). Expression in recombinant microbial hosts may be useful for the production of various PUFA pathway intermediates, or for the modulation of PUFA pathways already existing in the host for the synthesis of new products heretofore not possible using the host.

Microbial expression systems and expression vectors containing regulatory sequences that direct high level expression of foreign proteins are well known to those skilled in the art. Any of these could be used to construct chimeric genes for production of any of the gene products of the instant sequences. These chimeric genes could then be introduced into appropriate microorganisms via transformation to provide high-level expression of the encoded enzymes.

Vectors or DNA cassettes useful for the transformation of suitable host cells are well known in the art. The specific choice of sequences present in the construct is dependent upon the desired expression products (supra), the nature of the host cell and the proposed means of separating transformed cells versus non-transformed cells. Typically, however, the vector or cassette contains sequences directing transcription and translation of the relevant gene(s), a selectable marker and sequences allowing autonomous replication or chromosomal integration. Suitable vectors comprise a region 5' of the gene that controls transcriptional initiation and a region 3' of the DNA fragment that controls transcriptional termination. It is most preferred when both control regions are derived from genes from the transformed host cell, although it is to be understood that such control regions need not be derived from the genes native to the specific species chosen as a production host.

Initiation control regions or promoters which are useful to drive expression of the instant ORFs in the desired host cell are numerous and familiar to those skilled in the art. Virtually any promoter capable of directing expression of these genes in the selected host cell is suitable for the present invention. Expression in a host cell can be accomplished in a transient or stable fashion. Transient expression can be accomplished by inducing the activity of a regulatable promoter operably linked to the gene of interest. Stable expression can be achieved by the use of a constituitive promoter operably linked to the gene of interest. As an example, when the host cell is yeast, transcriptional and translational regions functional in yeast cells are provided, particularly from the host species. The transcriptional initiation regulatory regions can be obtained, for example, from: 1.) genes in the glycolytic pathway, such as alcohol dehydrogenase, glyceraldehyde-3-phosphate-dehydrogenase (see U.S. patent application Ser. No. 10/869,630), phosphoglycerate mutase (see U.S. patent application Ser. No. 10/869,630), fructose-bisphosphate aldolase (see U.S. patent application Ser. No. 60/519,971), phosphoglucose-isomerase, phosphoglycerate kinase, glycerol-3-phosphate O-acyltransferase (see U.S. Patent Application No. 60/610,060), etc.; or, 2.) regulatable genes such as acid phosphatase, lactase, metallothionein, glucoamylase, the translation elongation factor EF1-α (TEF) protein (U.S. Pat. No. 6,265,185), ribosomal protein S7 (U.S. Pat. No. 6,265,185), etc. Any one of a number of regulatory sequences can be used, depending upon whether constitutive or induced transcription is desired, the efficiency of the promoter in expressing the ORF of interest, the ease of construction and the like.

Nucleotide sequences surrounding the translational initiation codon ATG have been found to affect expression in yeast cells. If any of the instant Δ15 desaturases are poorly expressed in yeast, the nucleotide sequences of exogenous genes can be modified to include an efficient yeast translation initiation sequence to obtain optimal gene expression. For expression in yeast, this can be done by site-directed mutagenesis of an inefficiently expressed gene by fusing it in-frame to an endogenous yeast gene, preferably a highly expressed gene. Alternatively, one can determine the consensus translation initiation sequence in the host and engineer this sequence into heterologous genes for their optimal expression in the host of interest (see, e.g., U.S. patent application Ser. No. 10/840478 for specific teachings applicable for *Yarrowia lipolytica*).

The termination region can be derived from the 3' region of the gene from which the initiation region was obtained or from a different gene. A large number of termination regions are known and function satisfactorily in a variety of hosts (when utilized both in the same and different genera and species from where they were derived). The termination region usually is selected more as a matter of convenience rather than because of any particular property. Preferably, the termination region is derived from a yeast gene, particularly Saccharomyces, Schizosaccharomyces, Candida, Yarrowia or Kluyveromyces. The 3'-regions of mammalian genes encoding γ-interferon and α-2 interferon are also known to function in yeast. Termination control regions may also be derived from various genes native to the preferred hosts. Optionally, a termination site may be unnecessary; however, it is most preferred if included.

As one of skill in the art is aware, merely inserting a gene into a cloning vector does not ensure that it will be successfully expressed at the level needed. In response to the need for a high expression rate, many specialized expression vectors have been created by manipulating a number of different genetic elements that control aspects of transcription, translation, protein stability, oxygen limitation, and secretion from the host cell. More specifically, some of the molecular features that have been manipulated to control gene expression include: 1.) the nature of the relevant transcriptional promoter and terminator sequences; 2.) the number of copies of the cloned gene and whether the gene is plasmid-borne or integrated into the genome of the host cell; 3.) the final cellular location of the synthesized foreign protein; 4.) the efficiency of translation in the host organism; 5.) the intrinsic stability of the cloned gene protein within the host cell; and 6.) the codon usage within the cloned gene, such that its frequency approaches the frequency of preferred codon usage of the host cell. Each of these types of modifications are encompassed in the present invention, as means to further optimize expression of the Δ15 desaturases described herein.

Transformation of Microbial Hosts

Once the DNA encoding a polypeptide suitable for expression in an appropriate microbial host has been obtained, it is placed in a plasmid vector capable of autonomous replication in a host cell, or it is directly integrated into the genome of the host cell. Integration of expression cassettes can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

Where two or more genes are expressed from separate replicating vectors, it is desirable that each vector has a different means of selection and should lack homology to the other construct(s) to maintain stable expression and prevent reassortment of elements among constructs. Judicious choice of regulatory regions, selection means and method of propagation of the introduced construct(s) can be experimentally determined so that all introduced genes are expressed at the necessary levels to provide for synthesis of the desired products.

Constructs comprising the gene of interest may be introduced into a host cell by any standard technique. These techniques include transformation (e.g., lithium acetate transformation [*Methods in Enzymology*, 194:186-187 (1991)]), protoplast fusion, biolistic impact, electroporation, microinjection, or any other method that introduces the gene of interest into the host cell. More specific teachings applicable for oleaginous yeast (i.e., *Yarrowia lipolytica*) include U.S. Pat. Nos. 4,880,741 and 5,071,764 and Chen, D. C. et al. (*Appl Microbiol Biotechnol.* 48(2):232-235 (1997)).

For convenience, a host cell that has been manipulated by any method to take up a DNA sequence (e.g., an expression cassette) will be referred to as "transformed" or "recombinant" herein. The transformed host will have at least one copy of the expression construct and may have two or more, depending upon whether the gene is integrated into the genome, amplified, or is present on an extrachromosomal element having multiple copy numbers. The transformed host cell can be identified by selection for a marker contained on the introduced construct. Alternatively, a separate marker construct may be co-transformed with the desired construct, as many transformation techniques introduce many DNA molecules into host cells. Typically, transformed hosts are selected for their ability to grow on selective media. Selective media may incorporate an antibiotic or lack a factor necessary for growth of the untransformed host, such as a nutrient or growth factor. An introduced marker gene may confer antibiotic resistance, or encode an essential growth factor or enzyme, thereby permitting growth on selective media when expressed in the transformed host. Selection of a transformed host can also occur when the expressed marker protein can be detected, either directly or indirectly. The marker protein may be expressed alone or as a fusion to another protein. The marker protein can be detected by: 1.) its enzymatic activity (e.g., β galactosidase can convert the substrate X-gal [5-bromo-4-chloro-3-indolyl-β-D-galactopyranoside] to a colored product; luciferase can convert luciferin to a light-emitting product); or 2.) its light-producing or modifying characteristics (e.g., the green fluorescent protein of *Aequorea victoria* fluoresces when illuminated with blue light). Alternatively, antibodies can be used to detect the marker protein or a molecular tag on, for example, a protein of interest. Cells expressing the marker protein or tag can be selected, for example, visually, or by techniques such as FACS or panning using antibodies. For selection of yeast transformants, any marker that functions in yeast may be used. Desirably, resistance to kanamycin, hygromycin and the amino glycoside G418 are of interest, as well as ability to grow on media lacking uracil or leucine.

Following transformation, substrates suitable for the instant Δ15 desaturases (and, optionally other PUFA enzymes that are co-expressed within the host cell) may be produced by the host either naturally or transgenically, or they may be provided exogenously.

Metabolic Engineering of ω-3 and/or ω-6 Fatty Acid Biosynthesis in Microbes

Knowledge of the sequences of the present Δ15 desaturases will be useful for manipulating ω-3 and/or ω-6 fatty acid biosynthesis in oleaginous yeast, and particularly, in *Yarrowia lipolytica*. This may require metabolic engineering directly within the PUFA biosynthetic pathway or additional manipulation of pathways that contribute carbon to the PUFA biosynthetic pathway. Methods useful for manipulating biochemical pathways are well known to those skilled in the art.

Techniques to Up-Regulate Desirable Biosynthetic Pathways

Additional copies of desaturase (and optionally elongase) genes may be introduced into the host to increase the output of the ω-3 and/or ω-6 fatty acid biosynthesis pathways, typically through the use of multicopy plasmids. Expression of desaturase and elongase genes also can be increased at the transcriptional level through the use of a stronger promoter (either regulated or constitutive) to cause increased expression, by removing/deleting destabilizing sequences from either the mRNA or the encoded protein, or by adding stabilizing sequences to the mRNA (U.S. Pat. No. 4,910,141). Yet another approach to increase expression of heterologous desaturase or elongase genes is to increase the translational efficiency of the encoded mRNAs by replacement of codons in the native gene with those for optimal gene expression in the selected host microorganism.

Techniques to Down-Regulate Undesirable Biosynthetic Pathways

Conversely, biochemical pathways competing with the ω-3 and/or ω-6 fatty acid biosynthesis pathways for energy or carbon, or native PUFA biosynthetic pathway enzymes that interfere with production of a particular PUFA end-product, may be eliminated by gene disruption or down-regulated by other means (e.g., antisense mRNA). For gene disruption, a foreign DNA fragment (typically a selectable marker gene) is inserted into the structural gene to be disrupted in order to interrupt its coding sequence and thereby functionally inactivate the gene. Transformation of the disruption cassette into the host cell results in replacement of the functional native gene by homologous recombination with the non-functional disrupted gene (see, for example: Hamilton et al. *J. Bacteriol.* 171:4617-4622 (1989); Balbas et al. *Gene* 136:211-213 (1993); Gueldener et al. *Nucleic Acids Res.* 24:2519-2524 (1996); and Smith et al. *Methods Mol. Cell. Biol.* 5:270-277 (1996)).

Antisense technology is another method of down-regulating genes when the sequence of the target gene is known. To accomplish this, a nucleic acid segment from the desired gene is cloned and operably linked to a promoter such that the anti-sense strand of RNA will be transcribed. This construct is then introduced into the host cell and the antisense strand of RNA is produced. Antisense RNA inhibits gene expression by preventing the accumulation of mRNA that encodes the protein of interest. The person skilled in the art will know that special considerations are associated with the use of antisense technologies in order to reduce expression of particular genes. For example, the proper level of expression of antisense genes may require the use of different chimeric genes utilizing different regulatory elements known to the skilled artisan.

Although targeted gene disruption and antisense technology offer effective means of down-regulating genes where the sequence is known, other less specific methodologies have been developed that are not sequence-based. For example, cells may be exposed to UV radiation and then screened for the desired phenotype. Mutagenesis with chemical agents is also effective for generating mutants and commonly used substances include chemicals that affect nonreplicating DNA (e.g., $HNO_2$ and $NH_2OH$), as well as agents that affect replicating DNA (e.g., acridine dyes, notable for causing frameshift mutations). Specific methods for creating mutants using radiation or chemical agents are well documented in the art. See, for example: Thomas D. Brock in *Biotechnology: A Textbook of Industrial Microbiology*, $2^{nd}$ ed. (1989) Sinauer Associates: Sunderland, Mass.; or Deshpande, Mukund V., *Appl. Biochem. Biotechnol.*, 36:227 (1992).

Another non-specific method of gene disruption is the use of transposable elements or transposons. Transposons are genetic elements that insert randomly into DNA but can be later retrieved on the basis of sequence to determine where the insertion has occurred. Both in vivo and in vitro transposition methods are known. Both methods involve the use of a transposable element in combination with a transposase enzyme. When the transposable element or transposon is contacted with a nucleic acid fragment in the presence of the transposase, the transposable element will randomly insert into the nucleic acid fragment. The technique is useful for random mutagenesis and for gene isolation, since the disrupted gene may be identified on the basis of the sequence of the transposable element. Kits for in vitro transposition are commercially available [see, for example: 1.) The Primer Island Transposition Kit, available from Perkin Elmer Applied Biosystems, Branchburg, N.J., based upon the yeast Ty1 element; 2.) The Genome Priming System, available from New England Biolabs, Beverly, Mass., based upon the bacterial transposon Tn7; and 3.) the EZ::TN Transposon Insertion Systems, available from Epicentre Technologies, Madison, Wis., based upon the Tn5 bacterial transposable element].

Within the context of the present invention, it may be useful to modulate the expression of the fatty acid biosynthetic pathway by any one of the methods described above. For example, the present invention provides genes (i.e., Δ15 desaturases) encoding key enzymes in the biosynthetic pathways leading to the production of ω-3 and/or ω-6 fatty acids. It will be particularly useful to express these genes in oleaginous yeast that produce insufficient amounts of 18:3 fatty acids and to modulate the expression of this and other PUFA biosynthetic genes to maximize production of preferred PUFA products using various means for metabolic engineering of the host organism. Likewise, to maximize PUFA production with these genes, it may be necessary to disrupt pathways that compete for the carbon flux directed toward PUFA biosynthesis. In alternate embodiments, it may be desirable to disrupt the Δ15 desaturase herein, to promote synthesis of ω-6 fatty acids while simultaneously preventing co-synthesis of ω-3 fatty acids. In another alternate embodiment it will be possible to regulate the production of ω-3 and/or ω-6 fatty acids by placing any of the present Δ15 desaturase genes under the control of inducible or regulated promoters.

Preferred Hosts for Recombinant Expression of Δ15 Desaturases

Host cells for expression of the instant genes and nucleic acid fragments may include microbial hosts that grow on a variety of feedstocks, including simple or complex carbohydrates, organic acids and alcohols, and/or hydrocarbons over a wide range of temperature and pH values. Although the genes described in the instant invention have been isolated for expression in an oleaginous yeast, and in particular *Yarrowia lipolytica*, it is contemplated that because transcription, translation and the protein biosynthetic apparatus is highly conserved, any bacteria, yeast, algae and/or filamentous fungus will be a suitable host for expression of the present nucleic acid fragments.

Preferred hosts are oleaginous organisms, such as oleaginous yeast. These oleaginous organisms are naturally capable of oil synthesis and accumulation, wherein the oil can comprise greater than about 25% of the cellular dry weight, more preferably greater than about 30% of the cellular dry weight, and most preferably greater than about 40% of the cellular dry weight. Genera typically identified as oleaginous yeast include, but are not limited to: *Yarrowia, Candida, Rhodotorula, Rhodosporidium, Cryptococcus, Trichosporon* and *Lipomyces*. More specifically, illustrative oil-synthesizing yeast include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus, R. graminis* and *Yarrowia lipolytica* (formerly classified as *Candida lipolytica*).

Most preferred is the oleaginous yeast *Yarrowia lipolytica*; and, in a further embodiment, most preferred are the *Yarrowia lipolytica* strains designated as ATCC #76982, ATCC #20362, ATCC #8862, ATCC #18944 and/or LGAM S(7)1 (Papanikolaou S., and Aggelis G., *Bioresour. Technol.* 82(1): 43-9 (2002)).

Other preferred microbial hosts include oleaginous bacteria, algae and other fungi; and, within this group of microbial hosts, of particular interest are microorganisms that synthesize ω-6 fatty acids such as GLA and ARA. Thus, for example, transformation of *Mortierella alpina* (which is commercially used for production of ARA) with the any of the present Δ15 desaturase genes under the control of inducible or regulated promoters could yield a transformant organism capable of synthesizing EPA. Furthermore, one could improve the ratio of ω-3 to ω-6 fatty acids is this genetically engineered organism by transforming those strains having a disruption or mutation in their native Δ12 desaturase (e.g., by introducing any of the present Δ15 desaturases into the locus of the native Δ12 gene, using means well known in the art). The method of transformation of *M. alpina* described by Mackenzie et al. (*Applied and Environmental Microbiology* 66:4655 (2000)).

Fermentation Processes for PUFA Production

The transformed microbial host cell is grown under conditions that optimize activity of fatty acid biosynthetic genes and produce the greatest and the most economical yield of fatty acids (e.g., ALA, which can in turn increase the production of various ω-3 fatty acids). In general, media conditions which may be optimized include the type and amount of carbon source, the type and amount of nitrogen source, the carbon-to-nitrogen ratio, the oxygen level, growth temperature, pH, length of the biomass production phase, length of the oil accumulation phase and the time of cell harvest. Microorganisms of interest, such as oleaginous yeast, are grown in complex media (e.g., yeast extract-peptone-dextrose broth (YPD)) or a defined minimal media that lacks a component necessary for growth and thereby forces selection of the desired expression cassettes (e.g., Yeast Nitrogen Base (DIFCO Laboratories, Detroit, Mich.)).

Fermentation media in the present invention must contain a suitable carbon source. Suitable carbon sources may include, but are not limited to: monosaccharides (e.g., glucose, fructose), disaccharides (e.g., lactose or sucrose), oligosaccharides, polysaccharides (e.g., starch, cellulose or mixtures thereof), sugar alcohols (e.g., glycerol) or mixtures from renewable feedstocks (e.g., cheese whey permeate, cornsteep liquor, sugar beet molasses, barley malt). Additionally, carbon sources may include alkanes, fatty acids, esters of fatty acids, monoglycerides, diglycerides, triglycerides, phospholipids and various commercial sources of fatty acids including vegetable oils (e.g., soybean oil) and animal fats. Additionally, the carbon substrate may include one-carbon substrates (e.g., carbon dioxide or methanol) for which metabolic conversion into key biochemical intermediates has been demonstrated. Hence it is contemplated that the source of carbon utilized in the present invention may encompass a wide variety of carbon-containing substrates and will only be limited by the choice of the host organism. Although all of the above mentioned carbon substrates and mixtures thereof are expected to be suitable in the present invention, preferred carbon substrates are sugars and/or fatty acids. Most preferred is glucose and/or fatty acids containing between 10-22 carbons.

Nitrogen may be supplied from an inorganic (e.g., $(NH_4)_2SO_4$) or organic source (e.g., urea or glutamate). In addition to appropriate carbon and nitrogen sources, the fermentation media must also contain suitable minerals, salts, cofactors, buffers, vitamins, and other components known to those skilled in the art, suitable for the growth of the microorganism and promotion of the enzymatic pathways necessary for PUFA production. Particular attention is given to several metal ions (e.g., $Mn^{+2}$, $Co^{+2}$, $Zn^{+2}$, $Mg^{+2}$) that promote synthesis of lipids and PUFAs (Nakahara, T. et al. *Ind. Appl. Single Cell Oils*, D. J. Kyle and R. Colin, eds. pp 61-97 (1992)).

Preferred growth media in the present invention are common commercially prepared media, such as Yeast Nitrogen Base (DIFCO Laboratories, Detroit, Mich.). Other defined or synthetic growth media may also be used and the appropriate medium for growth of the particular microorganism will be known by one skilled in the art of microbiology or fermentation science. A suitable pH range for the fermentation is typically between about pH 4.0 to pH 8.0, wherein pH 5.5 to pH 7.0 is preferred as the range for the initial growth conditions. The fermentation may be conducted under aerobic or anaerobic conditions, wherein microaerobic conditions are preferred.

Typically, accumulation of high levels of PUFAs in oleaginous yeast cells requires a two-stage process, since the metabolic state must be "balanced" between growth and synthesis/storage of fats. Thus, most preferably, a two-stage fermentation process is necessary for the production of PUFAs in oleaginous yeast. In this approach, the first stage of the fermentation is dedicated to the generation and accumulation of cell mass and is characterized by rapid cell growth and cell division. In the second stage of the fermentation, it is preferable to establish conditions of nitrogen deprivation in the culture to promote high levels of lipid accumulation. The effect of this nitrogen deprivation is to reduce the effective concentration of AMP in the cells, thereby reducing the activity of the NAD-dependent isocitrate dehydrogenase of mitochondria. When this occurs, citric acid will accumulate, thus forming abundant pools of acetyl-CoA in the cytoplasm and priming fatty acid synthesis. Thus, this phase is characterized by the cessation of cell division followed by the synthesis of fatty acids and accumulation of oil.

Although cells are typically grown at about 30° C., some studies have shown increased synthesis of unsaturated fatty acids at lower temperatures (Yongmanitchai and Ward, *Appl. Environ. Microbiol.* 57:419-25 (1991)). Based on process economics, this temperature shift should likely occur after the first phase of the two-stage fermentation, when the bulk of the organisms' growth has occurred.

It is contemplated that a variety of fermentation process designs may be applied, where commercial production of omega fatty acids using the instant Δ15 desaturase genes is desired. For example, commercial production of PUFAs from a recombinant microbial host may be produced by a batch, fed-batch or continuous fermentation process.

A batch fermentation process is a closed system wherein the media composition is set at the beginning of the process and not subject to further additions beyond those required for maintenance of pH and oxygen level during the process. Thus, at the beginning of the culturing process the media is inoculated with the desired organism and growth or metabolic activity is permitted to occur without adding additional substrates (i.e., carbon and nitrogen sources) to the medium. In batch processes the metabolite and biomass compositions of the system change constantly up to the time the culture is terminated. In a typical batch process, cells moderate through a static lag phase to a high-growth log phase and finally to a stationary phase, wherein the growth rate is diminished or halted. Left untreated, cells in the stationary phase will eventually die. A variation of the standard batch process is the fed-batch process, wherein the substrate is continually added to the fermentor over the course of the fermentation process. A fed-batch process is also suitable in the present invention. Fed-Batch processes are useful when catabolite repression is apt to inhibit the metabolism of the cells or where it is desirable to have limited amounts of substrate in the media at any one time. Measurement of the substrate concentration in fed-batch systems is difficult and therefore may be estimated on the basis of the changes of measurable factors such as pH, dissolved oxygen and the partial pressure of waste gases (e.g., $CO_2$). Batch and fed-batch culturing methods are common and well known in the art and examples may be found in Thomas D. Brock in *Biotechnology: A Textbook of Industrial Microbiology*, $2^{nd}$ ed., (1989) Sinauer Associates: Sunderland, Mass.; or Deshpande, Mukund V., *Appl. Biochem. Biotechnol.*, 36:227 (1992), herein incorporated by reference.

Commercial production of omega fatty acids using the instant Δ15 desaturases may also be accomplished by a continuous fermentation process wherein a defined media is continuously added to a bioreactor while an equal amount of culture volume is removed simultaneously for product recovery. Continuous cultures generally maintain the cells in the log phase of growth at a constant cell density. Continuous or semi-continuous culture methods permit the modulation of one factor or any number of factors that affect cell growth or end product concentration. For example, one approach may limit the carbon source and allow all other parameters to moderate metabolism. In other systems, a number of factors affecting growth may be altered continuously while the cell concentration, measured by media turbidity, is kept constant. Continuous systems strive to maintain steady state growth and thus the cell growth rate must be balanced against cell loss due to media being drawn off the culture. Methods of modulating nutrients and growth factors for continuous culture processes, as well as techniques for maximizing the rate of product formation, are well known in the art of industrial microbiology and a variety of methods are detailed by Brock, supra.

Purification Of PUFAs

The PUFAs may be found in the host microorganism as free fatty acids or in esterified forms such as acylglycerols, phospholipids, sulfolipids or glycolipids, and may be extracted from the host cell through a variety of means well-known in the art. One review of extraction techniques, quality analysis and acceptability standards for yeast lipids is that of Z. Jacobs (*Critical Reviews in Biotechnology* 12(5/6):463-491 (1992)). A brief review of downstream processing is also available by A. Singh and O. Ward (*Adv. Appl. Microbiol.* 45:271-312 (1997)).

In general, means for the purification of PUFAs may include extraction with organic solvents, sonication, supercritical fluid extraction (e.g., using carbon dioxide), saponification, and physical means such as presses, or combinations thereof. Of particular interest is extraction with methanol and chloroform in the presence of water (E. G. Bligh & W. J. Dyer, *Can. J. Biochem. Physiol.* 37:911-917 (1959)). Where desirable, the aqueous layer can be acidified to protonate negatively-charged moieties and thereby increase partitioning of desired products into the organic layer. After extraction, the organic solvents can be removed by evaporation under a stream of nitrogen. When isolated in conjugated forms, the products may be enzymatically or chemically cleaved to release the free fatty acid or a less complex conjugate of interest, and can then be subject to further manipulations to produce a desired end product. Desirably, conjugated forms of fatty acids are cleaved with potassium hydroxide.

If further purification is necessary, standard methods can be employed. Such methods may include extraction, treatment with urea, fractional crystallization, HPLC, fractional distillation, silica gel chromatography, high-speed centrifugation or distillation, or combinations of these techniques. Protection of reactive groups, such as the acid or alkenyl groups, may be done at any step through known techniques (e.g., alkylation or iodination). Methods used include methylation of the fatty acids to produce methyl esters. Similarly, protecting groups may be removed at any step. Desirably, purification of fractions containing GLA, STA, ARA, DHA and EPA may be accomplished by treatment with urea and/or fractional distillation.

Production of ω-3 and/or ω-6 Fatty Acids in Plants

The coding regions of the invention can be expressed in plants, in particular, oilseed plants. This is accomplished by: 1.) construction of chimeric genes (comprising a Δ15 desaturase of the present invention under the control of suitable regulatory sequences such as promoters and 3' transcription terminators); 2.) transformation of the chimeric genes into appropriate plant hosts; and 3.) expression of said chimeric genes for production of PUFAs.

Thus, the instant invention concerns a recombinant construct for altering the total fatty acid profile of mature seeds of an oilseed plant to produce an oil having an omega 3:omega 6 ratio of greater than 0.4, said construct comprising an isolated nucleic acid fragment selected from the group consisting of:
 (a) an isolated nucleic acid fragment encoding all or part of the amino acid sequence as set forth in SEQ ID NO:2;
 (b) an isolated nucleic acid fragment that hybridizes with (a) when washed with 0.1×SSC, 0.1% SDS, 65° C.;
 (c) an isolated nucleic acid fragment encoding an amino acid sequence having at least 46.2% sequence identity with the amino acid sequences set forth in SEQ ID NOs:2, 6, 10, 14, 18 based on the Clustal V method of alignment; or
 (d) an isolated nucleic acid fragment that is completely complementary to (a), (b), or (c)
 wherein said isolated nucleic acid fragment is operably linked to at least one regulatory sequence.

The ratio of omega3 to omega6 can range from about 2:5 to at least about 45:1. Useful ratios include but are not limited to omega3 from about 3, 4, 5, 6, 7, 8, 9, 10, 11, 12, 13, 14, 15, 17, 18, 19, 20, 23, 24, 27, 29, 31, 36, 42 and 45, versus omega 6 of about one. Other useful omega3 to omega 6 ratios include, but are not limited to 2:5, 3:5, 4:5, 1:1, and 2:1. It is believed that any integer ratio of omega 3 to omega6 from at least about 2:5 to at least about 45:1 would be useful.

The isolated nucleic acid fragment described herein that was isolated from *Fusarium moniliforme* can be used to practice the invention.

This invention also concerns oilseed plants, plant cells, plant tissues and/or plant parts comprising in their genome the recombinant construct of the invention.

In still a further aspect, this invention also concerns seeds obtained from these transformed oilseed plants, oil obtained from these seeds, products obtained from the processing of the oil, use of this oil in food, animal feed or an industrial application, use of the by-products in food or animal feed.

The present invention provides a variety of plant hosts for transformation with the Δ-15 desaturases described herein. Plants so transformed can be monocotyledonous plants or dicotyledonous plants, and preferably they belong to a class of plants identified as oleaginous (e.g., oilseed plants). Examples of preferred oilseed plant hosts include, but are not limited to, soybean (*Glycine* and *Soja* sp.), corn (*Zea mays*), flax (*Linum* sp.), rapeseed (*Brassica* sp.), primrose, canola, maize, safflower (*Carthamus* sp.) and sunflower (*Helianthus* sp.).

Genetically, modified plants of the present invention are produced by overexpression of the instant Δ-15 desaturases. This may be accomplished by first constructing chimeric genes in which the Δ15 desaturase coding region is operably-linked to control sequences capable of directing expression of the gene in the desired tissues at the desired stage of development. These control sequences may comprise a promoter, enhancer, silencer, intron sequences, 3'UTR and/or 5'UTR regions, and protein and/or RNA stabilizing elements. Such elements may vary in their strength and specificity. For reasons of convenience, the chimeric genes may comprise promoter sequences and translation leader sequences derived from the same genes. 3' Non-coding sequences encoding transcription termination signals must also be provided. It is preferred that the chimeric gene be introduced via a vector and that the vector harboring the Δ15 desaturase sequence also contain one or more selectable marker genes so that cells transformed with the chimeric gene can be selected from non-transformed cells.

The present invention makes use of a variety of plant promoters to drive the expression of the Δ15 desaturase gene(s) described herein or functional fragments thereof. Any promoter functional in a plant will be suitable, including (but not limited to): constitutive plant promoters, plant tissue-specific promoters, plant development-stage specific promoters, inducible plant promoters, viral promoters, male germline-specific promoters, female germline-specific promoters, flower-specific promoters and vegetative shoot apical meristem-specific promoters.

As was noted above, a promoter is a DNA sequence that directs cellular machinery of a plant to produce RNA from the contiguous coding sequence downstream (3') of the promoter. The promoter region influences the rate, developmental stage, and cell type in which the RNA transcript of the gene is made. The RNA transcript is processed to produce messenger RNA (mRNA) which serves as a template for translation of the RNA sequence into the amino acid sequence of the encoded polypeptide. The 5' non-translated leader sequence is a region of the mRNA upstream of the protein coding region that may play a role in initiation and translation of the mRNA. The 3' transcription termination/polyadenylation signal is a non-translated region downstream of the protein coding region that functions in the plant cells to cause termination of the RNA transcript and the addition of polyadenylate nucleotides to the 3' end of the RNA.

The origin of the promoter chosen to drive expression of the coding sequence is not important as long as it has sufficient transcriptional activity to accomplish the invention by expressing translatable mRNA for the desired nucleic acid fragments in the desired host tissue at the right time. Either heterologous or non-heterologous (i.e., endogenous) promoters can be used to practice the invention.

Suitable promoters which can be used to practice the invention include, but are not limited to, the alpha prime subunit of beta conglycinin promoter, Kunitz trypsin inhibitor 3 promoter, annexin promoter, Gly1 promoter, beta subunit of beta conglycinin promoter, P34/Gly Bd m 30K promoter, albumin promoter, Leg A1 promoter and Leg A2 promoter. The level of activity of the annexin, or P34, promoter is comparable to that of many known strong promoters, such as the CaMV 35S promoter (Atanassova et al., (1998) *Plant Mol. Biol.* 37:275-285; Battraw and Hall, (1990) *Plant Mol. Biol.* 15:527-538; Holtorf et al., (1995) *Plant Mol. Biol.* 29:637-646; Jefferson et al., (1987) *EMBO J.* 6:3901-3907; Wilmink et al., (1995) *Plant Mol. Biol.* 28:949-955), the Arabidopsis oleosin promoters (Plant et al., (1994) *Plant Mol. Biol.* 25:193-205; Li, (1997) Texas A&M University Ph.D. dissertation, pp. 107-128), the Arabidopsis ubiquitin extension protein promoters (Callis et al., 1990), a tomato ubiquitin gene promoter (Rollfinke et al., 1998), a soybean heat shock protein promoter (Schoffl et al., 1989), and a maize H3 histone gene promoter (Atanassova et al., 1998).

Expression of chimeric genes in most plant cells makes the annexin or P34 promoter, which constitutes the subject matter of WO 2004/071178, published on Aug. 26, 2004 especially useful when seed specific expression of a target heterologous nucleic acid fragment is required. Another useful feature of the annexin promoter is its expression profile in developing seeds. The annexin promoter of the invention is most active in developing seeds at early stages (before 10 days after pollination) and is largely quiescent in later stages. The expression profile of the annexin promoter is different from that of many seed-specific promoters, e.g., seed storage protein promoters, which often provide highest activity in later stages of development (Chen et al., (1989) *Dev. Genet.* 10:112-122; Ellerstrom et al., (1996) *Plant Mol. Biol.* 32:1019-1027; Keddie et al., (1994) *Plant Mol. Biol.* 24:327-340; Plant et al., (1994) *Plant Mol. Biol.* 25:193-205; Li, (1997) Texas A&M University Ph.D. dissertation, pp.107-128). The P34 promoter has a more conventional expression profile but remains distinct from other known seed specific promoters. Thus, the annexin, or P34, promoter will be a very attractive candidate when overexpression, or suppression, of a gene in embryos is desired at an early developing stage. For example, it may be desirable to overexpress a gene regulating early embryo development or a gene involved in the metabolism prior to seed maturation.

The promoter is then operably linked in a sense orientation using conventional means well known to those skilled in the art.

Once the recombinant construct has been made, it may then be introduced into the oilseed plant cell of choice by methods well known to those of ordinary skill in the art including, for example, transfection, transformation and electroporation as described above. The transformed plant cell is then cultured and regenerated under suitable conditions permitting expression of the PUFA which is then recovered and purified.

The recombinant constructs of the invention may be introduced into one plant cell or, alternatively, each construct may be introduced into separate plant cells.

Expression in a plant cell may be accomplished in a transient or stable fashion as is described above.

The desired PUFAs can be expressed in seed. Also within the scope of this invention are seeds or plant parts obtained from such transformed plants.

Plant parts include differentiated and undifferentiated tissues, including but not limited to, roots, stems, shoots, leaves, pollen, seeds, tumor tissue, and various forms of cells and culture such as single cells, protoplasts, embryos, and callus tissue. The plant tissue may be in plant or in organ, tissue or cell culture.

Methods for transforming dicots, primarily by use of *Agrobacterium tumefaciens*, and obtaining transgenic plants have been published, among others, for cotton (U.S. Pat. No. 5,004,863, U.S. Pat. No. 5,159,135); soybean (U.S. Pat. No. 5,569,834, U.S. Pat. No. 5,416,011); Brassica (U.S. Pat. No. 5,463,174); peanut (Cheng et al. (1996) *Plant Cell Rep.* 15:653-657, McKently et al. (1995) *Plant Cell Rep.* 14:699-703); papaya (Ling, K. et al. (1991) *Bio/technology* 9:752-758); and pea (Grant et al. (1995) *Plant Cell Rep.* 15:254-258). For a review of other commonly used methods of plant transformation see Newell, C. A. (2000) *Mol. Biotechnol.* 16:53-65. One of these methods of transformation uses *Agrobacterium rhizogenes* (Tepfler, M. and Casse-Delbart, F. (1987) *Microbiol. Sci.* 4:24-28). Transformation of soybeans using direct delivery of DNA has been published using PEG fusion (PCT publication WO 92/17598), electroporation (Chowrira, G. M. et al. (1995) *Mol. Biotechnol.* 3:17-23; Christou, P. et al. (1987) *Proc. Natl. Acad. Sci. U.S.A.* 84:3962-3966), microinjection, or particle bombardment (McCabe, D. E. et. al. (1988) *Bio/Technology* 6:923; Christou et al. (1988) *Plant Physiol.* 87:671-674).

There are a variety of methods for the regeneration of plants from plant tissue. The particular method of regeneration will depend on the starting plant tissue and the particular plant species to be regenerated. The regeneration, development and cultivation of plants from single plant protoplast transformants or from various transformed explants is well known in the art (Weissbach and Weissbach, (1988) In.: Methods for Plant Molecular Biology, (Eds.), Academic Press, Inc., San Diego, Calif.). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant DNA fragments and recombinant expression constructs and the screening and isolating of clones, (see for example, Sambrook et al. (1989) Molecular Cloning: A Laboratory Manual, Cold Spring Harbor Press; Maliga et al. (1995) Methods in Plant Molecular Biology, Cold Spring Harbor Press; Birren et al. (1998) Genome Analysis: Detecting Genes, 1, Cold Spring Harbor, N.Y.; Birren et al. (1998) Genome Analysis: Analyzing DNA, 2, Cold Spring Harbor, N.Y.; Plant Molecular Biology: A Laboratory Manual, eds. Clark, Springer, New York (1997)).

In another aspect, this invention concerns a method for increasing the ratio of omega-3 fatty acids to omega-6 fatty acids in an oilseed plant comprising:
- a) transforming an oilseed plant cell of with the recombinant construct of the invention
- b) regenerating an oilseed plant from the transformed plant cell of step (a);
- c) selecting those transformed plants having an increased ratio of omega-3 fatty acids to omega-6 fatty acid compared to the ratio of omega-3 fatty acids to omega-6 fatty acid in an untransformed plant.

In still a further aspect, this invention concerns a method for producing alpha-linolenic acid in seed of an oilseed plant wherein the alpha-linolenic acid content of the oil in the seed is at least 25% of the total fatty acid content of the seed oil, said method comprising:
- a) transforming an oilseed plant cell of with the recombinant construct of the invention
- b) regenerating an oilseed plant from the transformed plant cell of step (a);
- c) selecting those transformed plants having at least 25% alpha-linolenic acid of the total fatty acid content of the seed oil.

The alpha-linolenic content of the oil in such seeds can range from at least 25% to about 89% or any integer percentage between 25% and 89%, e.g., 26%, 27%, etc.

The invention also concerns oilseed plants, plant cells, plant tissues and/or plant parts comprising in their genome the recombinant construct of the invention made by the methods of this invention.

In still a further aspect, this invention also concerns seeds obtained from these transformed oilseed plants, oil obtained from these seeds, products obtained from the processing of the oil, use of this oil in food, animal feed or an industrial application, use of the by-products in food or animal feed.

Methods of isolating seed oils are well known in the art: (Young et al, Processing of Fats and Oils, in "The Lipid Handbook" (Gunstone et al eds.) Chapter 5 pp 253-257; London, Chapman & Hall, 1994).

The altered seed oils can then be added to nutritional compositions such as a nutritional supplement, food products, infant formula, animal feed, pet food and the like.

Compared to other vegetable oils, the oils of the invention are believed to function similarly to other oils in food applications from a physical standpoint. Partially hydrogenated oils, such as soybean oil, are widely used as ingredients for soft spreads, margarine and shortenings for baking and frying.

Examples of food products or food analogs into which altered seed oils or altered seeds of the invention may be incorporated include a meat product such as a processed meat product, a cereal food product, a snack food product, a baked goods product, a fried food product, a health food product, an infant formula, a beverage, a nutritional supplement, a dairy product, a pet food product, animal feed or an aquaculture food product. Food analogs can be made use processes well known to those skilled in the art. U.S. Pat. Nos. 6,355,296 B1 and 6,187,367 B1 describe emulsified meat analogs and emulsified meat extenders. U.S. Pat. No. 5,206,050 B1 describes soy protein curd useful for cooked food analogs (also can be used as a process to form a curd useful to make food analogs). U.S. Pat. No. 4,284,656 to Hwa describes a soy protein curd useful for food analogs. U.S. Pat. No. 3,988,485 to Hibbert et al. describes a meat-like protein food formed from spun vegetable protein fibers. U.S. Pat. No. 3,950,564 to Puski et al. describes a process of making a soy based meat substitute and U.S. Pat. No. 3,925,566 to Reinhart et al. describes a simulated meat product. For example, soy protein that has been processed to impart a structure, chunk or fiber for use as a food ingredient is called "textured soy protein" (TSP). TSPs are frequently made to resemble meat, seafood, or poultry in structure and appearance when hydrated.

There can be mentioned meat analogs, cheese analogs, milk analogs and the like.

Meat analogs made from soybeans contain soy protein or tofu and other ingredients mixed together to simulate various kinds of meats. These meat alternatives are sold as frozen, canned or dried foods. Usually, they can be used the same way as the foods they replace. Meat alternatives made from soybeans are excellent sources of protein, iron and B vitamins. Examples of meat analogs include, but are not limited to, ham analogs, sausage analogs, bacon analogs, and the like.

Food analogs can be classified as initiation or substitutes depending on their functional and compositional characteristics. For example, an imitation cheese need only resemble the cheese it is designed to replace. However, a product can generally be called a substitute cheese only if it is nutritionally equivalent to the cheese it is replacing and meets the minimum compositional requirements for that cheese. Thus, substitute cheese will often have higher protein levels than imitation cheeses and be fortified with vitamins and minerals.

Milk analogs or nondairy food products include, but are not limited to, imitation milk, nondairy frozen desserts such as those made from soybeans and/or soy protein products.

Meat products encompass a broad variety of products. In the United States "meat" includes "red meats" produced from cattle, hogs and sheep. In addition to the red meats there are poultry items which include chickens, turkeys, geese, guineas, ducks and the fish and shellfish. There is a wide assortment of seasoned and processes meat products: fresh, cured and fried, and cured and cooked. Sausages and hot dogs are examples of processed meat products. Thus, the term "meat products" as used herein includes, but is not limited to, processed meat products.

A cereal food product is a food product derived from the processing of a cereal grain. A cereal grain includes any plant from the grass family that yields an edible grain (seed). The most popular grains are barley, corn, millet, oats, quinoa, rice, rye, sorghum, triticale, wheat and wild rice. Examples of a cereal food product include, but are not limited to, whole grain, crushed grain, grits, flour, bran, germ, breakfast cereals, extruded foods, pastas, and the like.

A baked goods product comprises any of the cereal food products mentioned above and has been baked or processed in a manner comparable to baking, i.e., to dry or harden by subjecting to heat. Examples of a baked good product include, but are not limited to bread, cakes, doughnuts, bread crumbs, baked snacks, mini-biscuits, mini-crackers, mini-cookies, and mini-pretzels. As was mentioned above, oils of the invention can be used as an ingredient.

In general, soybean oil is produced using a series of steps involving the extraction and purification of an edible oil product from the oil bearing seed. Soybean oils and soybean byproducts are produced using the generalized steps shown in the diagram below.

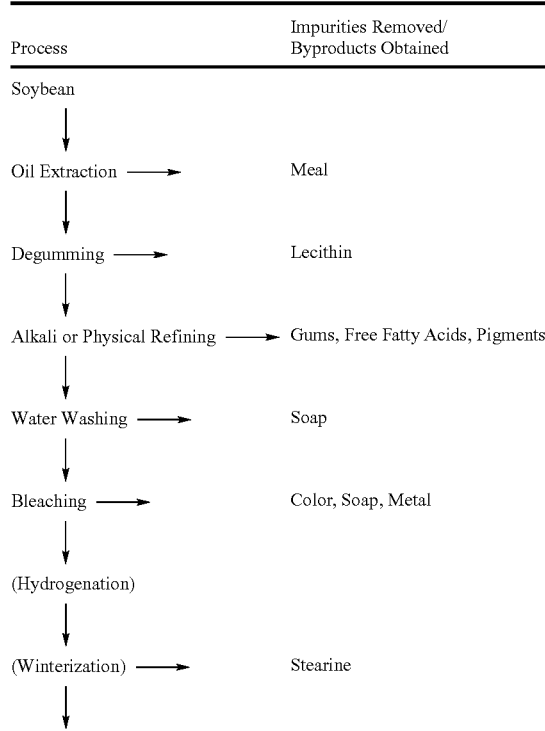

| Process | Impurities Removed/ Byproducts Obtained |
|---|---|
| Soybean | |
| ↓ | |
| Oil Extraction → | Meal |
| ↓ | |
| Degumming → | Lecithin |
| ↓ | |
| Alkali or Physical Refining → | Gums, Free Fatty Acids, Pigments |
| ↓ | |
| Water Washing → | Soap |
| ↓ | |
| Bleaching → | Color, Soap, Metal |
| ↓ | |
| (Hydrogenation) | |
| ↓ | |
| (Winterization) → | Stearine |
| ↓ | |

-continued

| Process | Impurities Removed/ Byproducts Obtained |
|---|---|
| Deodorization → | FFA, Tocopherols, Sterols, Volatiles |
| ↓ | |
| Oil Products | |

Soybean seeds are cleaned, tempered, dehulled, and flaked which increases the efficiency of oil extraction. Oil extraction is usually accomplished by solvent (hexane) extraction but can also be achieved by a combination of physical pressure and/or solvent extraction. The resulting oil is called crude oil. The crude oil may be degummed by hydrating phospholipids and other polar and neutral lipid complexes that facilitate their separation from the nonhydrating, triglyceride fraction (soybean oil). The resulting lecithin gums may be further processed to make commercially important lecithin products used in a variety of food and industrial products as emulsification and release (antisticking) agents. The term lecithin itself has different meanings when used in chemistry and biochemistry than when used commercially. Chemically, lecithin is phosphatidylcholine. Commercially, it refers to a natural mixture of neutral and polar lipids. Phosphatidylcholine, which is a polar lipid, is present in commercial lecithin in concentrations of 20 to 90%. Lecithins containing phosphatidylcholine are produced from vegetable, animal and microbial sources, but mainly from vegetable sources. Soybean, sunflower and rapeseed are the major plant sources of commercial lecithin. Soybean is the most common source. Plant lecithins are considered to be GRAS (generally regarded as safe). Degummed oil may be further refined for the removal of impurities; primarily free fatty acids, pigments, and residual gums. Refining is accomplished by the addition of a caustic agent that reacts with free fatty acid to form soap and hydrates phosphatides and proteins in the crude oil. Water is used to wash out traces of soap formed during refining. The soapstock byproduct may be used directly in animal feeds or acidulated to recover the free fatty acids. Color is removed through adsorption with a bleaching earth that removes most of the chlorophyll and carotenoid compounds. The refined oil can be hydrogenated resulting in fats with various melting properties and textures. Winterization (fractionation) may be used to remove stearine from the hydrogenated oil through crystallization under carefully controlled cooling conditions. Deodorization which is principally steam distillation under vacuum, is the last step and is designed to remove compounds which impart odor or flavor to the oil. Other valuable byproducts such as tocopherols and sterols may be removed during the deodorization process. Deodorized distillate containing these byproducts may be sold for production of natural vitamin E and other high-value pharmaceutical products. Refined, bleached, (hydrogenated, fractionated) and deodorized oils and fats may be packaged and sold directly or further processed into more specialized products. A more detailed reference to soybean seed processing, soybean oil production and byproduct utilization can be found in Erickson, 1995, Practical Handbook of Soybean Processing and Utilization, The American Oil Chemists' Society and United Soybean Board.

Soybean oil is liquid at room temperature because it is relatively low in saturated fatty acids when compared with oils such as coconut, palm, palm kernel and cocoa butter. Many processed fats, including spreads, confectionary fats, hard butters, margarines, baking shortenings, etc., require varying degrees of solidity at room temperature and can only be produced from soybean oil through alteration of its physical properties. This is most commonly achieved through catalytic hydrogenation.

Hydrogenation is a chemical reaction in which hydrogen is added to the unsaturated fatty acid double bonds with the aid of a catalyst such as nickel. High oleic soybean oil contains unsaturated oleic, linoleic, and linolenic fatty acids and each of these can be hydrogenated. Hydrogenation has two primary effects. First, the oxidative stability of the oil is increased as a result of the reduction of the unsaturated fatty acid content. Second, the physical properties of the oil are changed because the fatty acid modifications increase the melting point resulting in a semi-liquid or solid fat at room temperature.

There are many variables which affect the hydrogenation reaction which in turn alter the composition of the final product. Operating conditions including pressure, temperature, catalyst type and concentration, agitation and reactor design are among the more important parameters which can be controlled. Selective hydrogenation conditions can be used to hydrogenate the more unsaturated fatty acids in preference to the less unsaturated ones. Very light or brush hydrogenation is often employed to increase stability of liquid oils. Further hydrogenation converts a liquid oil to a physically solid fat. The degree of hydrogenation depends on the desired performance and melting characteristics designed for the particular end product. Liquid shortenings, used in the manufacture of baking products, solid fats and shortenings used for commercial frying and roasting operations, and base stocks for margarine manufacture are among the myriad of possible oil and fat products achieved through hydrogenation. A more detailed description of hydrogenation and hydrogenated products can be found in Patterson, H. B. W., 1994, Hydrogenation of Fats and Oils: Theory and Practice. The American Oil Chemists' Society.

Hydrogenated oils have also become controversial due to the presence of trans fatty acid isomers that result from the hydrogenation process. Ingestion of large amounts of trans isomers has been linked with detrimental health effects including increased ratios of low density to high density lipoproteins in the blood plasma and increased risk of coronary heart disease.

A snack food product comprises any of the above or below described food products.

A fried food product comprises any of the above or below described food products that has been fried.

A health food product is any food product that imparts a health benefit. Many oilseed-derived food products may be considered as health foods.

The beverage can be in a liquid or in a dry powdered form.

For example, there can be mentioned non-carbonated drinks; fruit juices, fresh, frozen, canned or concentrate; flavored or plain milk drinks, etc. Adult and infant nutritional formulas are well known in the art and commercially available (e.g., Similac®, Ensure®, Jevity®, and Alimentum® from Ross Products Division, Abbott Laboratories).

Infant formulas are liquids or reconstituted powders fed to infants and young children. They serve as substitutes for human milk. Infant formulas have a special role to play in the diets of infants because they are often the only source of nutrients for infants. Although breast-feeding is still the best nourishment for infants, infant formula is a close enough second that babies not only survive but thrive. Infant formula is becoming more and more increasingly close to breast milk.

A dairy product is a product derived from milk. A milk analog or nondairy product is derived from a source other than milk, for example, soymilk as was discussed above. These products include, but are not limited to, whole milk, skim milk, fermented milk products such as yogurt or sour milk, cream, butter, condensed milk, dehydrated milk, coffee whitener, coffee creamer, ice cream, cheese, etc.

A pet food product is a product intended to be fed to a pet such as a dog, cat, bird, reptile, fish, rodent and the like. These products can include the cereal and health food products above, as well as meat and meat byproducts, soy protein products, grass and hay products, including but not limited to alfalfa, timothy, oat or brome grass, vegetables and the like.

Animal feed is a product intended to be fed to animals such as turkeys, chickens, cattle and swine and the like. As with the pet foods above, these products can include cereal and health food products, soy protein products, meat and meat byproducts, and grass and hay products as listed above.

Aqualculture feed is a product intended to be used in aqua-farming which concerns the propagation, cultivation or farming of aquatic organisms, animals and/or plants in fresh or marine waters.

In yet another embodiment, this invention includes oil obtained from the seeds of such plants.

In yet another aspect, the invention concerns a recombinant construct for altering the total fatty acid profile of mature seeds of an oilseed plant to produce an oil having an omega 3 to omega 6 ratio greater than 2, wherein said oil has an eicosapentaenoic acid content greater than 2%, said construct comprising an isolated nucleic acid fragment selected from the group consisting of:

(a) an isolated nucleic acid fragment encoding all or part of the amino acid sequence as set forth in SEQ ID NO:2;

(b) an isolated nucleic acid fragment that hybridizes with (a) when washed with 0.1×SSC, 0.1% SDS, 65° C.;

(c) an isolated nucleic acid fragment encoding an amino acid sequence having at least 46.2% sequence identity with the amino acid sequences set forth in SEQ ID NOs:2, 6, 10, 14,18 based on the Clustal V method of alignment; or (d) an isolated nucleic acid fragment that is completely complementary to (a), (b), or (c)

wherein said isolated nucleic acid fragment is operably linked to at least one regulatory sequence.

Also, this invention concerns oilseed plants, plant cells, plant tissues, or plant parts comprising in their genomes the recombinant construct of the invention. The invention also concerns the seeds obtained from such plants, oil obtained from these seeds, use of this oil in food or animal feed, by-products obtained from the processing of this oil and use of these by-products in food or animal feed.

Additionally the invention provides microbial oils produced by the methods of the invention.

In still another aspect, the present invention concerns a method for producing eicosapentaenoic acid in seed of an oilseed plant to produce an oil having an omega 3 to omega 6 ratio greater than 2, wherein said oil has an eicosapentaenoic acid content greater than 2% of the total fatty acid content of the seed oil, said method comprising:

a) transforming an oilseed plant cell of with the recombinant construct of the present invention;

b) regenerating an oilseed plant from the transformed plant cell of step (a);

c) selecting those transformed plants having at least 2% eicosapentaenoic acid of the total fatty acid content of the seed oil.

Additionally, this invention concerns oilseed plants, plant cells, plant tissues, or plant parts comprising in their genomes the recombinant construct of the invention. The invention also concerns the seeds obtained from such plants, oil obtained from these seeds, use of this oil in food or animal feed, by-products obtained from the processing of this oil and use of these by-products in food or animal feed.

Additionally the invention provides microbial oils produced by the methods of the invention.

Various plasmids and vectors comprising the chimeric Δ15 desaturase genes can then be constructed, using methods which are well known to those skilled in the art; see, for example, the techniques described in Sambrook et al., *Molecular Cloning: A Laboratory Manual*, $2^{nd}$ ed., Cold Spring Harbor Laboratory: Cold Spring Harbor, N.Y., 1989 (hereinafter "Maniatus"); and by Ausubel et al., *Current Protocols in Molecular Biology*, published by Greene Publishing Assoc. and Wiley-Interscience (1987).

The choice of a plasmid vector depends upon the method that will be used to transform host plants. The skilled artisan is well aware of the genetic elements that must be present on the plasmid vector in order to successfully transform, select and propagate host cells containing the chimeric gene. For example, the termination signals usually employed are from the Nopaline Synthase promoter or from the CAMV 35S promoter. A plant translational enhancer often used is the tobacco mosaic virus (TMV) omega sequences; additionally, the inclusion of an intron (e.g., Intron-1 from the Shrunken gene of maize) has been shown to increase expression levels by up to 100-fold (Mait, *Transgenic Res.* 6:143-156 (1997); Ni, *Plant Journal* 7:661-676 (1995)). Additional regulatory elements may include transcriptional (as well as translational) enhancers.

In addition to the regulatory elements described above for a preferred expression vector, it is also useful for the vector to comprise a selectable and/or scorable marker. Preferably, the marker gene is an antibiotic resistance gene whereby the appropriate antibiotic can be used to select for transformed cells from among those cells that were not transformed. Selectable marker genes useful for the selection of transformed plant cells, callus, plant tissue and plants are well known to those skilled in the art. Examples include, but are not limited to: npt, which confers resistance to the aminoglycosides neomycin, kanamycin and paromycin; hygro, which confers resistance to hygromycin; trpB, which allows cells to utilize indole in place of tryptophan; hisD, which allows cells to utilize histinol in place of histidine (Hartman, *Proc. Natl. Acad. Sci. USA* 85:8047 (1988)); mannose-6-phosphate isomerase, which allows cells to utilize mannose (WO 94/20627); ODC (ornithine decarboxylase), which confers resistance to the ornithine decarboxylase inhibitor, 2-(difluoromethyl)-DL-ornithine (or "DFMO"; McConlogue, In: *Current Communications in Molecular Biology*, Cold Spring Harbor Laboratory: Cold Spring Harbor, N.Y. (1987)); and deaminase from *Aspergillus terreus*, which confers resistance to blasticidin S (Tamura, *Biosci. Biotechnol. Biochem.* 59 2336-2338 (1995)).

Useful scorable markers are also known to those skilled in the art and are commercially available, such as the genes encoding luciferase (Giacomin, *Pl. Sci.* 116:59-72 (1996); Scikantha, *J. Bact.* 178:121 (1996)), green fluorescent protein (Gerdes, *FEBS Lett.* 389:44-47 (1996)) or R-glucuronidase (Jefferson, *EMBO J.* 6:3901-3907 (1987)). This embodiment is particularly useful for simple and rapid screening of cells, tissues and organisms containing a vector comprising a Δ15 desaturase.

For some applications it may be useful to direct the Δ15 desaturase proteins to different cellular compartments. It is thus envisioned that the chimeric genes described above may be further modified by the addition of appropriate intracellular targeting sequences to their coding regions (and/or with targeting sequences that are already present removed). These additional targeting sequences include chloroplast transit peptides (Keegstra et al., *Cell* 56:247-253 (1989)), signal sequences that direct proteins to the endoplasmic reticulum (Chrispeels et al., *Ann. Rev. Plant Phys. Plant Mol.* 42:21-53 (1991)), and nuclear localization signals (Raikhel et al., *Plant Phys.*100:1627-1632 (1992)). While the references cited give examples of each of these, the list is not exhaustive and more targeting signals of utility may be discovered in the future which are useful in the invention.

A variety of techniques are available and known to those skilled in the art for introduction of constructs into a plant cell host. These techniques include transformation with DNA employing *Agrobacterium tumefaciens* or *A. rhizogenes* as the transforming agent. It is particularly preferred to use the binary type vectors of Ti and Ri plasmids of *Agrobacterium* spp. Ti-derived vectors transform a wide variety of higher plants, including monocotyledonous and dicotyledonous plants such as soybean, cotton, rape, tobacco and rice (Pacciotti et al., *Bio/Technology* 3:241 (1985); Byrne et al., *Plant Cell, Tissue and Organ Culture* 8:3 (1987); Sukhapinda et al., *Plant Mol. Biol.* 8:209-216 (1987); Lorz et al., *Mol. Gen. Genet.* 199:178 (1985); Potrykus, *Mol. Gen. Genet.* 199:183 (1985); Park et al., *J. Plant Biol.* 38(4):365-71 (1995); Hiei et al., *Plant J.* 6:271-282 (1994)). The use of T-DNA to transform plant cells has received extensive study and is amply described (EP 120516; Hoekema, In: *The Binary Plant Vector System*. Offset-drukkerij Kanters B. V.; Alblasserdam (1985), Chapter V; Knauf et al., *Genetic Analysis of Host Range Expression by Agrobacterum*, In: *Molecular Genetics of the Bacteria-Plant Interaction*, Puhler, A. Ed.; Springer-Verlag: New York, 1983, p 245; and An et al., *EMBO J.* 4:277-284 (1985)). For introduction into plants, the chimeric genes of the invention can be inserted into binary vectors as described in the Examples.

Other transformation methods are available to those skilled in the art, such as: 1.) direct uptake of foreign DNA constructs (see EP 295959); 2.) techniques of electroporation (see Fromm et al., *Nature* (London) 319:791 (1986)); 3.) high-velocity ballistic bombardment with metal particles coated with the nucleic acid constructs (see Kline et al., *Nature* (London) 327:70 (1987) and U.S. Pat. No. 4,945,050); or 4.) microinjection (see *Gene Transfer To Plants*, Potrykus and Spangenberg, Eds., Springer Verlag: Berlin, N.Y. (1995)). For a review of commonly used methods of plant transformation see Newell, C. A. (*Mol. Biotechnol.* 16:53-65 (2000)). The transformation of most dicotyledonous plants is possible with the methods described above; however, additional transformation techniques have been developed for the successful transformation of monocotyledonous plants. These include protoplast transformation and transformation by an in planta method using *Agrobacterium tumefaciens*. This in planta method (Bechtold and Pelletier, *C. R. Acad. Sci. Padis,* 316: 1194 (1993); or Clough S. J., Bent A. F.; *Plant Journal* 16(6): 735-43 (1998)) involves the application of *A. tumefaciens* to the outside of the developing flower bud and then introduction of the binary vector DNA to the developing microspore and/or macrospore and/or developing seed, so as to produce a transformed seed without the exogenous application of cytokinin and/or gibberellin. Those skilled in the art will be aware that the selection of tissue for use in such a procedure may vary; however, it is preferable generally to use plant material at the zygote formation stage for in planta transformation procedures.

Once transformed, there are a variety of methods for the regeneration of plants from plant tissue. The particular method of regeneration will depend on the starting plant tissue and the particular plant species to be regenerated. The regeneration, development and cultivation of plants from single plant protoplast transformants or from various transformed explants is well known in the art (Methods for Plant Molecular Biology; Weissbach and Weissbach, Eds., Academic: San Diego, Calif. (1988)). Of particular relevance are methods to transform foreign genes into commercially important oilseed crops, such as rapeseed (see De Block et al., *Plant Physiol.* 91:694-701 (1989); U.S. Pat. No. 5,463,174), sunflower (Everett et al., *Bio/Technology* 5:1201 (1987)), soybean (McCabe et al., *Bio/Technology*6:923 (1988); Hinchee et al., *Bio/Technology* 6:915 (1988); Chee et al., *Plant Physiol.* 91:1212-1218 (1989); Christou et al., *Proc. Natl. Acad. Sci USA* 86:7500-7504 (1989); EP 301749; U.S. Pat. No. 5,569,834; U.S. Pat. No. 5,416,011) and corn (Gordon-Kamm et al., *Plant Cell* 2:603-618 (1990); Fromm et al., *Biotechnology* 8:833-839 (1990)).

Typically, transgenic plant cells are placed in an appropriate selective medium for selection of transgenic cells that are then grown to callus. Shoots are grown from callus and plantlets generated from the shoot by growing in rooting medium. The various constructs normally will be joined to a marker for selection in plant cells. Conveniently, the marker may be resistance to a biocide (particularly an antibiotic such as kanamycin, G418, bleomycin, hygromycin, chloramphenicol, herbicide or the like). The particular marker used will allow for selection of transformed cells as compared to cells lacking the DNA that has been introduced.

One skilled in the art recognizes that the expression level and regulation of a transgene in a plant can vary significantly from line to line. Thus, one has to test several lines to find one with the desired expression level and regulation. The skilled artisan will also recognize that different independent transformation events will result in different levels and patterns of expression (Jones et al., *EMBO J.* 4:2411-2418 (1985); De Almeida et al., *Mol. Gen. Genetics* 218:78-86 (1989)), and thus that multiple events must be screened in order to obtain lines displaying the desired expression level and pattern. Such screening may be accomplished by Southern analysis of DNA blots (Southern, *J. Mol. Biol.* 98: 503 (1975)), Northern analysis of mRNA expression (Kroczek, *J. Chromatogr. Biomed. Appl.*, 618(1-2):133-145 (1993)), Western analysis of protein expression or phenotypic analysis. One particularly useful way to quantitate protein expression and to detect replication in different plant tissues is to use a reporter gene (e.g., GUS). Once transgenic plants have been obtained, they may be grown to produce plant tissues or parts having the desired phenotype. The plant tissue or plant parts may be harvested and/or the seed collected. The seed may serve as a source for growing additional plants with tissues or parts having the desired characteristics.

As was discussed above, methods of isolating seed oils are well known in the art (Young et al., In *The Lipid Handbook*; Gunstone et al., Eds.; Chapman & Hall: London, 1994; pp 253-257). The altered seed oils can then be used in various nutritional compositions (e.g., nutritional supplements, food products, infant formulas, animal feed, pet food, etc.).

The ultimate goal of the work described herein is the development of an organism that accumulates oils enriched in ω-3 PUFAs, wherein one preferred host is an oleaginous plant or an oleaginous yeast. Toward this end, desaturases must be identified that function efficiently to enable synthesis and high accumulation of preferred ω-3 PUFAs in these hosts. Identification of efficient Δ15 and ω-3 desaturases is also necessary for the manipulation of the ratio of ω-3 to ω-6 PUFAs produced in host cells.

In previous work, the native *Yarrowia lipolytica* Δ12 desaturase was isolated and over-expressed this protein, resulting in increased conversion of oleic acid to LA with respect to the wildtype cells (U.S. patent application Ser. No. 10/840325, incorporated entirely by reference; see also Example 2 herein and SEQ ID NOs:54 and 55). Despite the increased availability of LA within these host cells, however, it was desirable to obtain an even larger substrate pool suitable to enable high-level production of a variety of ω-3 PUFAs (e.g., EPA) within the *Y. lipolytica* transformant cells. Thus, expression of a heterologous protein having high-level Δ15 desaturase activity was therefore advantageous in the pathway engineering of the organism. Since previously isolated Δ15 desaturases from plant sources were not expected to function efficiently in oleaginous yeast, it was therefore an object of the present invention to isolate a fungal Δ15 desaturase. It was expected that over-expression of this fungal desaturase would increase substrate pools of ALA within oleaginous yeast hosts, thereby permitting synthesis and high accumulation of preferred ω-3 PUFAs (e.g., STA, ETA, EPA, DPA and DHA) in these hosts. Increased Δ15 desaturase activity would also enable modification of the ratio of ω-3 to ω-6 PUFAs.

To achieve these goals, in the present invention Applicants isolated and cloned a DNA fragment from *Fusatium moniliforme* that encodes a Δ15 desaturase enzyme ("Fm1"; SEQ ID NOs:1 and 2). Confirmation of this gene's activity as a Δ15 desaturase was provided based upon the production of ALA in wild type *Yarrowia lipolytica* cells upon transformation with a chimeric gene comprising the *F. moniliforme* Fm1 desaturase (Example 5, wherein the percent substrate conversion calculated as [18:3]/[18:2+18:3]*100) was 82.5%).

Surprisingly, however, the *F. moniliforme* Δ15 desaturase also has several unique characteristics, as compared to previously known Δ15 desaturases. Specifically, in addition to the novel sequence of the *F. moniliforme* Δ15 desaturase, it is also distinguished by its significant Δ12 desaturase activity (i.e. has the ability to use oleic acid as an enzymatic substrate), % ALA product accumulation and broad substrate specificity.

Significant Δ12 Desaturase Activity

As shown in the Examples, the *Fusarium moniliforme* Δ15 desaturase (Fm1) disclosed herein has significant Δ12 desaturase activity (see Table 9, Example 5), wherein a Δ12 desaturase-disrupted strain of *Yarrowia lipolytica* that was transformed with a chimeric gene encoding SEQ ID NO:2 was able to convert 24% of oleic acid to LA (percent substrate conversion calculated as ([18:2+18:3]/[18:1+18:2+18:3]) *100), in addition to 96% of LA to ALA (percent substrate conversion calculated as [18:3]/[18:2+18:3]*100)). This bifunctionality is in marked contrast to any other known Δ15 desaturase. And, although desaturases are known with specificity toward more than one substrate, the bifunctionality of the *F. moniliforme* desaturase (wherein the protein possesses both Δ12 and Δ15 desaturase activity) distinguishes it from any known Δ12 or Δ15 fatty acid desaturase identified to date.

Percent ALA Product Accumulation

The *Fusarium moniliforme* Δ15 desaturase disclosed herein enables extremely high synthesis of ALA when expressed in *Yarrowia lipolytica*, relative to that described for other heterologously expressed Δ15 desaturases (e.g., worms and plants). Specifically, the *Fusarium* enzyme was very active (i.e., *Yarrowia lipolytica* that was transformed with a chimeric gene encoding SEQ ID NO:2 was able to demonstrate a % product accumulation of ALA of 31%, relative to the total fatty acids in the transformant host cell (see Table 9, Example 5)). This represents a conversion efficiency to ALA of 83% (calculated as [18:3]/[18:2+18:3]*100). In the Δ12 desaturase-disrupted strain of *Yarrowia lipolytica* that was transformed with a chimeric gene encoding SEQ ID NO:2, a conversion efficiency to ALA of 96% was demonstrated. In contrast, the % product accumulation of ALA when expressing the *C. elegans* Δ15 desaturase in the non-oleaginous yeast *Sacchromyces cerevisiae* was only 4.1% (Meesapyodsuk et al., *Biochem.* 39:11948-11954 (2000)); and, the % product accumulation of ALA when expressing the *B. napus* Δ15 desaturase in *S. cerevisiae* was only 1.3% (Reed., D. W. et al., *Plant Physiol.* 122:715-720 (2000)).

The high efficiency of the *Fusarium moniliforme* Δ15 desturase, especially in the Δ12 desaturase-disrupted strain of *Y. lipolytica*, is the result of the protein's bifunctional Δ12 and Δ15 desaturase activity, whereby the product of the Δ12 desaturation is the substrate for the Δ15 desaturase. One skilled in the art would recognize that the ratio of 18:3/18:2 could be maximized by expression of the enzyme disclosed herein in host organisms having little or no ability to synthesize 18-2 (e.g. a Δ12 desaturase-null line in an oleaginous yeast or an Arabidopsis fad2 mutant).

Broad Substrate Specificity

Finally, the *Fusarium moniliforme* Δ15 enzyme has relatively broad substrate specificity on downstream ω-6 derivatives of 18:2; specifically, the Δ15 desaturase described herein is able to catalyze conversion of GLA to STA, DGLA to ETA, and ARA to EPA. In contrast to the heterologous expression of worm (*C. elegans*) and plant (*B. napus*) Δ15 desaturases in *S. cerevisae* (Meesapyodsuk et al., supra; Reed et al., supra), however, the Applicants' data herein demonstrate that the *Fusarium moniliforme* Δ15 desaturase converts the ω-6 substrates to their ω-3 counterparts much more efficiently, i.e., with higher % substrate conversion, when expressed in *Yarrowia* (Table 4).

TABLE 4

Qualitative Comparison Of Substrate Preferences Of Δ15 Desaturases From Worm, Plant And Fungus

| | Host Organism | | |
|---|---|---|---|
| | S. cerevisiae | S. cerevisiae | Y. lipolytica |
| | Δ15 desaturase source | | |
| ω-6 substrate | C. elegans | B. napus | F. moniliforme |
| | % substrate conversion | | |
| 18:2 (LA) | 11.1 | 2.6 | 81.6 |
| 18:3 (GLA) | 15.4 | 0.7 | 35.0 |
| 20:3 (DGLA) | 5.9 | 0.6 | 20.0 |
| 20:4 (ARA) | 1.9 | 0.7 | nd |

Note:
ω-6 substrate was fed in all cases except for 18:2 in *Y. lipolytica*;
Nd = not determined Thus, heterologous expression of the fungal Δ15 desaturase of the invention increases cellular carbon flow into the ω-3 fatty acid biosynthetic pathway, by enhancing the biosynthesis of ALA. As a result, the ratio of ω-3/ω-6 fatty acids is increased and production of more downstream ω-3 fatty acids (e.g., STA, ETA and EPA) is enabled, when other PUFA biosynthetic enzymes are co-expressed with the Δ15 desaturase herein. It is expected that these results will occur in any microorganism in which the Δ15 desaturase of the present invention is expressed. In alternative embodiments, the Applicants have demonstrated similar results by overexpression of the *Fusarium moniliforme* Δ15 desaturase in plant oilseed hosts. Therefore, expression of the present *Fusarium moniliforme* Δ15 desaturase in any host cell is expected to permit the host cell to produce ALA at levels greater than about 10% of the total fatty acids, where greater than about 30% is preferable and greater than about 50% is most preferred. Similarly, such transformants will demonstrate altered ratios of ALA to LA where ratios of ALA:LA of at least about 4 will be typical, ratios of at least 8 are preferred and ratios of at least 12 are most preferred. Microbial oils extracted from these transformants will contain greater than about 10% ALA, where greater than about 30% is equally expected and greater than 50% is expected to be typical.

Additionally, Applicants have also identified a suite of Δ15 desaturases orthologous to the *Fusarium moniliforme* protein described above from *Aspergillus nidulans*, *Neurospora crassa*, *Magnaporthe grisea*, and *Fusarium graminearium* (i.e., SEQ ID NOs:6, 14, 10 and 18, respectively). These fungal proteins are also expected to be useful for expression Δ15 desaturase activity in different host cells, including oleaginous yeast (e.g., *Yarrowia lipolytica*). These proteins (including the *Fusarium moniliforme* Δ12 desaturase (SEQ ID NO:2)) clustered within a distinct sub-family of proteins (referred to herein as "Sub-family 1") that are well-distinguished from the proteins clustered within "Sub-family 2" (i.e., SEQ ID NOs:4, 8, 12, 16 and 20, identified in co-pending U.S. Provisional Application No. 60/570679 as Δ12 desaturases), despite all proteins' identification as homologous to the *Y. lipolytica* Δ12 desaturase identified herein as SEQ ID NO:55 (characterized in co-pending U.S. patent application Ser. No. 10/840325). Together, the proteins of sub-family 1 (identified herein as Δ15 desaturases) represent a group of proteins having at least 46.2% identity to one another (Example 3) and they are well-distinguished by sequence homology from previously described Δ15 desaturases.

Functional characterization of the *Aspergillus nidulans* and *Neurospora crassa* proteins, which confirmed their activity as Δ15 desaturases, is described in WO 03/099216. Confirmation of the putative *Magnaporthe grisea* Δ5 desaturase ("Mg1"; SEQ ID NOs:9 and 10) gene's activity as a Δ15 desaturase was provided herein based upon the production of ALA in wild type *Yarrowia lipolytica* cells upon transformation with a chimeric gene comprising Mg1 (Example 6). Comparison of the activity of these Δ15 desaturases to that of the *Fusarium moniliforme* Δ15 desaturase described above, however, revealed that not all of the Δ15 desaturase proteins of sub-family 1 were characterized as having bifunctional Δ12/Δ15 desaturase activity. Specifically, based on the results provided in WO 2003/099216, the *Neurospora crassa* and *Aspergillus nidulans* proteins did not show bifunctional Δ12/Δ15 desaturase activity. In contrast, the Magnaporthe grisea protein behaved similarly to the *Fusarium moniliforme* protein, and thus both were classified as having bifunctional Δ12/Δ15 desaturase activity. It is hypothesized that the *Fusarium graminearium* ("Fg1"; SEQ ID NOs:17 and 18) will also have bifunctional Δ12/Δ15 desaturase activity, since Fg1 is most closely related to Fm1 (sharing 88.8% identity) while the bifunctional Fm1 and Mg1 are only 60.9% identical.

It is expected that this unique class of fungal Δ15 desaturases will be useful for expression in oleaginous yeast (e.g., *Yarrowia lipolytica*), and plants, as a means to alter the fatty acid composition, based on the expectation that they will function with high efficiency (i.e., percent substrate conversion, wherein % substrate conversion of LA to ALA of at least about 50% is useful, a conversion efficiency to ALA of at least about 80% is preferred, a % substrate conversion to ALA of at least about 90% is particularly suitable, and a % substrate conversion to ALA of at least about 95% is most preferred). Thus, one embodiment of the invention is a method of altering fatty acid profiles in an oleaginous yeast, whereby a Δ15 desaturase protein of sub-family 1 is expressed alone or in combination with other fatty acid biosynthetic genes (e.g., a Δ4 desaturase, a Δ5 desaturase, a Δ6 desaturase, a Δ12 desaturase, a Δ15 desaturase, a Δ17 desaturase, a Δ9 desaturase, a Δ8 desaturase and/or an elongase). A second embodiment is a method of altering fatty acid profiles in plants, whereby a whereby a Δ15 desaturase protein of sub-family 1 is expressed alone or in combination with other fatty acid biosynthetic genes to alter the omega3:omega6 ratios in the oils and/or to alter the accumulation or composition of plant PUFAs.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by: 1.) Sambrook, J., Fritsch, E. F. and Maniatis, T. *Molecular Cloning: A Laboratory Manual*; Cold Spring Harbor Laboratory: Cold Spring Harbor, N.Y. (1989) (Maniatis); 2.) T. J. Silhavy, M. L. Bennan, and L. W. Enquist, Experiments with Gene Fusions; Cold Spring Harbor Laboratory: Cold Spring Harbor, N.Y. (1984); and 3.) Ausubel, F. M. et al., Current Protocols in Molecular Biology, published by Greene Publishing Assoc. and Wiley-Interscience (1987).

Materials and methods suitable for the maintenance and growth of bacterial cultures are well known in the art. Techniques suitable for use in the following Examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, Eds), American Society for Microbiology: Washington, D.C. (1994)); or by Thomas D. Brock in *Biotechnology: A Textbook of Industrial Microbiology*, 2$^{nd}$ ed., Sinauer Associates: Sunderland, Mass. (1989). All reagents, restriction enzymes and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.), unless otherwise specified.

*E. coli* TOP10 cells and *E. coli* Electromax DH10B cells were obtained from Invitrogen (Carlsbad, Calif.). Max Efficiency competent cells of *E. coli* DH5α were obtained from GIBCO/BRL (Gaithersburg, Md.). *E. coli* (XL1-Blue) competent cells were purchased from the Stratagene Company (San Diego, Calif.). All *E. coli* strains were typically grown at 37° C. on Luria Bertani (LB) plates.

General molecular cloning was performed according to standard methods (Sambrook et al., supra). Oligonucleotides were synthesized by Sigma-Genosys (Spring, Tex.). PCR products were cloned into Promega's pGEM-T-easy vector (Madison, Wis.).

DNA sequence was generated on an ABI Automatic sequencer using dye terminator technology (U.S. Pat. No. 5,366,860; EP 272,007) using a combination of vector and insert-specific primers. Sequence editing was performed in Sequencher (Gene Codes Corporation, Ann Arbor, Mich.). All sequences represent coverage at least two times in both directions. Comparisons of genetic sequences were accomplished using DNASTAR software (DNASTAR Inc., Madison, Wis.).

The meaning of abbreviations is as follows: "sec" means second(s), "min" means minute(s), "h" means hour(s), "d" means day(s), "μl" means microliter(s), "mL" means milliliter(s), "L" means liter(s), "μM" means micromolar, "mM" means millimolar, "M" means molar, "mmol" means millimole(s), "μmole" mean micromole(s), "g" means gram(s), "μg" means microgram(s), "ng" means nanogram(s), "U" means unit(s), "bp" means base pair(s) and "kB" means kilobase(s).

Cultivation of *Yarrowia lipolytica*

*Yarrowia lipolytica* strains ATCC #76982 and ATCC #90812 were purchased from the American Type Culture Collection (Rockville, Md.). *Y. lipolytica* strains were usually grown at 28° C. on YPD agar (1% yeast extract, 2% bactopeptone, 2% glucose, 2% agar). For transformation selection, minimal medium (0.17% yeast nitrogen base (DIFCO Laboratories, Detroit, Mich.) without ammonium sulfate and without amino acids, 2% glucose, 0.1% proline, pH 6.1) was used. Supplements of adenine, leucine, lysine and/or uracil were added as appropriate to a final concentration of 0.01%.

Fatty Acid Analysis of *Yarrowia lipolytica*

For fatty acid analysis, cells were collected by centrifugation and lipids were extracted as described in Bligh, E. G. & Dyer, W. J. (*Can. J. Biochem. Physiol.* 37:911-917 (1959)). Fatty acid methyl esters were prepared by transesterification of the lipid extract with sodium methoxide (Roughan, G., and Nishida I. *Arch Biochem Biophys.* 276(1):38-46 (1990)) and subsequently analyzed with a Hewlett-Packard 6890 GC fitted with a 30-m×0.25 mm (i.d.) HP-INNOWAX (Hewlett-Packard) column. The oven temperature was from 170° C. (25 min hold) to 185° C. at 3.5° C./min.

For direct base transesterification, *Yarrowia* culture (3 mL) was harvested, washed once in distilled water and dried under vacuum in a Speed-Vac for 5-10 min. Sodium methoxide (100 μl of 1%) was added to the sample, and then the sample was vortexed and rocked for 20 min. After adding 3 drops of 1 M NaCl and 400 μl hexane, the sample was vortexed and spun. The upper layer was removed and analyzed by GC as described above.

Example 1

Construction of *Yarrowia* Expression Vectors

The present Example describes the construction of pY5-13 (comprising a chimeric TEF promoter:XPR terminator gene), pY5-13GPDN (comprising a chimeric GPD promoter:XPR terminator gene), and pY5-20 (comprising a chimeric hygromycin resistance gene).

Construction of Plasmid pY5-13

Figure 3:
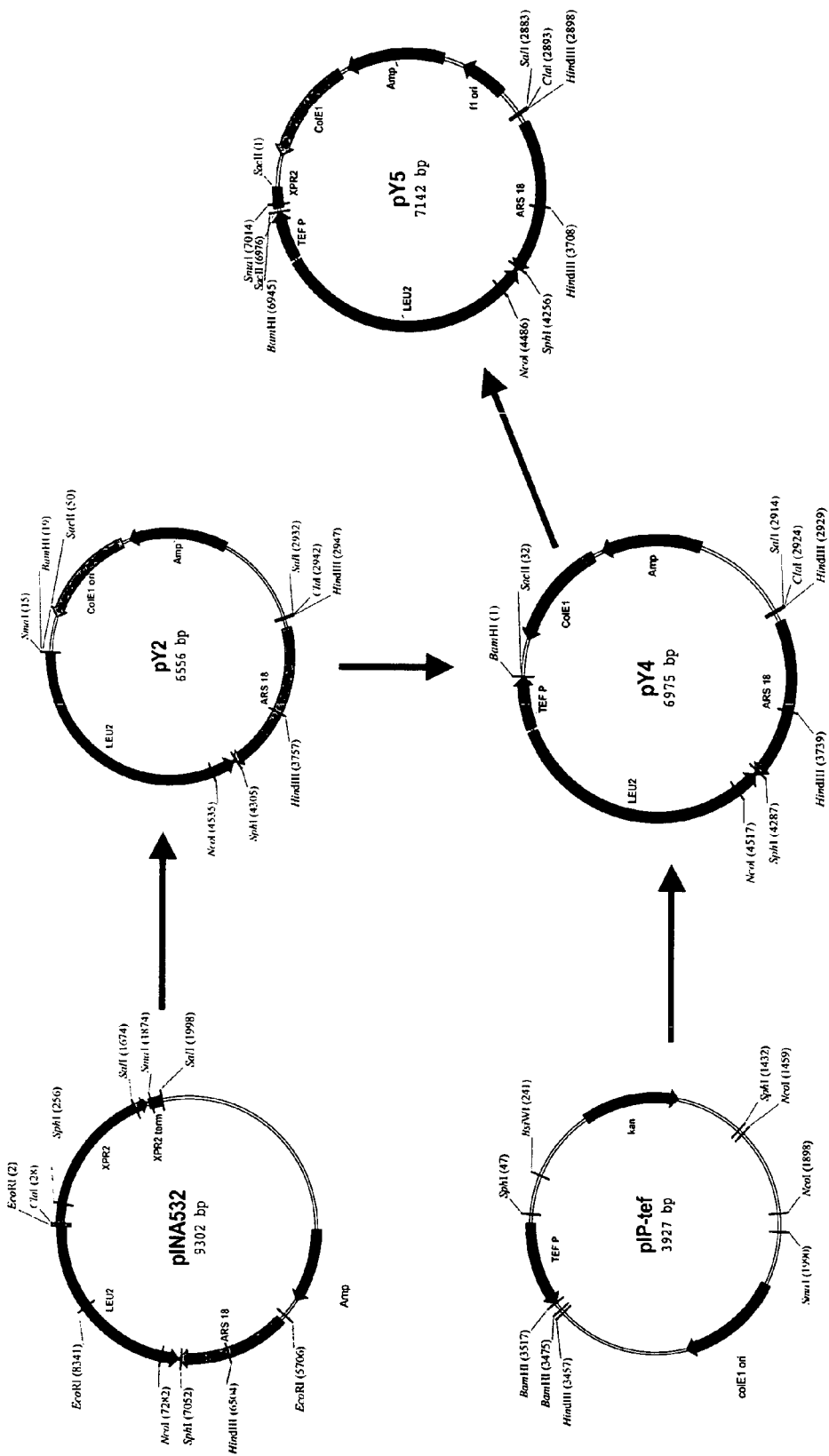
FIG. 3 illustrates the construction of the plasmid vector pY5 for gene expression in *Yarrowia lipolytica*.

The plasmid pY5, a derivative of pINA532 (a gift from Dr. Claude Gaillardin, Insitut National Agronomics, Centre de biotechnologie Agro-Industrielle, laboratoire de Genetique Moleculaire et Cellularie INRA-CNRS, F-78850 Thiverval-Grignon, France), was constructed for expression of heterologous genes in *Yarrowia lipolytica* (FIG. 3). First, the the partially-digested 3598 bp EcoRI fragment containing the ARS18 sequence and LEU2 gene of pINA532 was subcloned into the EcoRI site of pBluescript (Strategene, San Diego, Calif.) to generate pY2. The TEF promoter (Muller S., et al., *Yeast*, 14: 12671283 (1998)) was amplified from *Yarrowia lipolytica* genomic DNA by PCR using TEF5' (SEQ ID NO:21) and TEF3' (SEQ ID NO:22) as primers. PCR amplification was carried out in a 50 µl total volume containing: 100 ng *Yarrowia* genomic DNA, PCR buffer containing 10 mM KCl, 10 mM $(NH_4)_2SO_4$, 20 mM Tris-HCl (pH 8.75), 2 mM $MgSO_4$, 0.1% Triton X-100), 100 µg/mL BSA (final concentration), 200 µM each deoxyribonucleotide triphosphate, 10 pmole of each primer and 1 µl of PfuTurbo DNA polymerase (Stratagene, San Diego, Calif.). Amplification was carried out as follows: initial denaturation at 95° C. for 3 min, followed by 35 cycles of the following: 95° C. for 1 min, 56° C. for 30 sec, 72° C. for 1 min. A final extension cycle of 72° C. for 10 min was carried out, followed by reaction termination at 4° C. The 418 bp PCR product was ligated into pCR-Blunt to generate pIP-tef. The BamHI/EcoRV fragment of pIP-tef was subcloned into the BamHI/SmaI sites of pY2 to generate pY4.

The XPR2 transcriptional terminator was amplified by PCR using pINA532 as template and XPR5' (SEQ ID NO:23) and XPR3' (SEQ ID NO:24) as primers. The PCR amplification was carried out in a 50 µl total volume, using the components and conditions described above. The 179 bp PCR product was digested with SacII and then ligated into the SacII site of pY4 to generate pY5. Thus, pY5 (shown in FIG. 3) is useful as a *Yarrowia-E. coli* shuttle plasmid containing:

1.) a *Yarrowia* autonomous replication sequence (ARS18);
2.) a ColE1 plasmid origin of replication;
3.) an ampicillin-resistance gene ($Amp^R$), for selection in *E. coli*;
4.) a *Yarrowia* LEU2 gene, for selection in *Yarrowia*;
5.) the translation elongation promoter (TEF P), for expression of heterologous coding regions in *Yarrowia*; and
6.) the extracellular protease gene terminator (XPR2) for transcriptional termination of heterologous gene expression in *Yarrowia*.

Plasmid pY5-13 was constructed as a derivative of pY5 to facilitate subcloning and heterologous gene expression in *Yarrowia lipolytica*.

Specifically, pY5-13 was constructed by 6 rounds of site-directed mutagenesis using pY5 as template. Both SalI and ClaI sites were eliminated from pY5 by site-directed mutagenesis using oligonucleotides YL5 and YL6 (SEQ ID NOs:25 and 26) to generate pY5-5. A SalI site was introduced into pY5-5 between the Leu2 gene and the TEF promoter by site-directed mutagenesis using oligonucleotides YL9 and YL10 (SEQ ID NOs:27 and 28) to generate pY5-6. A PacI site was introduced into pY5-6 between the LEU2 gene and ARS18 using oligonucleotides YL7 and YL8 (SEQ ID NOs: 29 and 30) to generate pY5-8. A NcoI site was introduced into pY5-8 around the translation start codon of the TEF promoter using oligonucleotides YL3 and YL4 (SEQ ID NOs:31 and 32) to generate pY5-9. The NcoI site inside the Leu2 gene of pY5-9 was eliminated using YL1 and YL2 oligonucleotides (SEQ ID NOs:33 and 34) to generate pY5-12. Finally, a BsiWI site was introduced into pY5-12 between the ColEI and XPR region using oligonucleotides YL61 and YL62 (SEQ ID NOs:35 and 36) to generate pY5-13.

Construction of Plasmid pY5-13GPDN

A DNA fragment including the glyceraldehyde-3-phosphate-dehydrogenase (GPD) promoter region ("GPDPro"; see co-pending U.S. patent application Ser. No. 10/869630, herein incorporated by reference in its entirety) was amplified with oligonucleotides YL211 (SEQ ID NO:38) and YL212 (SEQ ID NO:39) as primers using *Yarrowia* genomic DNA as template. Briefly, this promoter fragment (SEQ ID NO:37) was comprised of the nucleotide region between the −968 to +3 region of the GPD gene, wherein the 'A' position of the 'ATG' translation initiation codon is designated as +1.

The amplified GPDPro DNA fragment was completely digested with SalI and then partially digested with NcoI. The SalI/NcoI fragment containing GPDPro was purified following gel electrophoresis in 1% (w/v) agarose and ligated to NcoI/SalI digested pY5-13 vector (wherein the NcoI/SalI digestion had excised the TEF promoter from the pY5-13 vector backbone) to yield pY5-13GPD. Thus, pY5-13GPD comprised a GPDPro:XPR terminator expression cassette.

The Nco I site at the 3' end of the promoter fragment in pY5-13GPD was converted to a Not I site to yield pY5-13GPDN. For this, GPDPro was re-amplified by PCR using GPDsense (SEQ ID NO:40) and GPDantisense (SEQ ID NO:41) primers with a Not I site. The resultant promoter fragment was digested with Sal I and Not I and cloned into the Sal/NotI site of pY5-13 (thus removing the TEF promoter) to produce pY5-13GPDN.

Construction of Plasmid PY5-20

Plasmid pY5-20 is a derivative of pY5. It was constructed by inserting a Not I fragment containing a chimeric hygromycin resistance gene into the Not I site of pY5. The chimeric gene had the hygromycin resistance ORF under the control of the *Yarrowia lipolytica* TEF promoter.

Example 2

Cloning of the *Yarrowia Lipolytica* Δ12 Desaturase and Disruption of the Endogenous Δ12 Desaturase Gene Based on the fatty acid composition of *Yarrowia lipolytica* (ATCC #76982) which demonstrated that the organism could make LA (18:2) but not ALA (18:3), it was assumed that *Y. lipolytica* would likely contain gene(s) having Δ12 desaturase activity but not Δ15 desaturase activity. Thus, the present Example describes the use of degenerate PCR primers to isolate a partial coding sequence of the *Yarrowia lipolytica* Δ12 desaturase, the use of the partial sequence to disrupt the native gene in *Yarrowia lipolytica*, and subsequent cloning of the full-length gene.

Cloning of a Partial Putative Δ12 Desaturase Sequence from *Yarrowia lipolytica* by PCR Using Degenerate PCR Primers Genomic DNA was isolated from *Yarrowia lipolytica* (ATCC #76982) using DNeasy Tissue Kit (Qiagen, Catalog #69504) and resuspended in kit buffer AE at a DNA concentration of 0.5 µg/µl. PCR amplifications were performed using the genomic DNA as template and several sets of degenerate primers made to amino acid sequences conserved between different Δ12 desaturases. The best results were obtained with a set of upper and lower degenerate primers, P73 and P76, respectively, as shown in the Table below.

TABLE 5

Degenerate Primers Used For Amplification Of A
Partial Putative Δ12 Desaturase

| Primer Set | Description | Degenerate Nucleotide Sequence | Corresponding Amino Acid Sequence |
|---|---|---|---|
| P73 | (32) 26-mers | 5'-TGGGTCCTGGGCCA YGARTGYGGNCA-3' (SEQ ID NO:42) | WVLGHECGH (SEQ ID NO:43) |
| P76 | (64) 30-mers | 5'-GGTGGCCTCCTCGG CGTGRTARAANGGNAT-3' (SEQ ID NO:44) | (M/I)PFVHAEEAT (SEQ ID NO:45) |

[Note: Abbreviations are standard for nucleotides and proteins. The nucleic acid degeneracy code used is as follows: R = A/G; Y = C/T; and N = A/C/G/T.]

The PCR was carried out in an Eppendorf Mastercycler Gradient thermocycler according to the manufacturer's recommendations. Amplification was carried out as follows: initial denaturation at 95° C. for 1 min, followed by 30 cycles of denaturation at 95° C. for 30 sec, annealing at 58° C. for 1 min, and elongation at 72° C. for 1 min. A final elongation cycle at 72° C. for 10 min was carried out, followed by reaction termination at 4° C.

The expected (ca. 740 bp) size PCR product was detected by agarose gel electrophoresis, isolated, purified, cloned into a pTA vector (Invitrogen), and sequenced. The resultant sequence had homology to known Δ12 desaturases, based on BLAST program analysis (Basic Local Alignment Search Tool; Altschul, S. F., et al., *J. Mol. Biol.* 215:403-410 (1993)).

Targeted Disruption of *Yarrowia lipolytica* Δ12 Desaturase Gene

Targeted disruption of the Δ12 desaturase gene in *Yarrowia lipolytica* ATCC #76982 was carried out by homologous recombination-mediated replacement of the Δ12 desaturase gene with a targeting cassette designated as pY23D12. pY23D12 was derived from plasmid pY5-20 (Example 1).

Specifically, pY23D12 was created by inserting a Hind III/Eco RI fragment into similarly linearized pY5-20. This 642 bp fragment consisted of (in 5' to 3' orientation): 3' homologous sequence from position +718 to +1031 (of the coding sequence (ORF) in SEQ ID NO:54), a Bgl II restriction site, and 5' homologous sequence from position +403 to +717 (of the coding sequence (ORF) in SEQ ID NO:54). The fragment was prepared by PCR amplification of 3' and 5' sequences from the 642 bp PCR product using sets of PCR primers P99 and P100 (SEQ ID NOs:46 and 47) and P101 and P102 (SEQ ID NOs:48 and 49), respectively.

pY23D12 was linearized by Bgl II restriction digestion and transformed into mid-log phase *Y. lipolytica* ATCC #76982 cells by the lithium acetate method according to the method of Chen, D. C. et al. (*Appl Microbiol Biotechnol.* 48(2):232-235 (1997)). Briefly, *Y. lipolytica* was streaked onto a YPD plate and grown at 30° C. for approximately 18 hr. Several large loopfuls of cells were scraped from the plate and resuspended in 1 mL of transformation buffer containing:

2.25 mL of 50% PEG, average MW 3350;
0.125 mL of 2 M Li acetate, pH 6.0;
0.125 mL of 2 M DTT; and
50 μg sheared salmon sperm DNA.

About 500 ng of plasmid DNA was incubated in 100 μl of resuspended cells, and maintained at 39° C. for 1 hr with vortex mixing at 15 min intervals. The cells were plated onto YPD hygromycin selection plates and maintained at 30° C. for 2 to 3 days.

Four hygromycin-resistant colonies were isolated and screened for targeted disruption by PCR. One set of PCR primers (P119 [SEQ ID NO:50] and P120 [SEQ ID NO:51]) was designed to amplify a specific junction fragment following homologous recombination. Another set of PCR primers (P121 [SEQ ID NO:52] and P122 [SEQ ID NO:53]) was designed to detect the native gene. Three of the four hygromycin-resistant colonies were positive for the junction fragment and negative for the native fragment, thus confirming targeted integration.

Determination of Fatty Acid Profile in the Δ12 Desaturase-Disrupted Strain

Disruption of the native Δ12 desaturase gene was further confirmed by GC analysis of the total lipids in one of the disrupted strains, designated as Q-d12D. Single colonies of wild type (ATCC #76982) and Q-d12D were each grown in 3 mL minimal media (formulation/L: 20 g glucose, 1.7 g yeast nitrogen base, 1 g L-proline, 0.1 g L-adenine, 0.1 g L-lysine, pH 6.1) at 30° C. to an $OD_{600}$~1.0. The cells were harvested, washed in distilled water, speed vacuum dried and subjected to direct transesterification and GC analysis (as described in the General Methods).

The fatty acid profile of wildtype Yarrowia and the transformant Q-d12D comprising the disrupted Δ12 desaturase are shown below in Table 6. Fatty acids are identified as 16:0 (palmitate), 16:1 (palmitoleic acid), 18:0, 18:1 (oleic acid) and 18:2 (LA) and the composition of each is presented as a % of the total fatty acids.

TABLE 6

Fatty Acid Composition (% Of Total Fatty Acids)
In Wildtype And Transformant *Yarrowia lipolytica*

| Strain | 16:0 | 16:1 | 18:0 | 18:1 | 18:2 |
|---|---|---|---|---|---|
| Wild type | 11 | 14 | 2 | 33 | 34 |
| Q-d12D disrupted | 6 | 15 | 1 | 74 | nd |

*nd = not detectable

Results indicated that the native Δ12 desaturase gene in the Q-d12D strain was inactivated. Thus, there is only one gene encoding a functional Δ12 desaturase in *Yarrowia lipolytica* ATCC #76982.

Plasmid Rescue of the *Yarrowia lipolytica* Δ12 Desaturase Gene

Since the Δ12 desaturase gene was disrupted by the insertion of the entire pY23D12 vector that also contained an *E. coli* ampicillin-resistant gene and *E. coli* ori, it was possible to rescue the flanking sequences in *E. coli*. For this, genomic DNA of Yarrowia lipolytica strain Q-d12D was isolated using the DNeasy Tissue Kit. Specifically, 10 μg of the genomic DNA was digested with 50 μl of restriction enzymes Age I, Avr II, Nhe I and Sph I in a reaction volume of 200 μl. Digested DNA was extracted with phenol:chloroform and resuspended in 40 μl deionized water. The digested DNA (10 μl) was self-ligated in 200 μl ligation mixture containing 3 U T4 DNA ligase. Ligation was carried out at 16° C. for 12 hrs. The ligated DNA was extracted with phenol:chloroform and resuspended in 40 μl deionized water. Finally, 1 μl of the resuspended ligated DNA was used to transform *E. coli* by electroporation and plated onto LB plates containing ampicillin (Ap). Ap-resistant colonies were isolated and analyzed for the presence of plasmids by miniprep. The following insert sizes were found in the recovered or rescued plasmids (Table 7):

TABLE 7

Insert Sizes Of Recovered Plasmids,
According To Restriction Enzyme

| Enzyme | plasmid insert size (kB) |
|---|---|
| AgeI | 1.6 |
| AvrII | 2.5 |
| NheI | 9.4 |
| SphI | 6.6 |

Sequencing of the plasmids was initiated with sequencing primers P99 (SEQ ID NO:46) and P102 (SEQ ID NO:49).

Based on the sequencing results, a full-length gene encoding the *Yarrowia lipolytica* Δ12 desaturase gene was assembled (1936 bp; SEQ ID NO:54). Specifically, the sequence encoded an open reading frame of 1257 bases (nucleotides +283 to +1539 of SEQ ID NO:54), while the deduced amino acid sequence was 419 residues in length (SEQ ID NO:55). This gene was also also publically disclosed as YALI-CDS3053.1 within the public *Y. lipolytica* protein database of the "Yeast project Genolevures" (Center for Bioinformatics, LaBRI, Talence Cedex, France) (see also Dujon, B. et al., *Nature* 430 (6995):35-44 (2004)).

Example 3

Identification of Δ15 Desaturases from Filamentous Fungi

The present Example describes the identification of Δ15 desaturases in various filamentous fungi. These sequences were identified based on their homology to the *Yarrowia lipolytica* Δ12 desaturase (Example 2); and, the sequences from each species fell into one of two "sub-families" based on phylogenetic analyses.

Homology Searches with Synechochytis Δ15 Desaturase

First, public databases of the filamentous fungi *Neurospora crassa* and *Magnaporthe grisea* sequences were subjected to BLAST searches (Basic Local Alignment Search Tool; Altschul, S. F., et al., *J. Mol. Biol.* 215:403-410 (1993)) using the *Synechochytis* Δ15 desaturase protein sequence (gene desB; GenBank Accession No. D90913) as the query sequence. Unexpectedly, these searches failed to identify any homologous sequence.

Homology Searches With *Yarrowia lipolytica* Δ12 Desaturase

Applicants then performed BLAST searches of the same databases with the *Yarrowia lipolytica* Δ12 desaturase protein sequence as the query sequence (SEQ ID NO:55). These searches resulted in the identification of two homologous sequences within each organism. Subsequently, SEQ ID NO:55 was used as a query against: 1.) public databases of *Aspergillus nidulans* and *Fusarium graminearium*; and 2.) a DuPont EST library of *Fusarium moniliforme* strain M-8114 (E. I. duPont de Nemours and Co., Inc., Wilmington, Del.) (*F. moniliforme* strain M-8114 available from the *Fusarium* Research Center, University Park, Pa.; see also *Plant Disease* 81(2): 211-216 (1997)). These searches also resulted in the identification of two homologs to the *Yarrowia lipolytica* Δ12 desaturase protein within each organism. The Table below summarizes details concerning each of these homologs.

TABLE 8

Description Of ORFs Having Homology To The
*Yarrowia lipolytica* Δ12 Desaturase

| SEQ ID NOs* | Source | Abbreviation | Organism |
|---|---|---|---|
| 1, 2 | EST sequence database, E. I. duPont de Nemours and Co., Inc. | Fm 1 | *Fusarium moniliforme* |
| 3, 4 | EST sequence database, E. I. duPont de Nemours and Co., Inc. | Fm 2 | *Fusarium moniliforme* |
| 5, 6 | Contig 1.122 (scaffold 9) in the *A. nidulans* genome project (sponsored by the Center for Genome Research (CGR), Cambridge, MA); see also WO 2003/099216 | An1 | *Aspergillus nidulans* |
| 7, 8 | Contig 1.15 (scaffold 1) in the *A. nidulans* genome project; AAG36933 | An2 | *Aspergillus nidulans* |
| 9, 10 | Locus MG08474.1 in contig 2.1597 in the *M. grisea* genome project (sponsored by the CGR and International Rice Blast Genome Consortium) | Mg1 | *Magnaporthe grisea* |
| 11, 12 | Locus MG01985.1 in contig 2.375 in the *M. grisea* genome project | Mg2 | *Magnaporthe grisea* |
| 13, 14 | GenBank Accession No. AABX01000577); see also WO 2003/099216 | Nc1 | *Neurospora crassa* |
| 15, 16 | GenBank Accession No. AABX01000374 | Nc2 | *Neurospora crassa* |
| 17, 18 | Contig 1.320 in the *F. graminearium* genome project (sponsored by the CGR and the International *Gibberella zeae* Genomics Consortium (IGGR); BAA33772.1) | Fg1 | *Fusarium graminearium* |
| 19, 20 | Contig 1.233 in the *F. graminearium* genome project | Fg2 | *Fusarium graminearium* |

*Note:
Odd SEQ ID NOs refer to ORF nucleotide sequences and even SEQ ID NOs refer to the deduced amino acid sequences.

All of the homologs were either unannotated or annotated as a Δ12 desaturase or fatty acid desaturase. Furthermore, the nucleotide sequences from *F. graminearium* were genomic with putative intron sequences; the Applicants made a tentative assembly of the deduced amino acids for comparison with amino acid sequences from the other homologs.

Figure 4:
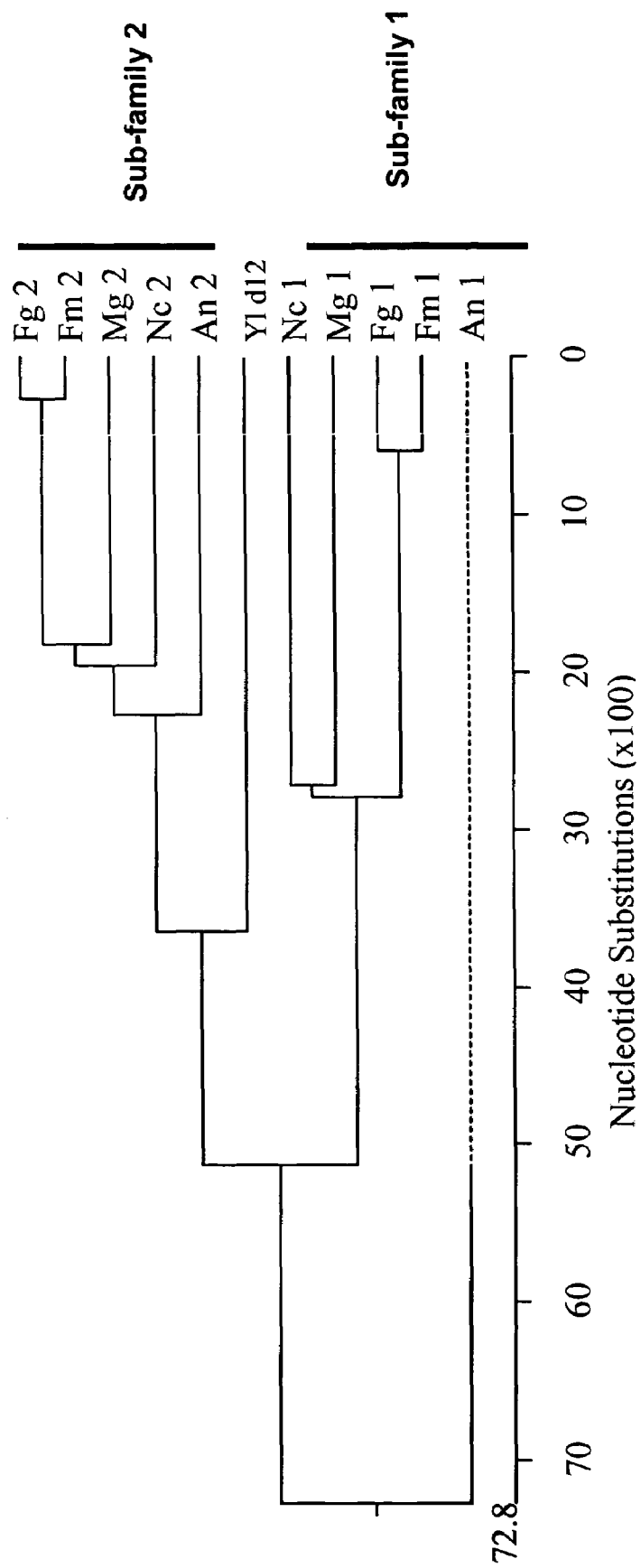
FIG. 4 shows a phylogenetic tree of proteins from different filamentous fungi (i.e., *Aspergillus nidulans, Fusarium moniliforme, F. graminearum, Magnaporthe grisea* and *Neurospora crassa*) having homology to the *Yarrowia lipolytica* Δ12 desaturase enzyme, and created using Megalign DNASTAR software.

Phylogenetic tree analysis of the Δ12 desaturase homologs from each species using the Megalign program of the LASERGENE bioinformatics computing suite (Windows 32 Megalign 5.06 1993-2003; DNASTAR Inc., Madison, Wis.) unexpectedly revealed two sub-families. As shown in FIG. 4, Nc1, Mg1, Fg1, Fm1 and An1 clustered in "sub-family 1" of the proteins having homology to the *Yarrowia lipolytica* Δ12 desaturase while Fg2, Fm2, Mg2, Nc2 and An2 clustered within "sub-family 2" of the *Yarrowia lipolytica* Δ12 desaturase protein homologs.

Each of the proteins having homology to the *Yarrowia lipolytica* Δ12 desaturase were then aligned using the method of Clustal W (slow, accurate, Gonnet option; Thompson et al., *Nucleic Acids Res.* 22:4673-4680 (1994)) of the Megalign program of DNASTAR software. The percent identities revealed by this method were used to determine whether the proteins were orthologs (FIG. 5). Specifically, the Figure shows: 1.) the percent identity among the proteins clustered within sub-family 1 (upper left-hand corner triangle, shown with a dark line); 2.) the percent identity between proteins in sub-family 1 and sub-family 2 (upper right-hand corner box, shown with a dotted line); and 3.) the percent identity among the proteins clustered within sub-family 2 (lower right-hand corner triangle). Thus, all proteins of sub-family 1 (SEQ ID NOs:2, 6, 10, 14 and 18) were at least 46.2% identical to each other and were less than 39.6% identical to the proteins of sub-family 2 (SEQ ID NOs:4, 8, 12, 16 and 20). Furthermore, the proteins of sub-family 2 were at least 56.3% identical to each other.

The analyses above clearly differentiated the two sub-families of proteins having homology to the *Yarrowia lipolytica* Δ12 desaturase (SEQ ID NO:55). Additionally, it was known that yeast such as *Y. lipolytica* can only synthesize 18:2 (but not 18:3), while each of the five filamentous fungi are able to synthesize both 18:2 and 18:3. Furthermore, a single Δ12 desaturase was isolated from Yarrowia, while all of the fungi had two homologs to the *Yarrowia* Δ12 desaturase. Thus, the Applicants postulated that one of the sub-families of desaturases in these organisms represented a Δ12 desaturase (permitting conversion of oleic acid to LA (18:2)) and the other represented a Δ15 desaturase (permitting conversion of LA to ALA (18:3)).

Finally, the *Fusarium moniliforme* Δ15 desaturase protein sequence was analyzed individually for its similarity using a ClustalW alignment algorithm (Megalign program of DNAS-TAR software, supra) to known Δ15 desaturase proteins from a wide range of species. The Fm1 amino acid sequence reported herein shares 25.4% identity with *C. elegans* Gen-Bank Accession No. L41807, 33.1% identity with *Synechosystis* desB (GI 1653388), 33.7% identity with the *Arabidopsis thaliana* fad2 gene, and 29.1% identity with the *Saprolegnia diclina* desaturase of U.S. 2003/0196217.

Example 4

Construction of Expression Plasmid pY34 (GPDPro:Fm1:XPR), Comprising the *Fusarium moniliforme* Desaturase of Sub-Family 1 (Encoding a Putative Δ15 Desaturase)

The present Example describes the construction of an expression plasmid comprising the Fusarium moniliforme Δ15 desaturase of sub-family 1 ("Fm1") identified in Example 3. Specifically, a chimeric gene was created, such that the putative Δ15 desaturase would be expressed under the control of the *Yarrowia* GPD promoter ("GPDPro"). This would enable subsequent determination of the protein's activity in *Yarrowia lipolytica*, by testing the ability of the expressed ORF to confer ALA production in the wild type strain and to complement a Δ12 desaturase-disrupted mutant (Example 2).

The ORF encoding the *F. moniliforme* Δ15 desaturase was PCR amplified using the cDNA clones ffm1c.pK001.g23 and ffm1c.pK013.n7 containing the full-length cDNA as the template and using upper and lower primers P192 (SEQ ID NO:56) and P193 (SEQ ID NO:57). The PCR was carried out in an Eppendorf Mastercycler Gradient Cycler using pfu polymerase, per the manufacturer's recommendations.

Amplification was carried out as follows: initial denaturation at 95° C. for 1 min, followed by 30 cycles of denaturation at 95° C. for 30 sec, annealing at 58° C. for 1 min and elongation at 72° C. for 1 min. A final elongation cycle at 72° C. for 10 min was carried out, followed by reaction termination at 4° C.

The correct-sized (ca.1240 bp) fragment was obtained from both templates. The fragment derived from clone ffm1c.pK001.g23 was purified from an agarose gel using a Qiagen DNA purification kit (Valencia, Calif.), digested with Not I and cloned into the Not I site between GPDPro and the XPR terminator of plasmid pY5-13GPDN (from Example 1). This resulted in creation of plasmid pY34, which contained a GPDPro:Fm1:XPR chimeric gene. The sequence of the Fm1 ORF in the resultant 8878 bp plasmid was confirmed. Plasmid pY34 additionally contained the *E. coli* origin of replication, the bacterial ampicillin resistance gene, a *Yarrowia* Leu 2 gene and the *Yarrowia* autonomous replication sequence (ARS).

Example 5

Expression of Plasmid PY34 (GPDPro:Fm1:XPR), Comprising The *Fusarium moniliforme* Desaturase of Sub-Family 1 (Encoding a Putative Δ15 Desaturase) in *Yarrowia lipolytica*

The present Example describes expression of plasmid pY34 (comprising the chimeric GPDPro:Fm1:XPR gene; from Example 4) in *Yarrowia lipolytica*. Specifically, the ability of the expressed *F. moniliforme* ORF to confer ALA production in the wild type strain of *Y. lipolytica* (thereby confirming the ORF's Δ15 desaturase activity) and to complement the Δ12 desaturase-disrupted mutant (from Example 2; thereby confirming the ORF's bifunctional Δ12/Δ15 desaturase activity) was tested.

Plasmids pY5 (vector alone control, from Example 1) and pY34 (GPDPro:Fm1:XPR) were each individually transformed into wild type (WT) and Δ12 desaturase-disrupted (Q-d12D) strains of *Yarrowia lipolytica* ATCC #76892, using the transformation procedure described in Example 2. Transformant cells were selected on Bio101 DOB/CSM-Leu plates.

Single colonies of wild type and transformant cells were each grown in 3 mL minimal media, harvested, washed, dried and analyzed, as described in Example 2 and the General Methods.

The fatty acid profile of wildtype Yarrowia and each of the transformants are shown below in Table 9. Fatty acids are identified as 16:0 (palmitate), 16:1 (palmitoleic acid), 18:0, 18:1 (oleic acid), 18:2 (LA) and 18:3 (ALA) and the composition of each is presented as a % of the total fatty acids. "d12d % SC" was calculated according to the following formula: ([18:2+18:3]/[18:1+18:2+18:3])*100 and represents percent substrate conversion to 18:2. "d15d % SC" was calculated according to the following formula: ([18:3]/[18:2+18:3])*100 and represents percent substrate conversion to ALA.

TABLE 9

Identification Of The *Fusarium moniliforme* Fm1 As A Bifunctional Δ12/Δ15 Desaturase

| Strain | % 16:0 | % 16:1 | % 18:0 | % 18:1 | % 18:2 | % ALA | d12d % SC | d15d % SC | Ratio ALA/LA |
|---|---|---|---|---|---|---|---|---|---|
| WT | 12.1 | 9.1 | 0.8 | 33.8 | 44.2 | 0.0 | 56.7 | 0 | — |
| WT + GPDPro::Fm1::XPR | 10.0 | 10.5 | 1.3 | 37.0 | 7.2 | 31.0 | 52.6 | 82.5 | 4.3 |

TABLE 9-continued

Identification Of The *Fusarium moniliforme* Fm1
As A Bifunctional Δ12/Δ15 Desaturase

| Strain | % 16:0 | % 16:1 | % 18:0 | % 18:1 | % 18:2 | % ALA | d12d % SC | d15d % SC | Ratio ALA/LA |
|---|---|---|---|---|---|---|---|---|---|
| Q-d12D | 3.3 | 13.9 | 0.3 | 82.4 | 0.0 | 0.0 | 0.0 | — | — |
| Q-d12D + GPDPro:: Fm1::XPR | 7.8 | 12.0 | 1.0 | 60.4 | 0.7 | 17.8 | 23.7 | 96.3 | 25.2 |

The results above demonstrated that the *F. moniliforme* ORF referred to herein as Fm1, and identified as a protein within sub-family 1 of those proteins having homology to the *Yarrowia lipolytica* Δ12 desaturase, is a Δ15 desaturase. Based on this confirmation, the Applicants predict that all other members of sub-family 1 (SEQ ID NOs:6, 10, 14 and 18) also will have Δ15 desaturase functionality.

Concerning the Δ15 desaturase activity of Fm1, it is noteworthy that the protein is even more efficient in its activity in *Yarrowia* (31% ALA accumulation) than previously expressed Δ15 desaturases in other yeast. Specifically, the % product accumulation of ALA when expressing the *C. elegans* Δ15 desaturase in the non-oleaginous yeast *Sacchromyces cerevisiae* was only 4.1% (Meesapyodsuk et al., *Biochem.* 39:11948-11954 (2000)), while the % product accumulation of ALA when expressing the *B. napus* Δ15 desaturase in *S. cerevisiae* was only 1.3% (Reed., D. W. et al., *Plant Physiol.* 122:715-720 (2000)). Based on the results provided herein, it would be expected that expression of the *Fusarium moniliforme* Δ15 desaturase, in combination of other genes for PUFA biosynthesis (e.g., a Δ6 desaturase, elongase, Δ5 desaturase, Δ17 desaturase, Δ9 desaturase, Δ8 desaturase, Δ4 desaturase, Δ12 desaturase), would result in higher production of ω-3 PUFAs than would result using any of the previously identified Δ15 desaturases.

Additionally, the results demonstrated that, unexpectedly, the *Fusarium moniliforme* Δ15 desaturase (Fm1) has some Δ12 desaturase activity. Specifically, expression of Fm1 in the Δ12 desaturase-disrupted strain of *Yarrowia lipolytica* (i.e., Q-d12D+GPDPro:Fm1:XPR) resulted in 24% substrate conversion of oleic acid to LA due to the Δ12 desaturase functionality of Fm1 (see "d12d % SC"). This was in addition to high substrate conversion of LA to ALA (96%, see "d15d % SC") due to the Δ15 desaturase functionality of Fm1. This bifunctionality is in marked contrast to any other known Δ12 or Δ15 desaturase. It will be obvious to one of skill in the art that expression of the *Fusarium moniliforme* Δ15 desaturase in a host organism that has low Δ12 desaturase activity (or lacks such activity entirely) will lead to maximized ratios of 18:3/18:2. It would be expected that when other genes for PUFA biosynthesis (e.g., a Δ6 desaturase, elongase, Δ5 desaturase, Δ17 desaturase) were expressed in this type of host organism with the *Fusarium moniliforme* Δ15 desaturase described above, an increased ratio of ω-3 to ω-6 fatty acids would result.

Example 6

Expression of *Magnaoorthe grisea* Desaturase of Sub-Family 1 (Encoding a Putative Δ15 Desaturase) in *Yarrowia lipolytica*

The present Example describes the contruction of an expression plasmid comprising the putative Magnaporthe grisea Δ15 desaturase ("Mg1") and the expression of this plasmid in *Yarrowia lipolytica*. This enabled confirmation of Mg1 as a Δ15 desaturase by testing the ability of the expressed ORF to confer ALA production in the wild type *Yarrowia lipolytica* strain and as a bifunctional Δ12/Δ15 desaturase by testing the ability of the expressed ORF to confer ALA production in the Δ12 desaturase-disrupted mutant of *Yarrowia lipolytica* (from Example 2).

Specifically, a chimeric TEF:Mg1 gene was constructed, wherein the putative Δ15 desaturase was expressed under the control of a *Yarrowia* TEF promoter (Muller S., et al., *Yeast*, 14: 12671283 (1998)). First, *Magnaporthe grisea* genomic DNA was isolated in a manner similar to that described for *Yarrowia lipolytica* in Example 2. Then, since the *Magnaporthe grisea* Mg1 gene encoding the putative Δ15 desaturase (SEQ ID NO:9) has two introns, these sequences were removed duing PCR amplification by first PCR-amplifying the three exons separately, and then PCR-amplifying the full length ORF by joining the three exons together using overlapping PCR primers. Thus, genomic DNA was used as the template in 3 separate PCR reactions, using the upper and lower primers shown below in Table 10.

TABLE 10

Primers For Amplification Of *Magnaporthe grisea* Exons Encoding Mg1

| Exon to be Amplified | Upper Primer | Lower Primer |
|---|---|---|
| Exon 1 | P186 (SEQ ID NO: 59) | P187 (SEQ ID NO: 60) |
| Exon 2 | P188 (SEQ ID NO: 61) | P189 (SEQ ID NO: 62) |
| Exon 3 | P190 (SEQ ID NO: 63) | P191 (SEQ ID NO: 64) |

Then, the full-length ORF was PCR-amplified using all three gel purified PCR products as templates and upper primer P186 and lower primer P191. Primers P186 and P191 contained Not I sites to facilitate cloning into the expression vector. Specifically, the correct-sized fragment was gel-purified, digested with NcoI and Not I, and cloned into Not I-cut *Yarrowia* expression vector pY5-13 (Example 1) under the control of the *Yarrowia* TEF promoter. The resultant clones were designated pY31.

Several pY31 clones were sequenced. As expected, all had a T-to-C substitution at position 3 of the ORF due to the NcoI site that was created in the upper primer to facilitate the cloning. This resulted in a change in the second amino acid from Ser to Ala. Three plasmid clones (i.e., pY31 plasmid clones #21, #24 and #28) were encoded by SEQ ID NO:10 (except for the second amino acid change described above); however, none of them had a nucleotide sequence identical to that of SEQ ID NO:9 (i.e., they had additional silent nucleotide substitutions that did not change the deduced amino acid sequence and most likely occurred by PCR errors). More specifically, plasmid clones #21, #24 and #28 all had the following base substitutions: a C-to-T substitution at position 309, a C-to-T substitution at position 390, a T-to-C substitution at position 549 and a G-to-C substitution at position 567. In addition, clone #24 had a T-to-A substitution at position 645, and both clones #21 and #28 had a C-to-T substitution at position 669.

The plasmids comprising the TEF:Mg1 chimeric genes (i.e., clones #21, #24 and #28) were each transformed into wildtype (Q) and the Δ12 desaturase-disrupted strain (Q-d12D) of Yarrowia lipolytica (ATCC #76982), according to the methodology described in Example 2. Three colonies (identified as "a", "b" and "c" in Table 11 below) from each transformation were picked and inoculated into 3 mL DOB/CSM medium and grown at 30° C. for 72 hrs, as described in General Methods. Cultures (1.5 mL) were harvested and subjected to direct trans-esterification and GC analysis (as described in Example 2 and the General Methods).

The fatty acid profile of wildtype Yarrowia and each of the transformants are shown below in Table 11. Fatty acids are identified as 16:0 (palmitate), 16:1 (palmitoleic acid), 18:0, 18:1 (oleic acid), 18:2 (LA) and 18:3 (ALA) and the composition of each is presented as a % of the total fatty acids (TFAs). "d12d % SC" was calculated according to the following formula: ([18:2+18:3]/[18:1+18:2+18:3])*100 and represents percent substrate conversion to 18:2. "d15d % SC" was calculated according to the following formula: ([18:3]/[18:2+18:3])*100 and represents percent substrate conversion to ALA.

As shown above, ALA is produced in both wildtype (Q) and Δ12 desaturase-disrupted strains (Q-d12D) of Yarrowia lipolytica that were transformed with the TEF:Mg1 chimeric gene. Thus, on the basis of these results, the identify of Mg1 as a desaturase having bifunctional Δ12/Δ15 activity is confirmed.

Example 7

Expression of Fusarium graminearium Desaturase of Sub-Family 1 (Encoding a Putative Δ15 Desaturase) In Yarrowia lipolytica The present Example describes the contruction of an expression plasmid comprising the putative Fusarium gramineΔ15 desaturase ("Fg1") and the expression of this plasmid in Yarrowia lipolytica. This would enable confirmation of Fg1 as a Δ15 desaturase by testing the ability of the expressed ORF to confer ALA production in the wild type Yarrowia lipolytica strain and as a bifunctional Δ12/Δ15 desaturase by testing the ability of the expressed ORF to confer ALA production in the Δ12 desaturase-disrupted mutant of Yarrowia lipolytica (from Example 2).

Specifically, a chimeric TEF:Fg1 gene will be synthesized, wherein the putative Δ15 desaturase would be expressed under the control of a Yarrowia TEF promoter. In a manner similar to that described in Example 6, three introns present in the Fusarium graminearium Fg1 gene encoding the putative Δ15 desaturase (SEQ ID NO:17) will be removed during PCR amplification, prior to expression of the Fg1 ORF. Thus,

TABLE 11

Identification Of The Magnaporthe grisea Mg1 As A Bifunctional Δ12/Δ15 Desaturase

| Strain | Plasmid, Transformant | TFA μg) | % 16:0 | % 16:1 | % 18:0 | % 18:1 | % 18:2 | % ALA | d12d % SC | d15d % SC |
|---|---|---|---|---|---|---|---|---|---|---|
| Q-D12 | None | 341 | 4.2 | 10.8 | 1.4 | 80.4 | 0.0 | 0.0 | 0 | |
| Q-D12 | pY31#21, a | 283 | 5.1 | 13.5 | 1.5 | 75.8 | 0.0 | 1.3 | 2 | 100 |
| Q-D12 | pY31#21, b | 257 | 5.1 | 13.2 | 1.4 | 76.0 | 0.0 | 1.4 | 2 | 100 |
| Q-D12 | pY31#21, c | 255 | 5.2 | 13.0 | 1.5 | 76.0 | 0.0 | 1.4 | 2 | 100 |
| Q-D12 | pY31#24, a | 261 | 5.1 | 13.6 | 1.5 | 75.5 | 0.0 | 1.3 | 2 | 100 |
| Q-D12 | pY31#24, b | 272 | 5.0 | 13.0 | 1.4 | 76.0 | 0.0 | 1.4 | 2 | 100 |
| Q-D12 | pY31#24, c | 321 | 5.3 | 12.7 | 1.4 | 76.0 | 0.0 | 1.6 | 2 | 100 |
| Q-D12 | pY31#28, a | 289 | 5.0 | 13.3 | 1.4 | 76.0 | 0.0 | 1.4 | 2 | 100 |
| Q-D12 | pY31#28, b | 317 | 5.0 | 13.3 | 1.4 | 76.1 | 0.0 | 1.3 | 2 | 100 |
| Q-D12 | pY31#28, c | 284 | 5.1 | 13.3 | 1.5 | 75.9 | 0.0 | 1.4 | 2 | 100 |
| Q | None | 258 | 7.1 | 13.0 | 1.3 | 46.6 | 29.2 | 0.0 | 39 | 0 |
| Q | pY31#21, a | 243 | 6.4 | 14.2 | 1.2 | 50.8 | 11.5 | 13.4 | 33 | 54 |
| Q | pY31#21, b | 297 | 6.4 | 14.0 | 1.3 | 51.0 | 11.5 | 13.4 | 33 | 54 |
| Q | pY31#21, c | 269 | 6.5 | 14.1 | 1.3 | 51.0 | 11.3 | 13.2 | 32 | 54 |
| Q | pY31#24, a | 240 | 6.6 | 13.9 | 1.4 | 50.8 | 10.9 | 14.0 | 33 | 56 |
| Q | pY31#24, b | 249 | 6.6 | 14.1 | 1.4 | 51.0 | 11.1 | 13.3 | 32 | 55 |
| Q | pY31#24, c | 219 | 6.5 | 14.1 | 1.4 | 50.9 | 11.2 | 13.4 | 33 | 55 |
| Q | pY31#28, a | 311 | 6.3 | 14.2 | 1.2 | 51.4 | 10.9 | 13.5 | 32 | 55 |
| Q | pY31#28, b | 296 | 6.0 | 14.1 | 1.2 | 51.7 | 11.0 | 13.6 | 32 | 55 |
| Q | pY31#28, c | 264 | 6.3 | 14.2 | 1.3 | 51.6 | 10.9 | 13.2 | 32 | 55 | genomic *F. graminearium* DNA will first be used as template in 4 separate PCR reactions using the upper and lower primers shown below in Table 12.

TABLE 12

Primers For Amplification Of *F. graminearium* Exons Encoding Fg1

| Exon to be Amplified | Upper Primer | Lower Primer |
|---|---|---|
| Exon 1 | PFg1UP1 (SEQ ID NO: 65) | PFg1LP1 (SEQ ID NO: 66) |
| Exon 2 | PFg1UP2 (SEQ ID NO: 67) | PFg1LP2 (SEQ ID NO: 68) |
| Exon 3 | PFg1UP3 (SEQ ID NO: 69) | PFg1LP3 (SEQ ID NO: 70) |
| Exon 4 | PFg1UP4 (SEQ ID NO: 71) | PFg1LP4 (SEQ ID NO: 72) |

Then, the full-length ORF will be PCR-amplified using all 4 gel purified PCR products as templates and upper primer PFg1 UP1 and lower primer PFg1LP4. Primers PFg1UP1 and PFg1LP4 contain Not I sites to facilitate cloning into the expression vector. The correct-sized fragment will be gel-purified, digested with Not I, and cloned into a Not I-cut *Yarrowia* expression vector, as described in Example 6 for the Mg1 coding region.

The plasmid comprising the TEF:Fg1 chimeric genes will be transformed into wild type (Q) and the Δ12 desaturase-disrupted (Q-d12D) strains of *Yarrowia lipolytica* (ATCC #76982). Following growth of single colonies of wild type and transformant cells in minimal media, the cells will be harvested and subjected to direct trans-esterification and GC analysis (as described in Example 2 and the General Methods).

ALA is expected to be produced in both wildtype and Δ12 desaturase-disrupted strains of *Yarrowia lipolytica* that were transformed with the TEF:Fg1 chimeric gene, thus confirming the identify of Fg1 as a bifunctional Δ12/Δ15 desaturase. This expectation is based on Fg1 protein sequence being closest to that of Fm1, based on a % identity comparison.

Example 8

Transformation of Arabidopsis Plants with a Chimeric Gene Comprising the *Fusarium moniliforme* Δ15 Desaturase of Sub-Family 1 (Fm1)

This Example describes methods that will be useful to transform wild type and fad2-1 mutant Arabidopsis with a chimeric gene containing the *Fusarium* Δ15 desaturase coding region.

Construction of an Arabidopsis Expression Vector Comprising Fm1

The NotI fragment of pY34 containing the Fm1 Δ15 desaturase coding region (Example 4) will be cloned into the NotI site of soybean expression vector pKR353. As described in Example 18 below, pKR353 contains a NotI site flanked by a seed-specific promoter from the Kti3 (kunitz trypsin inhibitor 3) gene and a Kti3 transcription terminator.

The chimeric Kti3 promoter:Fm1:Kti3 terminator gene will be isolated as an Asc 1 fragment from pKR353(Δ15) and cloned into the unique Asc 1 site in the binary vector pZBL11 (Asc1). pZBL11 (AscI) was derived from binary vector pZBL11 by adding an Asc I linker between the Pac I and Asp718 sites between the right and left T-DNA borders. pZBL11 (U.S. Pat. No. 5,968,793; EP 1003891; and WO 9859062) also contains a 35S:sulfonylurea resistant acetolactate synthase (ALS) transgene within the T-DNA borders that confers resistance to sulfonylurea herbicide and serves as the plant selectable marker. pZBL11 also has an origin of replication of both *E. coli* and *Agrobacterium tumefaciens*, and a bacterial ampicillin resistance gene.

The resultant binary plasmid, pZBLI(Δ15) will be transformed into *Agrobacterium* strain LBA4404. The transfected *Agrobacterium* will subsequently be used to transform wild type and a fad2-1 mutant (Okuley, J. et al., *Plant Cell* 6:147-158 (1994)) of *Arabidopsis thaliana* by the *Agrobacterium* dip method. Transformants will be selected on sulfonylurea and tested for ALA production in the seeds.

Wild type *Arabidopsis* transformed with the chimeric gene expressing the Δ15 desaturase will contain higher ALA content than untransformed plants. Fad2-1 plants transformed with the same chimeric gene will contain a higher ALA content than the untransformed mutant; and transformant fad2-1 plants will have a ratio of 18:3/18:2 that is higher than in the untransformed mutant as well as the wild-type transformant.

Example 9

Transformation of Somatic Soybean Embryo Cultures with a Chimeric Gene Comprising the Fusarium moniliforme Δ15 Desaturase of Sub-Family 1 (Fm1)

This Example describes methods that will be used for the cultivation of soybean, following their transformation with a chimeric gene containing the Fm1 Δ15 desaturase coding region.

Construction of a Soybean Expression Vector Comprising Fm1

Plasmid pKR353(Δ15) (created in Example 8) will also contain two cassettes comprising the hygromycin B phosphotransferase gene ("hpt"; Gritz, L. and J. Davies, *Gene* 25:179-188 (1983)):

(1) A T7 promoter:hpt:T7 terminator cassette—this cassette, in addition to a bacterial origin of replication (ori), enabled selection and replication in *E. coli*.

(2) A 35S promoter:hpt:NOS 3' transcription terminator cassette—this cassette enabled selection in soybean (35S, see Odell et al., *Nature* 313:810-812 (1985)); NOS 3', see Depicker et al., *J. Mol. Appl. Genet.* 1:561:570 (1982)).

Transformation of Somatic Soybean Embryo Cultures

Soybean embryogenic suspension cultures (cv. Jack) will be maintained in 35 mL liquid medium SB196 (infra) on a rotary shaker at 150 rpm and 26° C. with cool white fluorescent lights on a 16:8 hr day/night photoperiod with a light intensity of 60-85 μE/m$^2$/s.

| SB 196 - FN Lite Liquid Proliferation Medium (Per Liter): | |
|---|---|
| MS FeEDTA 100× Stock | 10 mL |
| MS Sulfate 100× Stock | 10 mL |
| FN Lite Halides 100× Stock | 10 mL |
| FN Lite P, B, Mo 100× Stock | 10 mL |
| B5 vitamins (1 mL/L) | 1.0 mL |
| 2,4-D (10 mg/L final concentration) | 1.0 mL |
| $KNO_3$ | 2.83 g |
| $(NH_4)_2SO_4$ | 0.463 g |
| Asparagine | 1.0 g |
| Sucrose (1%) | 10 g |
| pH 5.8 | |

| FN Lite Stock Solutions | 1000 mL | 500 mL |
|---|---|---|
| 1 MS Fe EDTA 100× Stock | | |
| Na$_2$ EDTA* | 3.724 g | 1.862 g |
| FeSO$_4$—7H$_2$O | 2.784 g | 1.392 g |
| 2 MS Sulfate 100× stock | | |
| MgSO$_4$—7H$_2$O | 37.0 g | 18.5 g |
| MnSO$_4$—H$_2$O | 1.69 g | 0.845 g |
| ZnSO$_4$—7H$_2$O | 0.86 g | 0.43 g |
| CuSO$_4$—5H$_2$O | 0.0025 g | 0.00125 g |
| 3 FN Lite Halides 100× Stock | | |
| CaCl$_2$—2H$_2$O | 30.0 g | 15.0 g |
| KI | 0.083 g | 0.0715 g |
| CoCl$_2$—6H$_2$O | 0.0025 g | 0.00125 g |
| 4 FN Lite P,B,Mo 100× Stock | | |
| KH$_2$PO$_4$ | 18.5 g | 9.25 g |
| H$_3$BO$_3$ | 0.62 g | 0.31 g |
| Na$_2$MoO$_4$—2H$_2$O | 0.025 g | 0.0125 g |

*Add first, dissolve in dark bottle while stirring

Cultures will be subcultured every 7-14 days by inoculating approximately 35 mg of tissue into 35 mL of fresh liquid SB196 (the preferred subculture interval is every 7 days).

Soybean embryogenic suspension cultures will be transformed with pKR353(Δ1 5) (supra) by the method of particle gun bombardment (Klein et al., *Nature*, 327:70 (1987)). A DuPont Biolistic PDS1000/HE instrument (helium retrofit) will be used for all transformations (E.I. duPont de Nemours and Co., Inc., Wilmington, Del.).

Soybean Embryogenic Suspension Culture Initiation

Soybean cultures will be initiated twice each month with 5-7 days between each initiation.

Between 45-55 days after planting, pods with immature seeds from available soybean plants will be picked and the seeds will be removed from their shells and placed into a sterilized magenta box. The soybean seeds will be sterilized by shaking for 15 min in the following solution: 95 mL of autoclaved distilled water plus 5 mL Clorox and 1 drop of soap. Seeds will be rinsed using two 1 L bottles of sterile distilled water and those less than 4 mm will be placed on individual microscope slides. The small end of the seed will be cut and the cotyledons pressed out of the seed coat. Cotyledons (25-30 per plate) will be transferred to plates containing SBI medium.

SBI Solid Medium (Per Liter):
  1 package MS salts (Gibco/BRL, Catalog #11117-066)
  1 mL B5 Vitamins Stock (infra)
  31.5 g sucrose
  2 mL 2,4-D (20 mg/L final concentration; 2,4-D stock is obtained premade from Phytotech, Catalog #D 295 as 1 mg/mL)
  pH to 5.7
  8 g TC agar B5 Vitamins Stock (Per 100 mL):
  10 g myo-inositol
  100 mg nicotinic acid
  100 mg pyridoxine HCl
  1 g thiamine

* Note: Store aliquots at −20° C.; If the solution does not dissolve quickly enough, apply a low level of heat via the hot stir plate.

Plates containing the cotyledons will be wrapped with fiber tape and stored for 8 wks. After this time, secondary embryos will be cut and placed into SB196 liquid media for 7 days.

Preparation of DNA for Bombardment

Either an intact plasmid or a DNA plasmid fragment containing the genes of interest and the selectable marker gene will be used for bombardment. Fragments are obtained by gel isolation of double digested plasmids. In each case, 100 μg of plasmid DNA is digested in 0.5 mL of the appropriate enzyme mix. The resulting DNA fragments are separated by gel electrophoresis on 1% SeaPlaque GTG agarose (BioWhittaker Molecular Applications, Rockland, Me.) and the DNA fragments containing chimeric genes are cut from the agarose gel. DNA is purified from the agarose using the GELase digesting enzyme following the manufacturer's protocol (EpiCentre, Madison, Wis.).

A 50 μl aliquot of sterile distilled water containing 3 mg of gold particles (3 mg gold) will be added to 5 μl of a 1 μg/μl DNA solution (either intact plasmid or DNA fragment prepared as described above), 50 μl 2.5 M CaCl$_2$ and 20 μl of 0.1 M spermidine. The mixture will be shaken 3 min on level 3 of a vortex shaker and spun for 10 sec in a bench microfuge. After a wash with 400 μl 100% ethanol, the pellet will be suspended by sonicaton in Ar 40 μl of 100% ethanol. Five μl of DNA suspension will be dispensed to each flying disk of the Biolistic PDS1000/HE instrument disk. Each 5 μl aliquot will contain approximately 0.375 mg gold per bombardment (i.e., per disk).

Tissue Preparation and Bombardment with DNA

Approximately 150-200 mg of 7 day old embryonic suspension cultures will be placed in an empty, sterile 60×15 mm petri dish and the dish will be covered with plastic mesh. Tissue will be bombarded 1 or 2 shots per plate with the membrane rupture pressure set at 1100 PSI and the chamber evacuated to a vacuum of 27-28 inches of mercury. Tissue will be placed approximately 3.5 inches from the retaining/stopping screen.

Selection of Transformed Embryos

Transformed embryos will be selected using hygromycin (when the hygromycin phosphotransferase, HPT, gene is used as the selectable marker) or chlorsulfuron (when the acetolactate synthase, ALS, gene is used as the selectable marker). In either case, the tissue will be placed into fresh SB1 96 media and cultured as described above following bombardment. Six days post-bombardment, the SB196 will be exchanged with fresh SB196 containing a selection agent of either 30 mg/L hygromycin or 100 ng/mL chlorsulfuron (chlorsulfuron stock: 1 mg/mL in 0.01 N ammonium hydroxide). The selection media will be refreshed weekly. Four to six weeks post-selection, green, transformed tissue may be observed growing from untransformed, necrotic embryogenic clusters. Isolated, green tissue will be removed and inoculated into multiwell plates containing SB196 to generate new, clonally propagated, transformed embryogenic suspension cultures.

Regeneration of Soybean Somatic Embryos into Plants

In order to obtain whole plants from embryogenic suspension cultures, the tissue must be regenerated.

Embryo Maturation: Embryos will be cultured for 4-6 wks at 26° C. in SB196 under cool white fluorescent (Phillips Cool White Econowalt F40/CW/RS/EW) and Agro (Phillips F40 Agro; 40 watt) bulbs on a 16:8 hr photoperiod with a fight intensity of 90120 μE/m$^2$/s. After this time, embryo clusters will be removed to SB166 solid agar media for 1-2 weeks.

SB 166 Solid Medium (Per Liter):
  1 package MS salts (Gibco/BRL, Cat#11117-066)
  1 mL B5 vitamins 1000X stock
  60 g maltose
  750 mg $MgCl_2$ hexahydrate
  5 g activated charcoal
  pH 5.7
  2 g gelrite Clusters are then subcultured to medium SB103 (media prepared the same as for SB 166, except no activated charcoal is included) for 3 weeks. During this period, individual embryos can be removed from the clusters and screened for alterations in their fatty acid compositions. It should be noted that any detectable phenotype, resulting from the expression of the genes of interest, could be screened at this stage. This would include, but not be limited to: alterations in fatty acid profile, protein profile and content, carbohydrate content, growth rate, viability or the ability to develop normally into a soybean plant.

Embryo Desiccation And Germination: Matured individual embryos will be desiccated by placing them into an empty, small petri dish (35×10 mm) for approximately 4-7 days. The plates are sealed with fiber tape (creating a small humidity chamber). Desiccated embryos are planted into SB71-4 medium where they are left to germinate under the same culture conditions described above.

SB 71-4 Solid Medium (Per Liter):
  1 bottle Gamborg's B5 salts w/sucrose (Gibco/BRL, Catalog #21153-036)
  pH 5.7
  5 g TC agar Germinated plantlets will be removed from germination medium and rinsed thoroughly with water and then planted in Redi-Earth in 24-cell pack trays covered with clear plastic domes. After 2 wks, the domes will be removed and plants hardened off for a further week. If plantlets look hardy, they are transplanted to 10" pots of Redi-Earth with up to 3 plantlets per pot. After 10-16 wks, mature seeds will be harvested, chipped and analyzed for fatty acids.

Example 10

Analysis of Somatic Soy Embryos Comprising the *Fusarium moniliforme* Δ15 Desaturase of Sub-Family 1 (Fm1)

This Example describes methods that will be useful to analyze fatty acid content in transformant soybean comprising a chimeric gene containing the Fm1 Δ15 desaturase coding region.

Theory

Mature somatic soybean embryos are a good model for zygotic embryos. While in the globular embryo state in liquid culture, somatic soybean embryos contain very low amounts of triacylglycerol or storage proteins typical of maturing, zygotic soybean embryos. At this developmental stage, the ratio of total triacylglyceride to total polar lipid (phospholipids and glycolipid) is about 1:4, as is typical of zygotic soybean embryos at the developmental stage from which the somatic embryo culture was initiated. At the globular stage as well, the mRNAs for the prominent seed proteins, α'-subunit of β-conglycinin, kunitz trypsin inhibitor 3, and seed lectin are essentially absent. Upon transfer to hormone-free media to allow differentiation to the maturing somatic embryo state, triacylglycerol becomes the most abundant lipid class; and, mRNAs for α'-subunit of β-conglycinin, kunitz trypsin inhibitor 3 and seed lectin become very abundant messages in the total mRNA population. On this basis, the somatic soybean embryo system behaves very similarly to maturing zygotic soybean embryos in vivo, and is therefore a good and rapid model system for analyzing the phenotypic effects of modifying the expression of genes in the fatty acid biosynthetic pathway. Most importantly, the model system is also predictive of the fatty acid composition of seeds from plants derived from transgenic embryos.

Fatty Acid Analysis

Transgenic somatic soybean embryos will be analyzed. For this, fatty acid methyl esters will be prepared from single, matured, somatic soy embryos by transesterification. Embryos will be placed in a vial containing 50 μL of trimethylsulfonium hydroxide (TMSH) and 0.5 mL of hexane and incubated for 30 min at room temperature while shaking. Fatty acid methyl esters (5 μL injected from hexane layer) will be separated and quantified using a Hewlett-Packard 6890 Gas Chromatograph fitted with an Omegawax 320 fused silica capillary column (Supelco Inc., Bellefonte, Pa.; Catalog #24152). A portion of the somatic embryos will have higher levels of ALA than in control somatic embryos.

Mature plants will be regenerated from transformed embryos, and the fatty acid analyses will be performed on the seeds that are produced by the regenerated plants. These plants will then be crossed with other transgenic plants expressing ω-3 fatty acid biosynthetic pathway genes (wherein the combined levels of EPA and DPA are frequently greater than 15%, and are as high as 23.5% of the total). Representative genes preferred for making long-chain PUFAs (e.g., EPA) include one or more of the following:

TABLE 13

EPA Biosynthetic Pathway Genes

| Gene | Organism | Plasmid Name | Reference |
|---|---|---|---|
| Δ6 desaturase | *S. diclina* | pRSP1 | WO 02/081668 |
| Δ6 desaturase | *M. alpina* | pCGR5 | U.S. Pat. No. 5,968,809 |
| Elongase | *M. alpina* | pRPB2 | WO 00/12720 |
| Elongase | *T. aureum* | pRAT-4-A7 | WO 02/08401 |
| Δ5 desaturase | *M. alpina* | pCGR4 | U.S. Pat. No. 6,075,183 |
| Δ5 desaturase | *S. diclina* | pRSP3 | WO 02/081668 |
| Δ4 desaturase | *S. aggregatum* | pRSA1 | WO 02/090493 |

Example 11

Cloning the Fusarium Δ15 Desaturase into a Soybean Expression Vector (PKR578)

This example describes the construction of pKR578, a vector for strong, seed-specific expression of the Δ15 desaturase in soybeans.

Vector pKS121 (WO 02/00904) contains a NotI site flanked by the Kunitz soybean Trypsin Inhibitor (KTi) promoter [Jofuku et al., (1989) *Plant Cell* 1:1079-1093] and the KTi 3' termination region, the isolation of which is described in U.S. Pat. No. 6,372,965 (KTi/NotI/KTi3' cassette). Vector pKR457 is a derivative of pKS121 where the restriction sites upstream and downstream of the Kti/NotI/Kti3' cassette have been altered through a number of subcloning steps. Vector pKR457 also contains the Soy albumin transcription terminator downstream of the Kti terminator to lengthen and strengthen termination of transcription. In pKR457, the BamHI site upstream of the Kti promoter in pKS121 was removed and a new sequence (SEQ ID NO:73) added containing a BsiWI, SalI, SbfI and HindIII site with the BsiWI site being closest the 5' end of the Kti promoter. In addition, the SalI site downstream of the Kti terminatior in pKS121 was removed and a new sequence (SEQ ID NO: 74) added containing an XbaI (closest to 3' end of Kti terminator), a BamHI site, the soy albumin transcription terminator sequence, a BsiWI site and another BamHI site (Kti/NotI/KtiSalb cassette). The albumin transcription terminator was previously amplified from soy genomic DNA using primer oSalb-12 (SEQ ID NO: 75), designed to introduce BamHI, XbaI and BsiWI sites at the 3' end of the terminator, and primer oSalb-13 (SEQ ID NO: 76), designed to introduce BamHI sites at the 5' end of the terminator.

A starting plasmid pKS123 (WO 02/08269, the contents of which are hereby incorporated by reference) contains the hygromycin B phosphotransferase gene (HPT) [Gritz, L. and Davies, J. (1983) *Gene* 25:179-188], flanked by the T7 promoter and transcription terminator (T7prom/hpt/T7term cassette), and a bacterial origin of replication (ori) for selection and replication in bacteria such as *E. coli*. In addition, pKS123 also contains the hygromycin B phosphotransferase gene, flanked by the 35S promoter [Odell et al., (1985) *Nature* 313:810-812] and NOS 3' transcription terminator [Depicker et al., (1982) *J. Mol. Appl. Genet* 1:561:570] (35S/hpt/NOS3' cassette) for selection in plants such as soybean. pKS123 also contains a NotI restriction site, flanked by the promoter for the α' subunit of β-conglycinin [Beachy et al., (1985) *EMBO J.* 4:3047-3053] and the 3' transcription termination region of the phaseolin gene [Doyle, J. J. et al. (1986) *J. Biol. Chem.* 261:9228-9238] thus allowing for strong tissue-specific expression in the seeds of soybean of genes cloned into the NotI site. Vector pKR72 is a derivative pKS123 where the HindIII fragment containing the β-conglycinin/NotI/phaseolin cassette has been inverted and a sequence (SEQ ID NO:77) containing SbfI, FseI and BsiWI restriction enzyme sites was introduced between the HindIII and BamHI sites in front of the β-conglycinin promoter. Vector pKR72 was digested with HindIII to remove the βcon/NotI/Phas3' cassette and give pKR325.

An intermediate cloning vector was formed by cloning the BsiWI fragment of pKR457, containing the Kti/NotI/KtiSalb cassette into the BsiWI site of pKR325. The NotI fragment of pY34 (see Example 4) containing the *Fusarium* Δ15 desaturase was then cloned into the NotI site of this intermediate vector to give pKR578. Plasmid pKR578 (SEQ ID NO:78) is shown in FIG. 6. Plasmid pKR578 has been deposited with the American Type Culture Collection (ATCC), 10801 University Boulevard, Manassas, Va. 20110-2209, bearing ATCC accession number PTA-6280 with a date of deposit of Nov. 4, 2004.

Example 12

Isolation of Soybean Seed-Specific Promoters

The cloning of soybean seed-specific promoters has been described in WO 04/071467 and is re-described here.

The soybean annexin and BD30 promoters (described in WO 04/071178, published on Aug. 26, 2004) were isolated with the Universal GenomeWalker system (Clontech) according to its user manual (PT3042-1). To make soybean GenomeWalker libraries, samples of soybean genomic DNA were digested with DraI, EcoRV, PvuII and StuI separately for two hours. After DNA purification, the digested genomic DNAs were ligated to the GenomeWalker adaptors AP1 and AP2.

Two gene specific primers (GSP1 and GSP2) were designed for soybean annexin gene based on the 5' coding sequences in annexin cDNA in DuPont EST database. The sequences of GSP1 and GSP2 are set forth in SEQ ID NOS:79 and 80.

The AP1 and the GSP1 primers were used in the first round PCR using the conditions defined in the GenomeWalker system protocol. Cycle conditions were 94° C. for 4 minutes; 94° C. for 2 second and 72° C. for 3 minutes, 7 cycles; 94° C. for 2 second and 67° C. for 3 minutes, 32 cycles; 67° C. for 4 minutes. The products from the first run PCR were diluted 50-fold. One microliter of the diluted products were used as templates for the second PCR with the AP2 and GSP2 as primers. Cycle conditions were 94° C. for 4 minutes; 94° C. for 2 second and 72° C. for 3 min, 5 cycles; 94° for 2 second and 67° C. for 3 minutes, 20 cycles; 67° C. for 3 minutes. A 2.1 kb genomic fragment was amplified and isolated from the EcoRV-digested GenomeWalker library. The genomic fragment was digested with BamH I and Sal I and cloned into Bluescript KS+ vector for sequencing. The DNA sequence of this 2012 bp soybean annexin promoter fragment is set forth in SEQ ID NO:81.

Two gene specific primers (GSP3 and GSP4) were designed for soybean BD30 based on the 5' coding sequences in BD30 cDNA in NCBI GenBank (J05560). The oligonucleotide sequences of the GSP3 and GSP4 primers have the sequences set forth in SEQ ID NOS:82 and 83.

The AP1 and the GSP3 primers were used in the first round PCR using the same conditions defined in the GenomeWalker system protocol. The cycle conditions used for soybean annexin promoter do not work well for the soybean BD30 promoter in GenomeWalker experiment. A modified touchdown PCR protocol was used. Cycle conditions were: 94° C. for 4 minutes; 94° C. for 2 second and 74° C. for 3 minutes, 6 cycles in which annealing temperature drops 1° C. every cycle; 94° C. for 2 second and 69° C. for 3 minutes, 32 cycles; 69° C. for 4 minutes. The products from the $1^{st}$ run PCR were diluted 50-fold. One microliter of the diluted products were used as templates for the $2^{nd}$ PCR with the AP2 and GSP4 as primers. Cycle conditions were: 94° C. for 4 minutes; 94° C. for 2 second and 74° C. for 3 min, 6 cycles in which annealing temperature drops 1° C. every cycle; 94° C. for 2 second and 69° C. for 3 minutes, 20 cycles; 69° C. for 3 minutes. A 1.5 kb genomic fragment was amplified and isolated from the PvuII-digested GenomeWalker library. The genomic fragment was digested with BamHI and SalI and cloned into Bluescript KS+ vector for sequencing. DNA sequencing determined that this genomic fragment contained a 1408 bp soybean BD30 promoter sequence (SEQ ID NO:84).

Based on the sequences of the soybean β-conglycinin β-subunit promoter sequence in NCBI database (S44893), two oligos with either BamHI or NotI sites at the 5' ends were designed to amplify the soybean β-conglycinin β-subunit promoter (SEQ ID NO:85). The oligonucleotide sequences of these two oligos are set forth in SEQ ID NOS: 86 and 87.

Based on the sequences of the soybean Glycinin Gy1 promoter sequence in the NCBI GenBank database (X15121), two oligos with either BamHI or NotI sites at the 5' ends were designed to amplify the soybean Glycinin Gy1 promoter (SEQ ID NO:88). The oligonucleotide sequences of these two oligos are set forth in SEQ ID NOS:89 and 90.

Example 13

Cloning the Fusarium Δ15 Desaturase into a Soybean Expression Vector for Co-expression with a Δ17 desaturase (pKR585)

This example describes the construction of pKR585, a vector for strong, seed-specific expression of the Fusarium Δ15 desaturase and *Saprolegnia diclina* Δ17 desaturase in soybeans. Construction of an intermediate cloning vector (pKR271), containing the *Saprolegnia diclina* Δ17 desaturase [Pereira et al. (2004) *Biochem. J.* 378, 665-671] under control of the soy annexin promoter, has previously been described in WO 04/071467 and is re-stated here.

The KTi/NotI/KTi3' cassette was PCR-amplified from pKS121 using primers oKTi5 (SEQ ID NO:91) and oKTi6 (SEQ ID NO:92), designed to introduce an XbaI and BsiWI site at both ends of the cassette. The resulting PCR fragment was subcloned into the XbaI site of the cloning vector pUC19 to give plasmid pKR124 thus adding a PstI and SbfI site at the 3' end of the Kti transcription terminator.

The SalI fragment of pJS93 containing soy BD30 promoter (WO 01/68887) was combined with the SalI fragment of pUC19 to give pKR227 thus adding a PstI and SbfI site at the 5' end of the BD30 promoter.

The BD30 3' transcription terminator was PCR-amplified from soy genomic DNA using primer oSBD30-1 (SEQ ID NO:93), designed to introduce an NotI site at the 5' end of the terminator, and primer oSBD30-2 (SEQ ID NO:94), designed to introduce a BsiWI site at the 3' end of the terminator.

The resulting PCR fragment was subcloned into the intermediate cloning vector pCR-Script AMP SK(+) (Stratagene) according the manufacturer's protocol to give plasmid pKR251r. The EcoRI/NotI fragment from pKR251r, containing the BD30 3' transcription terminator, was cloned into the EcoRI/NotI fragment of intermediate cloning vector pKR227 to give pKR256.

The annexin promoter (SEQ ID NO:81) from pJS92 was released by BamHI digestion and the ends were filled. The resulting fragment was ligated into the filled BsiWI fragment from the vector backbone of pKR124 in a direction which added a PstI and SbfI site at the 5' end of the annexin promoter to give pKR265. The annexin promoter was released from pKR265 by digestion with SbfI and NotI and was cloned into the SbfI/NotI fragment of pKR256, containing the BD30 3' transcription terminator, an ampicillin resistance gene and a bacterial ori region, to give pKR268.

The gene for the *Saprolegnia diclina* Δ17 desaturase was released from pKS203 [Pereira et al. (2004) *Biochem. J.* 378, 665-671] by partial digestion with NotI, and was cloned into the NotI site of pKR268 to give pKR271.

Figure 7:
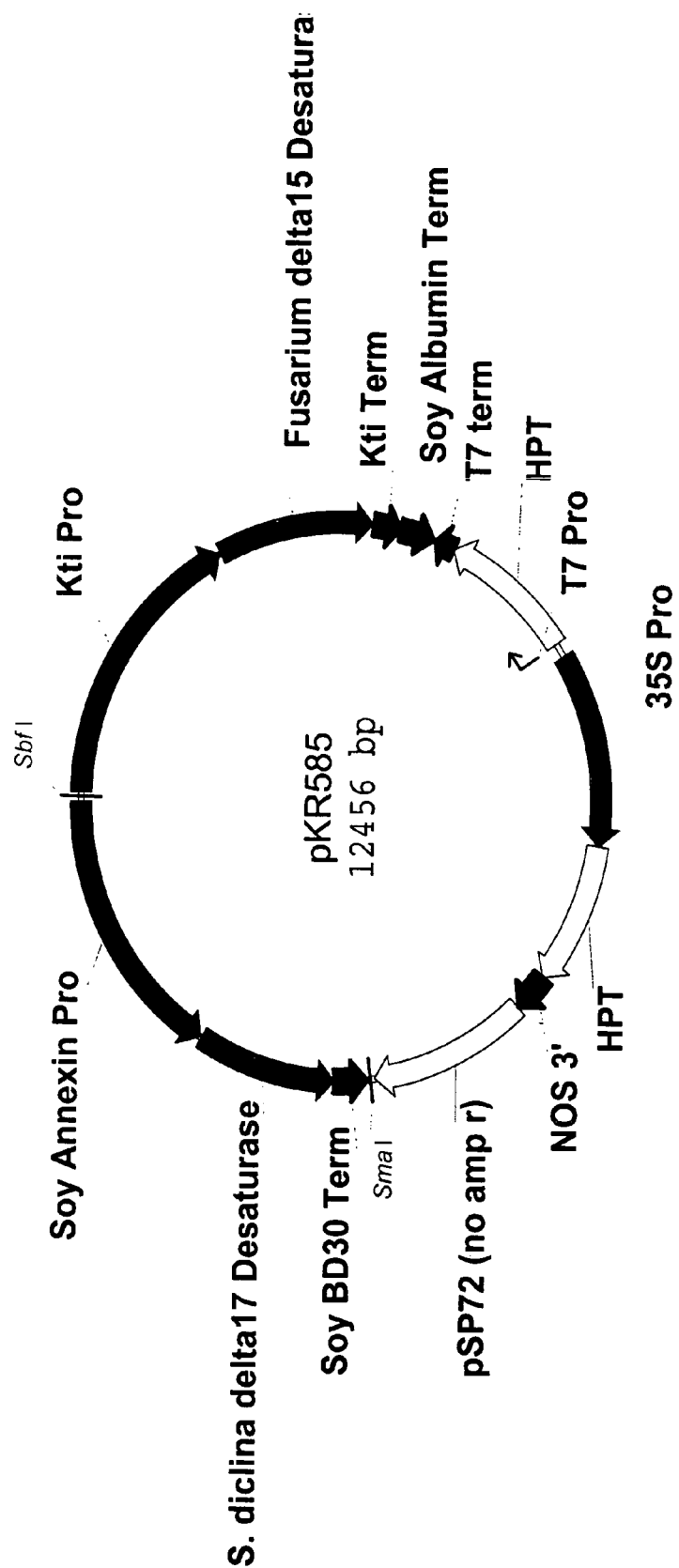
FIG. 7 is a schematic depiction of plasmid pKR585 (see Example 13).

Plasmid pKR271 was then digested with PstI and the fragment containing the *Saprolegnia diclina* Δ17 desaturase was cloned into the SbfI site of pKR578 to give pKR585. In this way, the *Fusarium* Δ15 desaturase could be co-expressed with the *Saprolegnia diclina* Δ17 desaturase behind strong, seed-specific promoters. A map of pKR585 (SEQ ID NO:95) is shown in FIG. 7. Plasmid pKR585 has been deposited with the American Type Culture Collection (ATCC), 10801 University Boulevard, Manassas, Va. 20110-2209, bearing ATCC accession number PTA-6279 with a date of deposit of Nov. 4, 2004.

Example 14

Assembling EPA Biosynthetic Pathway Genes for Expression in Soybeans (pKR274)

This example describes the construction of pKR274, a vector designed for strong, seed-specific expression of the *M. alpina* Δ6 desaturase (U.S. Pat. No. 5,968,809), *M. alpina* elongase (WO 00/12720) and *M. alpina* Δ5 desaturase (U.S. Pat. No. 6,075,183) in somatic soybean embryos and soybean seeds. Construction of this vector was previously described in WO 04/071467 and is re-stated here.

The Δ6 desaturase was cloned behind the promoter for the α subunit of β-conglycinin [Beachy et al., (1985) *EMBO J.* 4:3047-3053] followed by the 3' transcription termination region of the phaseolin gene [Doyle, J. J. et al. (1986) *J. Biol. Chem.* 261:9228-9238] (βcon/Mad6/Phas3' cassette).

The Δ5 desaturase was cloned behind the Kunitz soybean Trypsin Inhibitor (KTi) promoter [Jofuku et al., (1989) *Plant Cell* 1:1079-1093], followed by the KTi 3' termination region, the isolation of which is described in U.S. Pat. No. 6,372,965 (KTi/Mad5/KTi3' cassette).

The elongase was cloned behind the glycinin Gy1 promoter (SEQ ID NO:88) followed by the pea leguminA2 3' termination region (Gy1/Maelo/legA2 cassette).

All of these promoters exhibit strong tissue specific expression in the seeds of soybean. Plasmid pKR274 also contains the hygromycin B phosphotransferase gene [Gritz, L. and Davies, J. (1983) *Gene* 25:179-188] cloned behind the T7 RNA polymerase promoter and followed by the T7 terminator (T7prom/HPT/T7term cassette) for selection of the plasmid on hygromycin B in certain strains of *E. coli*, such as NovaBlue(DE3) (Novagen, Madison, Wis.), which is lysogenic for lambda DE3 (and carries the T7 RNA polymerase gene under lacUV5 control). In addition, plasmid pKR274 contains a bacterial origin of replication (ori) functional in *E. coli* from the vector pSP72 (Stratagene).

The gene for the *M. alpina* Δ6 desaturase was PCR-amplified from pCGR5 (U.S. Pat. No. 5,968,809) using primers oCGR5-1 (SEQ ID NO:96) and oCGR5-2 (SEQ ID NO:97), which were designed to introduce NotI restriction enzyme sites at both ends of the Δ6 desaturase and an NcoI site at the start codon of the reading frame for the enzyme.

The resulting PCR fragment was subcloned into the intermediate cloning vector pCR-Script AMP SK(+) (Stratagene) according the manufacturer's protocol to give plasmid pKR159.

The NotI fragment of pKR159, containing the *M. alpina* Δ6 desaturase gene, was cloned into NotI site of pZBL117 in the sense orientation to make plant expression cassette pZBL119.

Vector pKR197 was constructed by combining the AscI fragment from plasmid pKS102 (WO 02/00904), containing the T7prom/hpt/T7term cassette and bacterial ori, with the AscI fragment of plasmid pKR72, containing the βcon/NotI/Phas cassette.

Plasmid pKR159 was digested with NotI to release the *M. alpina* Δ6 desaturase, which was, in turn, cloned into the NotI site of the soybean expression vector pKR197 to give pKR269.

The glycininGy1 promoter was amplified from pZBL119 using primer oSGly-1 (SEQ ID NO:98), designed to introduce an SbfI/PstI site at the 5' end of the promoter, and primer oSGly-2 (SEQ ID NO:99), designed to introduce a NotI site at the 3' end of the promoter.

The resulting PCR fragment was subcloned into the intermediate cloning vector pCR-Script AMP SK(+) (Stratagene) according the manufacturer's protocol to give plasmid pSGly12.

The legA2 promoter was amplified from pea genomic DNA using primer LegPro5' (SEQ ID NO:100), designed to introduce XbaI and BsiWI sites at the 5' end of the promoter, and primer LegPro3' (SEQ ID NO:101), designed to introduce a NotI site at the 3' end of the promoter.

The legA2 transcription terminator was amplified from pea genomic DNA using primer LegTerm5' (SEQ ID NO:102), designed to introduce NotI site at the 5' end of the terminator, and primer LegTerm3' (SEQ ID NO:103), designed to introduce BsiWI and XbaI sites at the 3' end of the terminator.

The resulting PCR fragments were then combined and re-amplified using primers LegPro5' and LegTerm3', thus forming the legA2/NotI/legA23' cassette. The legA2/NotI/legA23' cassette PCR fragment was subcloned into the intermediate cloning vector pCR-Script AMP SK(+) (Stratagene) according the manufacturer's protocol to give plasmid pKR140. Plasmid pKR142 was constructed by cloning the BsiWI fragment of pKR140, containing the legA2/NotI/legA23' cassette, into the BsiWI site of pKR124, containing a bacterial ori and ampicillin resistance gene. The PstI/NotI fragment from plasmid pKR142 was then combined with the PstI/NotI fragment of plasmid pSGly12, containing the glycininGy1 promoter, to give pKR263.

The gene for the *M. alpina* Δ5 desaturase was amplified from pCGR4 (U.S. Pat. No. 6,075,183) using primers CGR4foward (SEQ ID NO:104) and CGR4reverse (SEQ ID NO:105) which were designed to introduce NotI restriction enzyme sites at both ends of the desaturase.

The resulting PCR fragment was digested with NotI and cloned into the NotI site of vector pKR124 to give pKR136.

The gene for the *Mortierella alpina* elongase was amplified from pRPB2 (WO 00/12720) using primers RPB2foward (SEQ ID NO:106) and RPB2reverse (SEQ ID NO:107) which were designed to introduce NotI restriction enzyme sites at both ends of the elongase. The resulting PCR fragment was digested with NotI and cloned into the NotI site of vector pKR263 to give pKR270.

The Gy1/Maelo/legA2 cassette was released from plasmid pKR270 by digestion with BsiWI and SbfI and was cloned into the BsiWI/SbfI sites of plasmid pKR269, containing the Δ6 desaturase, the T7prom/hpt/T7term cassette and the bacterial ori region. This was designated as plasmid pKR272.

Figure 8:
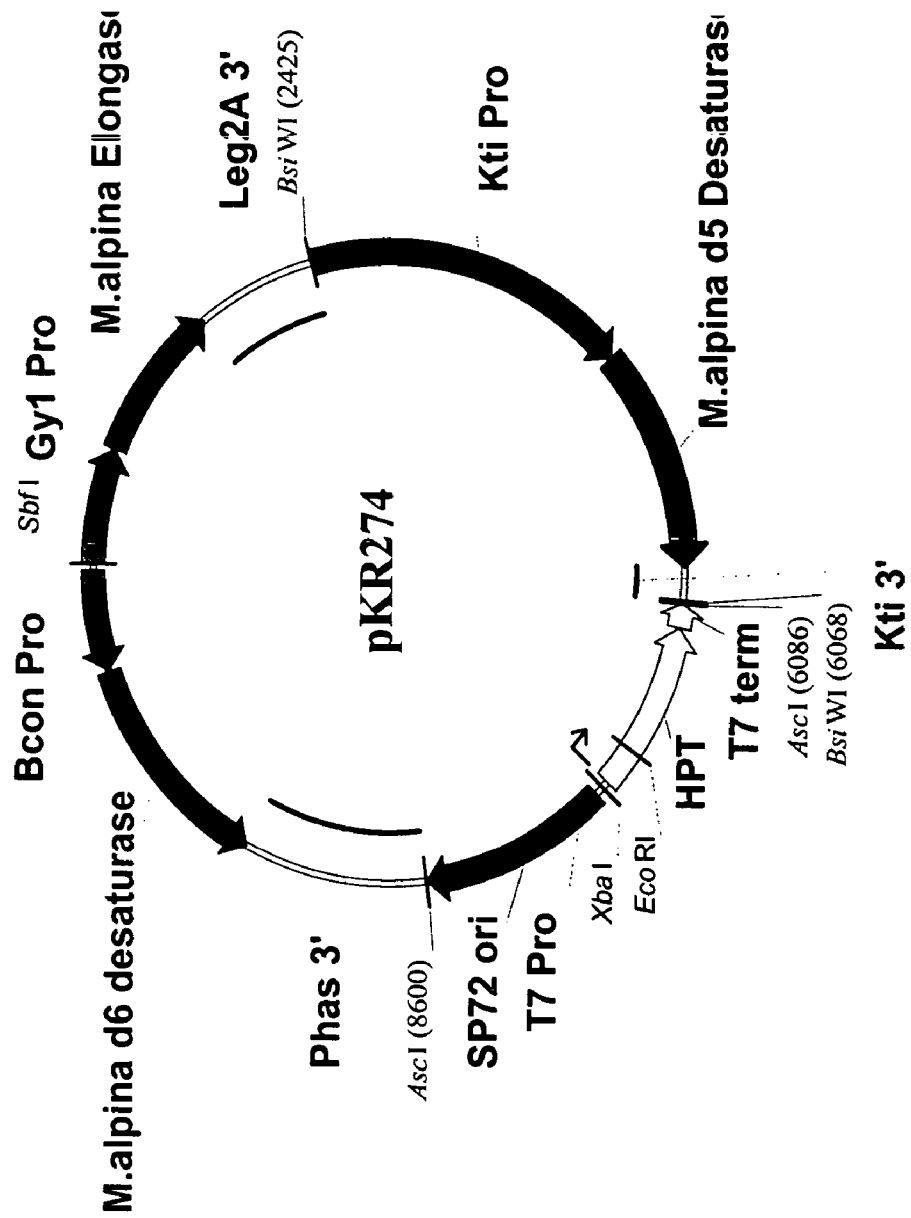
FIG. 8 is a schematic depiction of plasmid pKR274 (see Example 14).

The KTi/Mad5/KTi3' cassette, released from pKR136 by digestion with BsiWI, was then cloned into the BsiWI site of pKR272 to give pKR274 (FIG. 8).

Example 15

Assembling EPA Biosynthetic Pathway Genes for Expression in Soybeans (pKKE2)

This example describes the construction of pKKE2, a vector designed for strong, seed-specific expression of the *Saprolegnia diclina* Δ6 desaturase (WO 02/081668), *M. alpina* elongase (WO 00/12720) and *M. alpina* Δ5 desaturase (U.S. Pat. No. 6,075,183) in somatic soybean embryos and soybean seeds. This vector is identical to pKR274 except that the *M. alpina* Δ6 desaturase has been replaced with the the *Saprolegnia diclina* Δ6 desaturase. Construction of this vector was previously described in WO 04/071467 and is re-stated here.

The *S. diclina* Δ6 desaturase was removed from pRSP1 (WO 02/081668) by digestion with EcoRI and HindIII. The ends of the resulting DNA fragment were filled and the fragment was cloned into the filled NotI site of pKS123 to give pKS208.

The βcon/Sdd6/Phas3' cassette was released from plasmid pKS208 by digestion with HindIII and was cloned into the HindIII site of plasmid pKR272 to give pKR301.

Figure 9:
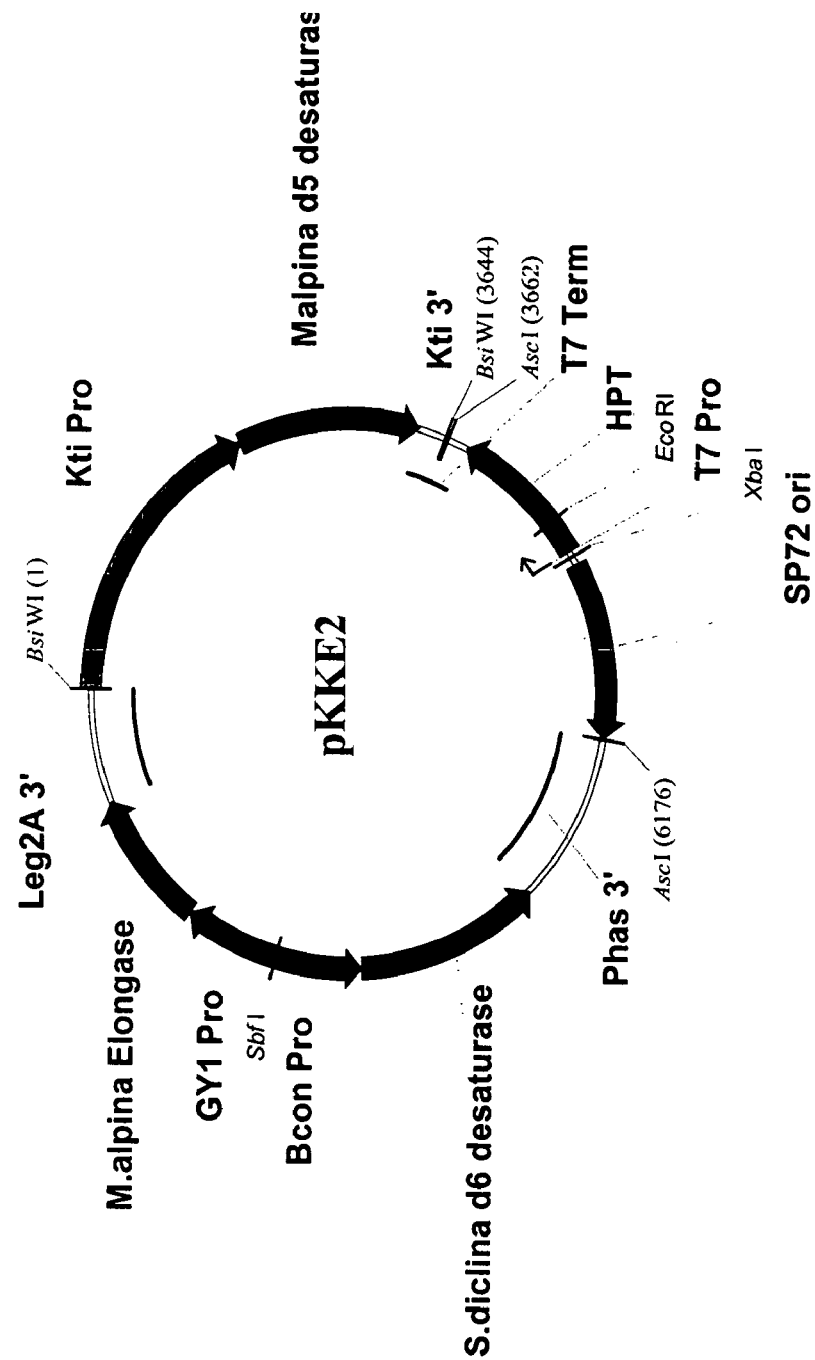
FIG. 9 is a schematic depiction of plasmid pKKE2 (see Example 15).

The KTi/Mad5/KTi3' cassette, released from pKR136, by digestion with BsiWI, was then cloned into the BsiWI site of pKR301 to give pKKE2 (FIG. 9).

Example 16

Transformation of Somatic Soybean Embryo Cultures Culture Conditions

Soybean embryogenic suspension cultures (cv. Jack) are maintained in 35 ml liquid medium SB196 (see recipes below) on a rotary shaker, 150 rpm, 26° C. with cool white fluorescent lights on 16:8 hr day/night photoperiod at light intensity of 60-85 μE/m2/s. Cultures are subcultured every 7 days to two weeks by inoculating approximately 35 mg of tissue into 35 ml of fresh liquid SB196 (the preferred subculture interval is every 7 days).

Soybean embryogenic suspension cultures are transformed with pKR353 (Δ15) plasmid described in the Example 18 by the method of particle gun bombardment (Klein et al. 1987; *Nature*, 327:70). A DuPont Biolistic PDS1000/HE instrument (helium retrofit) is used for all transformations.

Soybean Embryogenic Suspension Culture Initiation

Soybean cultures are initiated twice each month with 5-7 days between each initiation.

Pods with immature seeds from available soybean plants 45-55 days after planting are picked, the seeds removed from their shells and placed into a sterilized magenta box. The soybean seeds are sterilized by shaking them for 15 minutes in a 5% Clorox solution with 1 drop of ivory soap (95 ml of autoclaved distilled water plus 5 ml Clorox and 1 drop of soap). Mix well. Seeds are rinsed using 2 1-liter bottles of sterile distilled water and those less than 4 mm are placed on individual microscope slides. The small end of the seed is cut and the cotyledons pressed out of the seed coat. Cotyledons are transferred to plates containing SB1 medium (25-30 cotyledons per plate). Plates are wrapped with fiber tape and stored for 8 weeks. After this time secondary embryos are cut and placed into SB196 liquid media for 7 days.

Preparation of DNA for Bombardment

Either an intact plasmid or a DNA plasmid fragment containing the genes of interest and the selectable marker gene is used for bombardment. Fragments are obtained by gel isolation of double digested plasmids. In each case, 100 ug of plasmid DNA is digested in 0.5 ml of the appropriate enzyme mix. The resulting DNA fragments are separated by gel electrophoresis on 1% SeaPlaque GTG agarose (BioWhitaker Molecular Applications) and the DNA fragments containing chimeric genes are cut from the agarose gel. DNA is purified from the agarose using the GELase digesting enzyme following the manufacturer's protocol.

A 50 μl aliquot of sterile distilled water containing 3 mg of gold particles (3 mg gold) is added to 5 μl of a 1 μg/μl DNA solution (either intact plasmid or DNA fragment prepared as described above), 50 µl 2.5M $CaCl_2$ and 20 µl of 0.1 M spermidine. The mixture is shaken 3 min on level 3 of a vortex shaker and spun for 10 sec in a bench microfuge. After a wash with 400 µl 100% ethanol the pellet is suspended by sonication in 40 µl of 100% ethanol. Five µl of DNA suspension is dispensed to each flying disk of the Biolistic PDS1000/HE instrument disk. Each 5 µl, aliquot contains approximately 0.375 mg gold per bombardment (i.e. per disk).

Tissue Preparation and Bombardment with DNA

Approximately 150-200 mg of 7 day old embryonic suspension cultures are placed in an empty, sterile 60×15 mm petri dish and the dish covered with plastic mesh. Tissue is bombarded 1 or 2 shots per plate with membrane rupture pressure set at 1100 PSI and the chamber evacuated to a vacuum of 27-28 inches of mercury. Tissue is placed approximately 3.5 inches from the retaining/stopping screen.

Selection of Transformed Embryos

Transformed embryos are selected either using hygromycin (when the hygromycin phosphotransferase, HPT, gene is used as the selectable marker) or chlorsulfuron (when the acetolactate synthase, ALS, gene is used as the selectable marker).

Hygromycin (HPT) Selection

Following bombardment, the tissue is placed into fresh SB196 media and cultured as described above. Six days post-bombardment, the SB196 is exchanged with fresh SB196 containing a selection agent of 30 mg/L hygromycin. The selection media is refreshed weekly. Four to six weeks post selection, green, transformed tissue may be observed growing from untransformed, necrotic embryogenic clusters. Isolated, green tissue is removed and inoculated into multiwell plates to generate new, clonally propagated, transformed embryogenic suspension cultures.

Chlorsulfuron (ALS) Selection

Following bombardment, the tissue is divided between 2 flasks with fresh SB196 media and cultured as described above. Six to seven days post-bombardment, the SB196 is exchanged with fresh SB196 containing selection agent of 0.1 mg/L Chlorsulfuron. The selection media is refreshed weekly. Four to six weeks post selection, green, transformed tissue may be observed growing from untransformed, necrotic embryogenic clusters. Isolated, green tissue is removed and inoculated into multiwell plates containing SB196 to generate new, clonally propagated, transformed embryogenic suspension cultures.

Regeneration of Soybean Somatic Embryos into Plants

In order to obtain whole plants from embryogenic suspension cultures, the tissue must be regenerated.

Embryo Maturation

Embryos are cultured for 4-6 weeks at 26° C. in SB196 under cool white fluorescent (Phillips cool white Econowatt F40/CW/RS/EW) and Agro (Phillips F40 Agro) bulbs (40 watt) on a 16:8 hr photoperiod with light intensity of 90120 uE/m2s. After this time embryo clusters are removed to a solid agar media, SB166, for 1-2 weeks. Clusters are then subcultured to medium SB103 for 3 weeks. During this period, individual embryos can be removed from the clusters and screened for alterations in their fatty acid compositions. It should be noted that any detectable phenotype, resulting from the expression of the genes of interest, could be screened at this stage. This would include, but not be limited to, alterations in fatty acid profile, protein profile and content, carbohydrate content, growth rate, viability, or the ability to develop normally into a soybean plant.

Embryo Desiccation and Germination

Matured individual embryos are desiccated by placing them into an empty, small petri dish (35×10 mm) for approximately 4-7 days. The plates are sealed with fiber tape (creating a small humidity chamber). Desiccated embryos are planted into SB71-4 medium where they are left to germinate under the same culture conditions described above. Germinated plantlets are removed from germination medium and rinsed thoroughly with water and then planted in Redi-Earth in 24-cell pack trays, covered with clear plastic domes. After 2 weeks the domes are removed and plants hardened off for a further week. If plantlets look hardy they are transplanted to 10" pot of Redi-Earth with up to 3 plantlets per pot. After 10 to 16 weeks, mature seeds are harvested, chipped and analyzed for fatty acids.

Media Recipes

| SB 196 - FN Lite liquid proliferation medium (per liter) - | |
|---|---|
| MS FeEDTA - 100× Stock 1 | 10 ml |
| MS Sulfate - 100× Stock 2 | 10 ml |
| FN Lite Halides - 100× Stock 3 | 10 ml |
| FN Lite P,B,Mo - 100× Stock 4 | 10 ml |
| B5 vitamins (1 ml/L) | 1.0 ml |
| 2,4-D (10 mg/L final concentration) | 1.0 ml |
| KNO3 | 2.83 gm |
| (NH4)2 SO 4 | 0.463 gm |
| Asparagine | 1.0 gm |
| Sucrose (1%) | 10 gm |
| pH 5.8 | |

FN Lite Stock Solutions

| Stock # | 1000 ml | 500 ml |
|---|---|---|
| 1 MS Fe EDTA 100× Stock | | |
| $Na_2$ EDTA* | 3.724 g | 1.862 g |
| $FeSO_4$—$7H_2O$ | 2.784 g | 1.392 g |
| 2 MS Sulfate 100× stock | | |
| $MgSO_4$—$7H_2O$ | 37.0 g | 18.5 g |
| $MnSO_4$—$H_2O$ | 1.69 g | 0.845 g |
| $ZnSO_4$—$7H_2O$ | 0.86 g | 0.43 g |
| $CuSO_4$—$5H_2O$ | 0.0025 g | 0.00125 g |
| 3 FN Lite Halides 100× Stock | | |
| $CaCl_2$—$2H_2O$ | 30.0 g | 15.0 g |
| KI | 0.083 g | 0.0715 g |
| $CoCl_2$—$6H_2O$ | 0.0025 g | 0.00125 g |
| 4 FN Lite P,B,Mo 100× Stock | | |
| $KH_2PO_4$ | 18.5 g | 9.25 g |
| $H_3BO_3$ | 0.62 g | 0.31 g |
| $Na_2MoO_4$—$2H_2O$ | 0.025 g | 0.0125 g |

*Add first, dissolve in dark bottle while stirring

SB1 Solid Medium (Per Liter)
  1 pkg. MS salts (Gibco/BRL—Cat#11117-066)
  1 ml B5 vitamins 1000X stock
  31.5 g sucrose
  2 ml 2,4-D (20 mg/L final concentration)
  pH 5.7
  8 g TC agar SB 166 Solid Medium (Per Liter)
  1 pkg. MS salts (Gibco/BRL—Cat#11117-066)
  1 ml B5 vitamins 1000X stock 60 g maltose
750 mg MgCl2 hexahydrate
5 g activated charcoal
pH 5.7
2 g gelrite SB 103 Solid Medium (Per Liter)
  1 pkg. MS salts (Gibco/BRL—Cat#11117-066)
  1 ml B5 vitamins 1000X stock
  60 g maltose
  750 mg MgCl2 hexahydrate
  pH 5.7
  2 g gelrite SB 71-4 Solid Medium (Per Liter)
  1 bottle Gamborg's B5 salts w/sucrose (Gibco/BRL—Cat#21153-036)
  pH 5.7
  5 g TC agar 2,4-D Stock
  obtained premade from Phytotech cat# D 295—concentration is 1 mg/ml B5 Vitamins Stock (per 100 ml)—Store Aliquots at −20C
  10 g myo-inositol
  100 mg nicotinic acid
  100 mg pyridoxine HCl
  1 g thiamine
  If the solution does not dissolve quickly enough, apply a low level of heat via the hot stir plate.

Chlorsulfuron Stock
  −1 mg/ml in 0.01 N Ammonium Hydroxide

Example 17

Analysis of Somatic Soy Embryos Containing the
Fusarium Δ15 desaturase

Mature somatic soybean embryos are a good model for zygotic embryos. While in the globular embryo state in liquid culture, somatic soybean embryos contain very low amounts of triacylglycerol or storage proteins typical of maturing, zygotic soybean embryos. At this developmental stage, the ratio of total triacylglyceride to total polar lipid (phospholipids and glycolipid) is about 1:4, as is typical of zygotic soybean embryos at the developmental stage from which the somatic embryo culture was initiated. At the globular stage as well, the mRNAs for the prominent seed proteins, α'-subunit of β-conglycinin, kunitz trypsin inhibitor 3, and seed lectin are essentially absent. Upon transfer to hormone-free media to allow differentiation to the maturing somatic embryo state, triacylglycerol becomes the most abundant lipid class. As well, mRNAs for α'-subunit of β-conglycinin, kunitz trypsin inhibitor 3 and seed lectin become very abundant messages in the total mRNA population. On this basis somatic soybean embryo system behaves very similarly to maturing zygotic soybean embryos in vivo, and is therefore a good and rapid model system for analyzing the phenotypic effects of modifying the expression of genes in the fatty acid biosynthesis pathway (Example 3 in WO 02/00904). Most importantly, the model system is also predictive of the fatty acid composition of seeds from plants derived from transgenic embryos.

Transgenic somatic soybean embryos containing the constructs described above were analyzed in a similar way. For this, fatty acid methyl esters are prepared from single, matured, somatic soy embryos by transesterification. Embryos are placed in a vial containing 50 μL of trimethylsulfonium hydroxide (TMSH) and 0.5 mL of hexane and incubated for 30 minutes at room temperature while shaking. Fatty acid methyl esters (5 μL injected from hexane layer) are separated and quantified using a Hewlett-Packard 6890 Gas Chromatograph fitted with an Omegawax 320 fused silica capillary column (Supelco Inc., Cat#24152). The oven temperature was programmed to hold at 220° C. for 2.7 min, increase to 240° C. at 20° C./min and then hold for an additional 2.3 min. Carrier gas was supplied by a Whatman hydrogen generator. Retention times were compared to those for methyl esters of standards commercially available (Nu-Chek Prep, Inc. catalog #U-99-A).

Results for the best 10 lines containing pKR578 as well as those for a control embryo transformed with selection only are shown in Table 14. Although lines for only the best embryos are shown, other lines having ALA levels ranging from the control (22%) up to the best (89%) were obtained. Similarly, others lines having omega-3 to omega-6 ratios ranging from 0.4 to 45 were obtained. The best line had embryos with an average 18:3 content of 79% with the best embryo analyzed having 89% 18:3, versus the control which had an average 18:3 content of 19% and a best embryo of 22% 18:3. This corresponds to an average 4-fold improvement in 18:3 when compared to control embryos. The 18:3 content range in the lines transformed with pKR578 is 51-89%. This line also had an average ratio of omega-3:omega-6 fatty acids (18:3/18:2) of 24:1 with the best embryo having a ratio of 42:1, versus the control which had an average and best 18:3/18:2 ratio of 0.4. This corresponds to an average 66-fold improvement in omega-3:omega-6 ratios. The ratio range of omega-3:omega-6 fatty acids (18:3/18:2) in the lines transformed with pKR578 was 3:1-42:1.

TABLE 14

Accumulation of 18:3 (ALA) in lines transformed with pKR578

| Line* | 16:0 | 18:0 | 18:1 | 18:2 | 18:3 | 18:3 (ave) | 18:3 best | 18:3/ 18:2 | Ave ratio | Best ratio |
|---|---|---|---|---|---|---|---|---|---|---|
| Control | 1566: | | | | | | | | | |
| | 5-11-1 | 17 | 2 | 7 | 52 | 22 | | | 0.4 | | |
| | 5-11-2 | 17 | 2 | 9 | 53 | 19 | | | 0.4 | | |
| | 5-11-3 | 15 | 3 | 10 | 57 | 14 | 19 | 22 | 0.2 | 0.4 | 0.4 |
| | 5-11-4 | 17 | 3 | 8 | 53 | 18 | | | 0.3 | | |
| | 5-11-5 | 16 | 4 | 16 | 44 | 19 | | | 0.4 | | |

TABLE 14-continued

Accumulation of 18:3 (ALA) in lines transformed with pKR578

| Line* | 16:0 | 18:0 | 18:1 | 18:2 | 18:3 | 18:3 (ave) | 18:3 best | 18:3/ 18:2 | Ave ratio | Best ratio |
|---|---|---|---|---|---|---|---|---|---|---|
| +pKR578 1566: | | | | | | | | | | |
| 5-15-1 | 11 | 2 | 10 | 6 | 70 | | | 12 | | |
| 5-15-2 | 16 | 2 | 9 | 8 | 65 | | | 8 | | |
| 5-15-3 | 16 | 3 | 13 | 9 | 59 | 62 | 70 | 7 | 8 | 12 |
| 5-15-4 | 17 | 4 | 17 | 12 | 51 | | | 4 | | |
| 5-15-5 | 15 | 2 | 10 | 8 | 65 | | | 8 | | |
| +pKR578 1566: | | | | | | | | | | |
| 8-5-1 | 14 | 2 | 10 | 14 | 59 | | | 4 | | |
| 8-5-2 | 13 | 3 | 9 | 7 | 68 | | | 10 | | |
| 8-5-3 | 14 | 3 | 10 | 6 | 67 | 63 | 68 | 11 | 7 | 10 |
| 8-5-4 | 17 | 3 | 10 | 11 | 59 | | | 5 | | |
| 8-5-5 | 14 | 2 | 12 | 12 | 59 | | | 5 | | |
| +PKR578 1566: | | | | | | | | | | |
| 7-6-1 | 19 | 3 | 12 | 5 | 62 | | | 12 | | |
| 7-6-2 | 15 | 2 | 8 | 8 | 67 | | | 8 | | |
| 7-6-3 | 20 | 5 | 13 | 3 | 59 | 63 | 74 | 18 | 14 | 27 |
| 7-6-4 | 16 | 2 | 14 | 11 | 56 | | | 5 | | |
| 7-6-5 | 17 | 2 | 4 | 3 | 74 | | | 27 | | |
| +pKR578 1573: | | | | | | | | | | |
| 9-4-1 | 14 | 3 | 11 | 8 | 64 | | | 8 | | |
| 9-4-2 | 15 | 2 | 11 | 7 | 64 | | | 9 | | |
| 9-4-3 | 16 | 2 | 14 | 15 | 53 | 61 | 65 | 4 | 7 | 10 |
| 9-4-4 | 11 | 3 | 13 | 14 | 59 | | | 4 | | |
| 9-4-5 | 17 | 3 | 10 | 6 | 65 | | | 10 | | |
| +pKR578 1573: | | | | | | | | | | |
| 10-4-1 | 18 | 3 | 6 | 4 | 70 | | | 19 | | |
| 10-4-2 | 16 | 4 | 9 | 2 | 69 | 67 | 70 | 29 | 18 | 29 |
| 10-4-3 | 16 | 2 | 11 | 9 | 62 | | | 7 | | |
| 10-4-4 | 17 | 2 | 10 | 4 | 66 | | | 17 | | |
| +PKR578 1582: | | | | | | | | | | |
| 2-2-1 | 0 | 2 | 9 | 8 | 81 | | | 10 | | |
| 2-2-2 | 15 | 2 | 11 | 5 | 67 | | | 13 | | |
| 2-2-3 | 0 | 1 | 8 | 2 | 89 | 79 | 89 | 42 | 24 | 42 |
| 2-2-4 | 0 | 1 | 7 | 3 | 89 | | | 31 | | |
| 2-2-5 | 12 | 1 | 7 | 3 | 77 | | | 24 | | |
| 2-2-6 | 14 | 1 | 7 | 5 | 73 | | | 15 | | |
| +pKR578 1582: | | | | | | | | | | |
| 2-3-1 | 17 | 3 | 10 | 10 | 60 | | | 6 | | |
| 2-3-2 | 16 | 2 | 9 | 9 | 65 | | | 7 | | |
| 2-3-3 | 16 | 2 | 8 | 13 | 62 | 61 | 65 | 5 | 5 | 7 |
| 2-3-4 | 17 | 2 | 8 | 17 | 56 | | | 3 | | |
| 2-3-5 | 17 | 2 | 11 | 12 | 58 | | | 5 | | |
| 2-3-6 | 16 | 2 | 9 | 9 | 64 | | | 7 | | |
| +pKR578 1582: | | | | | | | | | | |
| 2-6-1 | 16 | 2 | 8 | 8 | 67 | | | 8 | | |
| 2-6-2 | 17 | 2 | 7 | 6 | 68 | | | 11 | | |
| 2-6-3 | 17 | 2 | 7 | 6 | 68 | 66 | 69 | 11 | 8 | 11 |
| 2-6-4 | 16 | 2 | 8 | 12 | 61 | | | 5 | | |
| 2-6-5 | 17 | 2 | 9 | 12 | 61 | | | 5 | | |
| 2-6-6 | 16 | 2 | 6 | 7 | 69 | | | 10 | | |
| +pKR578 1582: | | | | | | | | | | |
| 3-1-1 | 17 | 2 | 15 | 8 | 58 | | | 7 | | |
| 3-1-2 | 15 | 2 | 8 | 10 | 65 | | | 7 | | |
| 3-1-3 | 18 | 2 | 5 | 2 | 73 | 66 | 73 | 45 | 15 | 45 |
| 3-1-4 | 18 | 2 | 7 | 7 | 66 | | | 9 | | |
| 3-1-5 | 16 | 2 | 7 | 7 | 68 | | | 10 | | |
| 3-1-6 | 16 | 2 | 10 | 4 | 69 | | | 20 | | |
| +pKR578 1566: | | | | | | | | | | |
| 7-5-1 | 16 | 2 | 7 | 2 | 73 | | | 36 | | |
| 7-5-2 | 6 | 2 | 6 | 4 | 83 | | | 23 | | |
| 7-5-3 | 14 | 2 | 9 | 8 | 67 | 72 | 83 | 9 | 19 | 36 |
| 7-5-4 | 15 | 2 | 8 | 7 | 68 | | | 10 | | |
| 7-5-5 | 15 | 2 | 7 | 5 | 71 | | | 15 | | |
| 7-5-6 | 14 | 2 | 8 | 7 | 69 | | | 9 | | |

Results for the best line containing pKKE2 and pKR585 are shown in Table 15. The best line had embryos with an average omega-3 content of 63% and an average EPA content of 7%. The best omega-3 embryo analyzed had an omega-3 content of 72%. The best EPA embryo analyzed had EPA at 16% with the omega-3 content at 57%. This line also had an average ratio of omega-3:omega-6 fatty acids (18:3/18:2) of 8:1 with the best embryo having a ratio of 16:1. The best EPA embryo had an omega-3:omega-6 ratio of 4:1.

TABLE 15

Accumulation of omega-3 fatty acids in lines transformed with pKKE2 and pKR585

| Line | 16:0 | 18:0 | 18:1 | 18:2 | GLA | 18:3 | STA | DGLA | ARA | ETA | EPA | DPA | Other | Total ω3 | Total ω6 | ω3/ω6 |
|---|---|---|---|---|---|---|---|---|---|---|---|---|---|---|---|---|
| 1 | 14 | 3 | 4 | 7 | 1 | 59 | 3 | 1 | 0 | 1 | 6 | 0 | 3 | 71 | 8 | 9 |
| 2 | 18 | 4 | 7 | 11 | 8 | 24 | 8 | 2 | 1 | 3 | 12 | 0 | 2 | 48 | 22 | 2 |
| 3 | 15 | 2 | 4 | 4 | 1 | 62 | 3 | 1 | 0 | 2 | 4 | 0 | 2 | 72 | 6 | 11 |
| 4 | 16 | 3 | 3 | 6 | 0 | 58 | 4 | 0 | 0 | 2 | 6 | 0 | 2 | 71 | 7 | 10 |
| 5 | 15 | 3 | 6 | 6 | 1 | 57 | 2 | 1 | 0 | 2 | 5 | 0 | 2 | 68 | 9 | 8 |
| 6 | 15 | 2 | 4 | 7 | 4 | 39 | 9 | 2 | 0 | 4 | 12 | 0 | 2 | 65 | 13 | 5 |
| 7 | 20 | 6 | 8 | 11 | 7 | 18 | 7 | 3 | 1 | 4 | 14 | 1 | 3 | 44 | 22 | 2 |
| 8 | 18 | 5 | 7 | 4 | 6 | 17 | 14 | 3 | 0 | 7 | 16 | 2 | 1 | 57 | 13 | 4 |
| 9 | 20 | 5 | 3 | 9 | 2 | 36 | 5 | 2 | 1 | 4 | 10 | 1 | 3 | 58 | 15 | 4 |
| 10 | 16 | 3 | 6 | 4 | 0 | 63 | 1 | 0 | 0 | 0 | 1 | 0 | 4 | 70 | 5 | 16 |
| 11 | 17 | 4 | 6 | 5 | 0 | 61 | 2 | 0 | 0 | 0 | 2 | 0 | 3 | 68 | 5 | 13 |
| 12 | 18 | 5 | 9 | 4 | 0 | 56 | 1 | 0 | 0 | 0 | 1 | 0 | 6 | 64 | 4 | 16 |
| 13 | 15 | 5 | 8 | 5 | 0 | 57 | 1 | 0 | 0 | 1 | 4 | 1 | 4 | 67 | 5 | 13 |
| 14 | 20 | 7 | 3 | 7 | 1 | 42 | 4 | 1 | 0 | 2 | 7 | 1 | 5 | 61 | 9 | 7 |
| 15 | 17 | 3 | 6 | 5 | 1 | 55 | 3 | 1 | 0 | 1 | 6 | 0 | 2 | 68 | 6 | 11 |
| 16 | 18 | 4 | 5 | 9 | 2 | 47 | 3 | 1 | 0 | 2 | 7 | 1 | 3 | 61 | 12 | 5 |
| Ave.: | 17 | 4 | 6 | 6 | 2 | 47 | 4 | 1 | 0 | 2 | 7 | 1 | 3 | 63 | 10 | 8 |

Example 18

Transformation of Arabidopsis Plants

Vector pKR197 was digested with HindIII to remove the beta-glycinin conglycinin expression cassette and the vector backbone was re-ligated to give pKR277.

The Kti/NotI/Kti3' cassette from pKR124 was removed by digestion with BsiWI, the ends filled in and the fragment cloned into the filled HinIII site of pKR277 to give pKR353.

The NotI fragment of pY34 containing the *Fusarium* Δ15 desaturase was cloned into the NotI site of pKR353 to give pKR353 (Δ15).

Vector pHD1 was derived from binary vector pZBL11 [U.S. Pat. No. 5,968,793; EP 1003891; and WO 9859062] by adding an AscI linker between the PacI and Asp718 sites between the right and left T-DNA borders. The AscI linker was formed by annealing oligonucleotide Asc5 SEQ ID NO:108) with Asc3 (SEQ ID NO:109).

Vector pZBL11 [U.S. Pat. No. 5,968,793; EP 1003891; and WO 9859062] contains a 35S:sulfonylurea resistant acetolactate synthase (ALS) transgene within the T-DNA borders that confers resistance to sulfonylurea herbicide and serves as the plant selectable marker. pZBL11 also has an origin of replication for both *E. coli* and *Agrobacterium tumefaciens*, and a bacterial kanamycin resistance gene.

The chimeric gene Kti3 promoter:Fm Δ15 desaturase ORF:Kti3 terminator was isolated as an Asc1 fragment from pKR353 (Δ15) and cloned into the unique Asc1 site in the binary vector pHD1 to give pZBLI(D15).

Plasmid pZBLI(D15) was transformed into *Agrobacterium* strain NTL4 [Luo et. al. (2001) MPMI 14:98] and this culture was used to transform a fad2-1 mutant [Okuley et. al. (1994) Plant Cell 6: 147] of *Arabidopsis thaliana* by the *Agrobacterium* dip method. Transformants, given the designation NY, were selected on sulfonylurea, plants were grown and T2 seed was obtained. Transformation was also carried out using pHD1 as control in similar way. Lipid from bulk T2 seed batches (still segregating for the TDNA and sulfonylurea resistance) was analyzed as follows. Approximately 25-50 T2 seeds were broken in 50 uL of TMSH using a glass rod. After incubation at room temperature for approximately 15 minutes with constant agitation, 500 uL of hexane was added the samples incubated for an additional 15 minutes at room temperature with agitation. The hexane layer was then transferred to a separate GC vial and fatty acid methyl ester (FAME) analysis was carried out by GC as described (WO 04/071467). Results for multiple lines are shown in Table 16. The average 18:3 levels were approximately 1.5-fold higher in the Δ15-expressing lines (FmD15-NY) than in the empty vector control (HD1 control) lines, while the 18:3/18:2 ratios were 2-fold higher in the same lines. The n3/n6 ratio in wild type Arabidopsis is 0.61 [Shah et. al. (1997) *Plant Physiology* 114: 1533]. One skilled in the art would appreciate that the levels of ALA were underestimated because bulk seed was analyzed that contained segregating seed (includes wild-type, hemizygous and homozygous seed). One skilled in the art would also appreciate that a homozygous lines would contain two times more copies of Δ15 desaturase and thus, is expected to have higher levels of ALA than heterzygous lines (gene dosage effect).

TABLE 16

Accumulation of 18:3 in a Fad2-1 mutant *Arabidopsis* transformed with the *Fusarium* Δ15 Desaturase

| Sample | % 16:0 | % 18:0 | % 18:1 | % 18:2 | % 18:3 | % 20:0 | % 20:1 | ω3/ω 6 ratio |
|---|---|---|---|---|---|---|---|---|
| HD1 control-1 | 5.2 | 2.2 | 62.4 | 2.4 | 7.3 | 0.8 | 19.6 | 3.1 |
| HD1 control-2 | 5.3 | 2.2 | 63.1 | 2.2 | 7.1 | 0.9 | 19.3 | 3.3 |
| HD1 control-3 | 6.1 | 2.5 | 59.2 | 2.8 | 8.9 | 0.9 | 19.6 | 3.2 |
| HD1 control-4 | 5.5 | 2.3 | 60.9 | 2.3 | 8.0 | 1.0 | 20.0 | 3.4 |
| HD1 control-5 | 5.5 | 2.1 | 61.6 | 2.9 | 7.6 | 0.8 | 19.6 | 2.7 |

TABLE 16-continued

Accumulation of 18:3 in a Fad2-1 mutant *Arabidopsis* transformed with the *Fusarium* Δ15 Desaturase

| Sample | % 16:0 | % 18:0 | % 18:1 | % 18:2 | % 18:3 | % 20:0 | % 20:1 | ω3/ω6 ratio |
|---|---|---|---|---|---|---|---|---|
| HD1 control-6 | 5.4 | 2.3 | 61.8 | 2.1 | 7.2 | 0.9 | 20.2 | 3.4 |
| HD1 control-7 | 5.3 | 2.6 | 61.8 | 2.3 | 7.6 | 1.0 | 19.3 | 3.2 |
| HD1 control-8 | 5.2 | 2.0 | 63.0 | 2.9 | 7.5 | 0.8 | 18.6 | 2.6 |
| HD1 control-9 | 5.2 | 2.2 | 62.9 | 2.3 | 8.5 | 0.8 | 18.1 | 3.6 |
| HD1 control-10 | 5.7 | 2.3 | 61.1 | 2.5 | 8.3 | 0.9 | 19.3 | 3.3 |
| HD1 control-11 | 5.9 | 2.2 | 60.1 | 3.1 | 9.4 | 0.8 | 18.5 | 3.1 |
| HD1 control-12 | 5.6 | 2.1 | 61.7 | 2.6 | 8.6 | 0.8 | 18.6 | 3.4 |
| HD1 control-13 | 5.5 | 2.1 | 63.2 | 2.4 | 8.0 | 0.8 | 17.9 | 3.3 |
| HD1 control-14 | 5.6 | 2.3 | 61.7 | 2.8 | 7.8 | 0.8 | 19.1 | 2.8 |
| HD1 control-15 | 5.5 | 2.4 | 62.2 | 2.4 | 8.1 | 0.8 | 18.5 | 3.4 |
| HD1 control-16 | 5.6 | 2.7 | 60.8 | 2.5 | 8.0 | 0.9 | 19.5 | 3.2 |
| HD1 control-avg | 5.5 | 2.3 | 61.7 | 2.5 | 8.0 | 0.9 | 19.1 | 3.2 |
| Fm d15-NY-1 | 5.9 | 2.9 | 58.3 | 1.8 | 12.0 | 0.9 | 18.2 | 6.7 |
| Fm d15-NY-2 | 5.1 | 2.2 | 65.4 | 1.7 | 6.1 | 0.8 | 18.7 | 3.5 |
| Fm d15-NY-3 | 5.8 | 3.0 | 58.3 | 2.0 | 12.4 | 0.9 | 17.7 | 6.3 |
| Fm d15-NY-4 | 5.1 | 2.4 | 62.6 | 1.9 | 8.3 | 0.9 | 18.8 | 4.4 |
| Fm d15-NY-5 | 5.7 | 3.0 | 61.1 | 1.2 | 10.7 | 0.9 | 17.5 | 8.9 |
| Fm d15-NY-6 | 5.4 | 2.8 | 58.9 | 2.5 | 8.7 | 0.9 | 20.7 | 3.5 |
| Fm d15-NY-7 | 5.9 | 2.9 | 58.7 | 1.3 | 12.2 | 0.9 | 18.0 | 9.2 |
| Fm d15-NY-8 | 6.2 | 3.2 | 57.0 | 1.5 | 13.3 | 0.9 | 17.8 | 8.8 |
| Fm d15-NY-9 | 5.5 | 2.8 | 59.7 | 1.5 | 10.7 | 0.9 | 18.8 | 7.2 |
| Fm d15-NY-10 | 5.9 | 2.6 | 58.6 | 1.4 | 11.6 | 0.9 | 19.0 | 8.2 |
| Fm d15-NY-11 | 5.5 | 2.7 | 60.0 | 2.1 | 9.6 | 0.9 | 19.3 | 4.6 |
| Fm d15-NY-12 | 5.5 | 2.6 | 58.6 | 2.5 | 10.7 | 0.8 | 19.3 | 4.2 |
| Fm d15-NY-13 | 5.5 | 2.5 | 59.7 | 2.6 | 9.8 | 0.8 | 19.0 | 3.8 |
| Fm d15-NY-14 | 5.2 | 2.8 | 63.6 | 2.1 | 7.4 | 0.8 | 18.0 | 3.5 |
| Fm d15-NY-15 | 5.9 | 2.3 | 61.7 | 2.4 | 8.5 | 0.9 | 18.3 | 3.6 |
| Fm d15-NY-16 | 5.6 | 3.1 | 58.0 | 2.7 | 9.3 | 1.0 | 20.3 | 3.5 |
| Fm d15-NY-17 | 5.7 | 2.9 | 60.0 | 1.4 | 12.3 | 0.8 | 16.9 | 8.7 |
| Fm d15-NY-18 | 5.9 | 3.2 | 59.2 | 1.4 | 11.6 | 0.8 | 17.8 | 8.0 |
| Fm d15-NY-19 | 5.9 | 3.2 | 58.3 | 1.6 | 12.3 | 0.9 | 17.7 | 7.5 |
| Fm d15-NY-20 | 5.6 | 2.3 | 61.8 | 2.4 | 8.0 | 0.9 | 19.0 | 3.3 |
| Fm d15-NY-21 | 6.0 | 3.0 | 54.1 | 3.6 | 11.4 | 1.0 | 20.9 | 3.1 |
| Fm d15-NY-22 | 5.9 | 2.9 | 61.0 | 2.9 | 7.9 | 0.8 | 18.6 | 2.8 |
| Fm d15-NY-23 | 6.0 | 2.7 | 56.5 | 1.8 | 13.0 | 0.9 | 19.1 | 7.4 |
| Fm d15-NY-24 | 5.3 | 2.8 | 61.3 | 2.1 | 7.9 | 0.8 | 19.7 | 3.8 |
| Fm d15-NY-25 | 5.7 | 3.0 | 56.4 | 3.1 | 11.5 | 0.9 | 19.5 | 3.7 |
| Fm d15-NY avg | 5.7 | 2.8 | 59.6 | 2.1 | 10.3 | 0.9 | 18.8 | 5.5 |

Wild type *Arabidopsis* could also be transformed with the chimeric constructs expressing the Δ15 desaturase in a similar way and seeds from those plants will contain higher ALA content than untransformed plants.

Thus, the ratio of of ω3/ω6 fatty acids in plant oil can be improved by transforming the chimeric Δ15 desaturase gene either into wild type plants or into plants having reduced 18:2. The latter is the consequence of the *Fusarium* Δ15 desaturase being a bifunctional Δ12/Δ15 desaturase. Thus, one skilled in the art can transform the bifunctional Δ12/Δ15 desaturase into a mutant plant making little or no LA introduce or co-transform a wild type plant with the bifunctional Δ12/Δ15 desaturase and a DNA suppression construct designed to suppress the host's native Δ12 desaturase gene(s). The native Δ12 desaturase genes include genes encoding both extraplastidic and plastidic Δ12 desaturases.

What is claimed is:

1. An isolated nucleic acid fragment encoding a fungal Δ15 desaturase enzyme, selected from the group consisting of:
    (a) an isolated nucleic acid fragment encoding the amino acid sequence as set forth in SEQ ID NO:2;
    (b) an isolated nucleic acid fragment that hybridizes over the full length of the isolated nucleic acid fragment of (a) encoding the amino acid sequence of SEQ ID NO:2 under the following hybridization conditions: 0.1×SSC, 0.1% SDS, 65° C. and washed with 2×SSC, 0.1% SDS followed by 0.1×SSC, 0.1% SDS; and
an isolated nucleic acid fragment that is complementary over the full length of (a) or (b).

2. The isolated nucleic acid fragment of claim 1 as set forth in SEQ ID NO:1.

3. The isolated nucleic acid fragment of claim 1 isolated from *Fusarium moniliforme*.

4. An isolated nucleic acid fragment comprising a first nucleotide sequence encoding a Δ15 desaturase enzyme of at least 402 amino acids that has at least 90% identity based on the Clustal method of alignment when compared to a polypeptide having the sequence as set forth in SEQ ID NO:2; or a second nucleotide sequence comprising the complement of the first nucleotide sequence.

5. A chimeric gene comprising the isolated nucleic acid fragment of any of claims 1-4 operably linked to suitable regulatory sequences.

6. A transformed host cell comprising the isolated nucleic acid fragment of any of claims 1-4.

7. A transformed host cell according to claim 6 selected from the group consisting of: plant cells, algae, bacteria, yeast and fungal cells.

8. A transformed host cell according to claim 7 wherein the host cell is a plant cell from a plant selected from the group consisting of: soybean, corn, rapeseed, primrose, -flax, -canola, maize, safflower and sunflower.

9. A transformed host cell according to claim 7 wherein the host cell is a fungal cell from a fungus selected from the group consisting of: *Thraustochytrium Schizochytrium* and *Mortierella*.

10. A transformed host cell according to claim 7 wherein the yeast is an oleaginous yeast.

11. The transformed yeast of claim 10 wherein the oleaginous yeast is selected from the group consisting of: *Yarrowia, Candida, Rhodotorula, Rhodosporidium, Cryptococcus, Trichosporon* and *Lipomyces*.

12. The transformed yeast of claim 11 wherein the oleaginous yeast is *Yarrowia* sp.

13. A method for the production of α-linolenic acid comprising:
    a) providing a host cell comprising:
        (i) an isolated nucleic acid fragment encoding a protein having Δ15 desaturase activity that has at least 90% identity based on the Clustal method of alignment when compared to a polypeptide having the sequence as set forth in SEQ ID NO:2; and
        (ii) a source of linoleic acid;
    b) growing the host cell of step (a) under conditions wherein the nucleic acid fragment encoding a protein having Δ15 desaturase activity is expressed and the linoleic acid is converted to α-linolenic acid; and
    c) optionally recovering the α-linolenic acid of step (b).

14. A method for the production of α-linolenic acid comprising:
    a) providing a host cell comprising:
        (i) an isolated nucleic acid fragment encoding a protein having Δ15 desaturase activity that has at least 90% identity based on the Clustal method of alignment when compared to a polypeptide having the sequence as set forth in SEQ ID NO:2; and
        (ii) a source of oleic acid;
    b) growing the host cell of step (a) under conditions wherein the nucleic acid fragment encoding a protein having Δ15 desaturase activity is expressed and the oleic acid is converted to α-linolenic acid; and
    c) optionally recovering the α-linolenic acid of step (b).

15. A method according to claim 13 or 14 wherein the isolated nucleic acid fragment encoding a protein having Δ15 desaturase activity is isolated from a fungus selected from the group consisting of: *Fusarium moniliforme, Magnaporthe grisea, Neurospora crassa, Fusarium graminearium* and *Aspergillus nidulans*.

16. A method according to claim 13 or 14 wherein the isolated nucleic acid fragment encoding a protein having Δ15 desaturase activity encodes an amino acid sequence as set forth in SEQ ID NO:2.

17. A method according to claim 13 wherein the protein having Δ15 desaturase activity has a percent substrate conversion of linoleic acid to α-linolenic acid of at least about 50%.

18. A method according to claim 13 wherein the protein having Δ15 desaturase activity has a percent substrate conversion of linoleic acid to α-linolenic acid of at least about 80%.

19. A method according to claim 13 wherein the protein having Δ15 desaturase activity has a percent substrate conversion of linoleic acid to α-linolenic acid of at least about 90%.

20. A method according to claim 13 wherein the protein having Δ15 desaturase activity has a percent substrate conversion of linoleic acid to α-linolenic acid that is greater than at least about 95%.

21. A method according to claim 13 or 14 wherein the protein having Δ15 desaturase activity binds both oleic acid and linoleic acid as enzymatic substrates.

22. A method for the production of ω-3 fatty acids in a host cell comprising:
   a) providing a host cell comprising:
      (i) an isolated nucleic acid fragment encoding a protein having Δ15 desaturase activity that has at least 90% identity based on the Clustal method of alignment when compared to a polypeptide having the sequence as set forth in SEQ ID NO:2; and
      (ii) genes encoding a functional ω-3/ω-6 fatty acid biosynthetic pathway;
   b) providing a source of desaturase substrate consisting of oleic acid;
   c) growing the host cell of step (a) with the desaturase substrate of step (b) under conditions wherein ω-3 fatty acids are produced; and
   d) optionally recovering the ω-3 fatty acids of step (c).

23. A method of increasing the ratio of ω-3 fatty acids to ω-6 fatty acids in a host cell producing ω-3 fatty acids to ω-6 fatty acids comprising:
   a) providing a host cell producing ω-3 fatty acids and ω-6 fatty acids;
   b) introducing into the host cell of (a) an isolated nucleic acid fragment encoding a protein having at least 90% identity based on the Clustal method of alignment when compared to a polypeptide having the sequence as set forth in SEQ ID NO:2, wherein the polypeptide binds both oleic acid and linoleic acid as an enzyme substrate, wherein the ratio of ω-3 fatty acids to ω-6 fatty acids are increased.

24. A method according to claim 23 wherein the host cell producing ω-3 fatty acids and ω-6 fatty acids lacks a polypeptide having Δ12 desaturase activity.

25. A method according to claim 22 or 23 wherein the isolated nucleic acid fragment encoding a protein having Δ15 desaturase activity encodes an amino acid sequence as set forth in SEQ ID NOs:2.

26. A method according to claim 22 wherein the ω-3 fatty acids are selected from the group consisting of: α-linolenic acid, stearidonic acid, eicosatrienoic acid, eicosatetraenoic acid, eicosapentaenoic acid, docosapentaenoic acid and docosahexaenoic acid.

27. A method according to claim 22 wherein the genes encoding enzymes of the ω-3/ω-6 fatty acid biosynthetic pathway are selected from the group consisting of: a Δ6 desaturase, an elongase, a Δ5 desaturase, a Δ4 desaturase, a Δ8 desaturase, a Δ9 desaturase, a Δ9 elongase and a Δ17 desaturase.

28. A method according to any one of claims 13, 14, 22 and 23, wherein the host cell is selected from the group consisting of: plants, algae, bacteria, yeast and fungi.

29. A method according to claim 28 wherein the host cell is a plant selected from the group consisting of: soybean, corn, flax, rapeseed, primrose, canola, maize, safflower and sunflower.

30. A method according to claim 28 wherein the host cell is a fungus selected from the group consisting of: *Thraustochytrium* sp., *Schizochytrium* sp. and *Mortierella* sp.

31. A method according to claim 28 wherein the yeast is an oleaginous yeast.

32. A method according to claim 31 wherein the oleaginous yeast is selected from the group consisting of: *Yarrowia, Candida, Rhodotorula, Rhodosporidium, Cryptococcus, Trichosporon* and *Lipomyces*.

33. A method of obtaining a nucleic acid fragment encoding a Δ15 desaturase enzyme comprising:
   (a) probing a genomic library with the nucleic acid fragment of claim 1;
   (b) identifying a DNA clone that hybridizes with the nucleic acid fragment of claim 1; and
   (c) sequencing the genomic fragment that comprises the clone identified in step (b),
wherein the sequenced genomic fragment encodes a Δ15 desaturase enzyme.

34. The isolated nucleic acid fragment of either of claims 1 or 4 wherein the isolated nucleic acid fragment encodes a polypeptide having both a Δ15 desaturase activity and a Δ12 desaturase activity.

* * * * *

UNITED STATES PATENT AND TRADEMARK OFFICE
CERTIFICATE OF CORRECTION

PATENT NO. : 7,659,120 B2  
APPLICATION NO. : 10/985254  
DATED : February 9, 2010  
INVENTOR(S) : Yadav et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 555 days.

Signed and Sealed this

Thirtieth Day of November, 2010

David J. Kappos  
*Director of the United States Patent and Trademark Office*